(12) United States Patent
Chai et al.

(10) Patent No.: US 9,365,851 B2
(45) Date of Patent: Jun. 14, 2016

(54) SPALT-LIKE TRANSCRIPTION FACTOR 4 (SALL4) AND USES THEREOF

(71) Applicants: National University of Singapore, Singapore (SG); Brigham and Women's Hospital, Boston, MA (US)

(72) Inventors: Li Chai, Boston, MA (US); Todor Dimitrov, Boston, MA (US); Daniel Geoffrey Tenen, Singapore (SG); Kol Jia Yong, Singapore (SG); Bee Hui Liu, Singapore (SG)

(73) Assignees: National University of Singapore, Singapore (SG); Brigham and Women's Hospital, Boston, MA (US)

( * ) Notice: Subject to any disclaimer, the term of this patent is extended or adjusted under 35 U.S.C. 154(b) by 0 days.

(21) Appl. No.: 14/345,603

(22) PCT Filed: Sep. 20, 2012

(86) PCT No.: PCT/SG2012/000347
§ 371 (c)(1),
(2) Date: Mar. 18, 2014

(87) PCT Pub. No.: WO2013/043128
PCT Pub. Date: Mar. 28, 2013

(65) Prior Publication Data
US 2015/0080315 A1  Mar. 19, 2015

Related U.S. Application Data

(60) Provisional application No. 61/536,940, filed on Sep. 20, 2011.

(51) Int. Cl.
| | | |
|---|---|---|
| *A61K 38/10* | (2006.01) | |
| *C07K 16/18* | (2006.01) | |
| *C07K 7/08* | (2006.01) | |
| *C12N 15/113* | (2010.01) | |
| *A61K 38/17* | (2006.01) | |
| *G01N 33/574* | (2006.01) | |

(52) U.S. Cl.
CPC .......... *C12N 15/113* (2013.01); *A61K 38/1709* (2013.01); *C07K 7/08* (2013.01); *C07K 16/18* (2013.01); *G01N 33/57496* (2013.01); *C12N 2310/122* (2013.01); *C12N 2310/14* (2013.01); *C12N 2310/531* (2013.01)

(58) Field of Classification Search
CPC ... A61K 38/1709; A61K 38/10; C07K 16/18; C07K 7/08
USPC ...................................................... 514/19.3
See application file for complete search history.

(56) References Cited

U.S. PATENT DOCUMENTS

| | | | |
|---|---|---|---|
| 7,790,407 B2 * | 9/2010 | Ma ............... | A01K 67/0275 435/7.21 |
| 2007/0141066 A1 | 6/2007 | Phillips et al. | |
| 2007/0174923 A1 * | 7/2007 | Ma ............... | A01K 67/0275 800/14 |
| 2008/0241110 A1 | 10/2008 | Ma | |
| 2009/0232893 A1 | 9/2009 | Bader et al. | |
| 2009/0269763 A1 | 10/2009 | Eilertsen et al. | |

FOREIGN PATENT DOCUMENTS

| EP | 1 998 177 A2 | 12/1998 |
|---|---|---|
| WO | WO 2007/064696 A2 | 6/2007 |
| WO | WO 2009/057831 A1 | 5/2009 |
| WO | WO 2009/108917 A2 | 9/2009 |

OTHER PUBLICATIONS

Bard, J.D., et al., "Signal Transducer and Activator of Transcription 3 Is a Transcriptional Factor Regulating the Gene Expression of Sall", *The FASEB Journal*, 23: 1405-1414 (2009).
Ben-Porath, I., et al., "An Embryonic Stem Cell-Like Gene Expression Signature in Poorly Differentiated Aggressive Human Tumors", *Nature Genetics*, 40(5): 499-507 (2008).
Beroukhim, R., et al., "The Landscape of Somatic Copy-Number Alteration Across Human Cancers", *Nature*, 463: 899-905 (2010).
Cao, D., et al., "SALL4 Is a Novel Diagnostic Marker for Testicular Germ Cell Tumors", *Am J Surg Pathol*, 33(7): 1065-1077 (2009).
Cao, D., et al., "SALL4 Is a Novel Sensitive and Specific Marker for Metastatic Germ Cell Tumors, With Particular Utility in Detection of Metastatic Yolk Sac Tumors", *Cancer*, 115: 2640-2651 (2009).
Cao, D., et al., "SALL4 Is a Novel Sensitive and Specific Marker of Ovarian Primitive Germ Cell Tumors and Is Particularly Useful in Distinguishing Yolk Sac Tumor From Clear Cell Carcinoma", *Am J Surg Pathol*, 33(6):894-904 (2009).
Cerchietti, L.C., et al., "A Peptomimetic Inhibitor of BCL6 With Potent Antilymphoma Effects In Vitro and In Vivo", *Blood*, 113(15): 3397-3405 (2009).
Cerchietti, L.C., et al., "A Small Molecule Inhibitor of BCL6 Kills DLBCL Cells In Vitro and In Vivo", *Cancer Cell*, 17(4):400-41 1 (2010).
Chiba, T., et al., "The Polycomb Gene Products BMI1 Contributes to the Maintenance of Tumor-Initiating Side Population Cells in Hepatocellular Carcinoma", *Cancer Research*, 68(19): 774-7749 (2008).
Cui, W., et al., "Differential Expression of the Novel Oncogene, SALL4, in Lymphoma, Plasma Cell Myeloma, and Acute Lymphoblastic Leukemia", *Modern Pathology*, 19:1585-1592 (2006).

(Continued)

*Primary Examiner* — Julie Ha
(74) *Attorney, Agent, or Firm* — Hamilton, Brook, Smith & Reynolds, P.C.

(57) ABSTRACT

Described are methods of treating a solid tumor which expresses Spalt-Like Transcription Factor 4 (SALL4) and Phosphatase and Tensin Homolog (PTEN) in an individual in need thereof, comprising administering to the individual an effective amount of a composition that inhibits SALL4. In addition, the invention is directed to methods of detecting an aggressive cancer in an individual in need thereof as well as methods of detecting a poor prognosis of a patient with cancer in an individual in need thereof.

10 Claims, 98 Drawing Sheets

(56) References Cited

OTHER PUBLICATIONS

Daley, G.Q., "Common Themes of Dedifferentiation in Somatic Cell Reprogramming and Cancer", *CSHL Quant Biol*, 73: 171-174 (2008).

Deisch, J., et al., "Immunoexpression of SALL4 in Wilms Tumors and Developing Kidney", *Pathol Oncol Res*, 17(3):639-644 (2011).

Denslow, S.A. and Wade, P.A., "The Human Mi-2/NuRD Complex and Gene Regulation", *Oncogene*, 26:5433-5438 (2007).

Elit, L. and Hirte, H., "Current Status and Future Innovations of Hormonal Agents, Chemotherapy and Investigational AGents in Endometrial Cancer", *Curr Opin Obstet Gynecol*, 14: 67-73 (2002).

El-Serag, H.B., "Hepatocellular Carcinoma", *N Engl J Med*, 365:1118-1127 (2011).

Farazi, P.A. and DePhinho, R.A., "Hepatocellular Carcinoma Pathogenesis: From Genes to Environment", *Nat. Rev Cancer*, 6(9): 674-687 (2006).

Gao, C., et al., "The Role of Stem Cell Factor SALL4 in Leukemogenesis", *Crit Rev Oncog.*, 16(1-2):117-127 (2011).

Gao, C., et al., "Targeting Transcription Factor SALL4 in Acute Myeloid Leukemia by Interrupting Its Interaction With an Epigenetic Complex", *Blood*, 121(8):1413-1421 (2013).

Hermeking, H., "The MYC Oncogene as a Cancer Drug Target", *Current Cancer Drug Targets*, 3:163-175 (2003).

Hong, W., et al., "FOG-1 Recruits the NuRD Repressor Complex to Mediate Transcriptional Repression by GATA-1", *The EMBO Journal*, 24:2367-2378 (2005).

Jeong, H.W., et al., "SALL4, A Stem Cell Factor, Affects the Side Population by Regulation of the ATP-Binding Cassette Drug Transport Genes", *PLOS One*, 6(4): e18372, 11 pages (2011).

Keating, G.M. and Santoro, A., "Sorafenib: A Review of Its Use in Advanced Heptaocellular Carcinoma", *Drugs*, 69(2): 223-240 (2009).

Kiefer, S.M., et al., "Murine Sall1 Represses Transcription by Recruiting a Histone Deacetylase Complex", *The Journal of Biological Chemistry*, 277(17):14869-14876 (2002).

Knapp, D.C., et al., "Resistance to Chemotherapeutic Drugs Overcome by c-Myc Inhibition in a Lewis Lung Carcinoma Murine Model", *Anticancer Drugs*, 14: 39-47 (2003).

Kobayashi, D., et al., "SALL4 Is Essential for Cancer Cell Proliferation and Is Overexpressed at Early Clinical Stages in Breast Cancer", *International Journal of Oncology*, 38: 933-939 (2011).

Kobayashi, D., et al., "Overexpression of SALL4 in Lung Cancer and Its Importance in Cell Proliferation", *Oncology Reports*, 26: 965-970 (2011).

Levan, K., et al., "Identification of a Gene Expression Signature for Survival Prediction in Type 1 Endometrial Carcinoma", *Gene Expr*, 14(6): 361-370 (2010).

Lauberth, S.M. and Rauchman, M., "A Conserved 12-Amino Acid Motif in Sall1 Recruites the Nucleosome Remodleing and Deacetylase Corepressor Complex", *The Journal of Biological Chemistry*, 281(33): 23922-23931 (2006).

Lauberth, S.M., et al., "A Phosphomimetic Mutation in the Sall1 Repression Motif Disrupts Recruitment of the Nucleosome Remodeling and Deacetylase Complex and Repression of Gbx2", *The Journal of Biological Chemistry*, 282(48): 34585-34868 (2007).

Lee, J.S., et al., "A Novel Prognostic Subtype of Human Hepatocellular Carcinoma Derived From Hepatic Progenitor Cells", *Nature Medicine*, 12(4): 410-416 (2006).

Lejon, S., et al., "Insights Into Association of the NuRD Complex With FOG-1 From the Crystal Structure of an RbAp48•FOG-1 Complex", *The Journal of Biological Chemistry*, 286(2): 1196-1203 (2011).

Li, Y., et al., "Pretreatment With Phosphatase and Tensin Homolog Deleted on Chromosome 10 (PTEN) Inhibitor SF1670 Augments the Efficacy of Granulocyte Transfusion in a Clinically Relevant Mouse Model", *Blood*, 117(24): 6702-6713 (2011).

Liu, A., et al., "Diagnostic Utility of Novel Stem Cell Markers SALL4, OCT4, NANOG, SOX2, UTF1, and TCL1 in Primary Mediastinal Germ Cell Tumors", *Am J Surg Pathol*, 34(5):697-706 (2010).

Llovet, J.M. and Bruix, J., "Novel Advancements in the Management of Heptaocellular Carcinoma in 2008", *Journal of Hepatology*, 48:S20-S37 (2008).

Lu, J., et al., "Stem Cell Factor SALL4 Represses the Transcriptions of PTEN and SALL1 Throught an Epigenetic Repressor Complex", *PLOS One*, 4(5): e5577, 13 pages (2009).

Ma, Y., et al., "SALL4, A Novel Oncogene, Is Constitutively Expressed in Human Acute Myeloid Leukemia (AML) and Induces AML in Transgenic Mice", *Blood*, 108(8):2726-2735 (2006).

Mehlen, P. and Puisieux, A., "Metastasis: A Question of Life or Death", *Nature Reviews Cancer*, 6: 449-458 (2006).

Mei, K., et al., "Diagnostic Utility of SALL4 in Primary Germ Cell Tumors of the Central Nervous System: A Study of 77 Cases", *Modern Pathology*, 22:1628-1636 (2009).

Morris, M.C., "A Peptide Carrier for the Delivery of Biologically Active Proteins Into Mammalian Cells", *Nature Biotechnology*, 19(12): 1173-1176 (2001).

Oikawa, T., et al., "Sall4 Regulates Cell Fate Decision in Fetal Hepatic Stem/Progenitor Cells", *Gastroenterology*, 136: 1000-1011 (2009).

Oikawa, T., et al., "#1364 Down-Regulation of SALL4 Inhibits Tumor Growth in Hepatocellular Carcinoma", *The Liver Meeting 2010, The American Association for the Study of Liver Disease*.

Rao, S., et al., "Differential Roles of Sall4 Isoforms in Embryonic Stem Cell Pluripotency", *Molecular and Cellular Biology*, 30(22): 5364-5380 (2010).

Reya, T., et al., "Stem Cells, Cancer, and Cancer Stem Cells", *Nature*, 414: 105-111 (2001).

Sakaki-Yumoto, M., et al., "The Murine Homolog of SALL4, a Causative Gene in Okihiro Synddrome, Is Essential for Embryonic Stem Cell Prolieration, and Cooperates With Sall1 in Anorectal, Heart, Brain and Kidney Development", *Development*, 133:3005-3013 (2006).

Tabach, Y., et al., "Amplification of the 20q Chromosomal Arm Occurs Early in Tumorigenic Transformation and May Initiate Cancer", *PLOS One*, 6(11): e14632, 15 pages (2011).

Ushiku, T., et al., "SALL4 Represents Fetal Gut Differentiation of Gastric Cancer, and Is Diagnostically Useful in Distinguishing Hepatoid Gastric Carcinoma From Hepatocellular Carcinoma", *Am J Surg Pathol.*, 34(4): 533-540 (2010).

Van Waardenburg, R.C., et al., "Effects of C-MYC Oncogene Modulation on Drug Resistance in Human Small Cell Lung Carcinoma Cell Lines", *Anticancer Res.*, 16(4A): 1963-1970 (1996).

Wadia, J.S. and Dowdy, S.F., "Transmembrane Delivery of Protein and Peptide Drugs by TAT-Mediated Transduction in the Treatment of Cancer, *Adv Drug Deliv Rev*, 57(4): 579-596 (2004).

Wang, F., et al., "Diagnostic Utility of SALL4 in Extragonadal Yolk Sac Tumors", *Am J Surg Pathol*, 33(10):1529-1539 (2009).

Warren, M., et al., "A SAll4 Mutant Mouse Model Useful for Studying the Role of Sall4 in Early Embryonic Development and Organogenesis", *Genesis*, 45:51-58 (2007).

Woo, H.G., et al., "Identification of a Cholangiocarcinoma-Like Gene Expression Trait in Hepatocellular Carcinoma", *Cancer Res.*, 70(8): 3034-3041 (2010).

Wu, Q., et al., "Sall4 Interacts With Nanog and Co-Occupies Nanog Genomic Sites in Embryonic Stem Cells", *Journal of Biological Chemistry*, 281(34): 24090-24094 (2006).

Yang, J., et al., "SALL4 Is a Key Regulator of Survival and Apoptosis in Human Leukemic Cells", *Blood*, 112(3): 805-8213 (2008).

Yang, J.D., et al., "Epidemiology and Management of Hepatocellular Carcinoma", *Infect Dis Clin North Am.*, 24(4): 899-viii (2010).

Yang, J., et al., "A Novel SALL4/OCT4 Transcriptonal Feedback Network for Pluripotency of Embryonic Stem Cells", *PLOS One*, 5(5): e10766, 10 pages (2010).

Yang, J., et al., "Bmi-1 Is a Target Gene for SALL4 in Hematopoietic and Leukemic Cells", *PNAS*, 104(25): 10494-10499 (2007).

Yang, J., et al., "Genome-Wide Analysis Reveals Sall4 to Be a Major Regulator of Pluripotency in Murine-Embryonic Stem Cells", *PNAS*, 105(50): 19756-19761 (2008).

Yong, K.J., et al., "Oncofetal Gene SALL4 in Aggressive Hepatocellular Carcinoma", *The New England Journal of Medicine*, 368(24):2266-2276 (2013).

(56) References Cited

OTHER PUBLICATIONS

Zhang, J., et al., "PTEN Maintains Haematopoietic Stem Cells and Acts in Lineage Choice and Leukaemia Prevention", *Nature*, 441(7092): 518-522 (2006).

Zhang, J., et al., "Sall4 Modulates Embryonic Stem Cell Pluripotency and Early Embryonic Development by the Transcriptional Regulation of Pou5f1", *Nature Cell Biology*, 10 pages plus 9 supplemental figures, published online Sep. 17, 2006.

Zhu, X., et al., "PTEN Induces $G_1$ Cell Cycle Arrest and Decreases Cyclin D3 Levels in Endometrial Carcinoma Cells", *Cancer Research*, 61:4569-4575 (2001).

Notification of Transmittal of the International Search Report and the Written Opinion of the International Searching Authority for PCT/SG2012/000347, "SALL4 and Uses Thereof", mailed on Dec. 6, 2012.

International Preliminary Report on Patentability for PCT/SG2012/000347, "SALL4 and Uses Thereof", report completed on Oct. 1, 2013.

Shuai, X., et al., "Overexpression of the novel oncogene SALL4 and activation of the Wnt/β-catenin pathway in myelodysplastic syndromes", *Cancer Genetics and Cytogenetics* 194(2): 119-124 (2009).

Böhm, J., et al., "Synergistic cooperation of Sall4 and Cyclin D1 in transcriptional repression", *Biochemical and Biophysical Research Communications*, 356(3): 773-779 (2007).

Lim, CY, et al., "SALL4 Regulates Distinct Transcription Circuitries in Different Blastocyst-Derived Stem Cell Lineages", *Cell Stem Cell*, 3(5): 543-554 (2008).

Li, A., et al., "SALL4 is a new target in endometrial cancer", *Oncogene*, (2013) 1-10.

\* cited by examiner

Figures 1A-1D
A
MSRRKQAKPQHI-wt
MSRRAQAKPQHI-mutant
SRMRQKIHPKIQ-Scramble
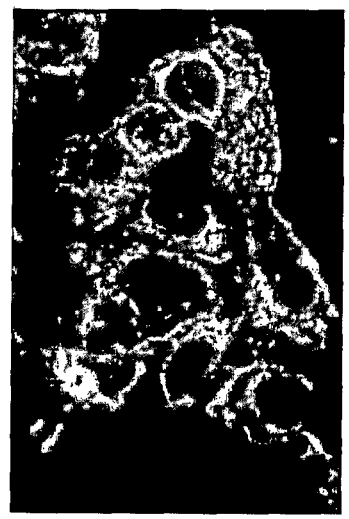
HDAC activity pulldown
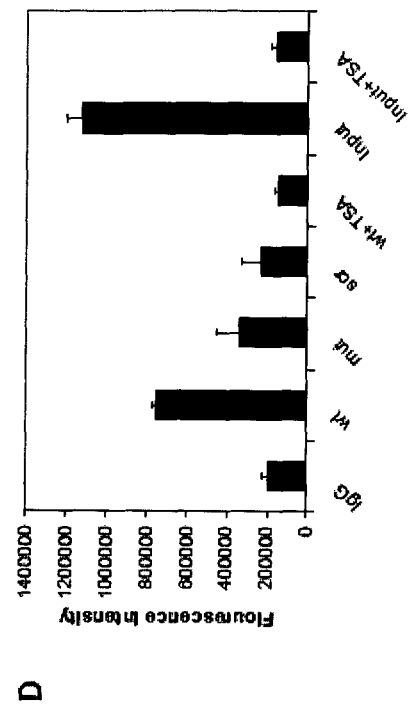
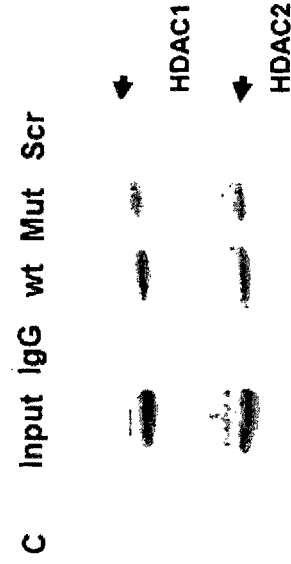

FIGS. 11A-11D
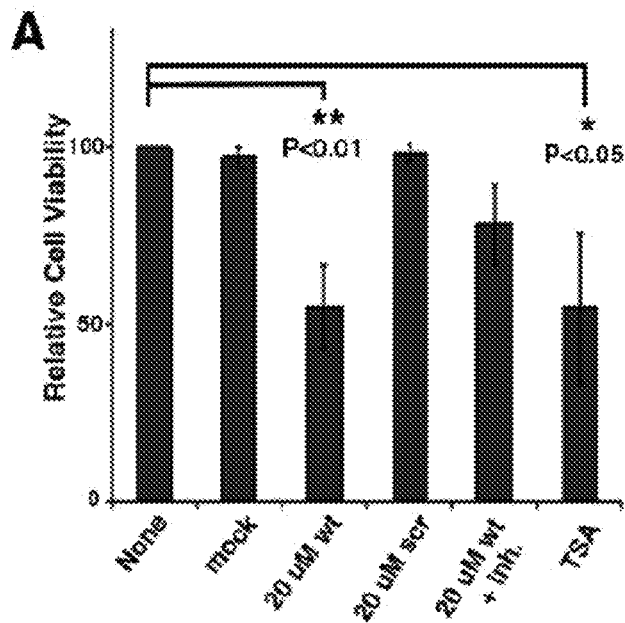
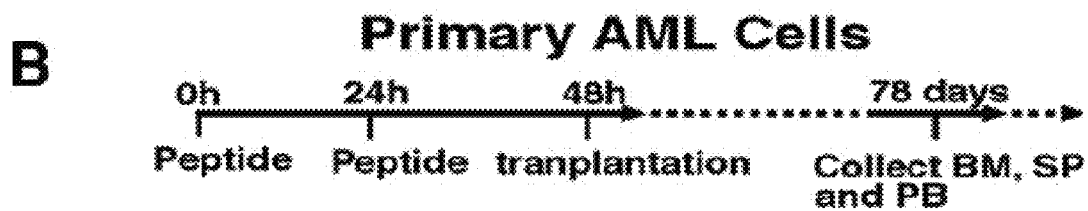
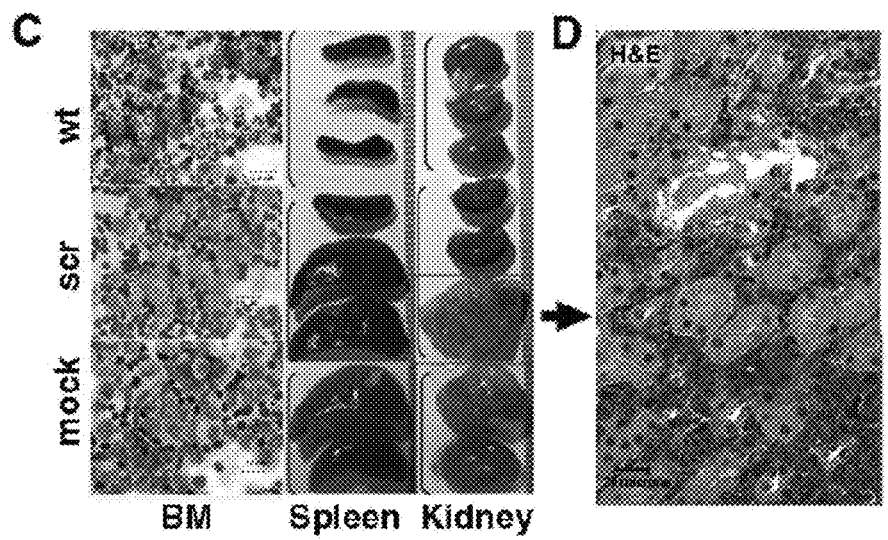

FIGS. 12D-12F
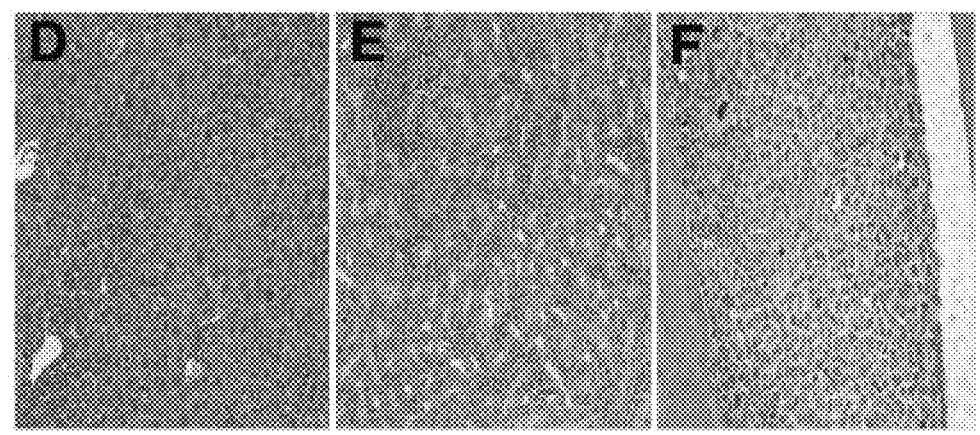
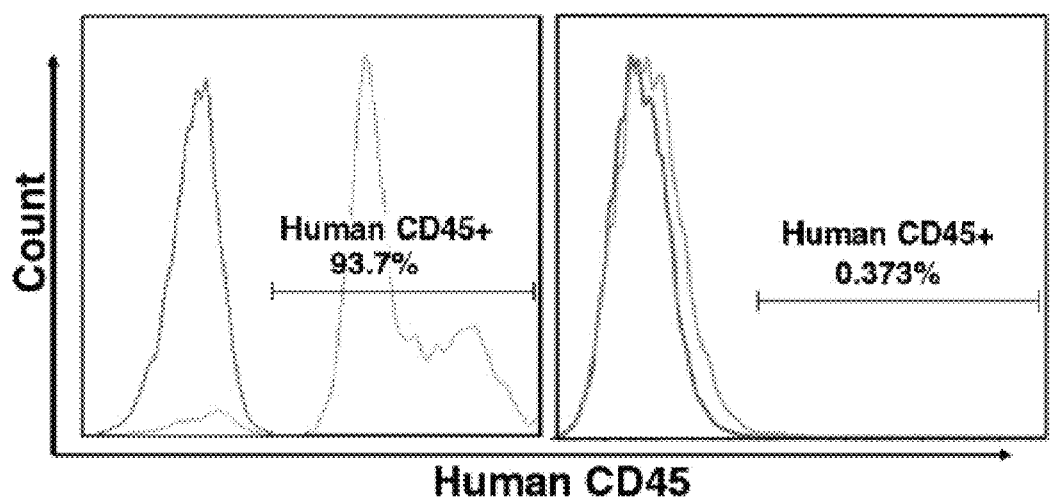

FIGS. 24B-24F

B: (BrdU staining) SALL4 *in vitro* overexpression – THLE-2 and/ or THLE-3 and SNU-387

C: (*in vivo* xenotransplant assay) SALL4 *in vitro* overexpression – THLE-2 and/ or THLE-3 and SNU-387

D: SALL4B transgenic model – with or without 2-stage chemical carcinogenesis protocol E: SALL4 *in vivo* overexpression model – Alb-TVA SALL4 overexpression model F: Liver injury (hepatectomy and/ or chemical-induced) model(s)

C

D

Figures 46A-46B
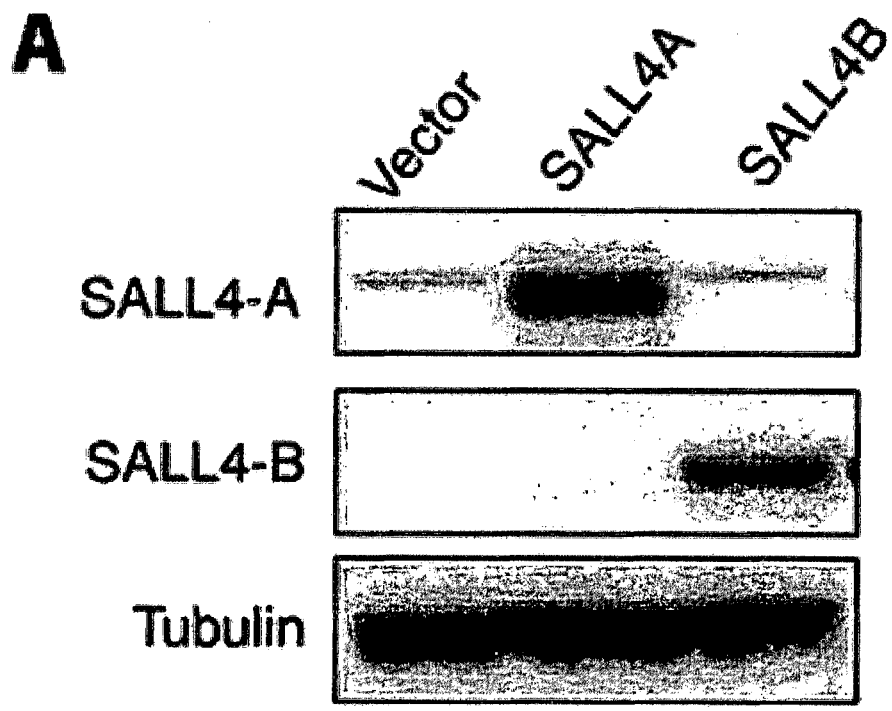
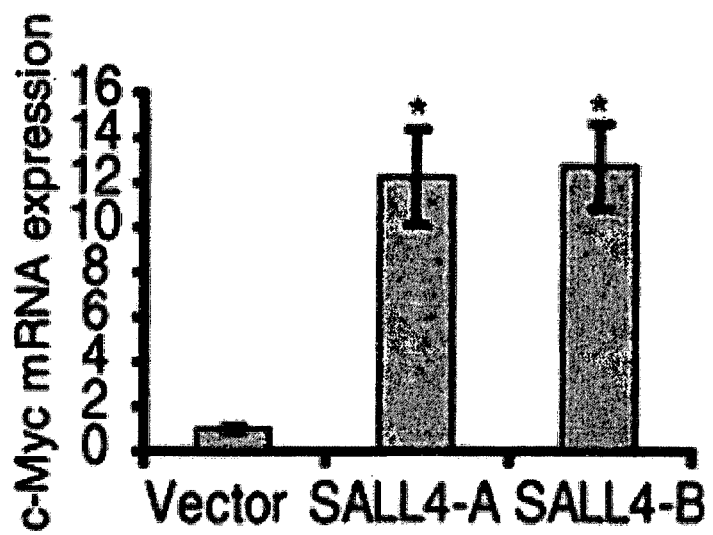

Table S3. List of primers used in ChIP-qPCR

| Primer | Sequence |
|---|---|
| cMyc-PI-f | AAGGAGGTGGCTGGAAACTT |
| cMyc-PI-r | CGTTCAGGTTTGCGAAAGTA |
| cMyc-PII-f | GGAAAGAGGACCTGGAAAGG |
| cMyc-PII-r | GGGACCGGACTTCCTAAAAG |
| Negative-f | AGCAGGTGGATCATGAGGTC |
| Negative-r | CTGGAGTGCAGTGGTGTGAT |

Figure 50

SPALT-LIKE TRANSCRIPTION FACTOR 4 (SALL4) AND USES THEREOF

RELATED APPLICATION(S)

This application is the U.S. National Stage of International Application No. PCT/SG2012/000347, filed Sep. 20, 2012, which designates the U.S., published in English, and claims the benefit of U.S. Provisional Application No. 61/536,940, filed on Sep. 20, 2011.

The entire teachings of the above application(s) are incorporated herein by reference.

GOVERNMENT SUPPORT

This invention was made with government support under P01 DK080665, R01HL092437, R01HL092437-A1S1 and P01HL095489 awarded by the National Institutes of Health. The government has certain rights in the invention.

INCORPORATION BY REFERENCE OF MATERIAL IN ASCII TEXT FILE

This application incorporates by reference the Sequence Listing contained in the following ASCII text file:

a) File name: 44591030002SEQLIST.txt; created 11-19-2014, 4 KB in size.

BACKGROUND OF THE INVENTION

Over the past few years, much effort has been expended to develop anticancer drugs on the basis of cell permeable peptides. Such complex formation is a difficult target for small molecules since the interacting surfaces lack specific interaction pockets typical for surface molecules and receptors.

A need exists for improved drugs that can be used to treat cancer.

SUMMARY OF THE INVENTION

Described herein is the identification of SALL4 as a molecular target for targeted cancer therapy of a subtype of solid tumors, including some clinically challenging cancers, and use of short hairpin ribonucleic acid (shRNA) and a 12 amino acid (12-AA) peptide as agents for treating SALL4-expressing solid tumors. Specifically, using shRNAs and a 12-AA peptide, it was shown herein that SALL4 can be used as a therapeutic target in a subgroup of solid tumors that expresses SALL4. Also shown herein, is that SALL4 is a molecular target in a subgroup of solid tumors that have aberrant SALL4 expression.

Accordingly, in one aspect, the invention is directed to a method of treating a solid tumor which expresses SALL4 and Phosphatase and Tensin Homolog (PTEN) in an individual in need thereof, comprising administering to the individual an effective amount of a composition that inhibits SALL4.

In another aspect, the invention is directed to a method of treating a liver tumor which expresses SALL4 in an individual in need thereof comprising administering to the individual an effective amount of a composition that inhibits SALL4.

In yet another aspect, the invention is directed to a method of treating an endometrial tumor which expresses SALL4 in an individual in need thereof comprising administering to the individual an effective amount of a composition that inhibits SALL4.

In another aspect, the invention is directed to a method of treating an ovarian epithelial tumor which expresses SALL4 in an individual in need thereof comprising administering to the individual an effective amount of a composition that inhibits SALL4.

The invention is also directed to a method of detecting an aggressive liver cancer in an individual in need thereof comprising detecting whether one or more liver cancer cells of the individual expresses SALL4, wherein if SALL4 is detected in the one or more liver cancer cells, then an aggressive liver cancer is detected in the individual.

The invention is also directed to a method of detecting a poor prognosis of a patient with liver cancer in an individual in need thereof, comprising detecting whether one or more liver cancer cells of the patient expresses SALL4, wherein if SALL4 is detected in the one or more liver cancer cells of the patient, then a poor prognosis is detected in the patient.

The invention is also directed to a method of detecting an aggressive endometrial cancer in an individual in need thereof comprising detecting whether one or more endometrial cancer cells of the individual expresses SALL4, wherein if SALL4 is detected in the one or more endometrial cancer cells, then an aggressive endometrial cancer is detected in the individual.

The invention is also directed to a method of detecting a poor prognosis of a patient with endometrial cancer in an individual in need thereof, comprising detecting whether one or more endometrial cancer cells of the patient expresses SALL4, wherein if SALL4 is detected in the one or more endometrial cancer cells of the patient, then a poor prognosis is detected in the patient.

SALL4 has been proposed to be a diagnostic marker for certain cancers by other groups, but its role as a therapeutic target has not been investigated. Other molecules, mostly kinases, have been proposed to be targets for cancer therapy. However, prior to the data described herein, SALL4 was not identified as a therapeutic target in solid tumors. Some molecules that are important in carcinogenesis are not druggable, or difficult to target. SALL4 on the other hand, can be targeted by various means as shown herein. Most importantly, the effects of targeting SALL4 are specific only for SALL4-expressing cancer cells, most of the adult tissues do not have SALL4 expression.

BRIEF DESCRIPTION OF THE DRAWINGS

FIGS. 1A-1D: Peptide derived from N-terminus of SALL4 penetrates through cell and nuclear membranes and interacts with the proteins from the NuRD complex. (1A) Amino acid composition of the peptides used in this study (SEQ ID NOS: 1, 6 and 7). (1B) Confocal micrograph of the distribution of FITC labeled wild-type peptide in MCF7 cells. (1C) Association of the wild type peptide with HDAC1 and HDAC2 in vitro. Nuclear extracts from SNU 398 cells were immunoprecipitated with anti FITC antibody followed by Western blotting with anti HDAC 1 and HDAC 2 antibodies. (1D) Nuclear extracts from SNU398 cells were incubated with wt, Mut and scr peptides, N-terminally conjugated with FITC. Extracts were subsequently immunoprecipitated with anti FITC antibody and the complexes pulled down were subjected to HDAC activity assay following the recommendations of the manufacturer (Active Motif).

FIGS. 11A-11F: Down-regulation of SALL4 by shRNA leads to decreased cell viability of primary human AML cells in culture and reduced leukemic development in vivo. (11A) Down-regulation of SALL4 RNA in primary AML cells using shRNA. Control scrambled shRNA-infected cells and SALL4 shRNA30 infected cells were analyzed 48 h post-transduction. The expression of SALL4 RNA in AML cells infected with SALL4 shRNAs-expressing retroviruses was reduced to 35% of those infected with scrambled pRS control vectors, evaluated by qRT-PCR after normalized to GAPDH. (N=3 biological samples, Error Bars: +/−SD). (11B) Increased apoptosis and cell death were observed via flow cytometry analysis of Annexin V/PI staining in AML cells upon SALL4 knock down. Data were derived from three independent experiments. Viable cells were defined as the double negative (Annexin V−/PI−) population. The viability was set as 100 for control group. (11C) Xenotransplantation showed increased survival of mice receiving SALL4-reduced leukemic cells. 1.5 million primary human AML cells were transduced as described in the methods and cultured for 48 hours prior to transplantation via tail vein injection. While the median survival of recipient mice with control scrambled shRNA retrovirus-transduced primary human AML cells (n=7) was 33 days, the median survival of recipient mice with SALL4 shRNA retrovirus-infected primary human AML cells (N=6) was 109 days. The p value using Log rank (Mantel-Cox) was 0.03 and the p-value using Gehan-Breslow-Wilcoxon was 0.01. (11D-11F) Leukemia development in xenotransplant recipient mice. AML is defined as blast count more than 20% in peripheral blood and/or bone marrow with multiple organ involvements observed in recipient mice. Blasts were present in liver (11D, ×200), spleen (11E, ×200), and bone marrow (11F, ×200), as assessed by hematoxylin and eosin staining. AML cells in xenograft recipients were human CD45 positive. Flow cytometry was performed on bone marrow from recipients following transduction with control scrambled or SALL4 shRNA retrovirus.

FIGS. 12A-12F: Treatment of SALL4 peptide in primary human AML cells induces reduced cell viability in culture and impaired leukemic engraftment in vivo. (12A) Wild type peptide treatment reduces cell viability of human AML cells in culture, and this effect can be reversed in part by the PTEN inhibitor SF1670. 1×106 AML cells were treated with nothing (None), Pep-1 alone (Mock), or 20 µM wild type (wt), or scrambled peptide (scr), or wt peptide with 400 nM PTEN inhibitor SF1670 (wt+inh) or with 100 nM TSA for 48 hours, as described in the Methods. Cell viability of untreated primary AML cells is set as 100. (N=3 biological samples, Error Bars: +/−SD) (12B) Schematic diagram shows the steps and time course of the peptide treatment in the xenotransplantation assay. 1 million of primary human leukemic cells were treated twice with peptides at a 24 h interval, followed by transplantation into sublethally irradiated NSG mice. Mice were killed when ill. (12C) Wright-Giemsa staining of a cytospin preparation of bone marrows (BM) from scr- or carrier alone-treated mice shows marked expansion of immature blasts, which is not present in the wt-treated recipient BM (left panel, bar, 10 µm). The scr- or Pep-1 carrier alone-treated mice also have enlarged spleen (middle panel) and kidney (right panel), while the wt-treated recipient mice show normal spleen and kidney. (12D) Histology section of the kidney (arrow) shows effacement of normal architecture by leukemic infiltration (Bar, 20 µm). (12E-12F) SALL4 wild type peptide (wt) treatment significantly impaired human AML cell engraftments in NSG mice analyzed at 78 days post-transplantation. Percentage of human CD45+ cells engrafted in BM, spleen (SP) and peripheral blood (PB) was determined by flow cytometry. Representative FACS results from wt, scr and Pep-1 carrier only (mock) treatments are shown in (12E), and statistical summary is shown in (12F). N=5 mice per group, P<0.01 in BM, or P<0.05 in SP and PB, ANOVA with Tukey's multiple comparison test.

FIGS. 24A-24F: SALL4 overexpression in HCC leads to increased cell proliferation and (induces tumor formation). (24A) SNU-398 cells have higher proliferation rate compared to SNU-387 cells. (24B) (BrdU) in vitro SALL4 overexpression in THLE-2 and/or THLE-3 and SNU-387 (24C) (in vivo xenotransplantation assay) in vitro SALL4 overexpression in THLE-2 and/or THLE-3 and SNU-387 (24D) SALL4B transgenic model, with or without 2-stage chemical carcinogenesis model (24E) SALL4 in vivo overexpression (somatic gene transfer) Alb-TVA model. (24F) Liver injury models (hepatectomy and/or chemical-induced liver injury).

Arrow shows subcutaneous tumor formation at right flank of the mouse. Graph showing tumor volume ($cm^3$) measured at various time point after transplantation (n=3). Tumor volume ($cm^3$) was derived by the formula volume=$\pi/6$×larger diameter×(smaller diameter). (25G) Kaplan-Meier curve shows poorer survival advantage for mice harboring SNU-398 or HuH-7 cells infected with scrambled control shRNA as compared to mice harboring cells infected with SALL4-specific E5 shRNA. n=12; p=0.036.

Figure 26A:
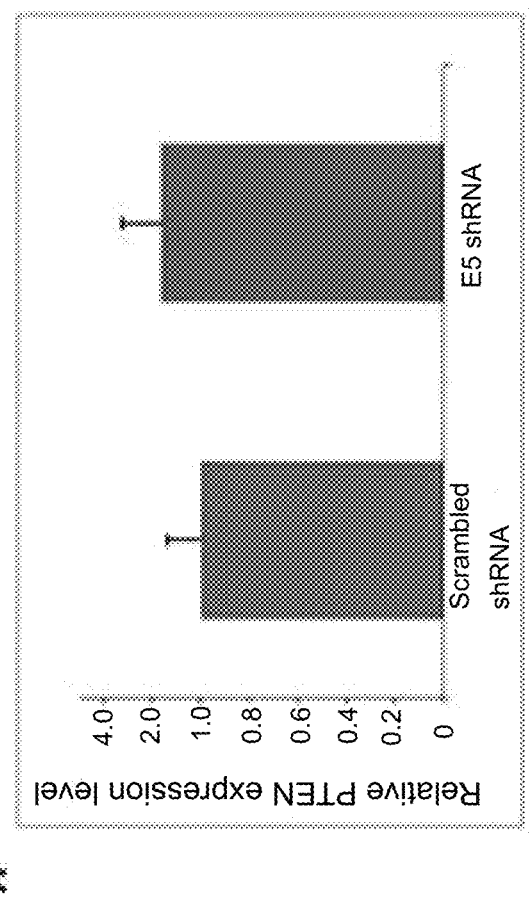
Figure 26B:
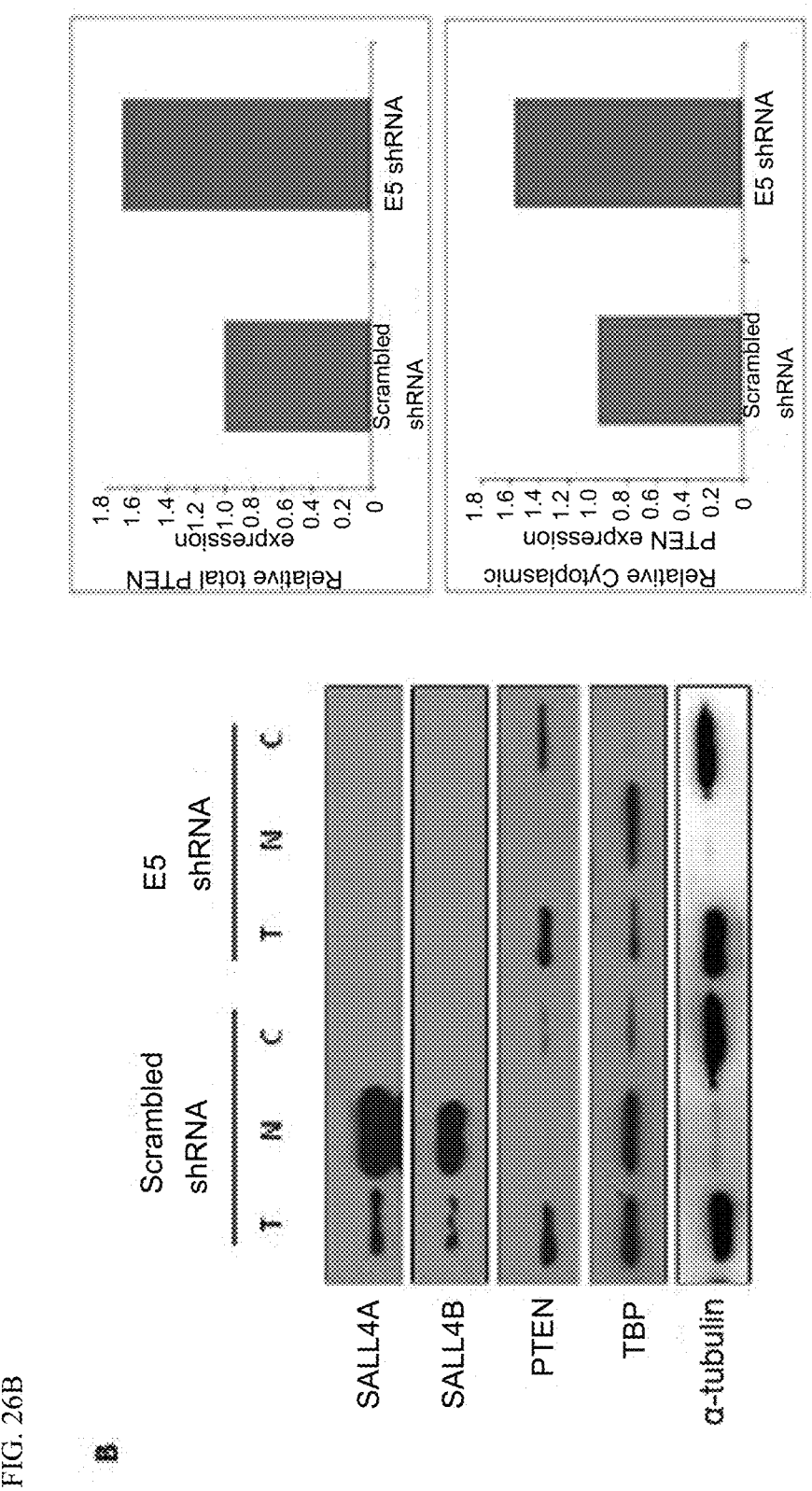
Figure 26C:
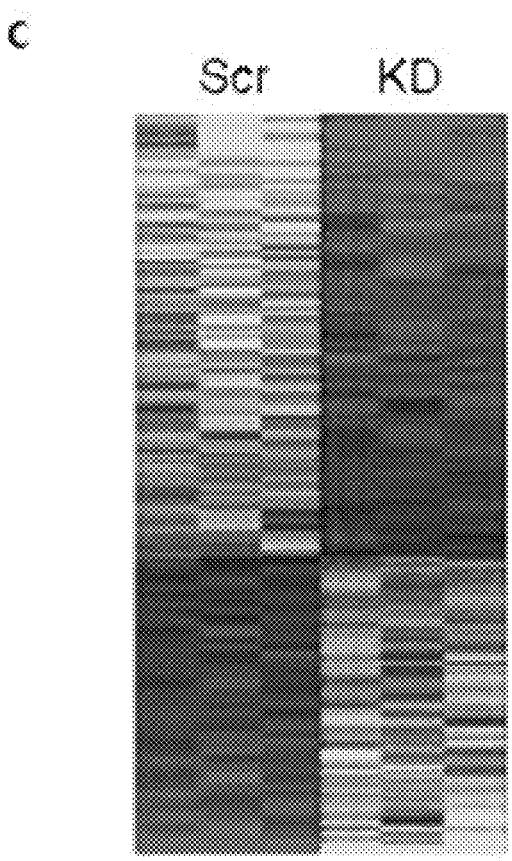

FIGS. 26A-26C: PTEN repression as a mechanism of SALL4-induced HCC. (26A) qPCR analysis of PTEN expression upon SALL4 gene knockdown. An increase of 16.5% of PTEN was observed four days after transduction. E5 shRNA is a shRNA specifically targets SALL4. (26B) Western blot analysis of PTEN protein expression upon SALL4 gene knockdown using fractionated nuclear (N) and cytoplasmic (26C) lysates. A total cell lysate (T) was used for protein expression analysis too. SALL4 is exclusively present in cell nuclei (left). Densitometry analysis of total PTEN expression (top right) and cytoplasmic PTEN expression (bottom right).

FIGS. 27A-27D: SALL4 peptide specifically and effectively target SALL4 in SALL4-overexpressed HCC cells. (27A) CitoTox 96 cell viability assay analysis of the effects of SALL4 peptide on high endogenous SALL4 SNU-398 cells. Absorbance at 490 nm is directly correlated to cell viability. Wildtype functional SALL4 peptide (wt), mutant non-functional SALL4 peptide (Mut.), trichostatin A (TSA), scrambled control peptide (Scr.), wildtype peptide+PTEN inhibitor (wt+Inh.) were given to SNU-398 cells at the indicated concentration. (27B) CitoTox 96 cell viability assay analysis of the effects of SALL4 peptide on low/no endogenous SALL4 SNU-387 cells. Absorbance at 490 nm is inversely correlated to cell viability. Wildtype functional SALL4 peptide (wt), mutant non-functional SALL4 peptide (Mut.), trichostatin A (TSA), scrambled control peptide (Scr.), wildtype peptide+PTEN inhibitor (wt+Inh.) were given to SNU-387 cells at the indicated concentration. (27C) Western blot analysis of the effects of peptides on PTEN expression. Wildtype functional SALL4 peptide (wt), trichostatin A (TSA), scrambled control peptide (Scr.), wildtype peptide+PTEN inhibitor (wt+Inh.) were given to SNU-398 or SNU-387 cells prior to protein expression analysis. (27D) Western blot analysis of the effects of peptides on phosphos-AKT (pAKT) expression. Wildtype functional SALL4 peptide (wt), trichostatin A (TSA) and scrambled control peptide (Scr.) were given to SNU-398 cells prior to protein expression analysis.

FIGS. 28A-28F: SALL4 is expressed in human fetal livers, silenced in adult livers and re-activated in a subgroup of human HCCs. (28A) Representative SALL4 IHC images of formalin-fixed paraffinembedded (FFPE) human fetal liver (left) and human adult liver (right). SALL4 expression is indicated by brown staining. (28B) Representative SALL4 IHC images of HCC (right) and the matched nonneoplastic (left) livers on tissue microarrays. SALL4 expression was detected in the HCC tissue and localized in the nucleus as indicated by the brown staining. Scale bar=100 µm. (28C) Differential SALL4 expression in 228 matched HCC and non-tumor livers from the Hong Kong cohort of primary clinical specimens as determined by microarray. P<0.0001. (28D) Microarray SALL4 expression of primary HCC and non-tumor livers extracted from public databases. P=0.003. (28E) Quantitative RTPCR analysis of SALL4A (left) and SALL4B (right) expression in 10 human HCC cell lines and two immortalized non-transformed hepatocyte cell lines, THLE-2 and THLE-3. All values were normalized to beta-actin and plotted relative to the expression of THLE-2 cell line. Error bars indicate standard error of three replicates. (28F) SALL4 CNV significantly and positively correlates with SALL4 gene expression in other cohorts of primary HCC tissues. Data were extracted from the GEO and the TCGA databases and HCC samples with SALL4 expression exceeded the threshold of expression intensity of 40 were included in the analysis. n=97, P<0.0001, R2=0.5411.

Figures 29A, 29B:
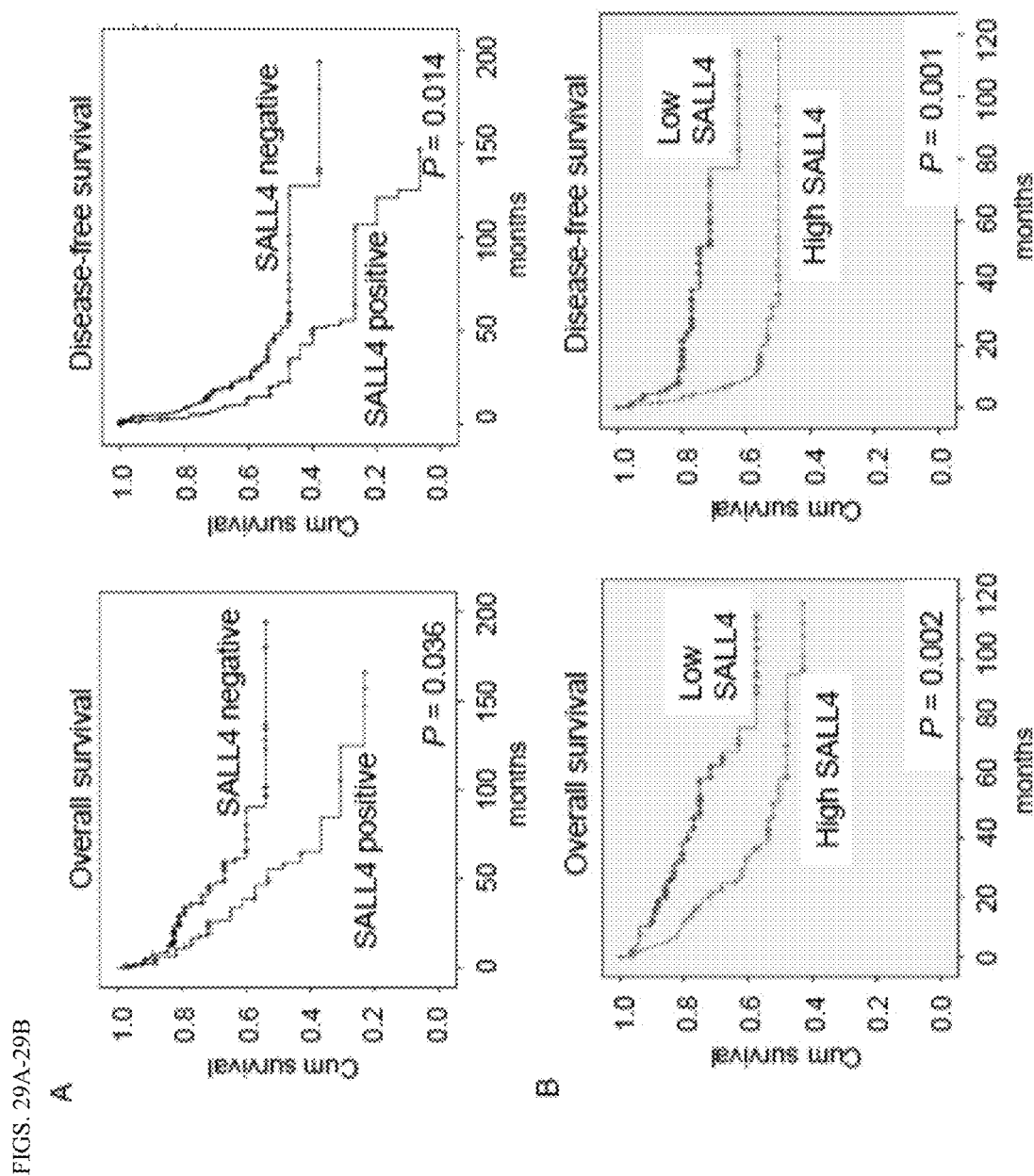
Figure 29:
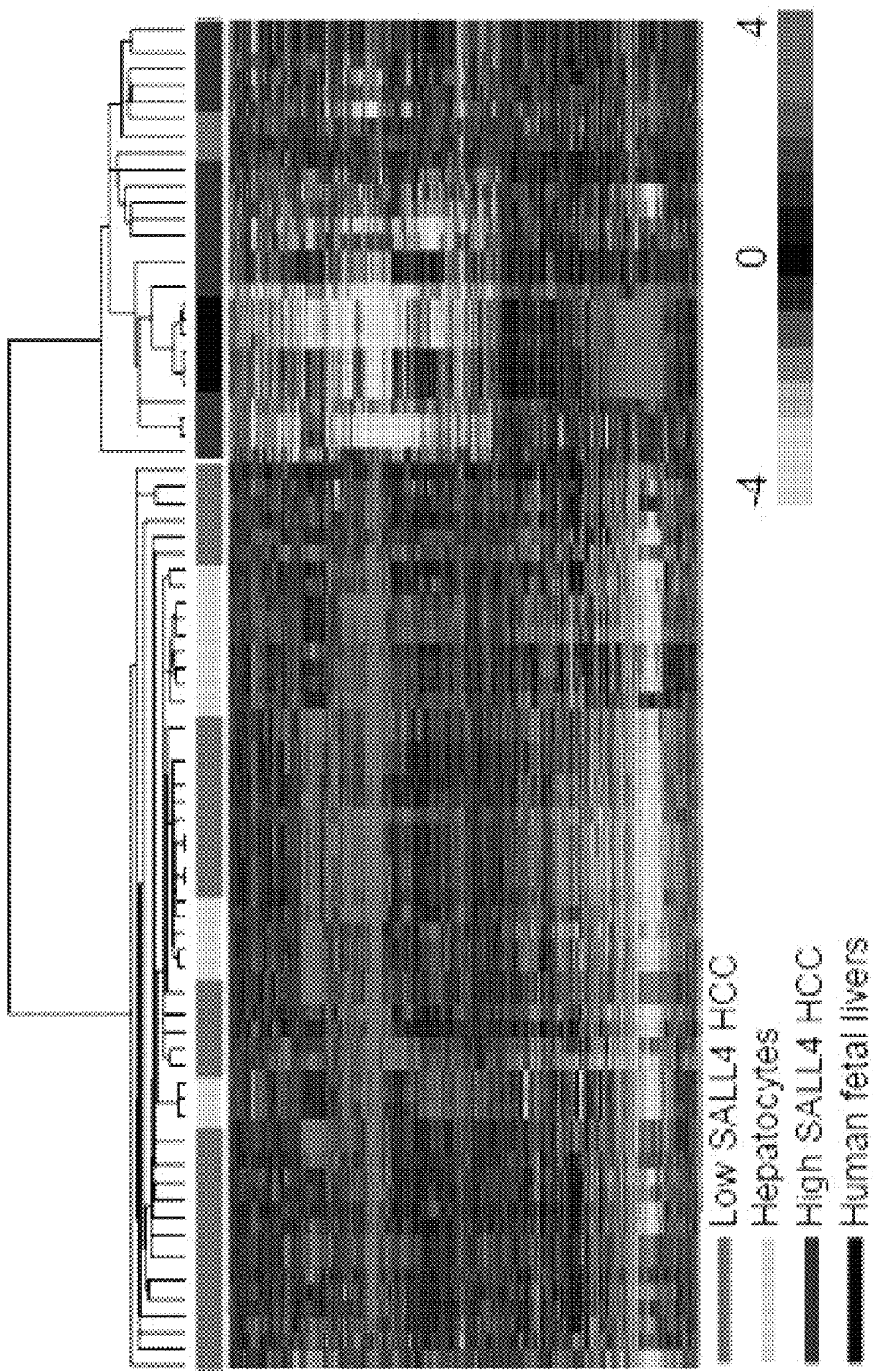
Figure 29C:
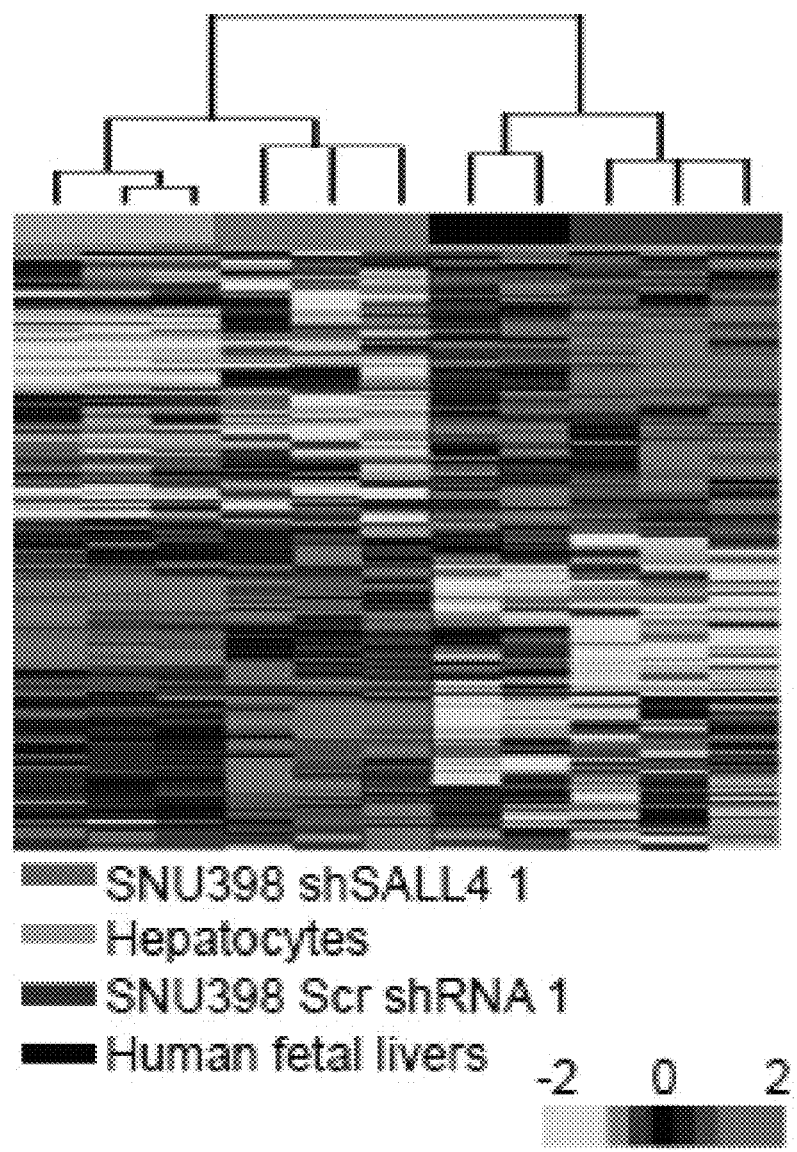

FIGS. 29A-29C: SALL4 expression in HCC predicts poor prognosis. (29A) Kaplan-Meier curve shows poorer overall (left) and disease-free (right) survival advantages for SALL4-positive HCCs, as compared to SALL4-negative HCCs in primary HCC cases from Singapore. Poverall=0.036; PDisease-free=0.014. (29B) Kaplan-Meier curves show poorer overall (left) and disease-free (right) survival advantages for SALL4-high HCCs in the cohort of primary HCC specimens from Hong Kong. Poverall=0.002; PDisease-free=0.001. (29C) Dendrogram and heatmap show the hierarchical cluster analysis of gene expression data from primary human hepatocytes, human fetal livers and human HCC samples extracted from public databases. Columns represent individual samples and rows represent each gene. Each cell in the matrix represents the expression level of a gene in an individual sample. Scale bar indicates the expression levels, red and green knot shown) reflect high and low expression levels, respectively.

FIGS. 30A-30E: Loss of SALL4 leads to decreased HCC cell viability and tumorigenicity. (30A) Left panel: qPCR analysis of relative SALL4, SALL4A and SALL4B expression in SNU-398 cells four days post-transduction. Error bars indicate standard error of three replicates; expression was normalized to beta-actin and plotted relative to scrambled controls. *** P<0.001. Right panels: Western blot analysis of SALL4 expression in SNU-398 and HuH-7 cells four days post-transduction. (30B) MTS analysis of HCC cell viability upon SALL4 gene knockdown by scrambled control shRNAs (Scr shRNA) or SALL4-specific shRNAs (shSALL4) in SNU-398 (left), HuH-7 (middle) and SNU-387 (right) cells. Error bars indicate standard error of three replicates. * P<0.05; * P<0.0001. (30C) Growth curve of SNU-398.  P<0.01. (30D) Caspase 3/7 assay shows an increase in apoptosis in SALL4-knockdown SNU-398 cells at day 4 post-transduction.  P<0.01; * P<0.0001. (30E) Western blot shows the expression of total caspase 3 and cleaved caspase 3 in SNU-398 cells four days posttransduction. Effects of SALL4 gene knockdown on tumorigenicity of HCC cells. (Top left) Representative images show immunocompromised mice transplanted with Scr shRNA 1- or shSALL4.1-treated HuH-7 cells. Arrow shows subcutaneous tumor on the right flank of the mouse. (Top right) Tumor volumes of the subcutaneous tumors. Significance of the last time point could not be determined because there was only one mouse left in the Scr group. * P<0.05. (Bottom) Kaplan-Meier plot shows poorer survival advantage for mice harboring SNU-398 or HuH-7 cells infected with scrambled control shRNA as compared to mice harboring cells infected with shSALL4. n=12; P=0.036. Dendrogram and heatmap show the hierarchical cluster analysis of gene expression data from primary human hepatocytes, human fetal livers and SNU-398 cells transduced with Scr shRNA 1 or shSALL4.1.

FIGS. 31A-31H: SALL4 peptide specifically and effectively targets SALL4 in high SALL4-expressing HCC cells leading to decreased cell viability and tumorigenicity. MTS cell viability assay shows the effects of SALL4 peptide on high endogenous SALL4 SNU-398 cells (31A) and SNU-387 cells with undetectable SALL4 expression (31B). Cell viability was determined 72 hours after peptide treatments. Absorbance at 490 nm is directly correlated to cell viability. Wild type functional SALL4 peptide (wt), mutant non-functional SALL4 peptide (Mut.), trichostatin A (TSA), scrambled control peptide (Scr.), wild type peptide+PTEN inhibitor SF1670 (wt+Inh.) were given to the cells at the indicated concentration. PTEN inhibitor concentration was 400 nM. (31C, 31D) Western blot analyses of the effects of peptides on PTEN, AKT, and pAKT expression on SNU-398 (31C) and SNU-387 (31D) cells 72 hours following peptide treatments. 20 µM of wt or Scr. peptide or 100 nM of TSA was used. PTEN inhibitor concentration was 400 nM. (31E) Representative images show NOD/SCID mice transplanted with Scr peptide- and wt peptide-treated SNU-398 cells (left) and the dissected subcutaneous tumors (right). Arrow indicates subcutaneous tumor. (31F) Growth curve of subcutaneous tumors (left panel) and tumor weight of tumors dissected at day 26 post-transplantation (right panel). Results are mean±s.d. n=5; * P<0.05. (31G) Representative images show NOD/SCID mice transplanted with 3 million SNU-398 cells at the left flank and treated intraperitoneally for five consecutive days with 56 mg/kg body weight TAT-Mut. peptide or 60 mg/kg body weight wt peptide (top panel) and the dissected subcutaneous tumors (bottom). (31H) Tumor weight of tumors dissected at day 18 post-transplantation and post-treatment of mice treated intraperitoneally with TAT fusion peptides as described in 5 g. Results are mean±s.d. n=5; * P<0.05.

FIGS. 32A-32F: Further data showing that SALL4 peptide specifically and effectively targets SALL4 in high SALL4-expressing HCC cells leading to decreased cell viability and tumorigenicity.

Figure 33:
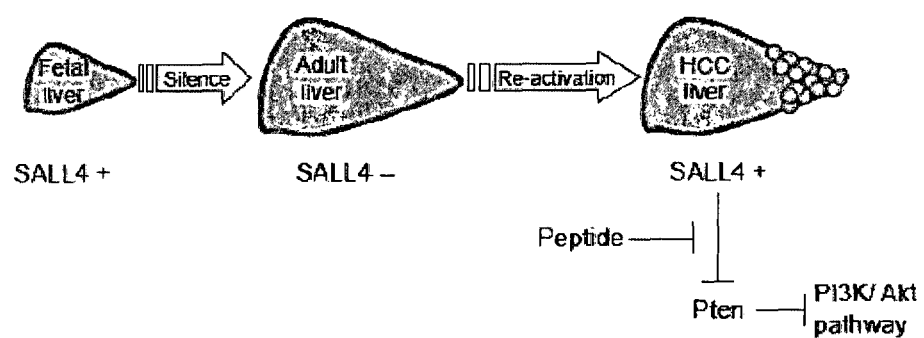

FIG. 33 shows the unique expression pattern of SALL4 in human livers.

Figures 34A, 34B:
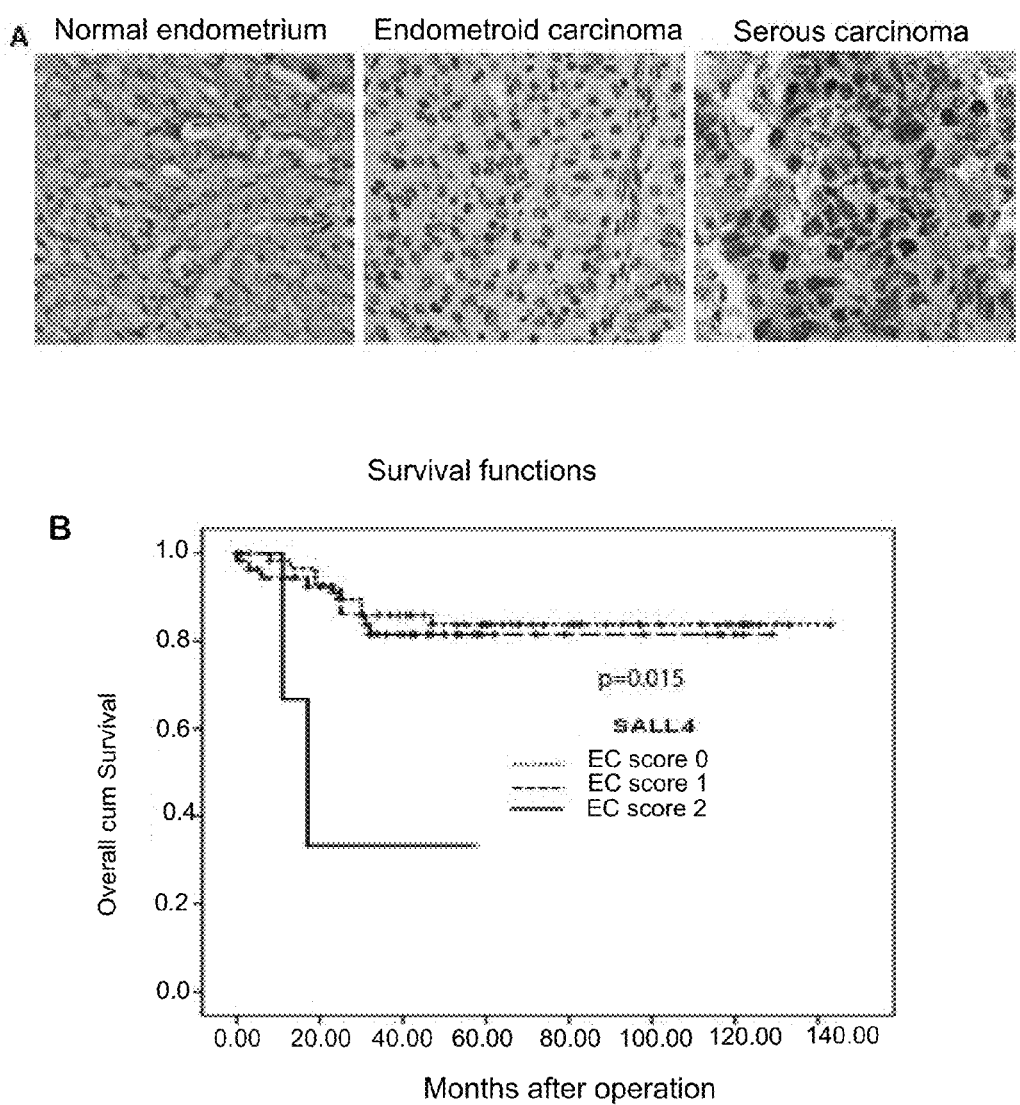
Figure 34C:
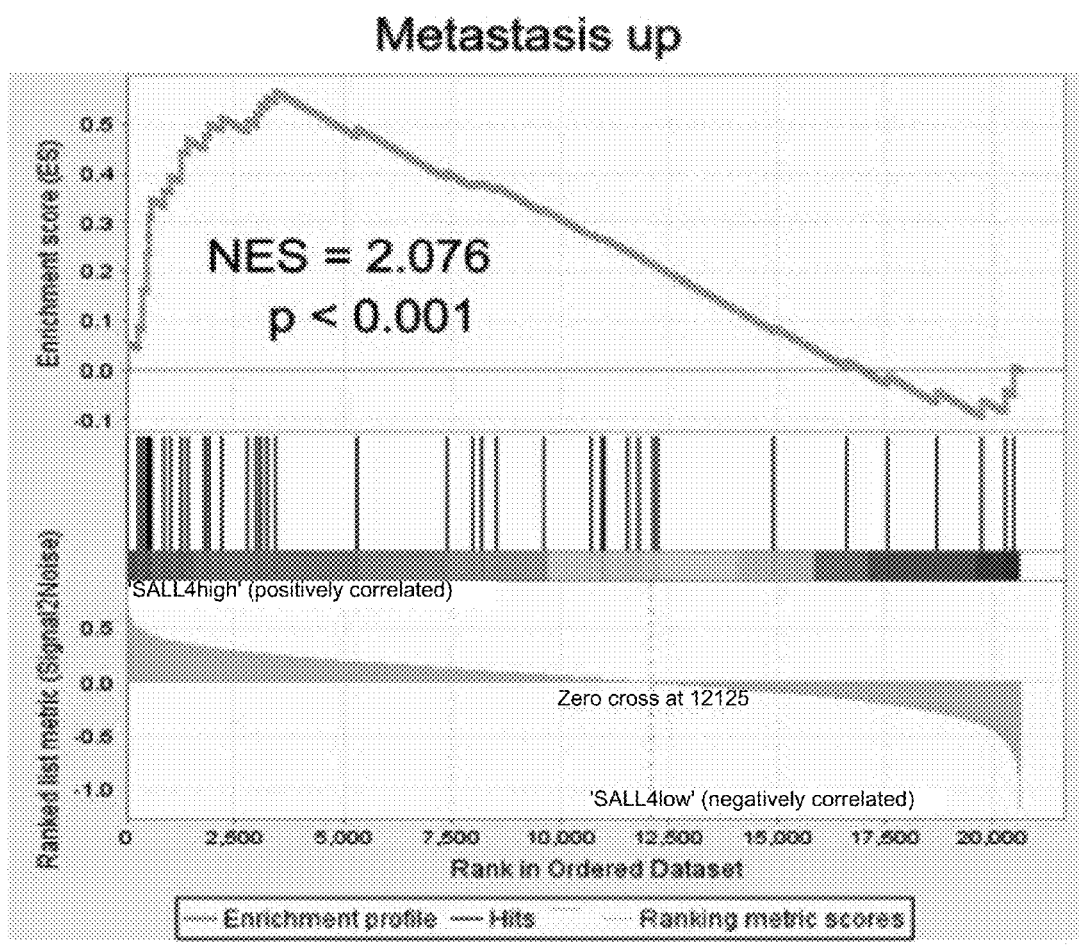
Figure 34C:
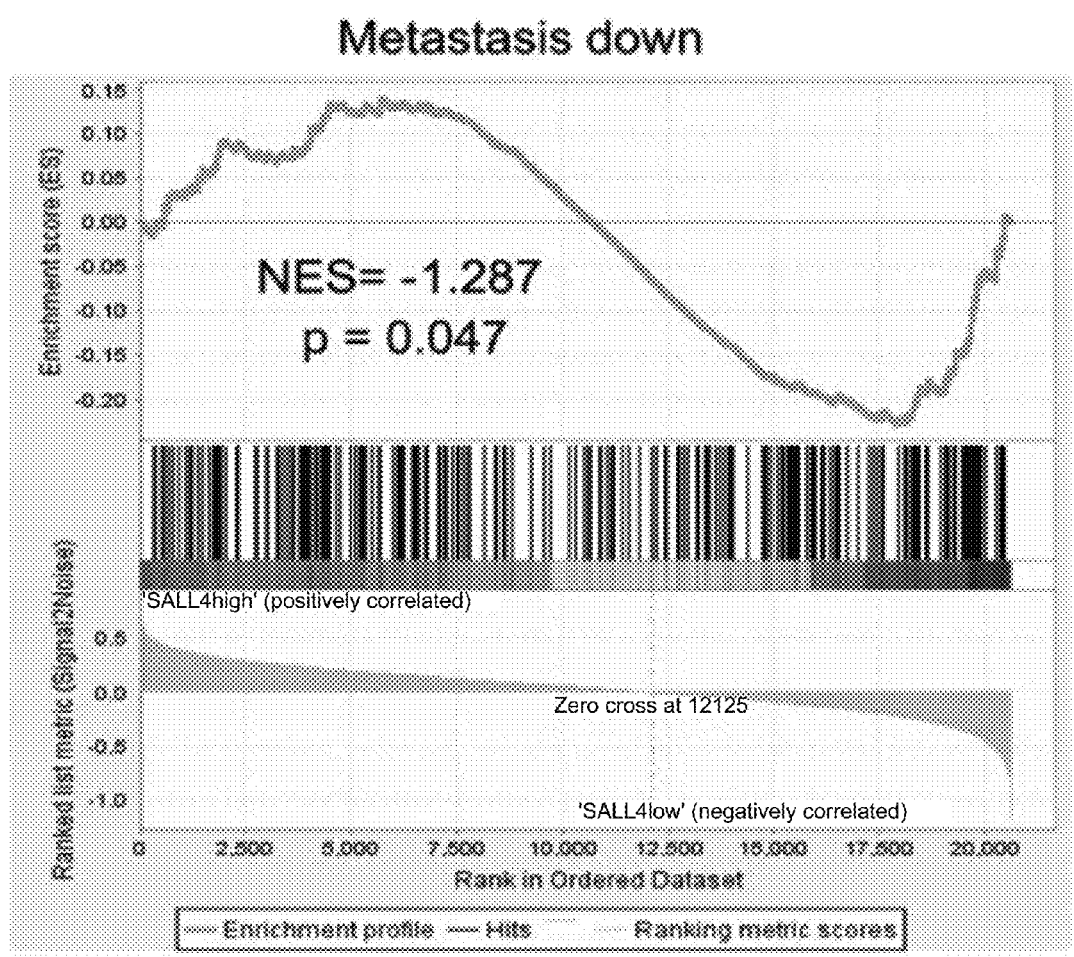

FIGS. 34A-34C: SALL4 expression is associated with poor survival and metastis in endometrial cancer patients. (34A) Representative IHC images show higher SALL4 expression in endometrial cancer and absence in normal endometrial. (34B) Clinicopathological analysis showing that SALL4 expression is significantly correlated with worse survival of EC patients p=0.015. (34C) Gene Set Enrichment Analysis (GSEA) showing that enrichment of gene sets upregulated in cancers with metastasis in SALL4-expression endometrial carcinoma (left panel p<0.001); and gene sets that are enriched in cancers without metastasis are enriched in SALL4-negative endometrial carcinoma (right panel p=0.047).

FIGS. 35A-35F: SALL4 depletion decreases cell viability and tumorigenicity by inhibiting proliferation and triggering cell apoptosis in vitro and in vivo. (35A) Western blot analysis shows downregulation of SALL4 expression in AN3CA cells as a result of lentiviral-mediated RNA interference. (35B) MTS assay shows downregulation of SALL4 decrease cell viability in AN3CA cells (upper panel) and HEC-1A cells (lower panel). (35C) Cells stably expressing SALL4 shRNAs or scramble shRNA were pulse-labeled with BrdU for 1 hr, followed by analysis of DNA replication with anti-BrdU antibody and flow cytometry analysis to measure proliferating cells. (35D) shRNA-treated cells were collected, stained with PI and Annexin V, and processed for analysis by flow cytometry to measure the apoptotic cells. (35E) Graph showing tumor volume (mm3) measured at various time points after transplantation (n=5) Error bars indicate standard error from five mice. Tumor volume (mm3) was calculated by the following formula: length×width×hight/2. (35F) AN3CA tumor sections had reduced proliferation and increased apoptosis as measured by IHC Ki-67 and TUNEL staining, respectively. Error bars indicate standard error of three replicates (n=3), (For B, C, D & E, *p<0.05, Student's t test).

FIGS. 36A-36E: SALL4 depletion inhibits endometrial cancer cells migration, invasion and metastasis. (36A) Phase contrast microscopy images show impaired AN3CA and HEC-1A cells wound closure rate as a result of loss of SALL4. (36B) Representative transwell cell migration and matrigel cell invasion images. (36C) and (36D) Migration and invasion capacities were quantified after the cells were stained with crystal violet solution data are presented as the OD600 nm. Error bars indicate standard error of three replicates (n=3), (*p<0.05). (36E) Liver tissues from mice retroorbitally injected with SALL4-knockdown or scramble control shRNA-treated AN3CA cells. Upper panel, gross liver tissue pictures; lower panel, representative H&E staining on liver tissues. Arrows indicate metastatic tumor region. Scale bar represents 50 µm, * p<0.05.

FIGS. 37A-37D: Change of SALL4 expression leads to alterations in cMyc transcriptional activity and drug sensitivity of endometrial cancer cells to carboplatin. (37A) ChIP assay was performed using SALL4-specific antibody in AN3CA cells. Immunoprecipitated DNA was analyzed by quantitative PCR using specific primers. qChIP values were expressed as percentage of input chromatin as reported by others (34). Data represent the average and standard deviation from three parallel experiments. (37B) Western blot shows that SALL4 depletion significantly down-regulated c-Myc expression in AN3CA and HEC-1A cell lines, and overexpression of SALL4 up-regulated c-Myc expression in Ishikawa cells. (37C) Clonogenic assays of Ishikawa cells overexpressing SALL4A or SALL4B treated with indicated carboplatin concentrations, images show colonies stained with crystal violet solution. (37D) Overexpression of SALL4 rendered Ishikawa more resistant to carboplatin treatment (40 µg/ml carboplatin treated for 72 hrs), by upregulating proliferation and downregulating apoptosis, as measured by Ki-67 and TUNEL staining * p<0.05.

Figures 38A, 38B:
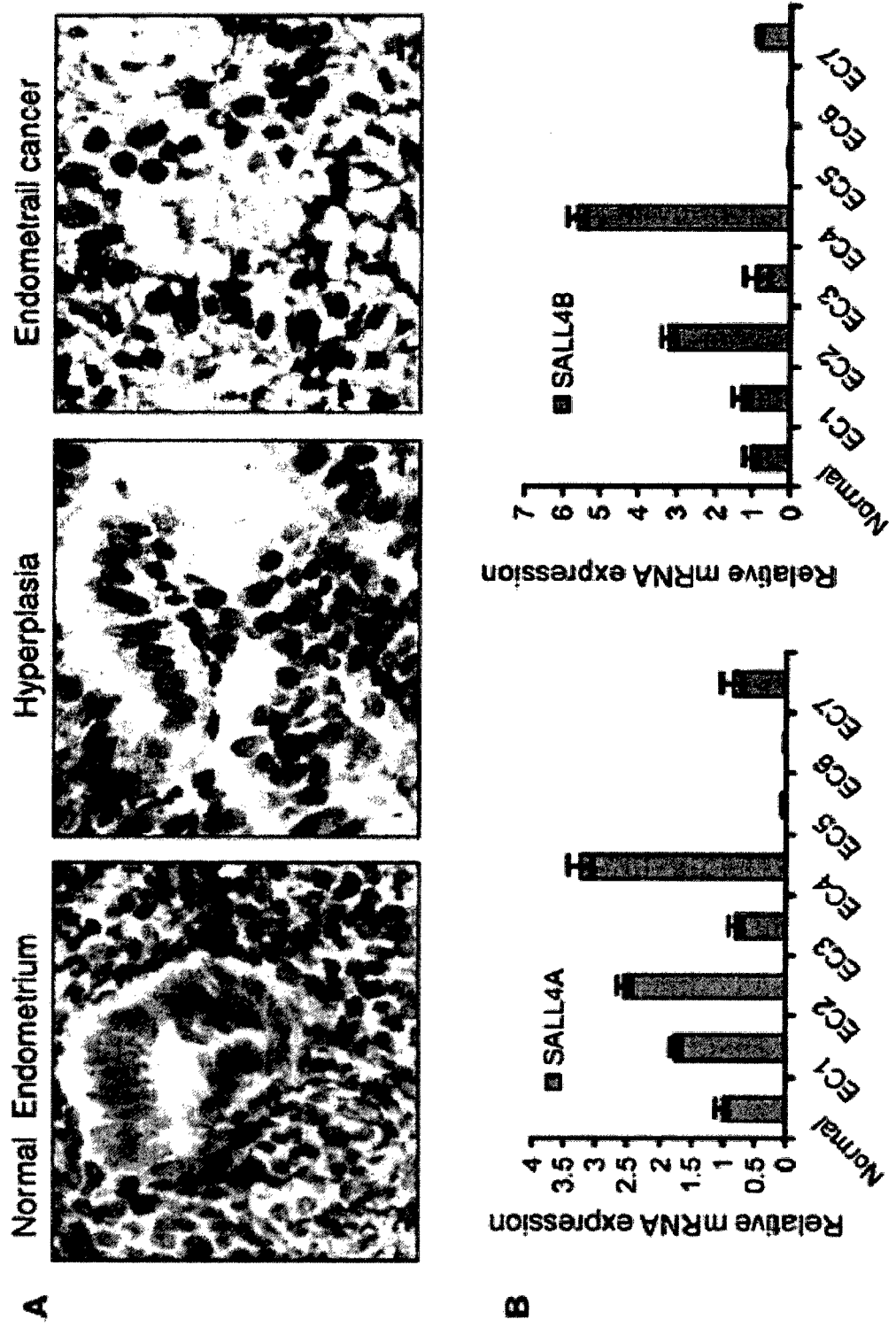

FIGS. 38A-38B: SALL4 expression in endometrial carcinoma. (38A) Immunohistochemical analysis of SALL4 expression using SALL4-specific antibody on formalin-fixed, paraffin-embedded endometrial samples. Representative images show positive SALL4 nuclear stain only in the endometrial cancer cells, but not detectable in hyperplasia and normal endometrium. Bars represent 10 µm (IHC). (38B) QRT-PCR analysis of SALL4A and SALL4B expression in 7 snap-frozen endometrial cancer samples compared with normal endometrial tissues. All values were normalized to GAPDH. Experiments were done in triplicates, data represent mean±SD.

Figure 39A:
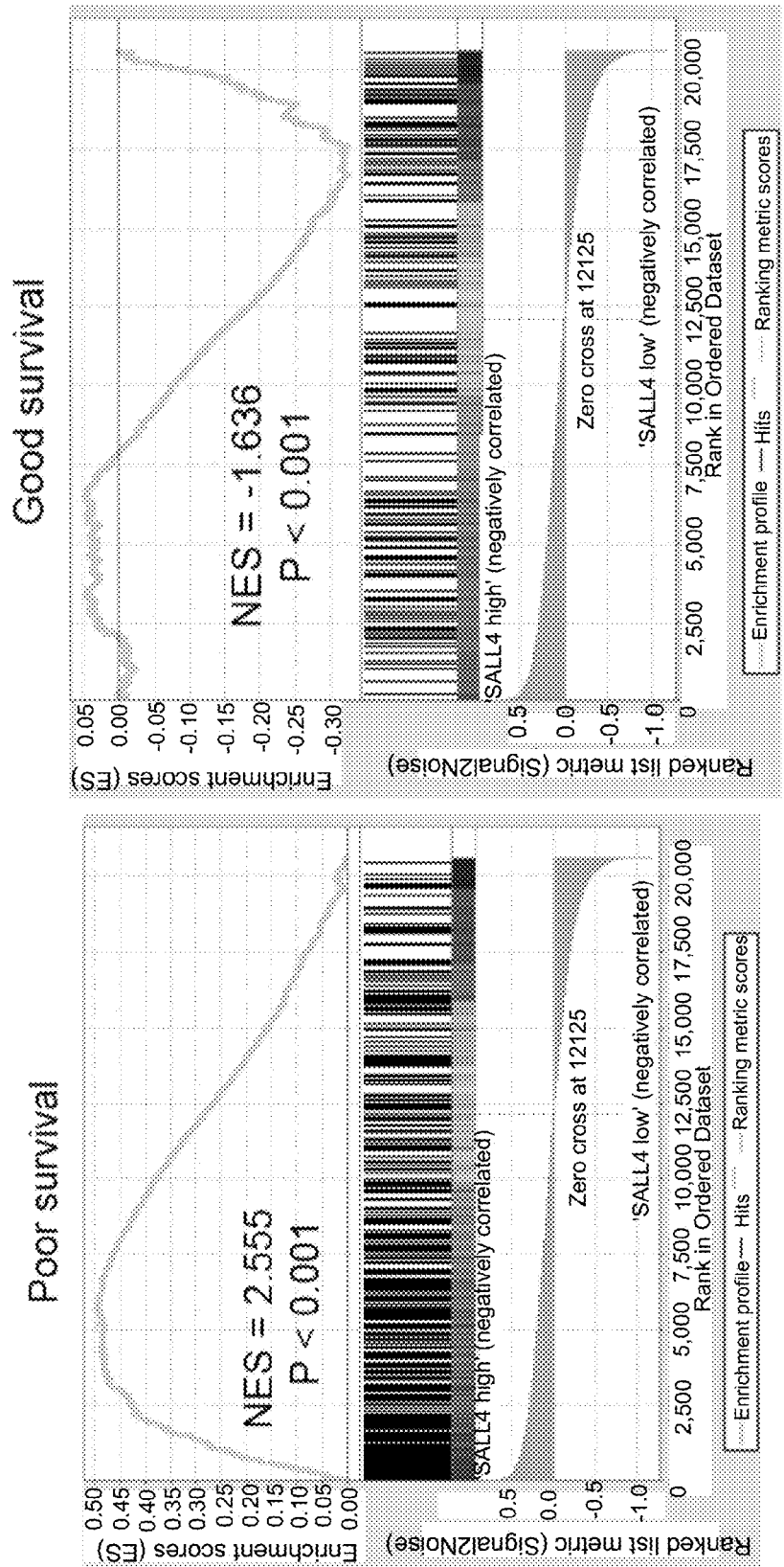
Figure 39B:
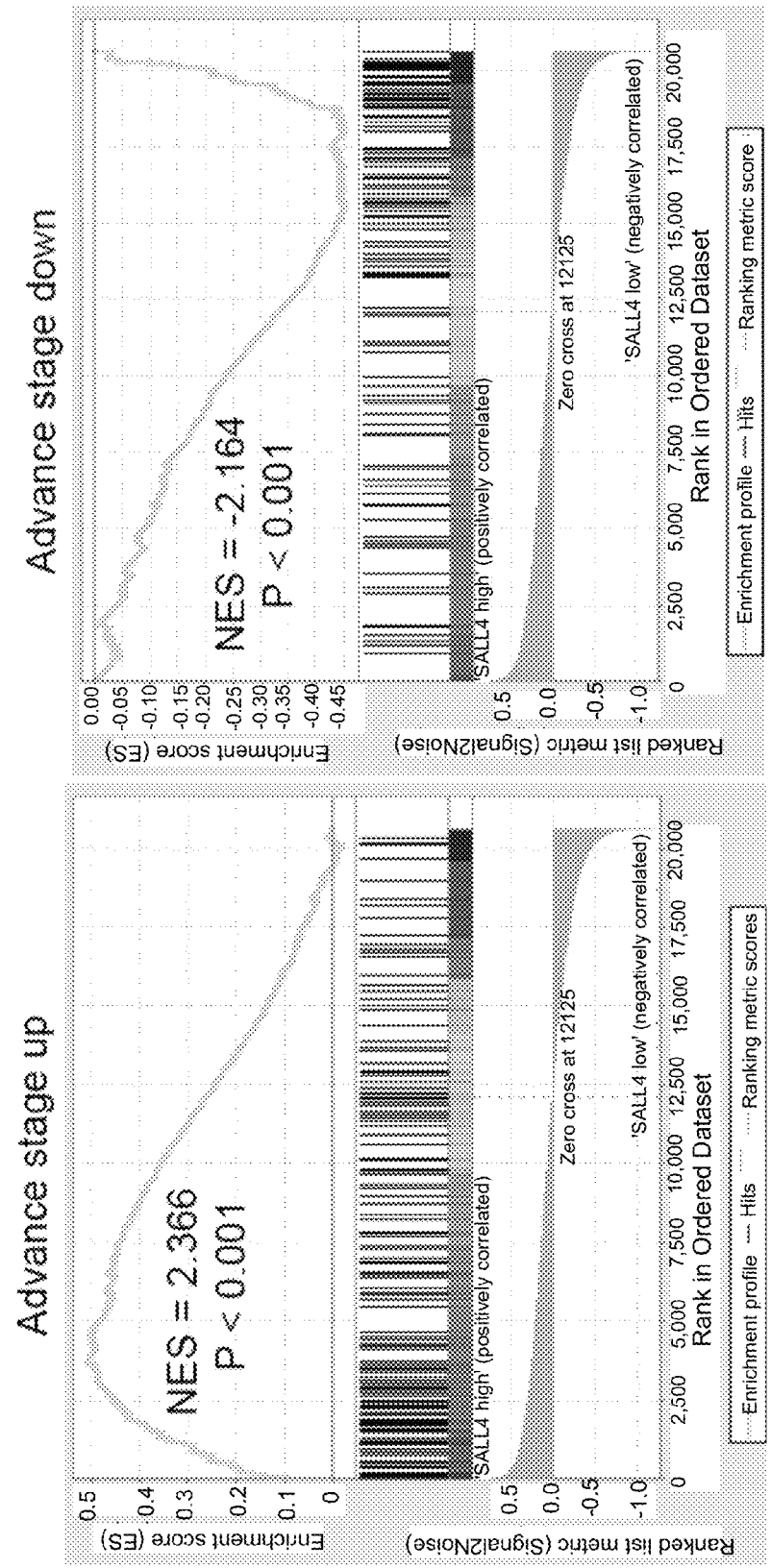
Figure 39C:
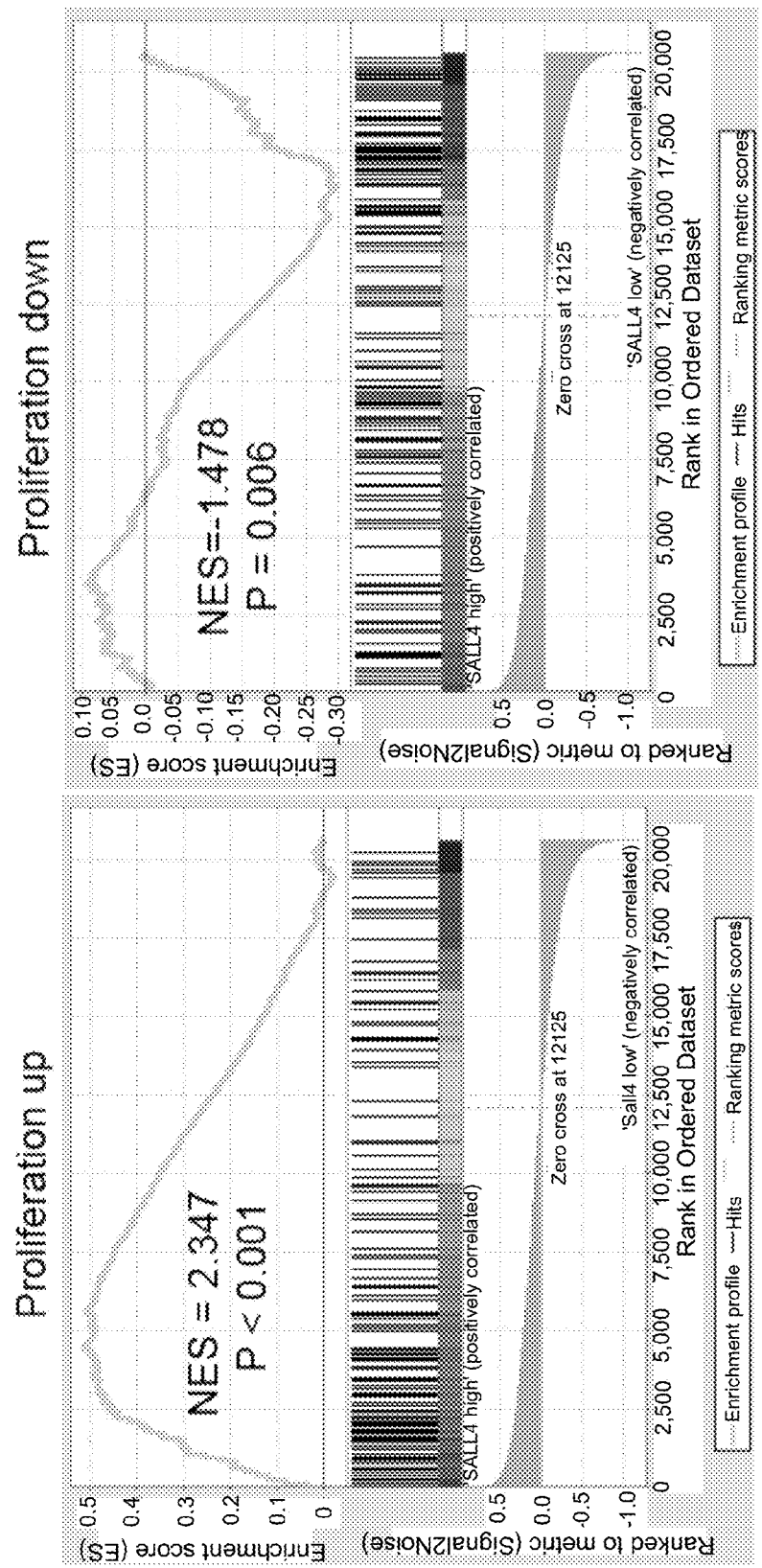

FIGS. 39A-39C: Gene Set Enrichment Analysis (GSEA): (39A) enrichment of gene sets upregulated in cancers with poor survival in SALL4-expression endometrial carcinoma (left panel p<0.001); and gene sets that are enriched in cancers with good survival are enriched in SALL4-negative endometrial carcinoma (right panel p<0.001). (39B) Enrichment of gene sets upregulated in cancers with advanced tumor stage in SALL4-expression endometrial carcinoma (left panel p<0.001); gene sets that are downregulated in advanced tumor stage are enriched in SALL4-negative endometrial carcinoma (right panel p<0.001). (39C) Enrichment of gene sets upregulated in cancers with proliferating tumors in SALL4-expression endometrial carcinoma (left panel p<0.001); and gene sets that are downregulated in proliferating tumor cells are enriched in enriched in SALL4-negative endometrial carcinoma (right panel p=0.006).

Figure 40:
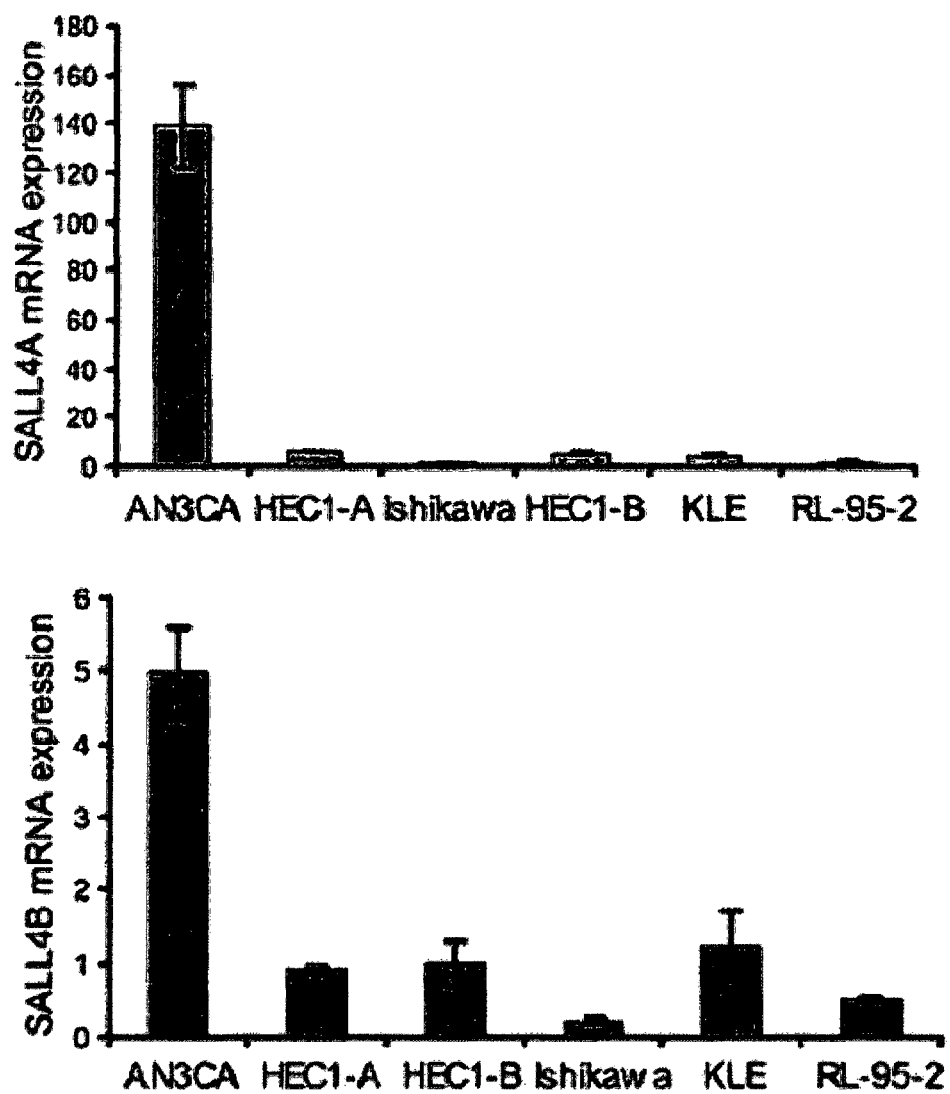

FIG. 40: SALL4 mRNA expression in endometrial carcinoma cell lines. All values were normalized to GAPDH. Experiments were done in triplicates, data represent mean±SD.

Figure 41:
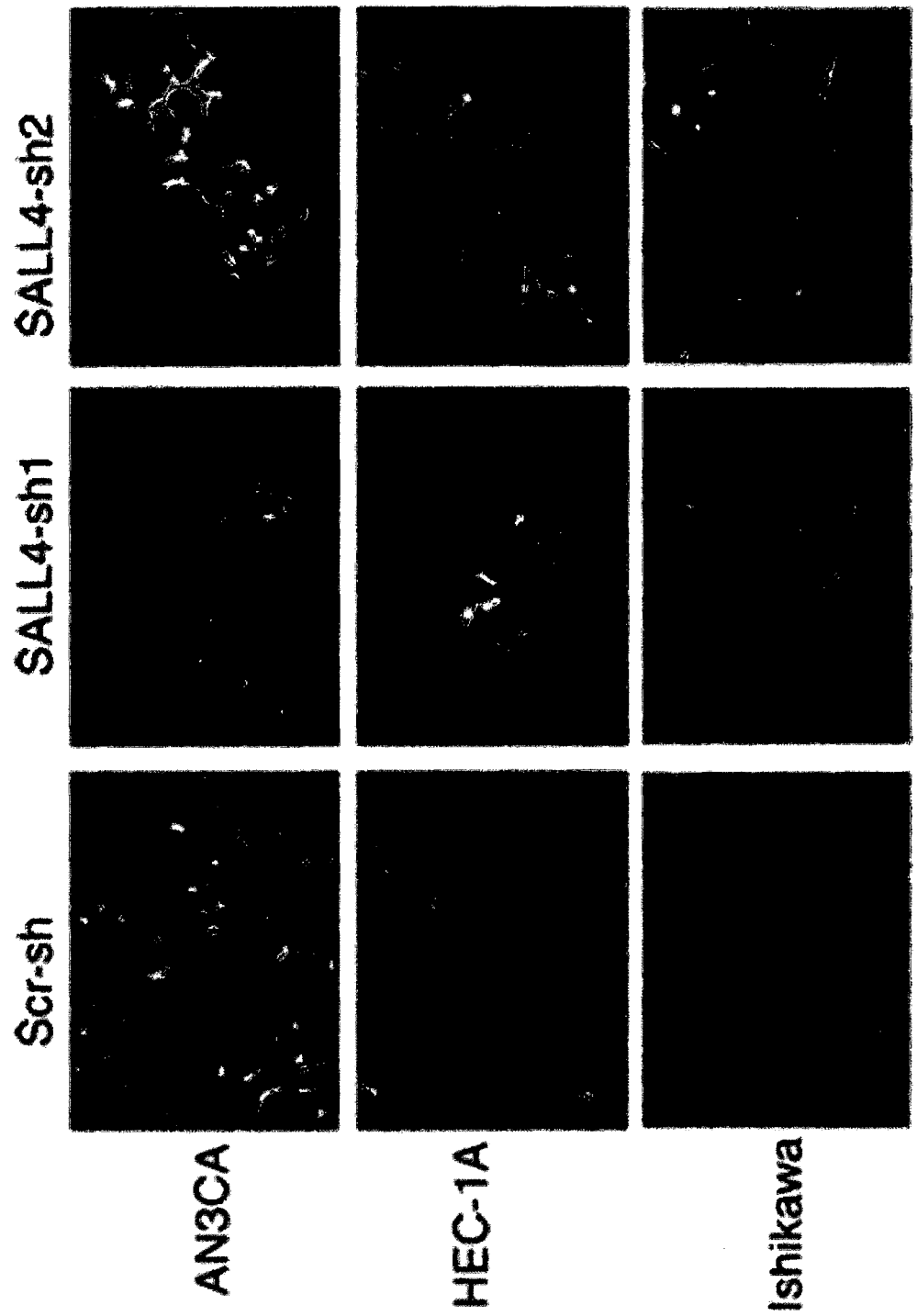

FIG. 41: Phase-contrast photomicrographs showing cell decreased viable cells by morphology after SALL4 knockdown.

Figure 42:
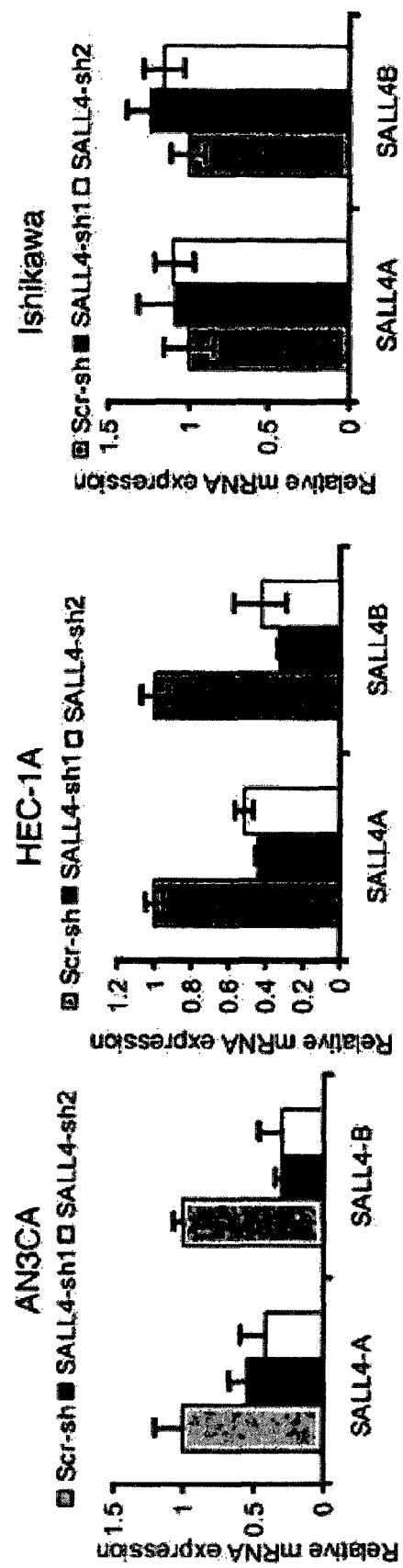

FIG. 42: qRT-PCR assay shows downregulation of SALL4 expression in AN3CA and HEC-1A cells, but not in Ishikawa cell as a result of shRNA targeting.

Figures 43A, 43B, 43C:
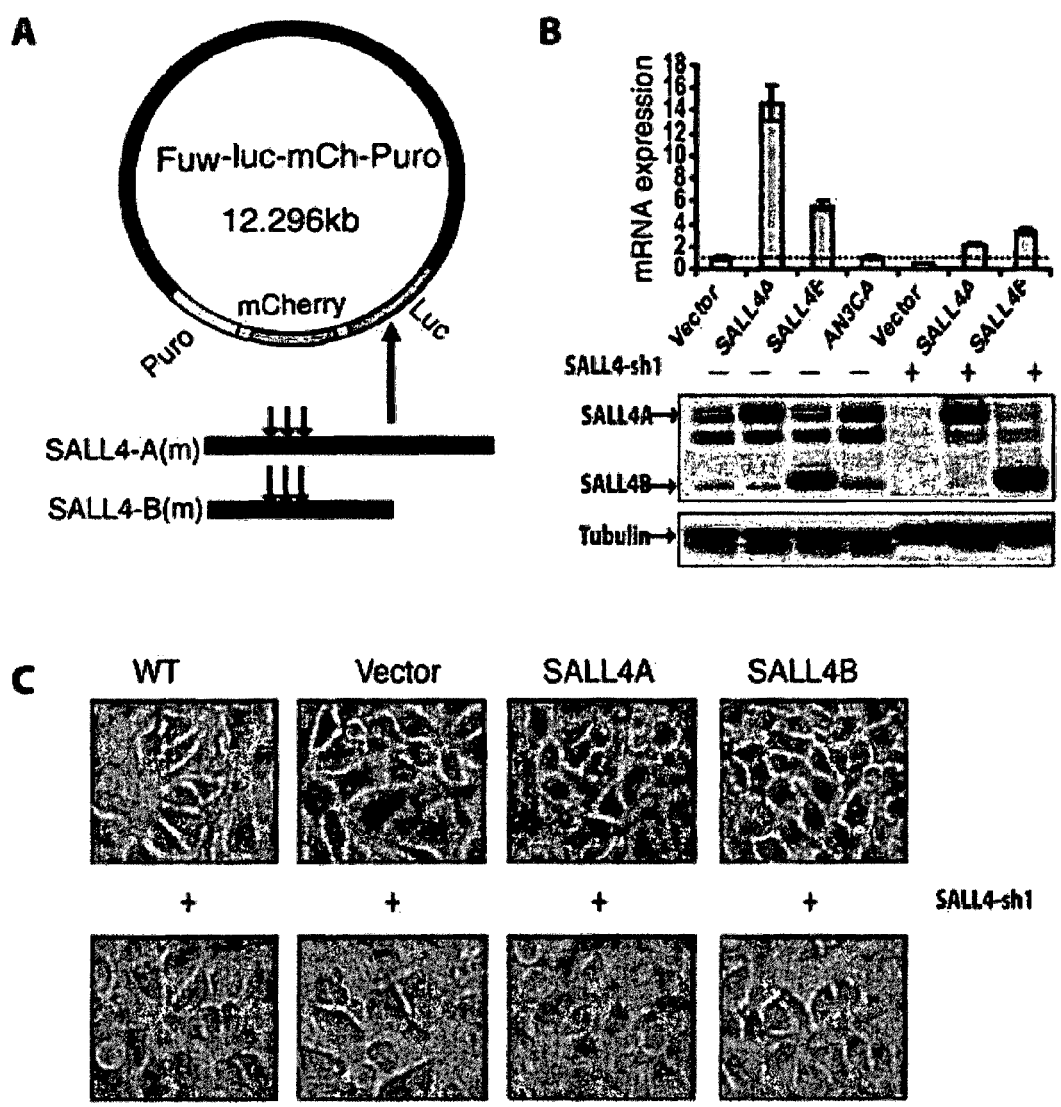

FIGS. 43A-43C: Overexpression of mutant SALL4 isoforms to rescue SALL4 knockdown phenotype. (43A) Vector map of SALL4 overexpression. (43B) Western blot and real-time PCR showing that SALL4A or B expression levels after co-infection of AN3CA cell with virus expressing SALL4shRNA1 and SALL4A mutant or SALL4B mutant. (43C) Phase-contrast photomicrographs showing that overexpression of either SALL4A mutant or SALL4B mutant alone could partially rescue SALL4 knockdown phenoptype.

Figure 44:
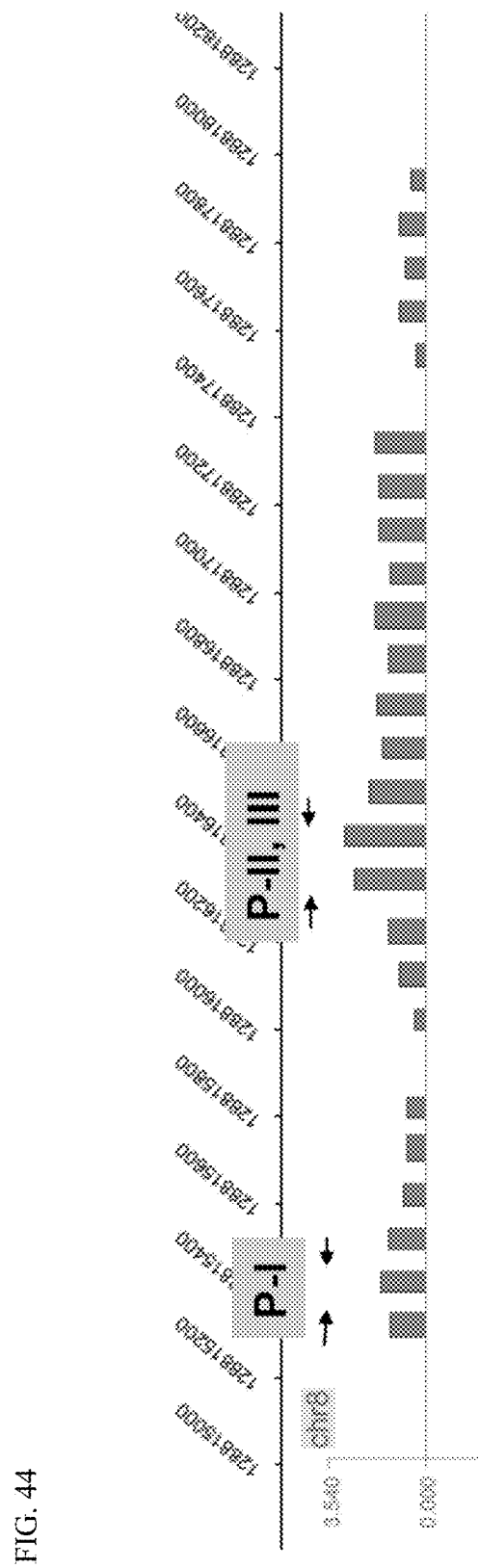

FIG. 44: ChIP-on-Chip analysis of SALL4 binding on c-Myc promoter region in NB4.

Figure 45:
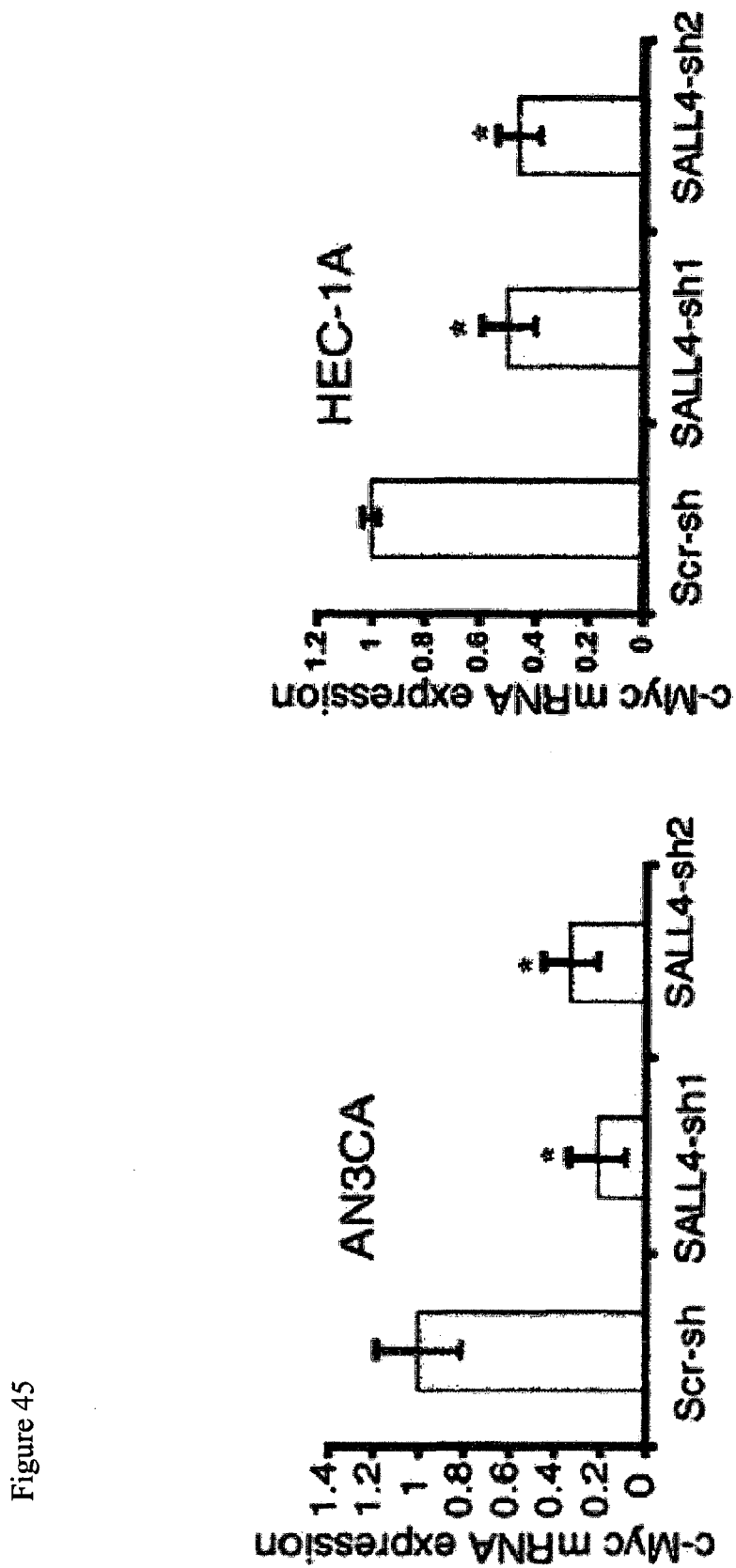

FIG. 45: Knock down of SALL4 downregulates cMyc expression. Real time RT-PCR analysis shows that the mRNA of c-Myc was downregulated by SALL4 knockdown in AN3CA and HEC-1A * p<0.05.

FIGS. 46A-46B: Overexpression of SALL4 upregulates cMyc expression. (A) Western blot shows ectopic overexpression of SALL4 in Ishikawa cells. (B) Real time RT-PCR analysis shows that the mRNA of c-Myc was up-regulated by SALL4 overexpression in Ishikawa cells * p<0.05.

Figure 47:
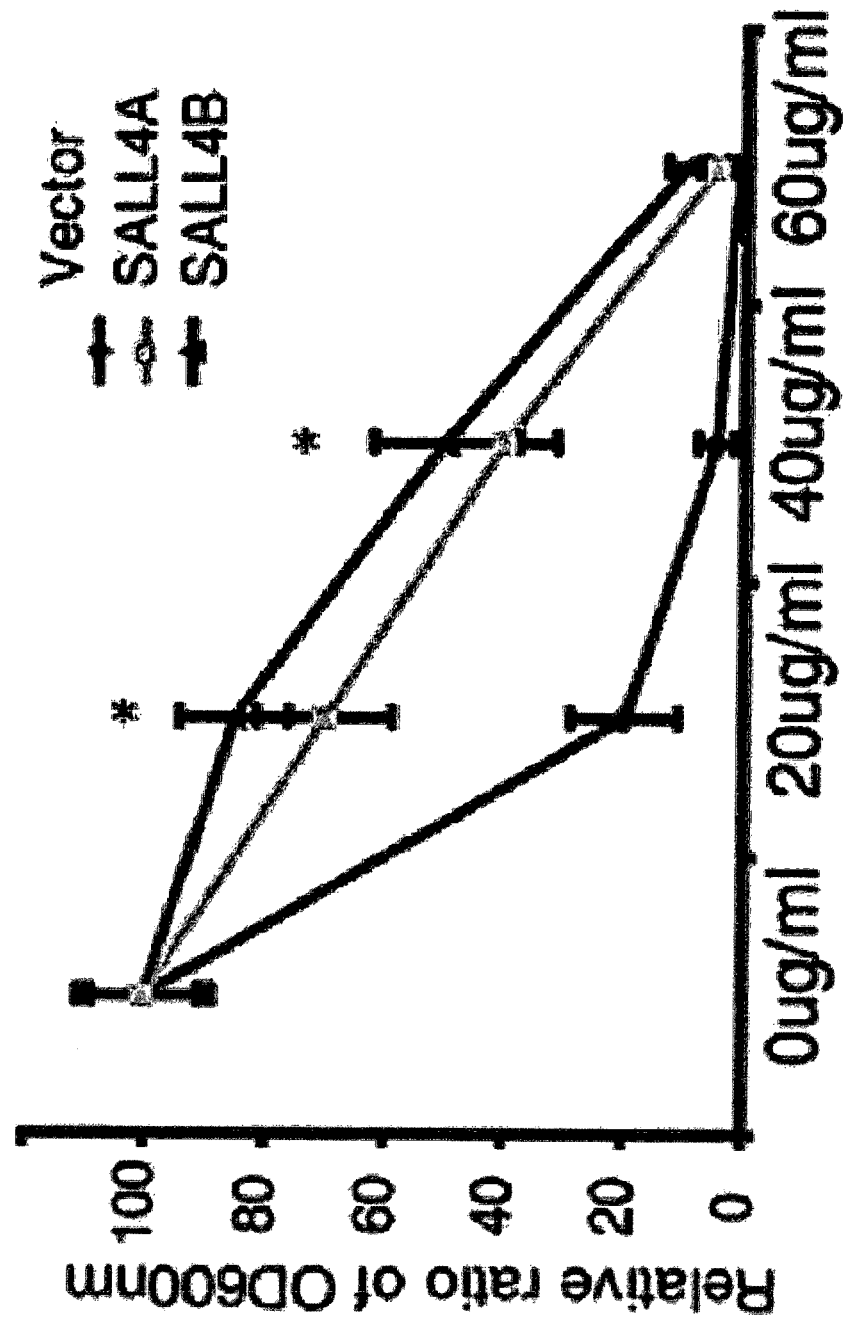

FIG. 47: Overexpression of SALL4 increase colony information after carboplatin treatment. Quantification of the relative colony formation in empty vector control group versus SALL4 overexpression groups following drug treatments. * p<0.05.

Figures 48A, 48B:
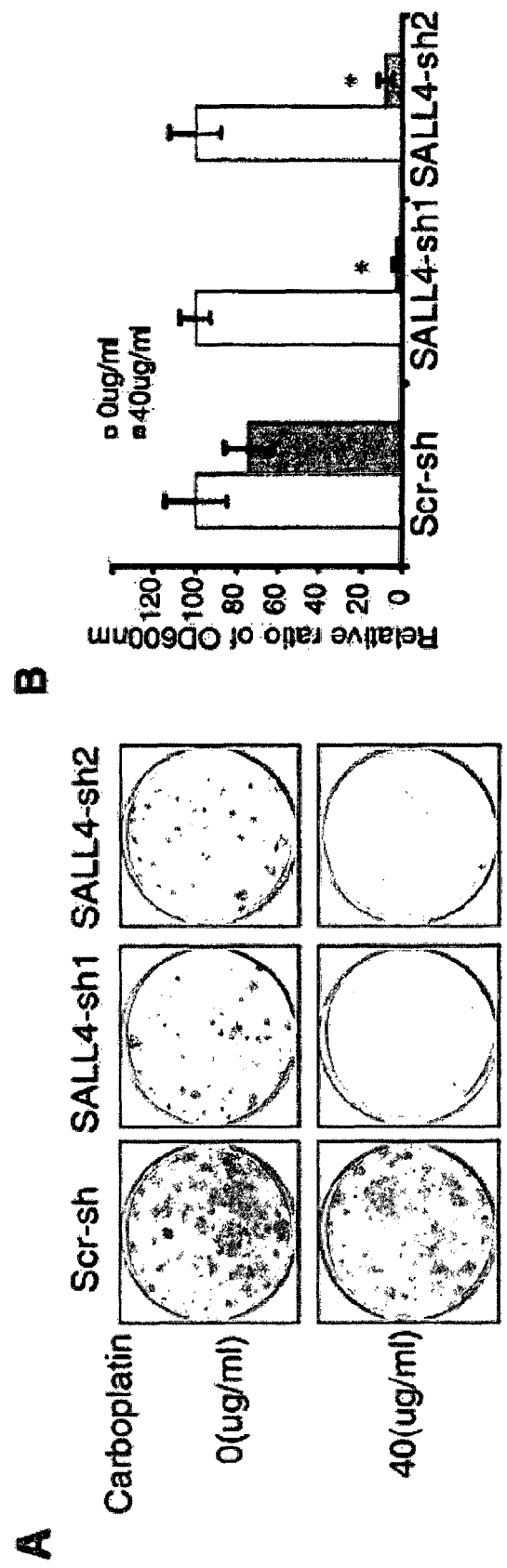

FIGS. 48A-48B: Stable knockdown of SALL4 sensitized carboplatin-resistant cell line HEC-1A to carboplatin treatment, as shown by decreased colony formation. (48A) Image shows colony number differences between SALL4 knock down and scramble control. (48B) Quantification of relative colony formation in control versus SALL4 knockdown HEC-1A cells with and without 40 µg/ml carboplatin treatment. * p<0.05.

Figure 49:
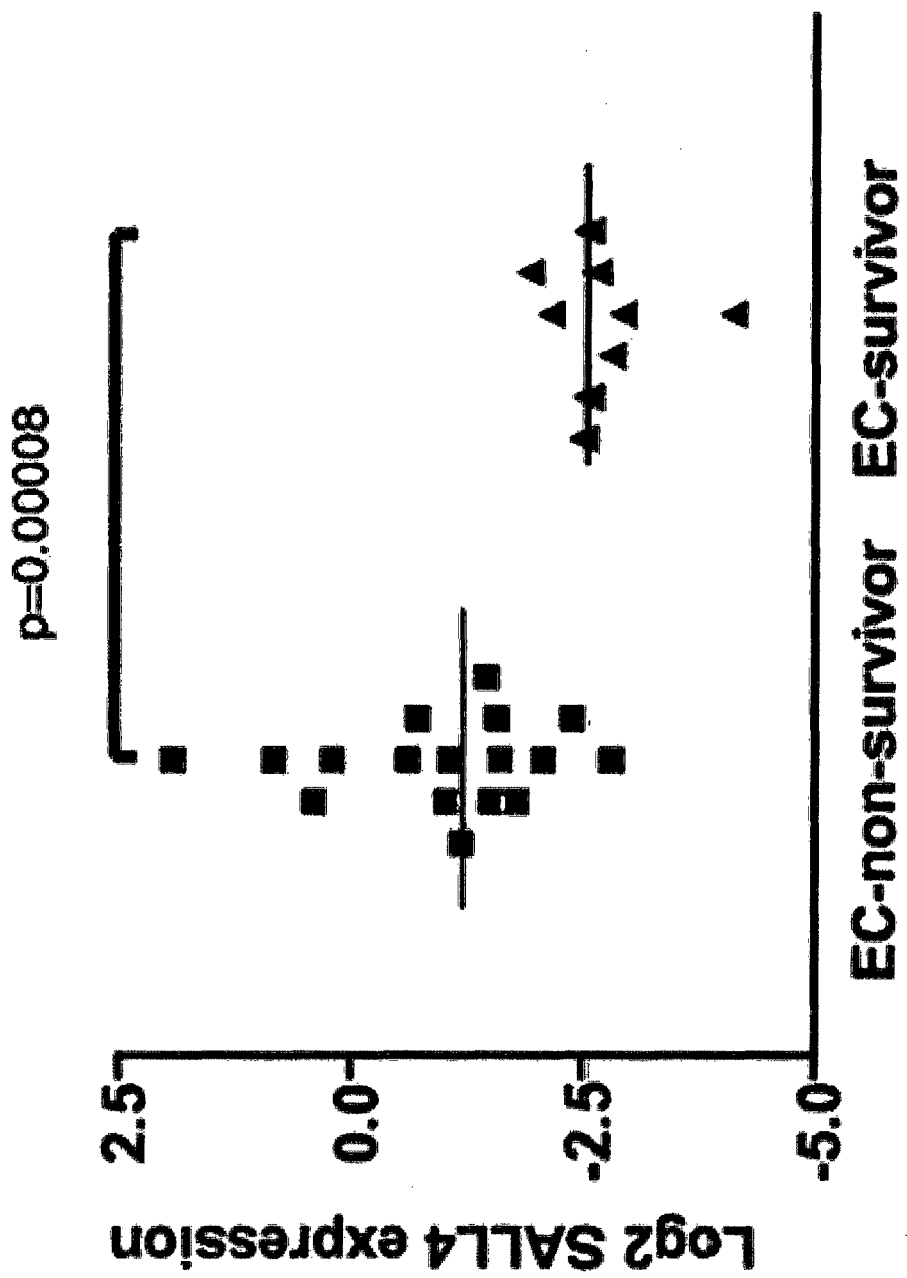

FIG. 49: Microarray analysis showed that SALL4 expression was significantly higher in non-survivor compared to survivor of endometrial cancer.

FIG. 50: shows a list of primer used in ChIP-qPCR (SEQ ID NOs: 8-13).

Figure 51:
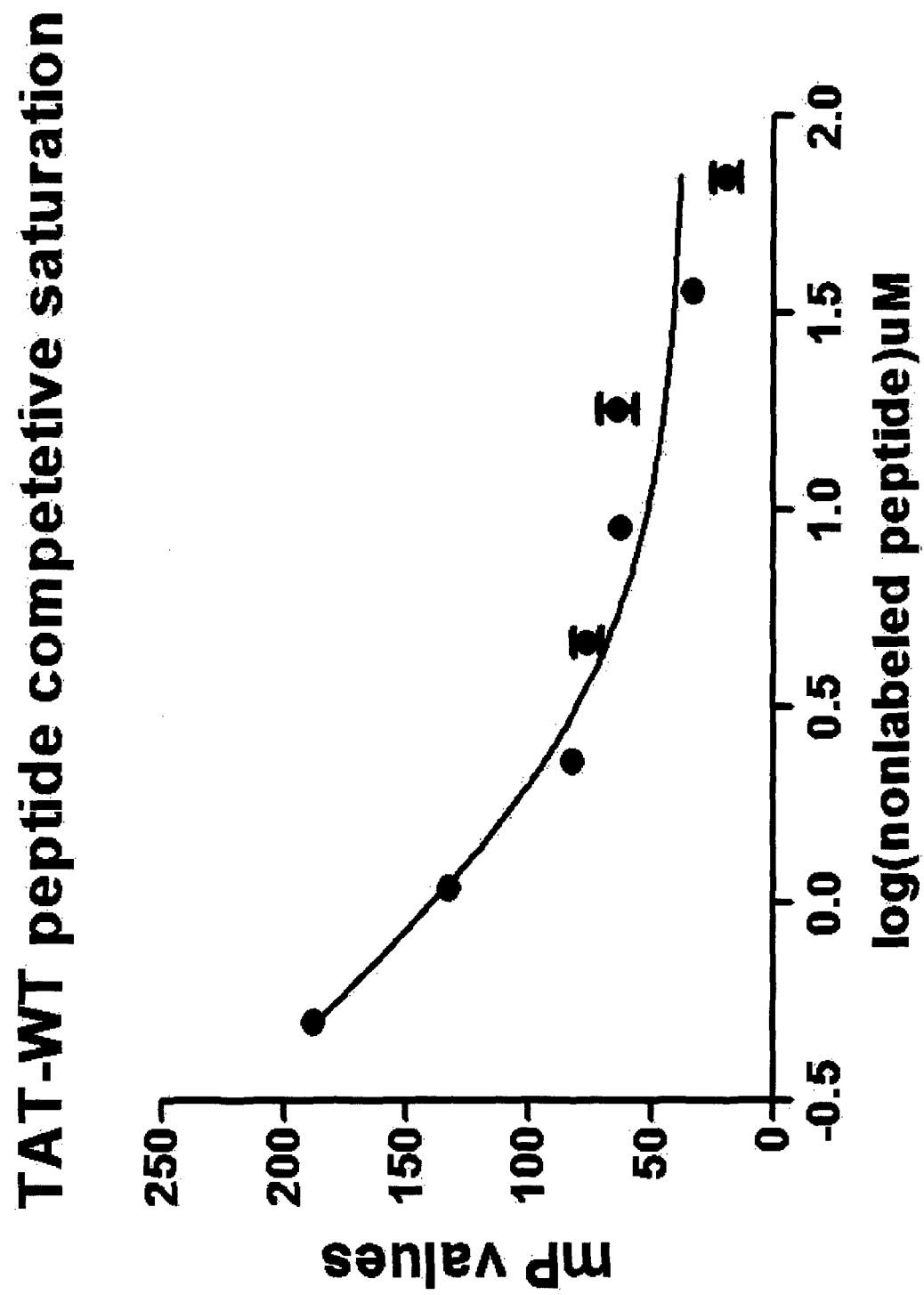

FIG. 51: Binding affinity of TATWT peptide tested by FP reveals the IC50 of 8.

Figure 52:

FIG. 52: Nuclear (blue—not shown) and TAT-peptide (green—not shown) colocalized 15 mins after treatment within SNU398 cells.

Figure 53:
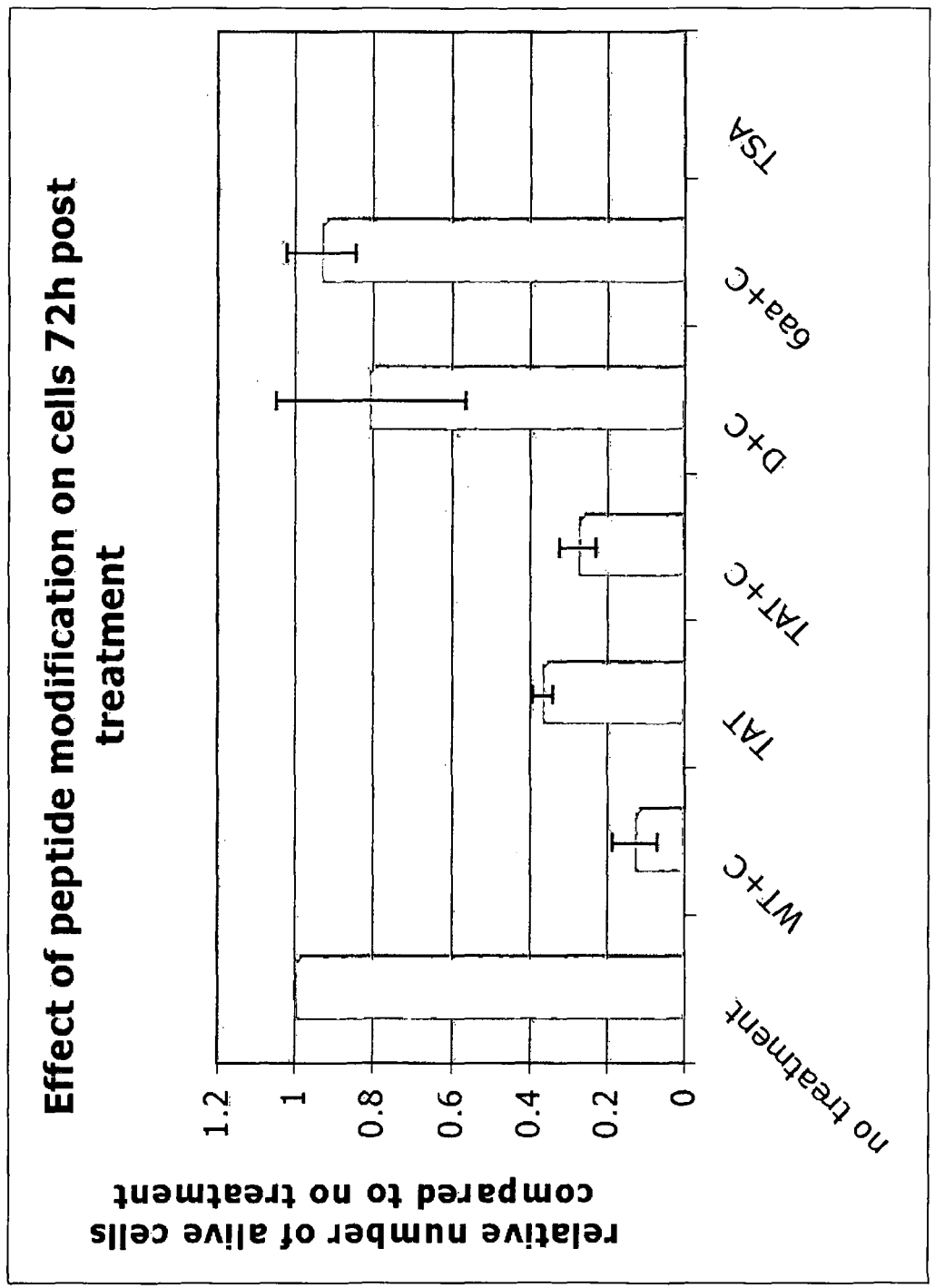

FIG. 53: MTS results on various peptide treatments on SNU397 cells after 72 hours along the carrier (C).

Figures 54A, 54B, 54C:
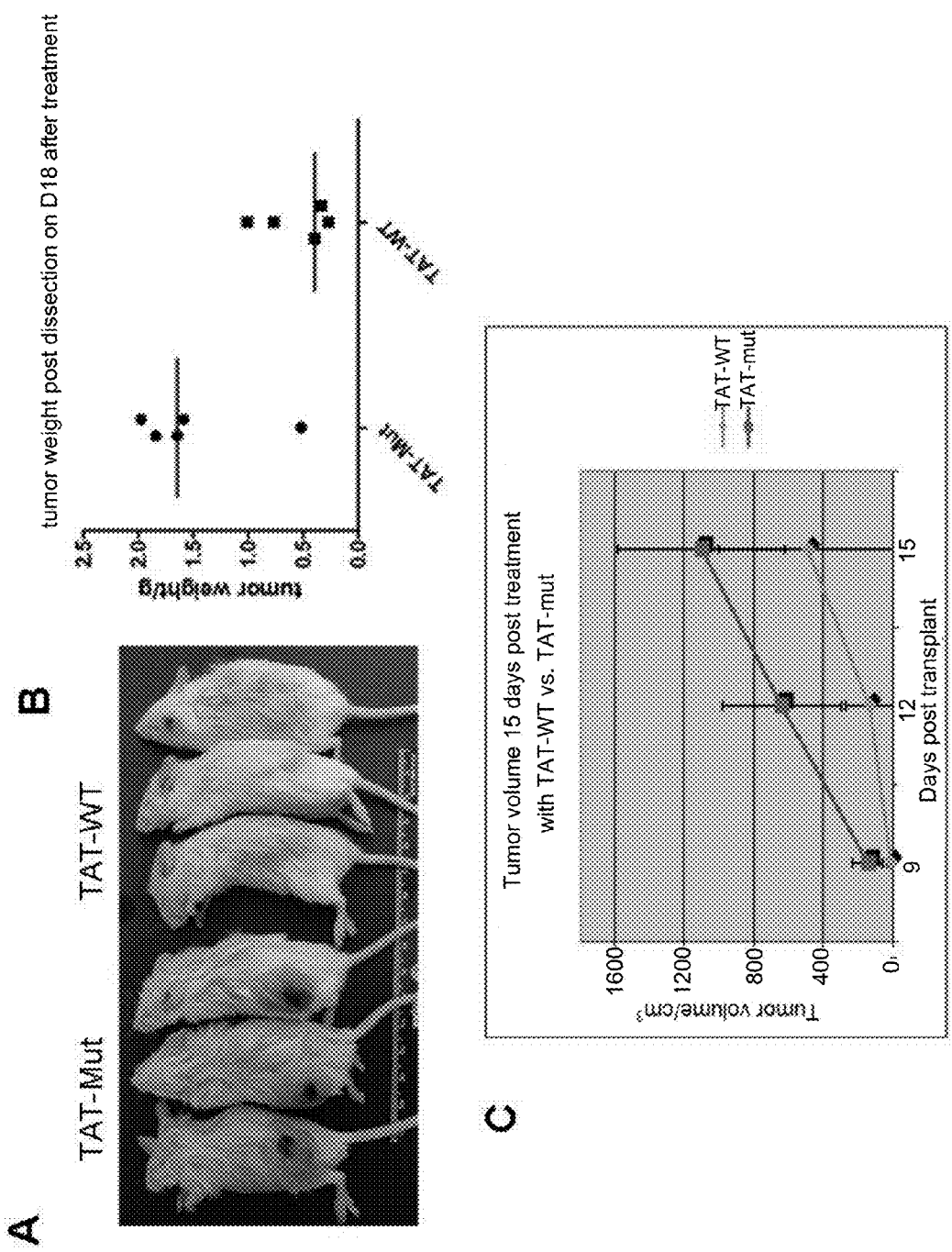

FIG. 54A-54C: TAT-WT and TAT-Mut peptides admitted IP into mice inoculated with SNU398 cells daily for 5 days. Mice were analyzed and tumors were measured.

Figures 55A, 55B:
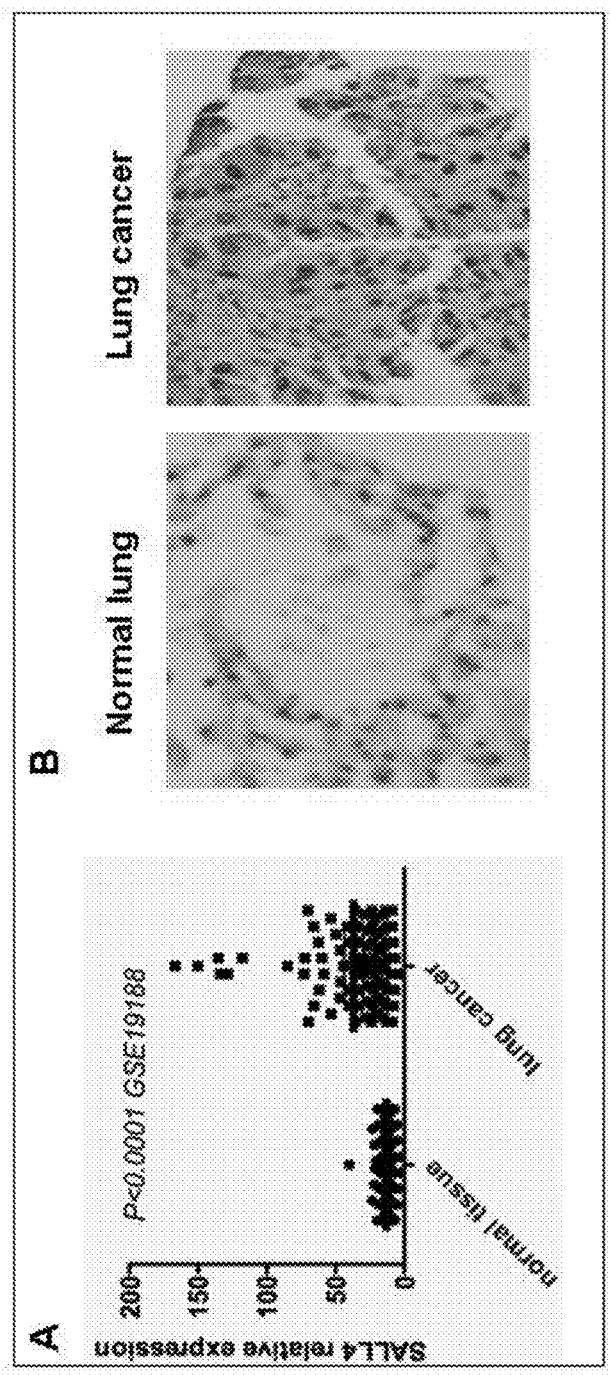
Figures 56A, 56B, 56C, 56D:
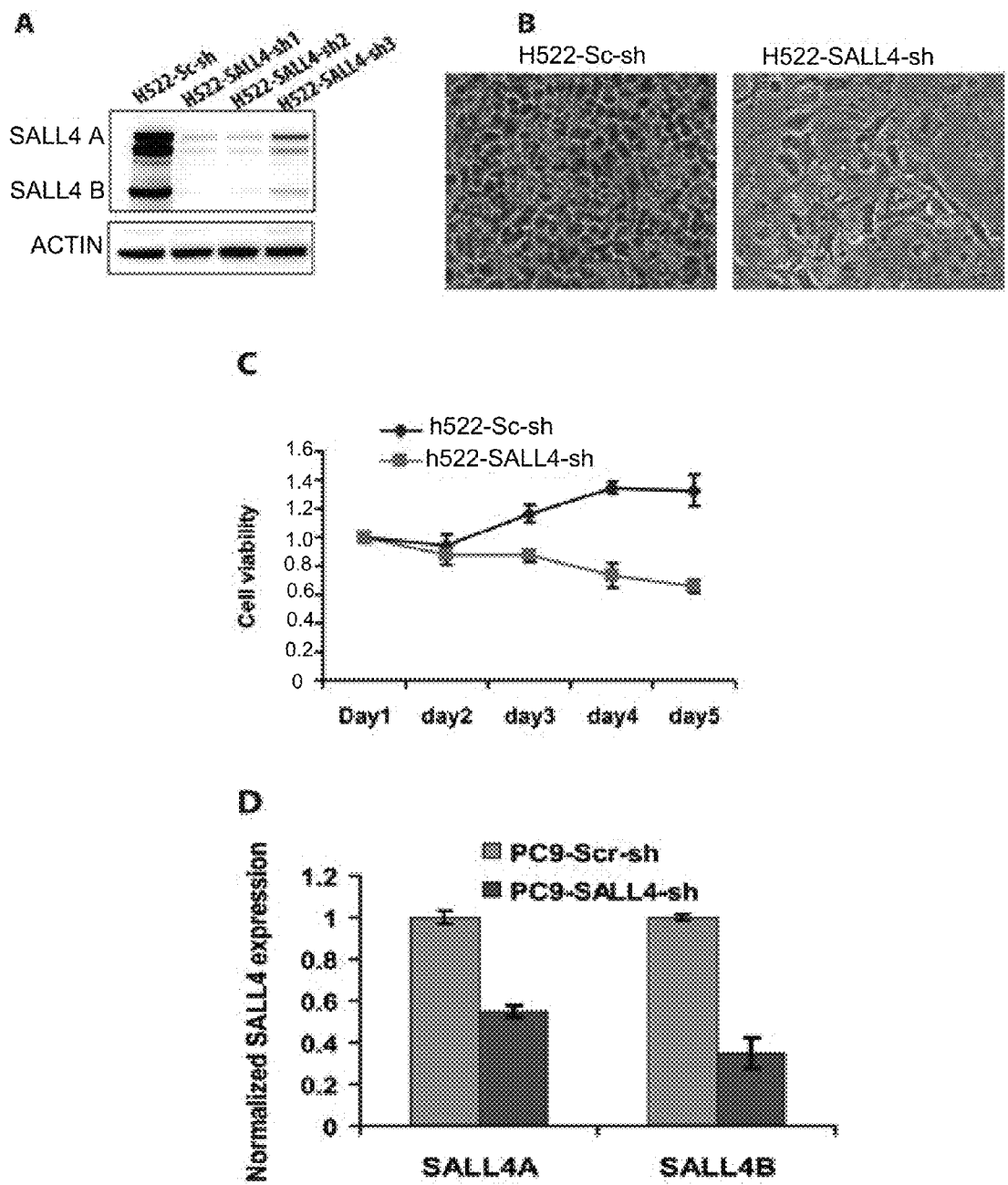
Figure 56E:
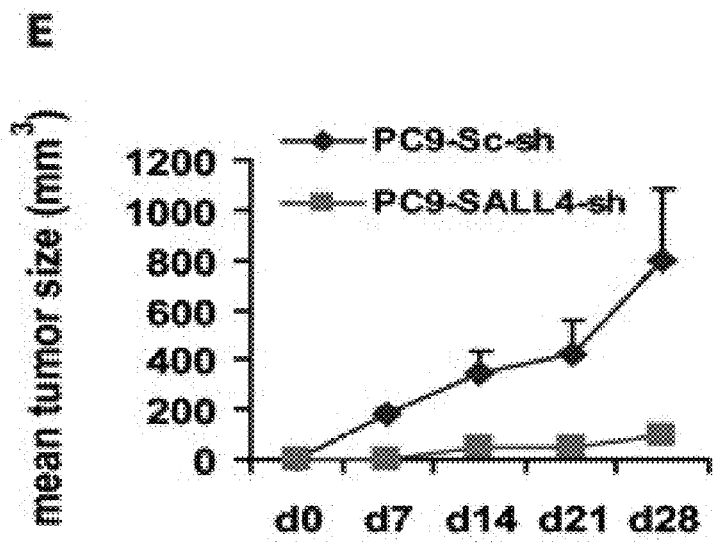
Figure 56F:
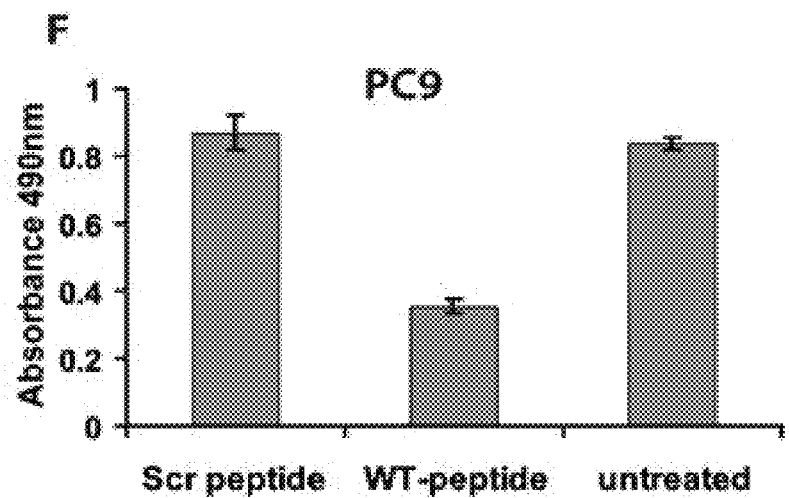

FIGS. 55A-55B: SALL4 expression in lung cancer. 55A: gene expression profiling analysis of GSE database. 55B: IHC data showing SALL4 aberrant expression in subsets of lung cancer sample compared to normal lung tissue.

FIGS. 56A-56F: Knockdown SALL4 resulted in completely cell growth arrest and dramatic cell apoptosis. 56A: Western blot demonstrates SALL4 knock down in lung cancer cell line H522. 56B: Cell image after SALL4 knockdown in H522 cells. 56C: MTS assay showing cell growth arrest of H522 after SALL4 knock down. 56D: Real-time PCR shows that SALL4 knockdown in PC9 cells. 56E: Xenograft studies data show that SALL4 knock down in PC9 cells inhibits tumor growth. 56F: SALL4 peptide (Wt) treatment leads to cell growth arrest in PC9 cells. Scr (scramble) peptide treatment shows no effect on the cells when compared to control untreated cells.

Figures 57A, 57B, 57C:
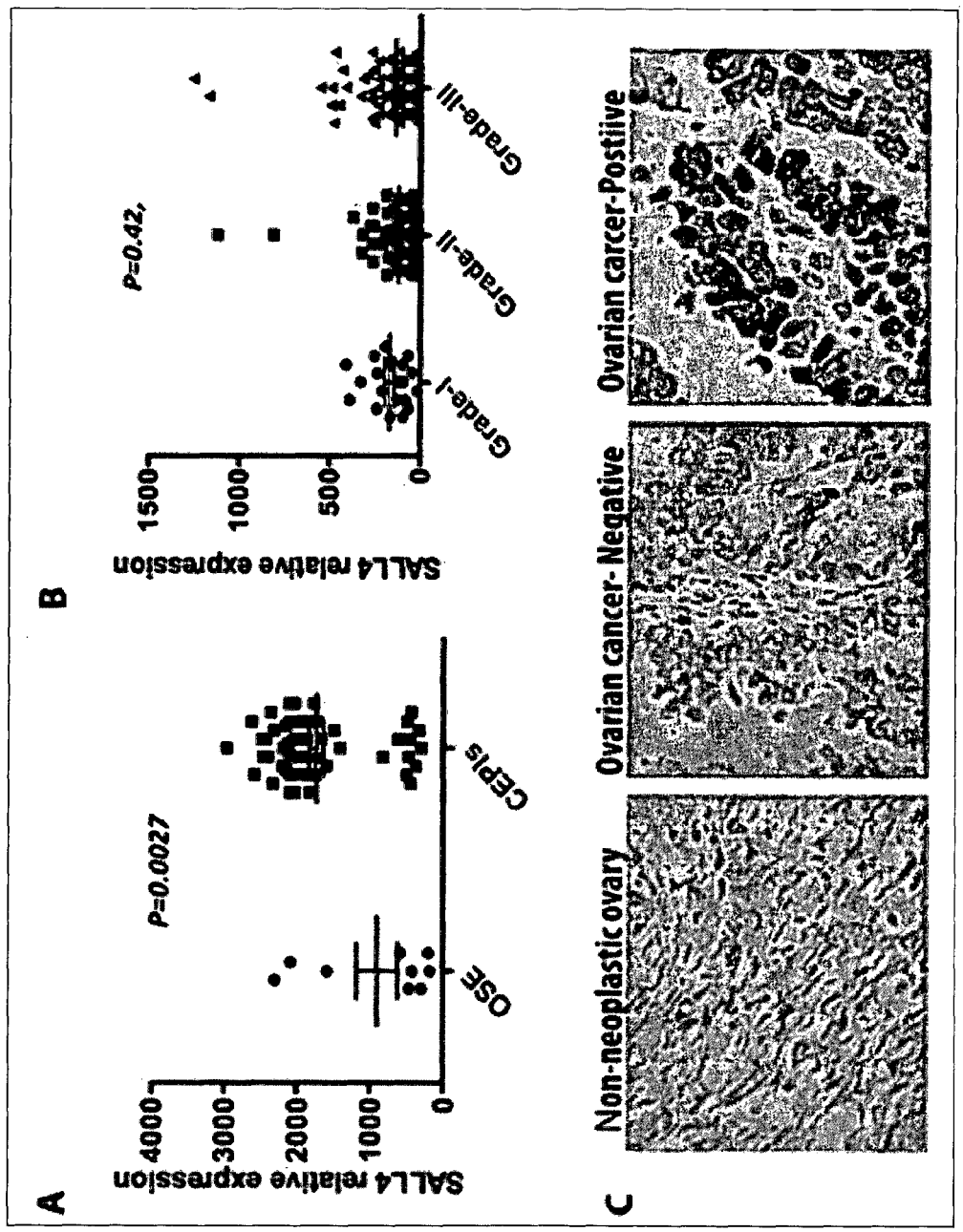

FIGS. 57A-57C: Characterization of SALL4 expression in ovarian epithelial carcinoma. 57A and 57B: Gene expression data analysis reveals that higher level of SALL4 expression in ovarian cancer epithelial cells (CEPIs) than ovarian surface epithelial cells (OSE). 57C: Representative IHC images showing the SALL4 expression in ovarian epithelial cancer, but not in the matched non-neoplastic ovarian.

Figures 58A, 58B:
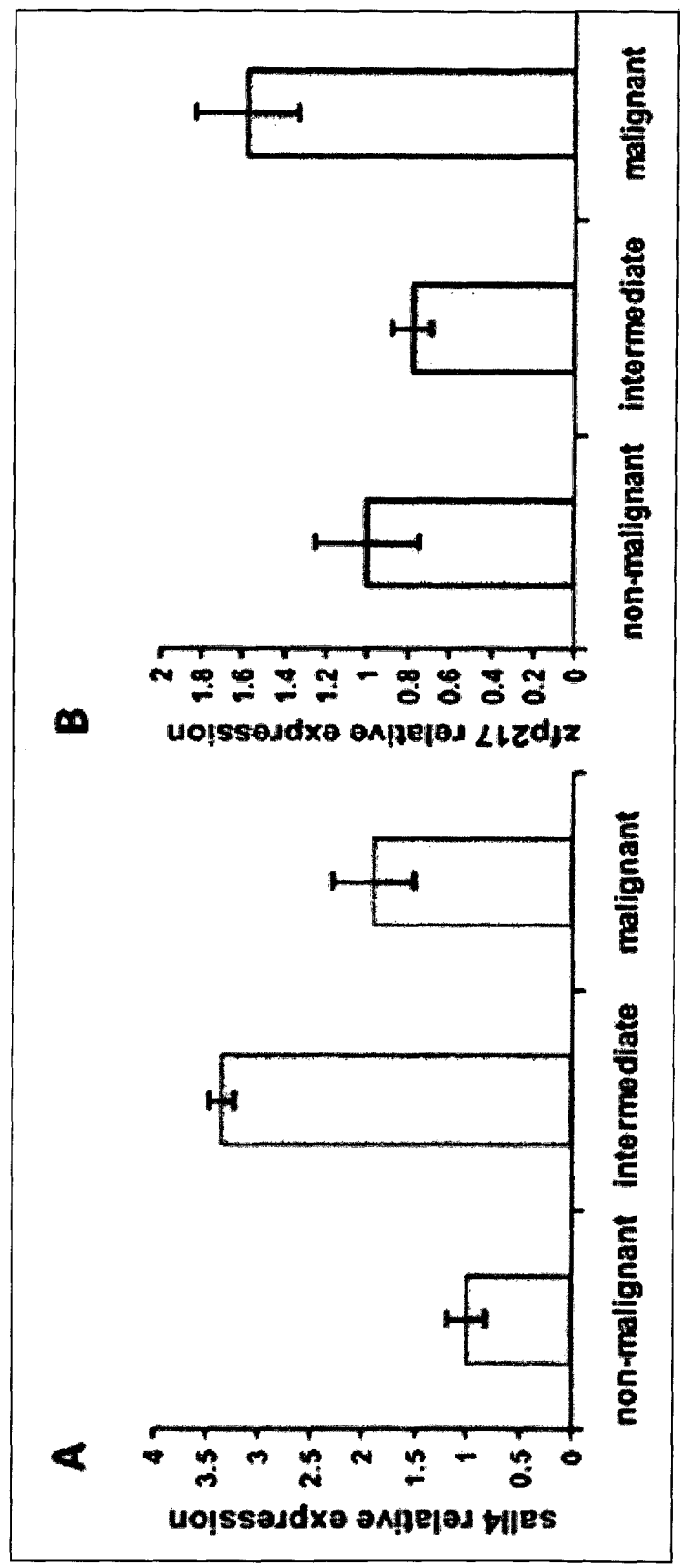

FIGS. 58A-58B Q-RT-PCR showing that gene expression in cultured MOSE cells. 58A: Mouse Sall4 expression in different stages of MOSE cells. 58B: Mouse zfp217 expression in different stages of MOSE cells.

Figures 59A, 59B, 59C:
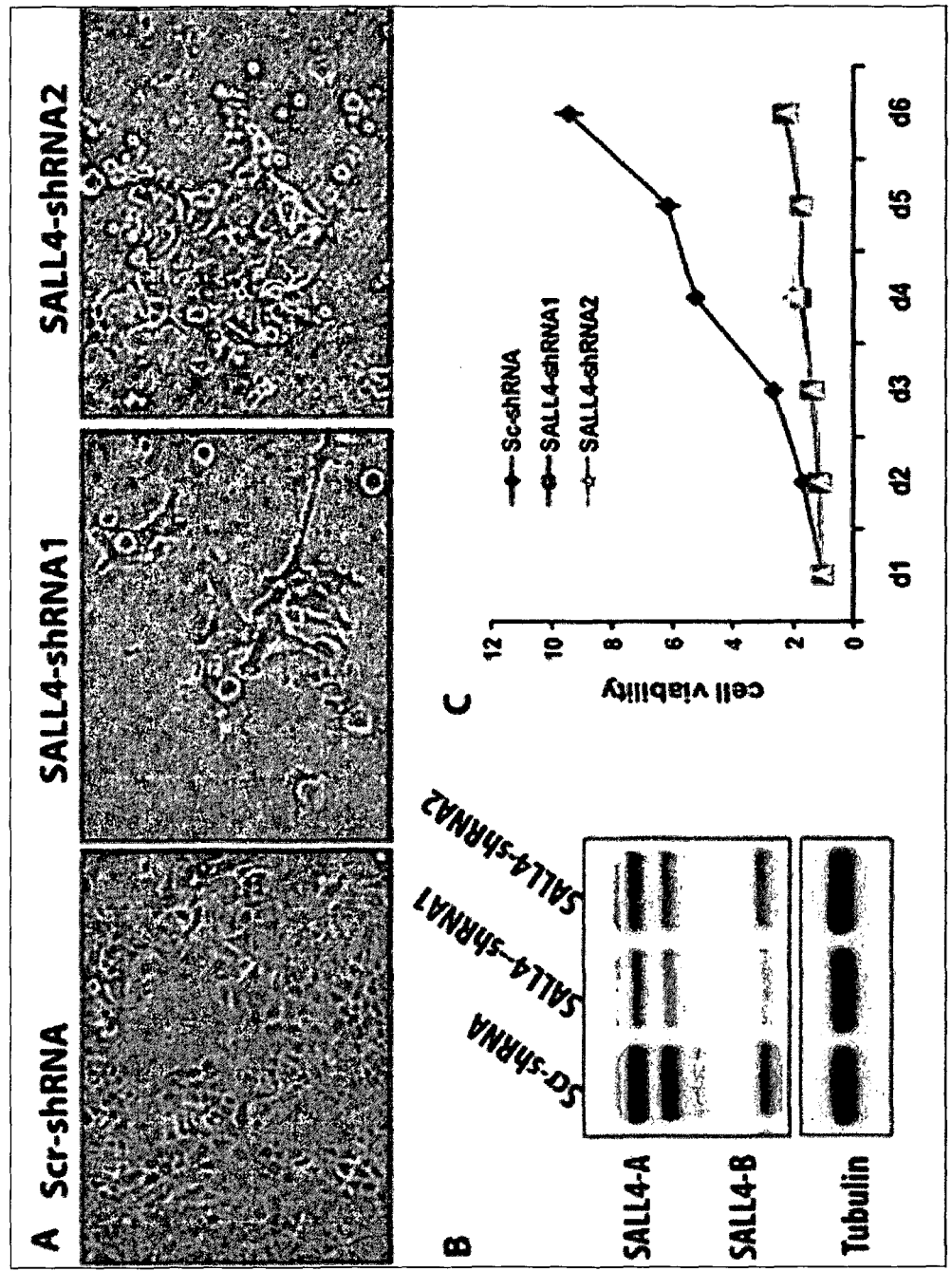

FIGS. 59A-59C: Down-regulation of SALL4 significantly induces cell death and growth arrest. 59A: Representative cell images after SALL4 knockdown in OV90 cells. 59B: Western blot showing the down regulation of SALL4 protein in SALL4 specific shRNAs treated OV90 cells. 59C: MTS assay shows that the decrease in cell viability of SALL4-shRNAs treated OV90 cells compared to Scr-treated control.

The above data suggests that SALL4 may also play an important role in maintenance of ovarian tumor.

Figure 60:

FIG. 60: Peptide treatment on OV90 leads to decreased living cells. Mut-peptide: mutant peptide; WT-peptide: wild-type peptide.

Figure 61:
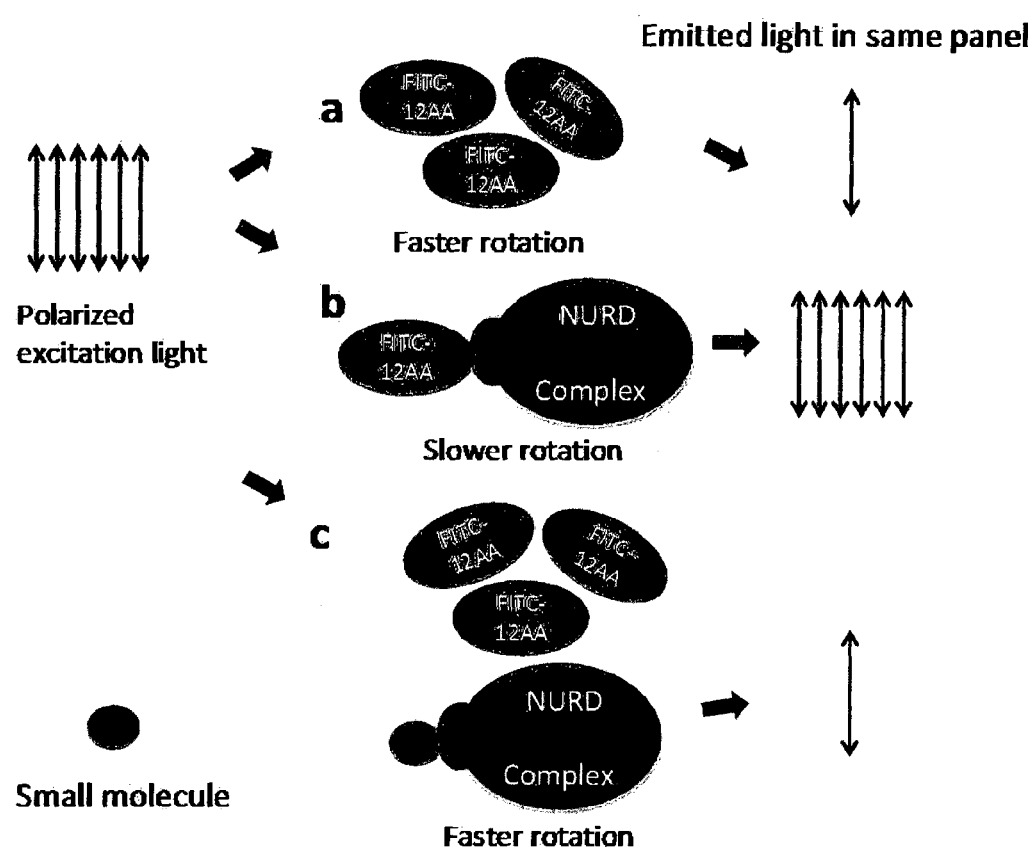

FIG. 61: The signal measured with this technology is a weighted value of free and bound ligand. 12AA peptide will be labeled with an appropriate fluorophor and the binding of the NuRD complex counterpart affinity will be antagonized with the above library (FIG. 11).

DETAILED DESCRIPTION OF THE INVENTION

SALL4, a zinc finger transcription factor, forms a core transcriptional network with Oct4, Nanog and Sox2, which governs the self-renewal property of murine embryonic stem cells (ESCs). In addition, SALL4 is aberrantly expressed in human acute myeloid leukemia (AML), and transgenic SALL4 mice develop myelodysplastic syndrome (MDS) and AML. Loss of function studies have demonstrated that SALL4 is a key regulator in leukemic cell survival and down-regulation of SALL4 can lead to significant apoptosis of leukemic cells in a cell line model. In addition, SALL4 is aberrantly expressed in solid tumors such as breast cancer, ovary cancer, gastric cancer, Wilms tumor and germ cell tumor.

A "SALL4 leukemic initiation signature" was characterized in a SALL4 transgenic murine model and it was found that SALL4 mainly acts as a repressor by interacting with the nucleosome remodeling and deacetylase (NuRD) complex containing histone deacetylase 1 (HDAC1) and HDAC2. Phosphatase and tensin homolog deletion on chromosome 10 (Pten), one of the factors that are essential for the self-renewal of leukemic stem cells (LSCs), is repressed by SALL4 through the NuRD complex.

Described herein is the study of whether blocking the SALL4/NuRD interaction exerts a biological effect on cancer cells, using AML cells and hepatocarcinoma cells. Shown herein is that the NuRD recruiting region of SALL4 contains 12 amino acids (AA), and this 12-AA peptide demonstrated growth inhibition of leukemic cells similar to that of classic HDAC inhibitors such as trichostatin A (TSA) as well as that of down-regulation of SALL4 gene by shRNA. The antitumor effect of this peptide can be rescued by a Pten inhibitor.

Accordingly, in one aspect, the invention is directed to a method of treating a (one or more) solid tumor which expresses SALL4 and Phosphatase and Tensin Homolog (PTEN) in an individual in need thereof, comprising administering to the individual an effective amount of a (one or more) composition that inhibits SALL4.

In a particular aspect, the invention is directed to a method of treating a liver tumor which expresses SALL4 in an individual in need thereof comprising administering to the individual an effective amount of a composition that inhibits SALL4.

In another aspect, the invention is directed to a method of treating an endometrial tumor which expresses SALL4 in an individual in need thereof comprising administering to the individual an effective amount of a composition that inhibits SALL4.

In yet another aspect, the invention is directed to a method of treating an ovarian epithelial tumor which expresses SALL4 in an individual in need thereof comprising administering to the individual an effective amount of a composition that inhibits SALL4.

Also shown herein is that SALL4 is a prognostic marker for cancer. Thus, the invention is also directed to methods of detecting an aggressive cancer in an individual in need thereof comprising detecting whether one or more cancer cells of the individual expresses SALL4, wherein if SALL4 is detected in the one or more cancer cells, then an aggressive cancer is detected in the individual. The invention is also directed to a method of detecting a poor prognosis of a patient with cancer in an individual in need thereof, comprising detecting whether one or more cancer cells of the patient expresses SALL4, wherein if SALL4 is detected in the one or more cancer cells of the patient, then a poor prognosis is detected in the patient.

In a particular aspect, the invention is directed to a method of detecting an aggressive liver cancer in an individual in need thereof comprising detecting whether one or more liver cancer cells of the individual expresses SALL4, wherein if SALL4 is detected in the one or more liver cancer cells, then an aggressive liver cancer is detected in the individual. The invention is also directed to a method of detecting a poor prognosis of a patient with liver cancer in an individual in need thereof, comprising detecting whether one or more liver cancer cells of the patient expresses SALL4, wherein if SALL4 is detected in the one or more liver cancer cells of the patient, then a poor prognosis is detected in the patient.

In yet another aspect, the invention is directed to a method of detecting an aggressive endometrial cancer in an individual in need thereof comprising detecting whether one or more endometrial cancer cells of the individual expresses SALL4, wherein if SALL4 is detected in the one or more endometrial cancer cells, then an aggressive endometrial cancer is detected in the individual. The invention is also directed to a method of detecting a poor prognosis of a patient with endometrial cancer in an individual in need thereof, comprising detecting whether one or more endometrial cancer cells of the patient expresses SALL4, wherein if SALL4 is detected in the one or more endometrial cancer cells of the patient, then a poor prognosis is detected in the patient.

As used herein, SALL4 refers to a zinc finger transcription factor essential in the developmental stage, as it is a potent stem cell factor. SALL4 forms a core transcriptional network with Oct4, Nanog and Sox2, and governs the self-renewal property of murine embryonic stem cells (ESCs). In humans, during normal hematopoiesis, SALL4 is preferentially expressed in CD34+CD38− hematopoietic stem cells (HSCs) and down-regulated in the CD34+CD38+ hematopoietic progenitor cells (HPCs). In disease state, SALL4 is aberrantly expressed in human acute myeloid leukemia (AML). Transgenic SALL4 mice (that overexpress SALL4) develop MDS and AML, suggesting a role for SALL4 in leukemogenesis. Loss of function studies demonstrated that SALL4 is a key regulator of cell survival and apoptosis in leukemic cells. The important role of SALL4 in normal HSC and leukemic stem or initiating cells (LICs) is supported by its interactions with several key players implicated in self-renewal of HSCs and LICs—Wnt/β-catenin, Bmi1, and Pten (phosphatase and tensin homolog deletion on chromosome 10).

In addition, SALL4 is found to be aberrantly expressed in solid tumors such as breast cancer, lung cancer, ovary cancer, liver cancer, gastric cancer, brain and germ cell tumors (FIG. 8). Loss of function studies demonstrated that SALL4-expressing liver or lung cancer cells had decreased viability, in part due to cell cycle arrest and increased apoptosis, upon SALL4 gene knockdown (FIGS. 9 and 10).

A role for SALL4 as a therapeutic target for a subtype of solid tumors that expresses a high level of SALL4, including some clinically challenging cancers like liver cancers (that has no established molecular classification to date) and EGFR-negative lung cancer, is described herein.

SALL4 has a role in leukemogenesis i.e. behaving like an oncogene. Associated proteins of SALL4 have been identified using tandem mass spectrometry as described herein, which led to the development of a cancer treatment which targets SALL4. Components of the NuRD complex were found in SALL4-immunocomplexes along with HDAC activity in ESCs with endogenous SALL4 expression and 293T cells overexpressing SALL4. SALL4-mediated transcriptional regulation was tested on one potential target gene—referred to herein as PTEN or Pten. Pten has been confirmed to be a SALL4 downstream target by chromatin-immunoprecipitation (ChIP) assay, and its expression level, when tested by quantitative reverse transcription polymerase chain reaction (qRT-PCR), was decreased in 293T cells overexpressing SALL4, indicating that SALL4 transcriptionally repressed Pten expression. As used herein, Pten refers to a protein that is encoded by the Pten gene and which acts as a tumor suppressor.

In addition, SALL4 binding sites at the promoter regions of Pten were co-occupied by NuRD components, indicating that SALL4 represses the transcription of PTEN through its interactions with NuRD. The in vivo repressive effect(s) of SALL4 was evaluated in SALL4 transgenic mice, in which decreased expression of Pten was associated with MDS and AML. In short, shown herein is that SALL4 exerts its oncogenic role, in part, by transcriptional repression of tumor suppressor genes e.g. PTEN, through its interactions with NuRD complex.

As also shown herein, one of the mechanisms underlying SALL4-induced tumorigenesis is the suppression of tumor suppressor gene PTEN through its interaction with NuRD complex. A 12-AA SALL4 peptide (FIG. 1) was used as a therapeutic peptide for solid tumors that express high level of SALL4. The 12-AA SALL4 peptide effectively disrupted the interaction of SALL4 with NuRD complex and hence released the transcriptional repressive effects of SALL4 on PTEN, and thereby reversed tumorigenesis.

Figures 12A, 12B, 12C:
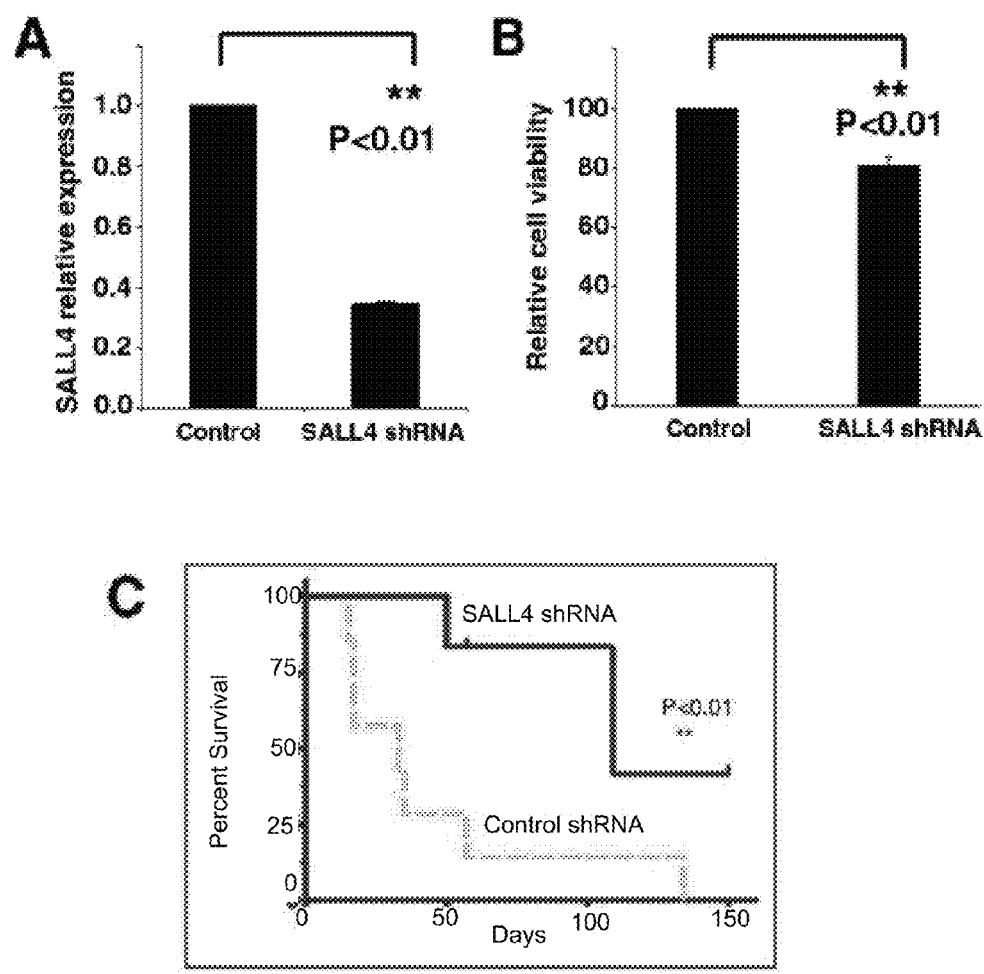
Figure 13:
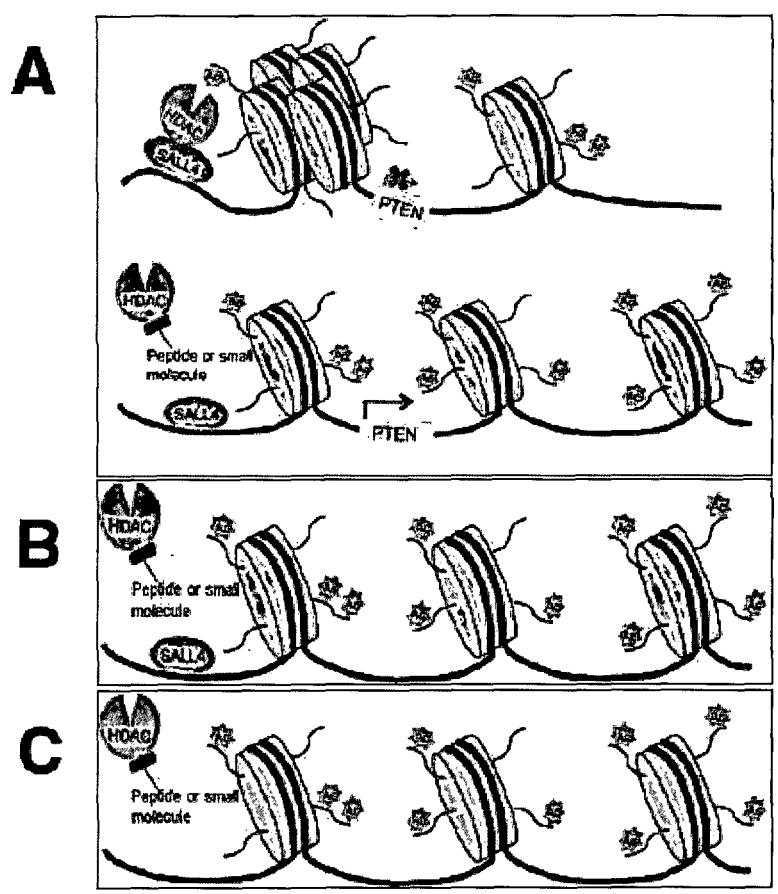
FIGS. 13A-13C: Working model of the novel peptide or a small molecule that targets the interaction between the HDAC complex and its transcription factor recruiter SALL4. (13A) Upper panel: SALL4 represses its downstream targets by recruiting a HDAC complex NuRD to specific promoter regions, such as the PTEN promoter, resulting in histone deacetylation, a more compact chromatin structure, and transcription repression. Lower panel: The wild type peptide (or a small molecule) competes with SALL4 in interacting with NuRD. The repression of PTEN by SALL4 is therefore lost, and the PTEN expression is up-regulated, leading to tumor growth inhibition. (13B) In some tumor cells (such as the human endometrioid cancer line AN3CA), PTEN is deleted, hence the disruption of the SALL4/HDAC complex does not affect cell growth. (13C) Some tumors do not express SALL4 (such as KBM5), in which case, PTEN will be regulated independent of SALL4 and the wild type peptide will not have any effects on cell growth.
Figure 14A:
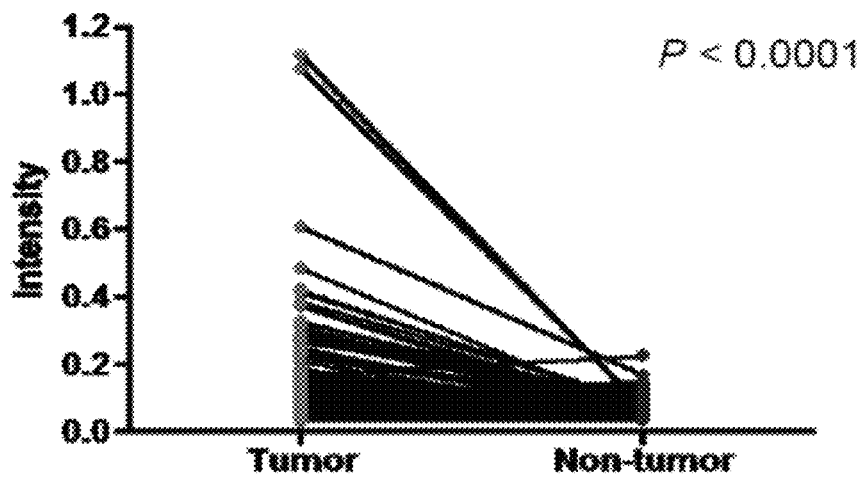
FIGS. 14A-14F: SALL4 expression is constantly elevated in a subgroup of solid tumors; analysis of SALL4 expression in (14A) primary HCC and adjacent normal liver samples, (14B) primary endometrial carcinoma samples, (14C) primary gastric cancer samples, (14D) primary lung cancer samples, (14E) lung cancer subtypes, and (14F) brain tumors.
Figure 14B:
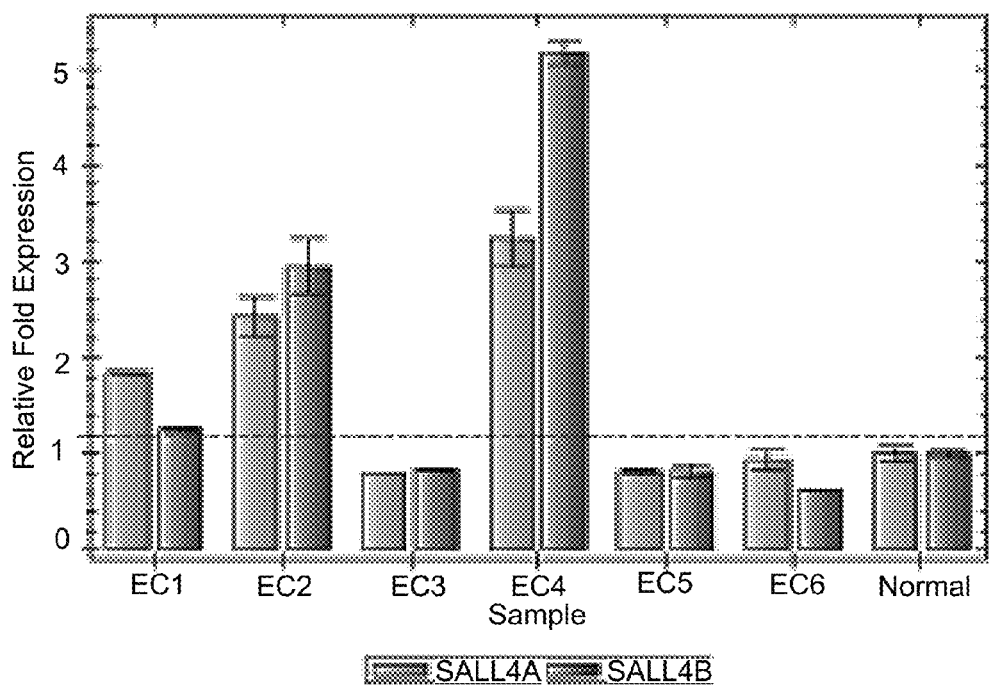
Figures 14C, 14D:
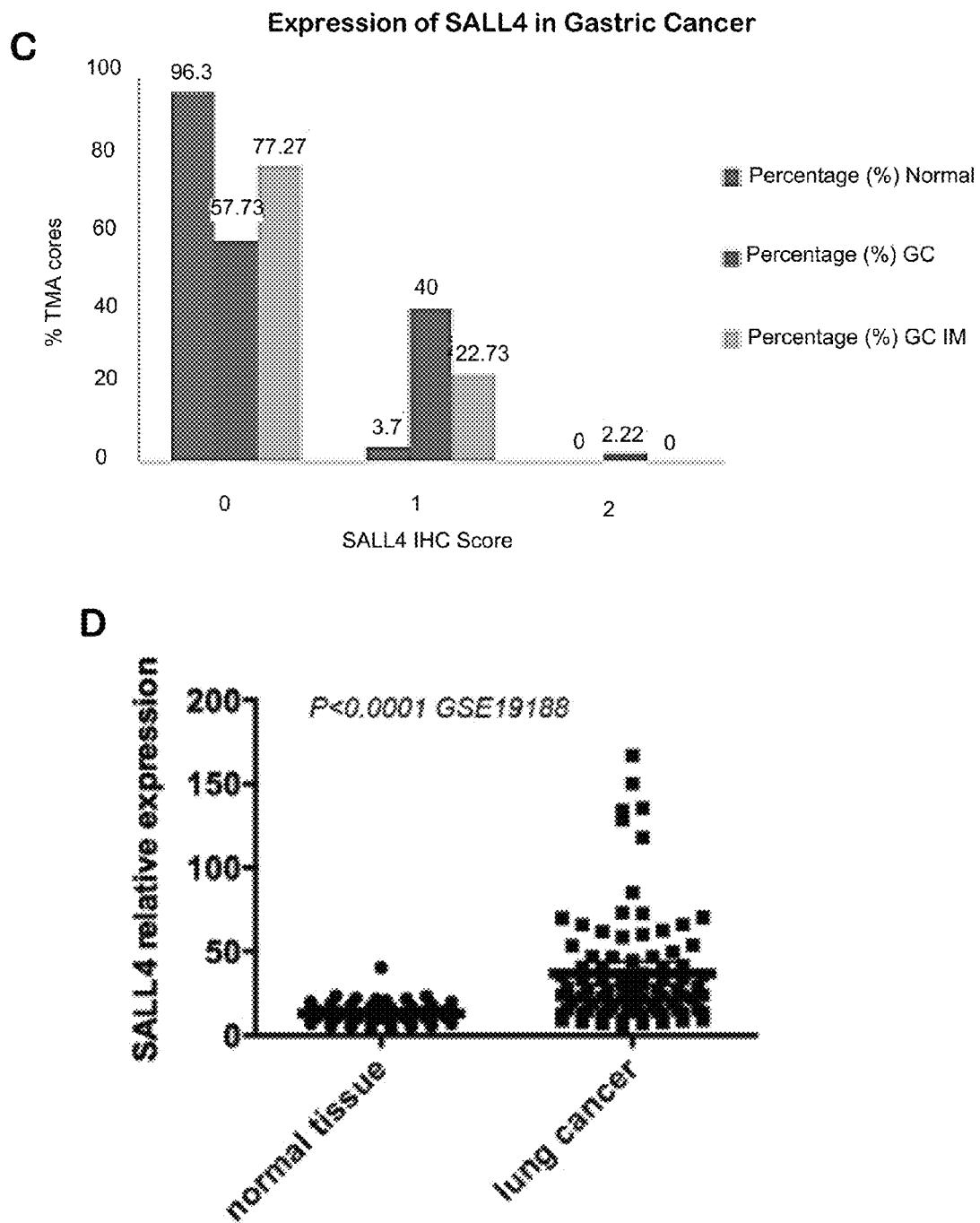
Figure 14E:
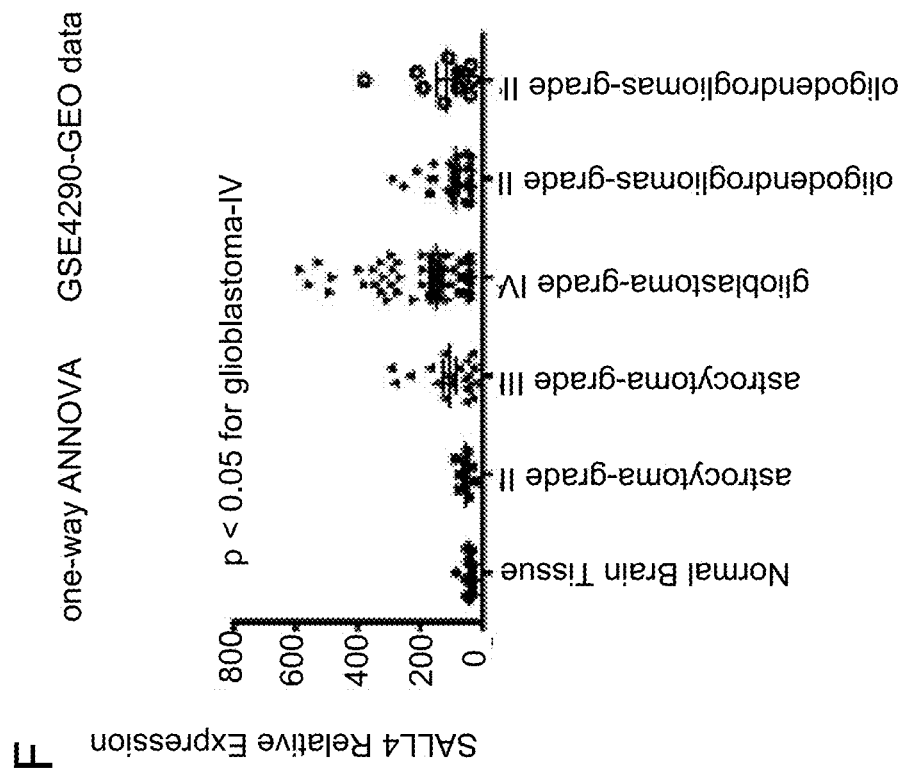
Figure 14F:
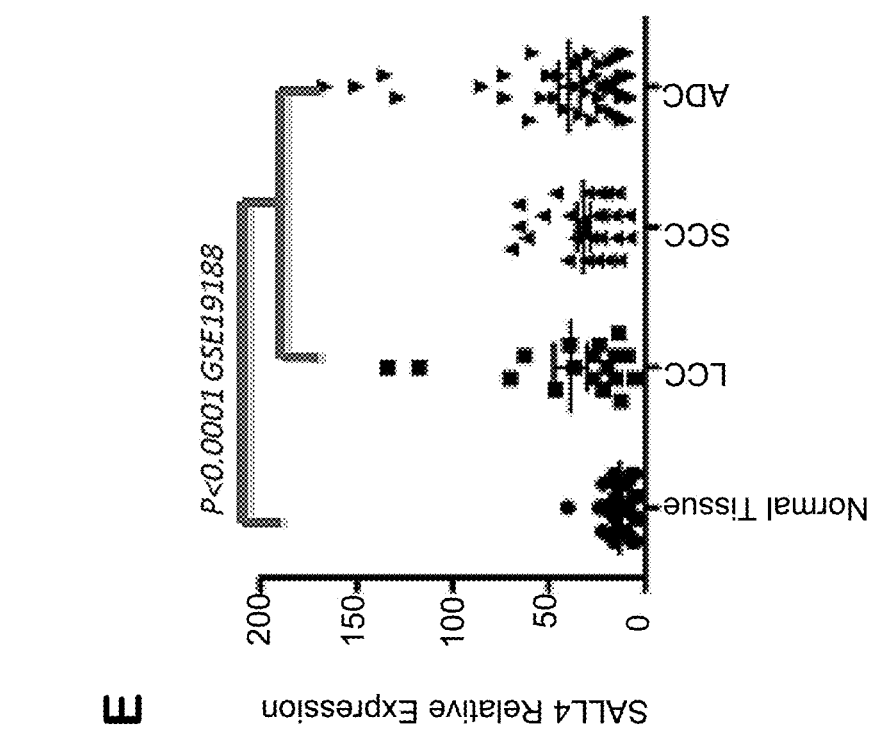
Figures 15A, 15B:
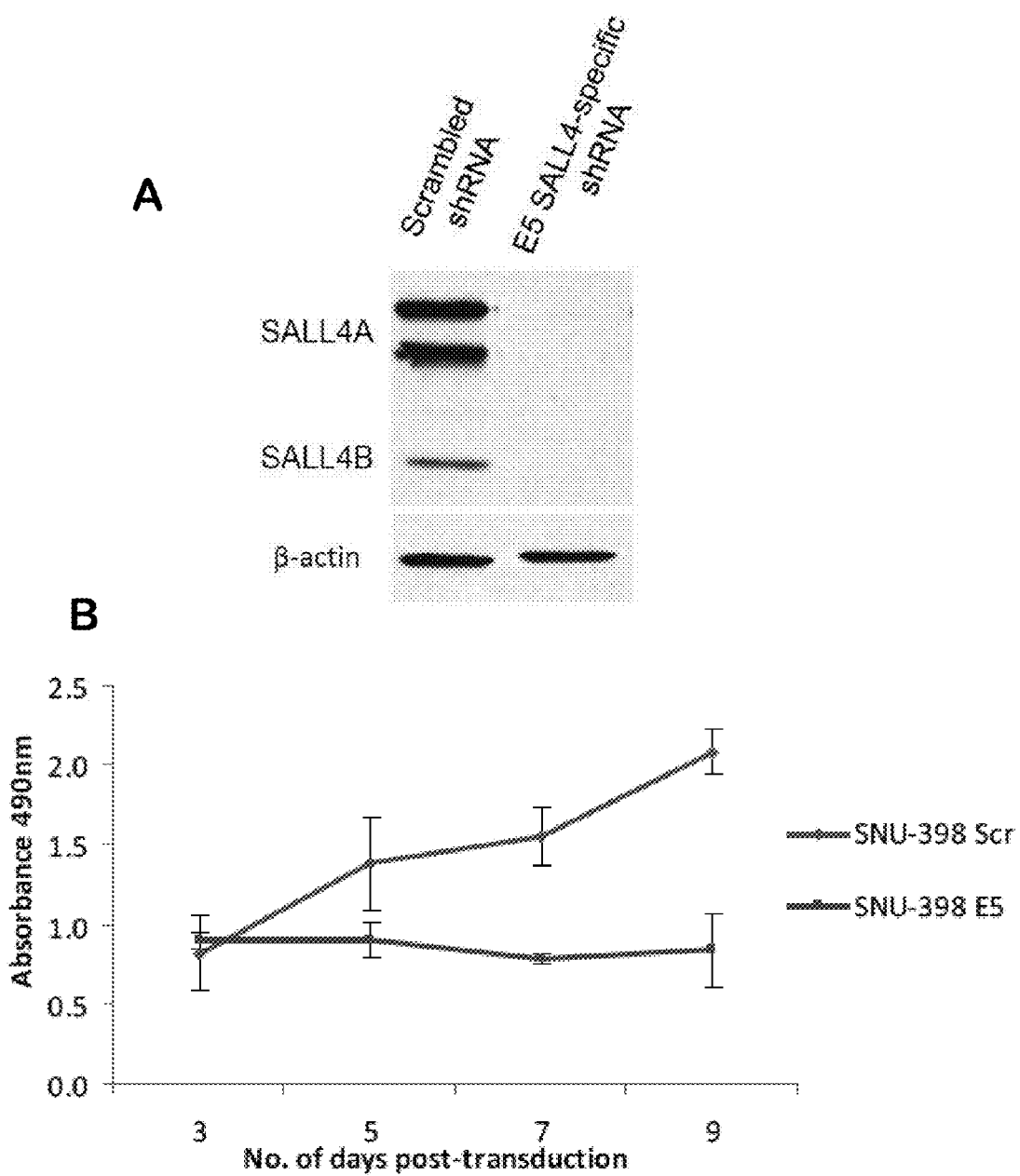
FIGS. 15A-15D: Loss of SALL4 in HCC cells that express high level of SALL4 (15A-15C) decreases cell viability, in part due to increased apoptosis. (15A) Western blot analysis showing downregulation of SALL4 protein level by SALL4-specific shRNA, (15B) MTS assay showing decreased cell viability upon SALL4 gene knockdown (SNU-398 E5); the viability of HCC cells were not affected by the infection of virus expressing scrambled shRNA (SNU-398 Scr), as an increase in the number of viable HCC cells was observed. (15C) Caspase 3/7 assay showing increased apoptosis in SALL4-knockdown cells, as observed by the increase in capase 3/7 activity for four days and six days post-transduction. (15D) No significant change in cell viability of cancer cells that express low/no SALL4, upon SALL4 gene knockdown by RNAi using shRNA, as seen from MTS assay.
Figures 15C, 15D:
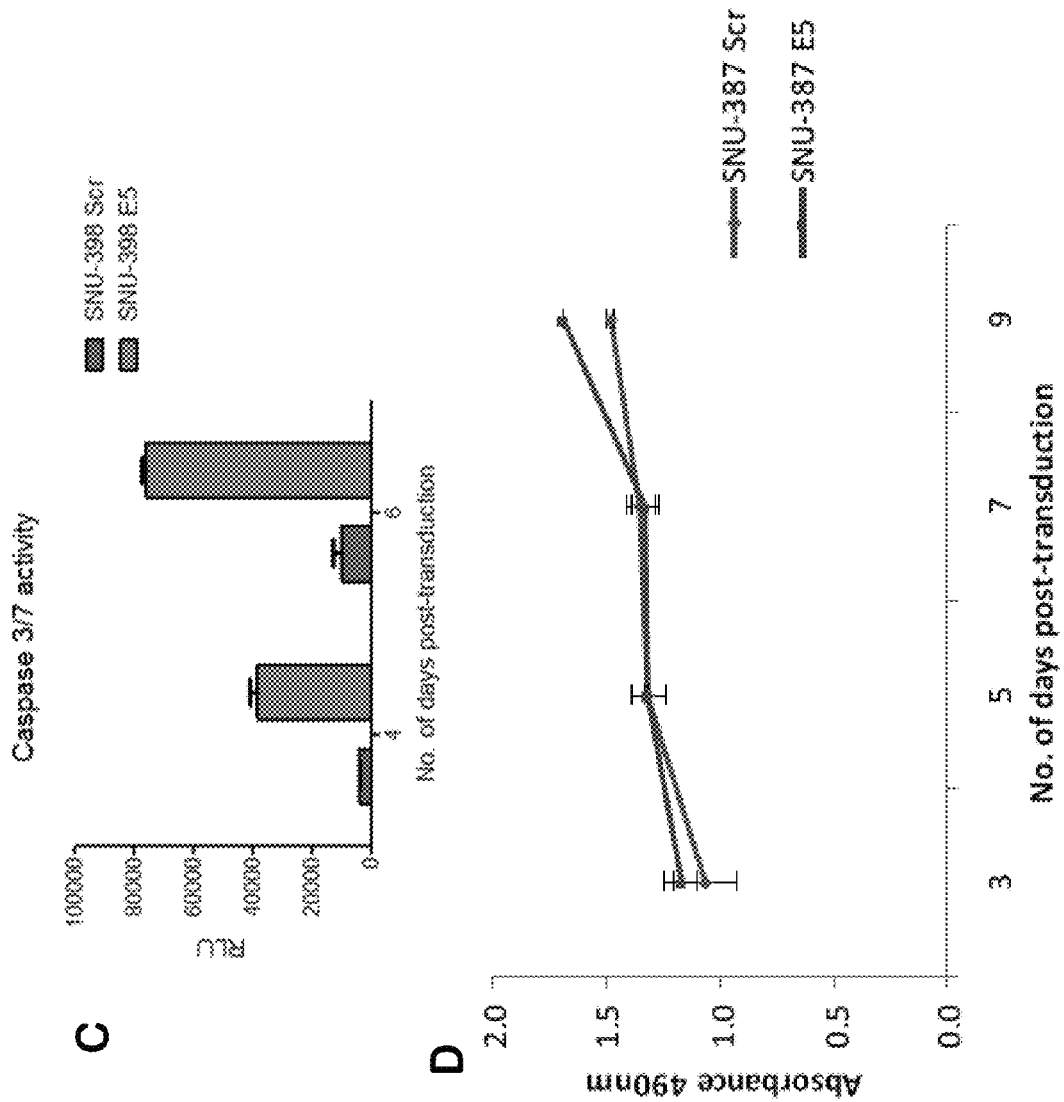
Figures 16A, 16B:
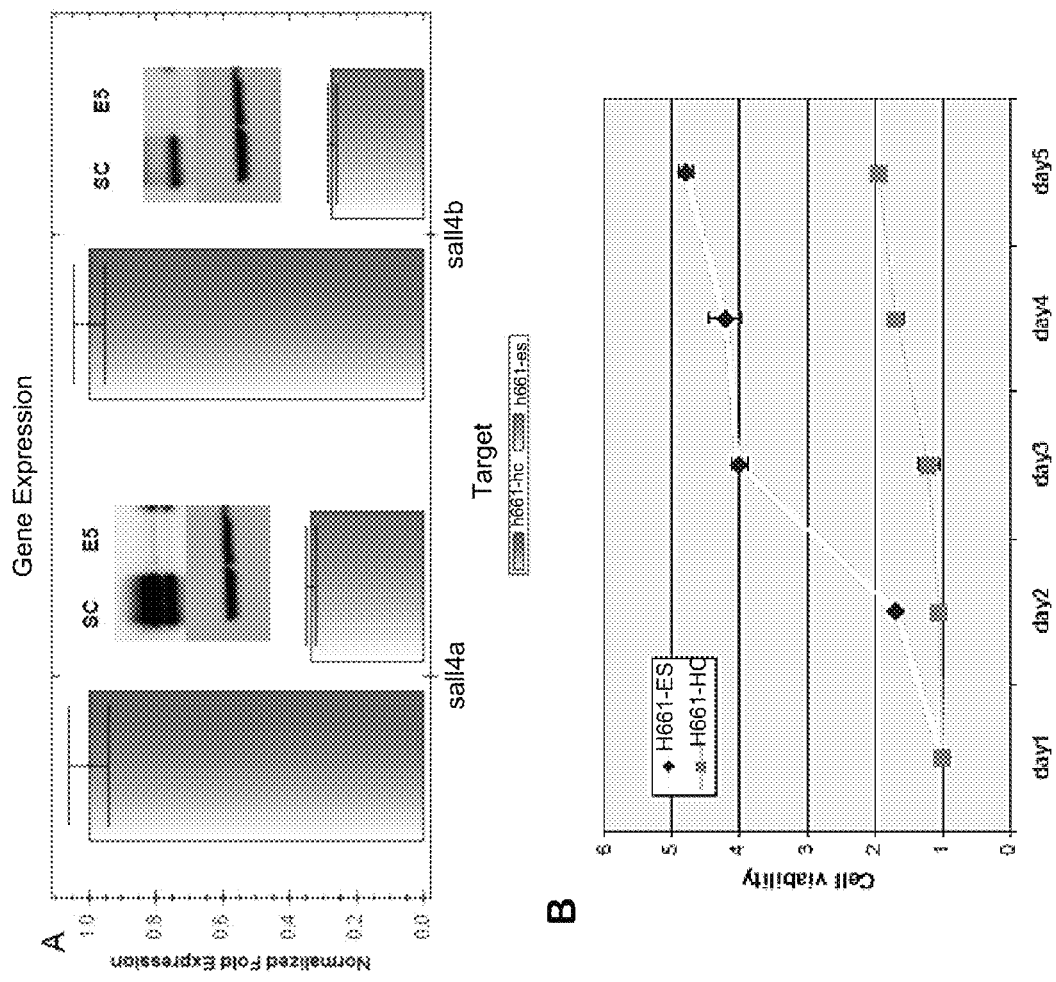
FIGS. 16A-16B: Loss of SALL4 in lung cancer cells that express high level of SALL4 decreases cell viability. (16A) qPCR (bar chart) and western blot were done to confirm the dwonregulation of SALL4 RNA (qPCR) and protein (western blot) expression levels upon SALL4 gene knockdown by shRNA (E5) compared to the control (SC). (16B) MTS assay showing the decrease of cell viability of H661 lung carcinoma cells upon SALL4 gene knockdown (H661-E5).
Figure 17:
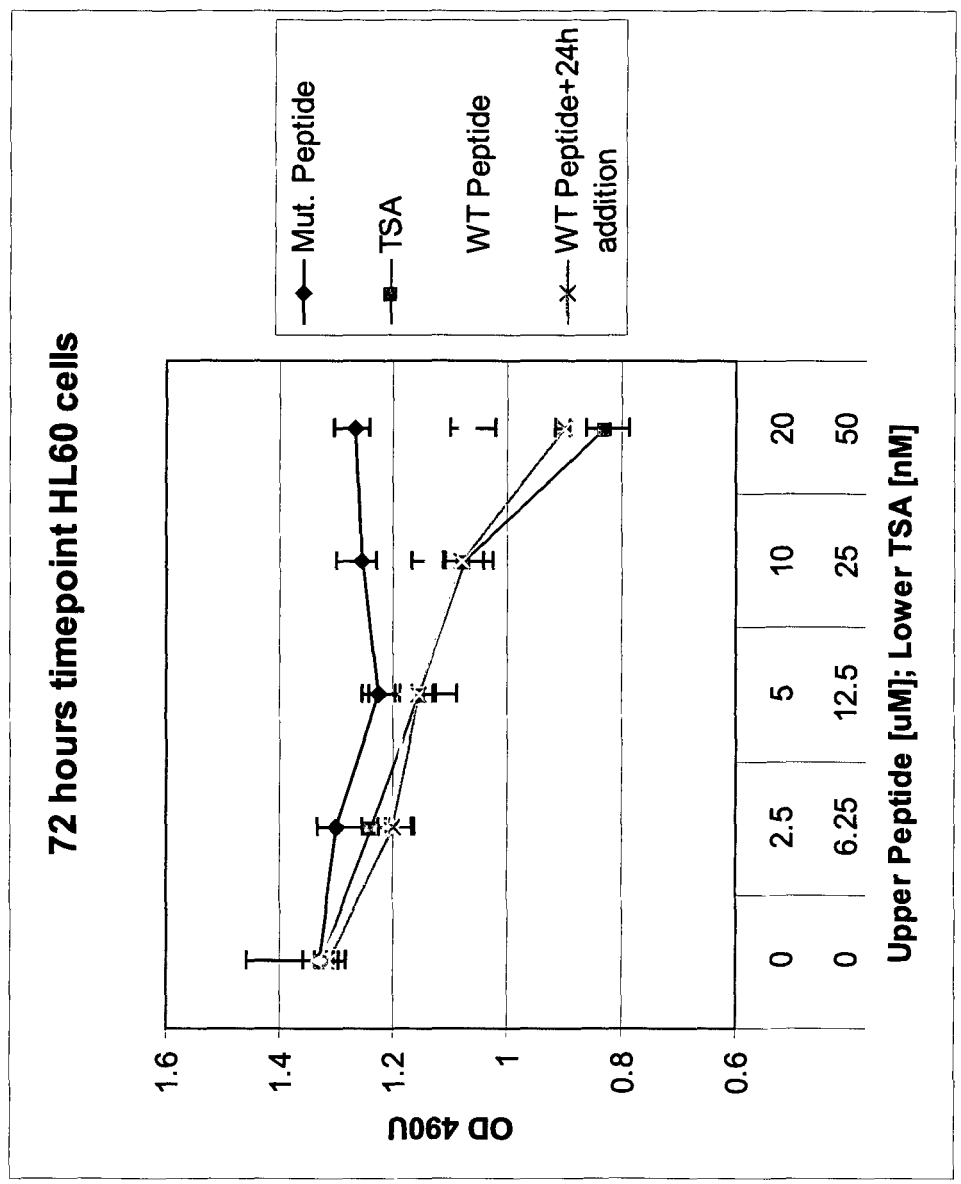
FIG. 17: SALL4 peptide reduces the viability of leukemic HL-60 cells. HL60 human acute promyelocytic leukemia cells (ATCC), were cultured in RPMI medium with 10% FBS (Invitrogen). 5000 cells/well were seeded in 96 well plate. Peptides: MSRRKQAKPQHI-wt (SEQ ID NO: 1) and MSR-RAQAKPQHI-mutant (SEQ ID NO: 6) were synthesized by Biosynthesis Inc. to 85% purity. Peptides and TSA were re-suspended in PBS and added to the final concentration as indicated. WT peptide was re-added 24 hours after the initial addition as indicated. Experiment was performed in triplicate. MTS assay was performed by adding 20 ul of the Cell-Titer 96® AQueous One Solution Reagent (Promega) directly to the cells in medium, incubating for 2 hours and then recording absorbance at 490 nm with a 96-well plate reader. The quantity of formazan product as measured by the amount of 490 nm absorbance is directly proportional to the number of living cells in culture.
Figure 18:
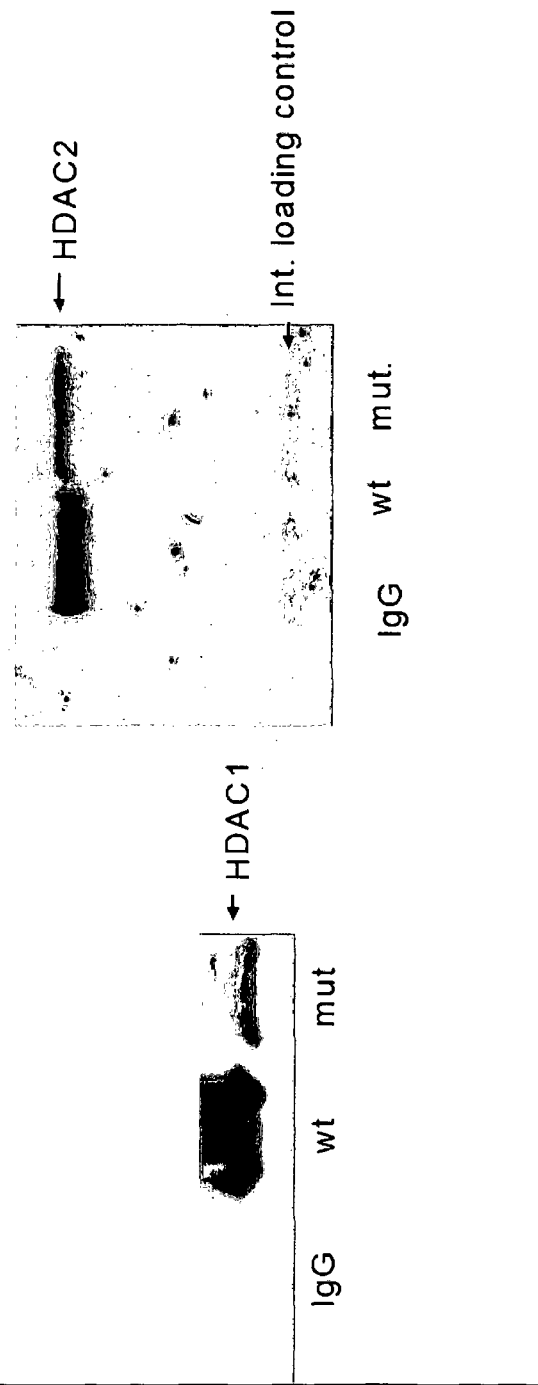
FIG. 18: SALL4 peptide interacts with various components of the NuRD complex. Cell lysates from HL60 cells were mixed with wild type (wt) or mutant (mut) peptides end-labeled with FITC and immunoprecipitated with anti-FITC antibody (Santa Cruz). The complexes were pulled down with Dynabeads Antibody Coupling Kit (Invitrogen) according to the manufacturer's instructions. The samples were immunoblotted and probed for HDAC1 and HDAC2. The wild type peptide binds to both HDACs with several folds higher activity than the mutant. The specificity was tested with mouse IgG instead of anti-FITC antibody.
Figure 19:
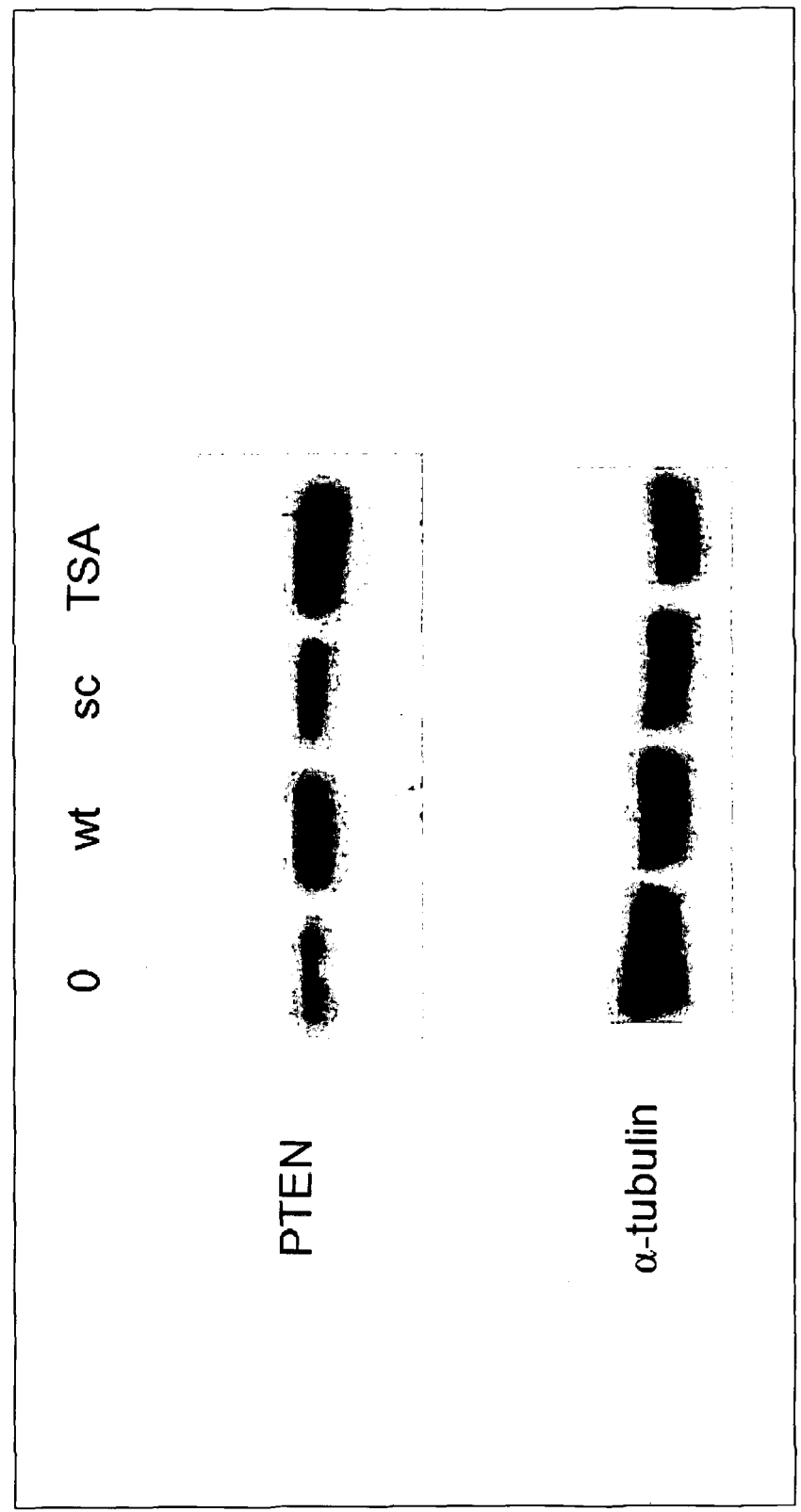
FIG. 19: SALL4 peptide induces an increase in PTEN expression level. SNU-398 (HCC cells) was treated for 24 h with wt and scrambled peptides and the levels of PTEN expression was evaluated. More than 2 times elevated level was observed in the cells treated with the wt peptide, consistent with the levels of induction related with the SALL4 suppression in the same cell type. The scrambled (mutant) peptide does not exhibit the same properties. For a positive control for the PTEN induction Trichostatin A—a potent HDAC inhibitor was used. The levels of PTEN were elevated upon drug treatment. Induction was calculated in comparison with the levels of the house keeping gene alfa-tubulin in the same sample.
Figures 20A, 20B:
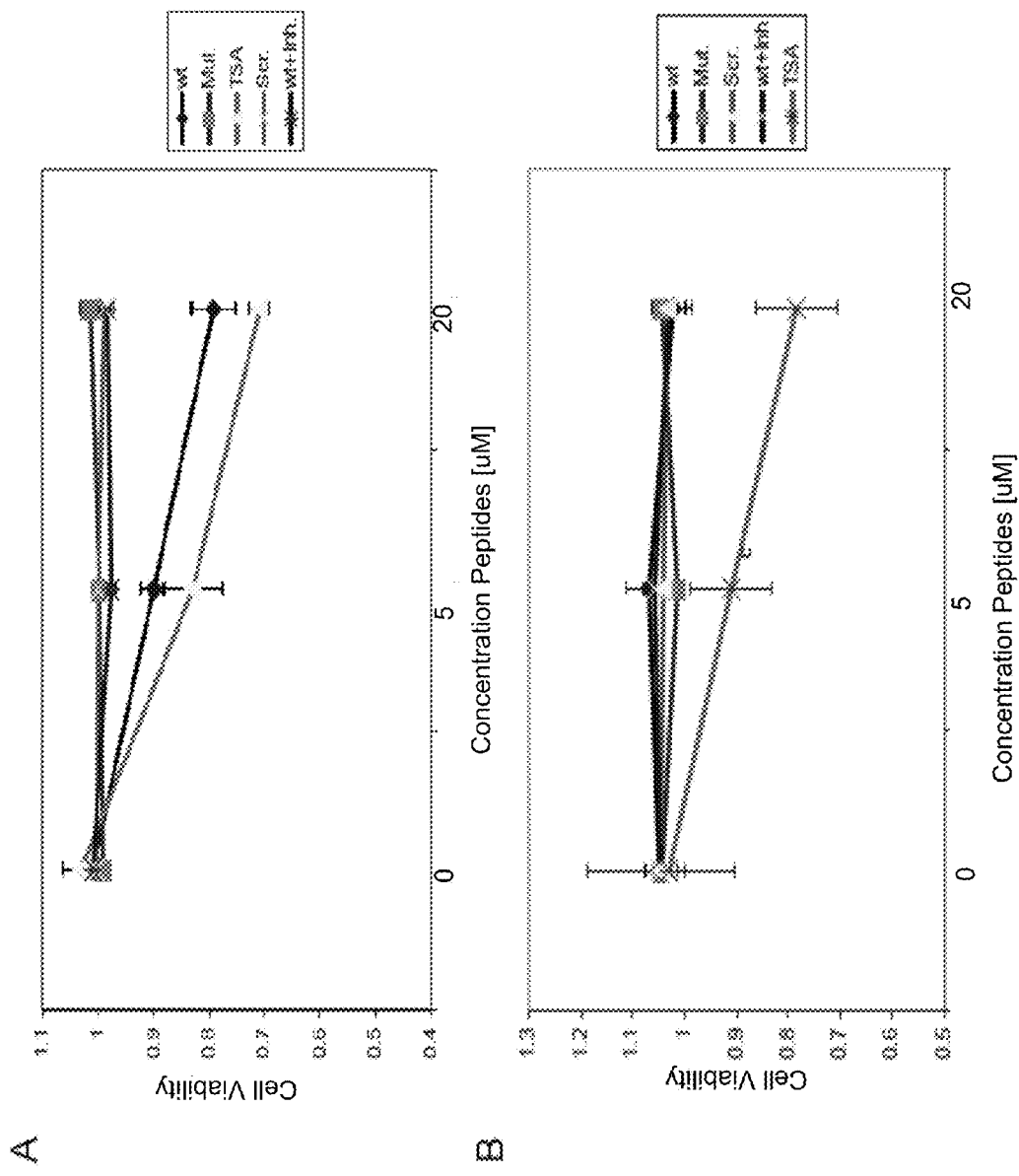
FIGS. 20A-20B: Therapeutics targeting SALL4 are specific. (20A) SALL4 peptide treatment triggered loss of cell viability in HCC cells that express high SALL4 level, similar to the effect of TSA treatments. (20B) No effect on cell viability upon SALL4 peptide treatment on HCC cells that express low/no SALL4; wt: wildtype SALL4 peptide, Mut: mutant peptide, TSA: Trichostatin A, Scr: scrambled peptide, inh: PTEN inhibitor.

Specifically to further characterize the interaction of SALL4 and NuRD, the N-terminal 12 amino acid (12-AA) peptide of SALL4 was examined. This region has been implicated in recruiting NuRD in another SALL gene family member, SALL1. This 12-AA (WT) and its mutant (Mut) was synthesized for further analyses. Mut lacks interaction with NuRD. Leukemic HL-60 cells were treated with WT, Mut and HDAC inhibitor (TSA) for 72 hours. The WT-treated HL-60 cells showed a decrease in cell viability similar to that of the ISA-treated cells (FIG. 11). A similar phenotype was observed in a panel of solid tumors tested (e.g., HL-60, MCF7, SNU-398, SNU-387). By pull down assay, it was confirmed that the peptide recruits some components of the NuRD complex with the same affinity as SALL4 itself (FIG. 12). Moreover, it was confirmed that the WT peptide can increase PTEN expression by western blot analysis (FIG. 13). Unlike HDAC inhibitors (e.g. Trichostatin A, TSA in short) that inhibit HDAC activity (one of the components in NuRD complex), SALL4 peptide is specific for cancer cells that express SALL4 (FIG. 14). Specificity of a drug is one of the important criteria for any therapeutic agents, as the more specific a drug is, the fewer side effects it brings about. Furthermore, as a stem cell factor implicated in normal development, SALL4 is shut down in most of the adult tissues, a fact that confers more specificity for therapeutics targeting SALL4.

As shown herein, the 12-AA peptide also caused cell death in HCC cells with high expression of SALL4, similar to the effect of knocking down this gene, but not in the SALL4 low or non-expressing HCC lines. It is likely that this 12-AA competed with SALL4 protein in interacting with NuRD, and thus, functioned as a tissue-specific gene-specific HDCA inhibitor, and released SALL4 in repressing Pten. Data proving this hypothesis is provided herein, e.g., after this 12-AA treatment, an increase in Pten expression which led to cell death was observed.

SALL4 has multiple functions. It can activate genes or repress genes. Though in theory, this 12-AA can bind to NuRD, it was not known whether it would function as a competitor or enhancer to the SALL4/Pten pathway, particularly in cells.

Thus, the present invention discloses the use of SALL4 as a therapeutic target for a subtype of solid tumors, including some clinically challenging cancers. In one aspect, the solid tumor expresses SALL4. In another aspect, the solid tumor expresses SALL4 and Pten. In yet another aspect, the solid tumor expresses high levels of SALL4.

As will be appreciated by those of skill in the art, high levels of SALL4 refer to increased amounts of SALL4 as compared to the level of SALL4 in a normal (e.g., healthy) cell (e.g., a non-tumor cell) or in a normal individual (an individual that does not have a tumor). For example, a high level of SALL4 refers to an increased level of SALL4 present in an individual that has a liver tumor (e.g., a tissue and/or cell from an individual's liver tumor) when compared to the level of SALL4 present in an individual that does not have a liver tumor (e.g., a tissue and/or cell from an individual's liver wherein the individual does not have a liver tumor, such as a healthy individual).

As will be appreciated by those of skill in the art, a solid tumor that can be treated using the methods described herein include a breast tumor, a lung tumor, an ovarian tumor, a liver tumor (e.g., hepatocellular carcinoma), a gastric tumor, a brain tumor, a germ cell tumor etc. In one aspect, the solid tumor is a tumor. In another aspect, the solid tumor is a lung tumor (e.g., NSCLC). In a particular aspect, the lung tumor comprises cells that are epidermal growth factor receptor (EGFR)-mutation positive, EGFR-mutation negative or a combination thereof. In another aspect, the solid tumor is a brain tumor. In a particular aspect, the brain tumor is a glioblastoma multiforme brain tumor. In yet another aspect, the solid tumor is not a tumor of stem cell or progenitor cell origin.

Although the methods of treating a solid tumor which expresses SALL4 has been demonstrated using the 12-AA peptide and shRNA, it will be appreciated by those of skill in the art that other compositions that inhibit SALL4 can be used. In the methods described herein, inhibiting SALL4 can include inhibiting the activity of SALL4, the expression of SALL4 or a combination thereof. That is, the composition can partially or completely down regulate (decrease) SALL4 expression and/or activity.

Examples of a (one or more) composition include nucleic acid, proteins, peptides, small molecules and combinations thereof. In one aspect, the composition comprises a nucleic acid that inhibits expression of SALL4. For example, the composition can be a short hairpin ribonucleic acid (shRNA) that specifically targets SALL4, thereby knocking down expression of SALL4. In a particular aspect, the shRNA comprises the nucleic acid sequence of E5: CTATTTAGC-CAAAGGCAAA (SEQ ID NO: 2). In another aspect, the shRNA comprises the nucleic acid sequence of 507: GCCT-TGAAACAAGCCAAGCTA (SEQ ID NO: 3). In yet another aspect, the shRNA comprises the nucleic acid sequence of 7210: GCCGACCTATGTCAAGGTTGAAGTTCCTG (SEQ ID NO: 4). In still another aspect, the shRNA comprises the nucleic acid sequence of 7412: GATGCCTTGAAA-CAAGCCAAGCTACCTCA (SEQ ID NO: 5).

In another aspect, the composition comprises a protein or peptide that inhibits SALL4 activity. In a particular aspect, the peptide is the 12-AA SALL4 peptide shown herein to be a therapeutic peptide for solid tumors that express SALL4 which comprises the amino acid sequence MSRRKQAK-PQHI (SEQ ID NO: 1). In other aspects, the 12-AA peptide can be used as a fusion protein, For example, the 12-AA peptide can be fused to the HIV TAT peptide.

The (one or more) compound used in the methods described herein can be administered to a subject as part of a pharmaceutical composition. Formulations will vary according to the route of administration selected (e.g., solution, emulsion or capsule). A "pharmaceutical composition" comprises a (one or more) chemical compound described herein as the active ingredient and inert ingredient(s), such as pharmaceutically acceptable excipients, that make up the carrier. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

Any suitable route of administration can be used, for example, oral, dietary, topical, transdermal, rectal, parenteral (e.g., intravenous, intraarterial, intramuscular, subcutaneous injection, intradermal injection), inhalation (e.g., intrabronchial, intranasal or oral inhalation, intranasal drops), ocular, pulmonary, nasal, and the like may be employed. Administration can be local or systemic as indicated. The preferred mode of administration can vary depending on the particular agent chosen. Suitable dosage forms include tablets, troches, dispersions, suspensions, solutions, capsules, creams, ointments, aerosols, and the like.

As described herein, the invention is directed to treating a solid tumor. In one aspect, treating a solid tumor refers to ameliorating the symptoms associated with the tumor in an individual. In another aspect, treating a solid tumor refers to decreasing the size of (shrinking) a tumor or arresting the growth of a tumor in an individual. In yet other aspects, treating a solid tumor refers to eradicating a tumor in an individual.

The invention is also directed to use of SALL4 as a prognostic to detect an aggressive cancer and/or detect a poor prognosis in an individual in need thereof. As will be appreciated by those of skill in the art, in the methods of detection SALL4 can be detected in a variety of ways. For example, all or a portion (e.g., biologically active portion) of a SALL 4 nucleic acid, a SALL4 protein or a combination thereof can be detected. SALL4 nucleic acid includes SALL4 DNA, SALL4 RNA, SALL4 mRNA and combinations thereof.

The methods of detection can further comprise obtaining a sample that comprises one or more cancer cells from the individual. In particular aspects, the sample can be contacted with an agent that detects the expression of SALL4, the activity of SALL4 or a combination thereof. In one aspect, the agent specifically binds to SALL4. Examples of such agents include an antibody (e.g., polyclonal, monclonal) that specifically binds to SALL4. The methods can further comprise comparing SALL4 detected in the one or more cancer cells of the individual to a control. An example of a suitable control is a normal (non-cancerous) cell.

The methods of detection can further comprise altering the treatment based on the aggressiveness and/or prognosis of the cancer.

As used herein an "individual" refers to an animal, and in a particular aspect, a mammal. Examples of mammals include primates, a canine, a feline, a rodent, and the like. Specific examples include humans, dogs, cats, horses, cows, sheep, goats, rabbits, guinea pigs, rats and mice.

The term "individual in need thereof" refers to an individual who is in need of treatment or prophylaxis as determined by a researcher, veterinarian, medical doctor or other clinician. In one embodiment, an individual in need thereof is a mammal, such as a human.

The need or desire for administration according to the methods of the present invention is determined via the use of well known risk factors. The effective amount of a (one or more) particular compound is determined, in the final analysis, by the physician in charge of the case, but depends on factors such as the exact tumor to be treated, the severity of the tumor from which the patient suffers, the chosen route of administration, other drugs and treatments which the patient may concomitantly require, and other factors in the physician's judgment.

As used herein, "effective amount" or "therapeutically effective amount" means an amount of the active compound that will elicit the desired biological or medical response in a tissue, system, subject, or human, which includes alleviation of the symptoms, in whole or in part, of the tumor being treated.

The compound can be administered in a single dose (e.g., in a day) or in multiple doses. In addition, the compound can be administered in one or more days (e.g. over several consecutive days or non-consecutive days).

In other aspects, the invention is directed to a composition which inhibits SALL4 for use as a medicament in therapy. For example, the composition can be used in the treatment of a solid tumor. In addition, the composition can be used in the manufacture of a medicament for the treatment of a solid tumor.

EXEMPLIFICATION

Example 1

A Peptide Blocking Transcription Factor SALL4 Interaction with an Epigenetic Complex Induces Cell Death in Acute Myeloid Leukemia Stem cell factor SALL4 plays a key role in leukemia development. The mechanism of SALL4 in leukemogenesis is at least in part mediated by its repression of the Pten (phosphatase and tensin homolog) expression through its interaction with the nucleosome remodeling and deacetylase (NuRD) complex. Demonstrated herein is that a peptide competed with SALL4 in interacting with NuRD complex and reversed its effect on Pten repression. Treating SALL4 expressing leukemic and solid tumor cell lines with this peptide led to cell death which was rescued with a Pten inhibitor. The anti-leukemic effect of this peptide was also confirmed on primary leukemia cells, and this effect was identical to that of down-regulation of SALL4 in these cells using a shRNA approach. In summary, demonstrated herein is a peptide that blocked the interaction between transcription factor SALL4 and its epigenetic complex NuRD in regulating its target gene Pten, and thus, can be used to target SALL4 in cancers such as leukemia and solid tumors (e.g., liver cancer).

Methods:
Cells and Peptides:

Cells used in the experiments were standard ATCC cell lines and the culture conditions were exactly the same as required in the suppliers manual. Peptides were synthesized by Biosynthesis Inc., Lewisville, Tex. using standard solid face peptide synthesis chemistry and purified by the manufacturer typically to 75% purity. Peptides were dissolved in deionized $H_2O$ to concentration of 20 mM and then further diluted in sterile PBS to final concentration of 2 mM. In this concentration peptides were liquoted and stored at −80 C.

Peptide Delivery:

Cells were grown typically in 6 well plates (35 mm dish) to 50-70% confluence. Usually the transfect ion efficiency is somehow cell type specific. 2 mM peptide was diluted 4 times in PBS (2 ul+6 ul) (For FITC peptidedo not dilute the 2 mM stock). For each transfection reaction tube with 100 ul PBS+1 ul diluted peptide was set up. Chariot reagent was diluted 1:10 in ddH2O and for each transfection a 94 ul $H_2O$ tube+6 ul diluted Chariot was prepared (No master mix for more than 4 transfections). The 2 tubes were carefully mixed by pipetting up and down and incubated 30 min. at room temperature. Medium was aspirated from the dish (well) and cells were overlay with the mix. 400 ul serum free medium was added and cells were incubated further for 1 h 37 C (cell incubator). 500 ul complete medium (with 10% serum) was finally added. If cells are not very sensitive to serum starvation (cancer cell lines) 5% serum could be used.

Western Blot:

For the pull down assay FITC-labeled version of the peptides and anti-FITC antibody (Santa Kruz, Calif.) was used. The antibody was immobilized covalently on the surface of Dinabeads (Invitrogen). The magnetic beads were than used in the pull down reaction according to the instruction of the manufacturer with the following minor modifications: 1 mM DTT, 0.1 mM NaF, 1 mM PMSF, 1 mM Na orthovanadate, and 1:100 final dilution of protease inhibitor, (Sigma Co.) was added to the extraction buffer. The NaCl concentration was optimized to 100 mM. Eluted proteins were submitted to Western blotting using standard procedure and the protein bands were visualized using antibodies to HDAC1 and 2 (Sigma)

Microscopy:

Fluorescent and Confocal microscopy was performed on cells treated with FITC labeled peptides with or without of transfection reagent depending on the cell type. Cells were mounted on cover slips using mounting media with DAPI (Invitrogen) and in some cases cytoskeleton dye (Invitrogen).

Cell Viability Assay:

Cell viability assay (MTT) (Invitrogen) was performed according to the manufacturer's instructions. Briefly—10000 cells were seeded in 100 ul medium in 96 well plates. The next day cells were treated as indicated on the figures. At the designated time after the treatment 20 ul of 5 mg/ml MTT solution was added to each well. After 3.5 h incubation at 37 C the medium was removed and the reaction was terminated with a solution of 4 mM HCl, 0.1% Nondet P-40 (NP40) all in isopropanol in dark on orbital shaker for 15 mM. at room temperature. The absorbance was read at 590 nm with a reference filter of 620 nm in Spectromax M3 (ABI) spectrophotometer.

HDAC Assay

Assay was performed with the Fluorescent HDAC Assay Kit (Active Motif) having the following modifications: Following the pull down described in Western Blotting section the proteins bound to the beads were eluted in buffer containing 20 mM HEPES (pH 7.5) 350 mM NaCl, 20% glycerol, 1% Igepal CA-630, 1 mM MgCl2, 5 mM DTT and Protease inhibitors (Sigma). The eluates were used as an HDAC enzyme source in an enzymatic reaction for 2 h at 37 C. The HDAC reactions were performed twice on various samples, and each time in triplicate.

Culture of Primary AML Samples

Primary leukemic patient samples (AML samples) were obtained from Brigham and Women's Hospital under IRB approval. Cells were maintain in a serum free medium (StemSpan-H3000, StemCell Technologies) supplied with StemSpan CC 100 cytokine cocktail (StemCell Technologies) to support 50-60% viability for 3-4 days post-thaw culturing.

Lentivirual Virus Production and Infection

SALL4 shRNA lentiviral constructs was made based the sequence of our previous published 7412 (sequence). Scrambled pGFP were used as control. Lentiviral supernatants were obtained in 293T cells by cotransfection of the shRNA plasmids and packaging plasmids containing VSV-G and pHR8.9. For lentiviral infection of primary AML patient cell, $10^5$ cells were seeded in 12-well plates (200 ul per well) in the above-mentioned culture media. Polybrene (hexadimerthrine bromide; Sigma-Aldrich, St Louis, Mo.) was added at a final concentration of 8 ug/ml). After adding 1 ml of lentiviral particles (titer of each lentiviral shRNA construct adjusted to $1\times10^6$ transducing unit/ml to achieve a multiplicity of infection of 10 transducing units/cells), spinoculation was performed at 1800 rpm for 90 minutes at 37° C. Then cells were brought back to 500 ul in volume using the appropriate fresh culture media and incubated at 37° C., 5% $CO_2$ until use for subsequent applications.

Results

Cellular Characterization of the Peptide

SALL4 interacts with NuRD, and it has been suggested that another SALL gene family member, SALL1, can use its N-terminus 12-AA to recruit the NuRD complex. Since there is high homology shared between SALL1 and SALL4 at the N-terminus, there is a high probability that the N-terminus 12-AA of SALL4 is involved in NuRD recruiting as well. Herein, this 12-AA of SALL4 is referred to as wild type peptide (wt). It has been shown by others that mutating amino acid 2 to 5 at this N-terminus 12-AA can affect its binding property to the NuRD complex. Among these three amino acids, mutation of amino acid 5 (Lys) can abolish the NuRD interacting capacity to the most extent. As described herein, a mutated peptide at this 5 AA (Lys) site was made and referred to as Mut. A scramble peptide (Scr) was designed to eliminate the residual capacity of the Mut peptide, and was used as a second control (FIG. 1A). This Scr has the same 12-AA sequences as that of wt, however, the order of AA in this 12-AA is scrambled. The Scr was designed to maintain the overall net charge of this peptide. A positive net charge is important for peptide to enter into the cells. Although the uptake of peptides into cells has been studied extensively in the last decade, the mechanism(s) are still unclear. The general rule however states that the more positively charged (basic) the molecule is, the better chances are for unaided entry through the cell and nuclear membrane.

In order to evaluate their cellular uptake and localization, the N terminus of these peptides was labeled with fluorescein isothiocyanate (FITC). Despite the net positive charge of these peptides, their uptake by the cells is cell-type specific. Some cell lines such as HL-60 (an AML cell line) allowed the peptide to enter the cells without any modification or carrier, and some cell lines were not penetrable at all. In order to achieve a similar level of peptide delivery in most cell types, a Chariot Transfection Reagent (Active Motif) was used as a peptide carrier, as directed from the manufacturer. The overall success rate of peptide uptake by the cells was between 50 to 80%, and is summarized in Table 1. All cell types used in the study described herein were subjected to individual evaluation of the percentage of the cells in which the peptide was delivered as well as the duration of time during which they sustained the labeled peptide in the cells. After Chariot treatment, confocal microscopy studies confirmed uptake of these peptides throughout the cell, including nuclei (as evidenced by DAPI overlay, FIG. 1B).

The Wt 12-AA can Compete with SALL4 in HDAC Interaction and Pten Repression

Next tested was whether this wt 12-AA could compete with SALL4 in interacting with NuRD. A hepatocellular carcinoma cell line SNU-398 with abundant SALL4 expression was chosen for the following groups of experiences. Whether the wt 12-AA or its control (Mut and Scr) can bind to HDAC1 and HDAC2, the two NuRD components, was first evaluated. Pull-down by an anti-FITC antibody from the nuclear extracts of the SNU-398 cells treated with either FITC-labeled wt, Mut or scramble peptides revealed that HDAC1 and HDAC2 could only be detected in the nuclear complex obtained from the wt, and to a much less degree from Mut peptide, but never from Scr peptide (FIG. 1C). If the peptide interacts with HDAC1 and HDAC2, it is possible that the peptide pull-down can exhibit some HDAC activities. The histone deacetylase activity of the peptide pull-down complex was then measured using a Fluorescent Assay kit (Active Motif) (FIG. 1D). The active enzymatic activity of the HDACs tested by this assay corresponds to the amount of the HDAC proteins in the sample. The wt pull-down had the most HDAC activity, and the Mut pull-down had some residual HDAC activity, however, the Scr pull-down had no HDAC activity when compared to the negative IgG control.

Figure 2:
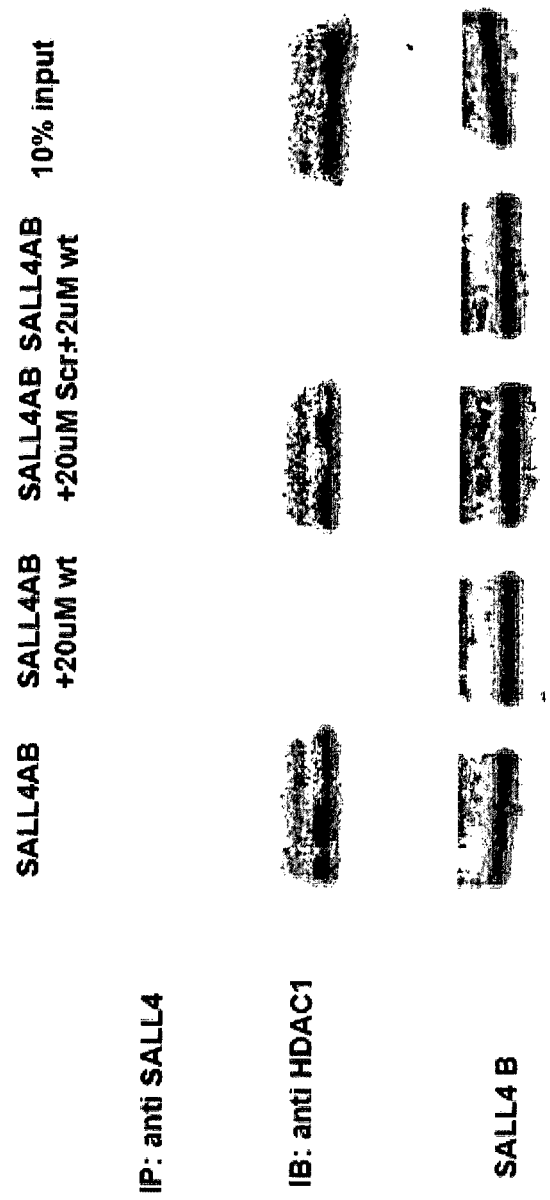
FIG. 2: The wt 12-AA can compete with SALL4 in Pten repression. SALL4 was immunoprecipitated from SNU398 nuclear extracts using an anti SALL4 antibody (Santa Cruz). HDAC1 was recovered from the complex. The interaction was completely abrogated by addition of 2 different concentrations of WT peptide to the nuclear extracts; (lane 2 and 4) addition of scrambled peptide in high concentration does not affect the interaction (lane 3).

Furthermore, whether wt peptide can compete with endogenous SALL4 in interacting with HDAC1 was tested. SNU-398 cells were treated with wt or Scr peptides. Binding of HDAC1 by endogenous SALL4 was completely abrogated when tested by a SALL4 C-terminus antibody after the cells were treated with the wt peptide. This effect was not observed with the SNU-398 cells treated with Scr peptide and HDAC1 was still present in the endogenous SALL4 pull-down (FIG. 2). This result indicates that wt peptide can compete with SALL4 in recruiting HDACs.

Whether this peptide can reverse the repressive effect of SALL4 on its target genes was then tested. Pten was chosen as an example since it is one of genes implicated in SALL4-mediated leukemogenesis. In addition, it was previously reported that SALL4 and NuRD component HDAC2 shared the same binding site at a specific Pten promoter region identified by a ChIP assay. When SALL4 was overexpressed in 293T cells, an enrichment of SALL4 as well as HDAC2 but a decreased H3 acetylation at this binding site were observed, which was correlated with a decreased Pten mRNA expression. It is likely that SALL4 recruits the NuRD complex in repressing Pten expression. If this model of the role of wt peptide is correct, then it could compete with endogenous SALL4 in recruiting NuRD to the binding site on Pten promoter. Therefore, wt peptide treatment of SALL4 expressing cells would lead to a decreased HDCA2 binding or an increased H3 acetylation at this same binding site, and would lead to an increased Pten expression at the mRNA level. SNU-398 cells were treated with Scr or wt peptide and then evaluated for the Pten mRNA expression, as well as the status of HDAC2 binding and H3 acetylation at the Pten promoter region. Wt treated SNU-398 cells had increased Pten mRNA expression level, as well as increased H3 acetylation at the Pten promoter region.

Anti-Proliferative Effect of 12-AA Peptide on SALL4/Pten Expressing Cancer Cells Multiple cell lines with or without SALL4 expression were chosen to test the biological effect(s) of this wt peptide. Wt or its control (Scr or Mut) peptide was delivered into tumor cells at various concentrations, and their effects on cells were evaluated at 48 or 72 hours post treatment by a MTT assay (Manufacture name). Most SALL4-expressing leukemic or solid tumor cell lines such as HL-60, MCF (breast cancer line) and SNU-398 (FIGS. 3A-3F) exhibited a decreased cell viability when treated with wt peptide but remained unaffected with treatment of Scr or Mut peptide. Since, as proposed herein, wt peptide can compete with SALL4 and release it from recruiting HDAC complex NuRD, the wt peptide would likely work as a HDAC inhibitor. Therefore, as a positive control, TSA, a broad HDAC inhibitor, was used in the same group of experiments along with the wt and Scr peptide. Not surprisingly, the TSA treatment resulted in a similar anti-proliferative or killing effect on these cancer cells. The effect of wt peptide seemed to be specific to SALL4 since it had no effects on SNU387, another hepatocelluar carcinoma cell line, which had no detectable endogenous SALL4 protein expression.

Figures 3A, 3B:
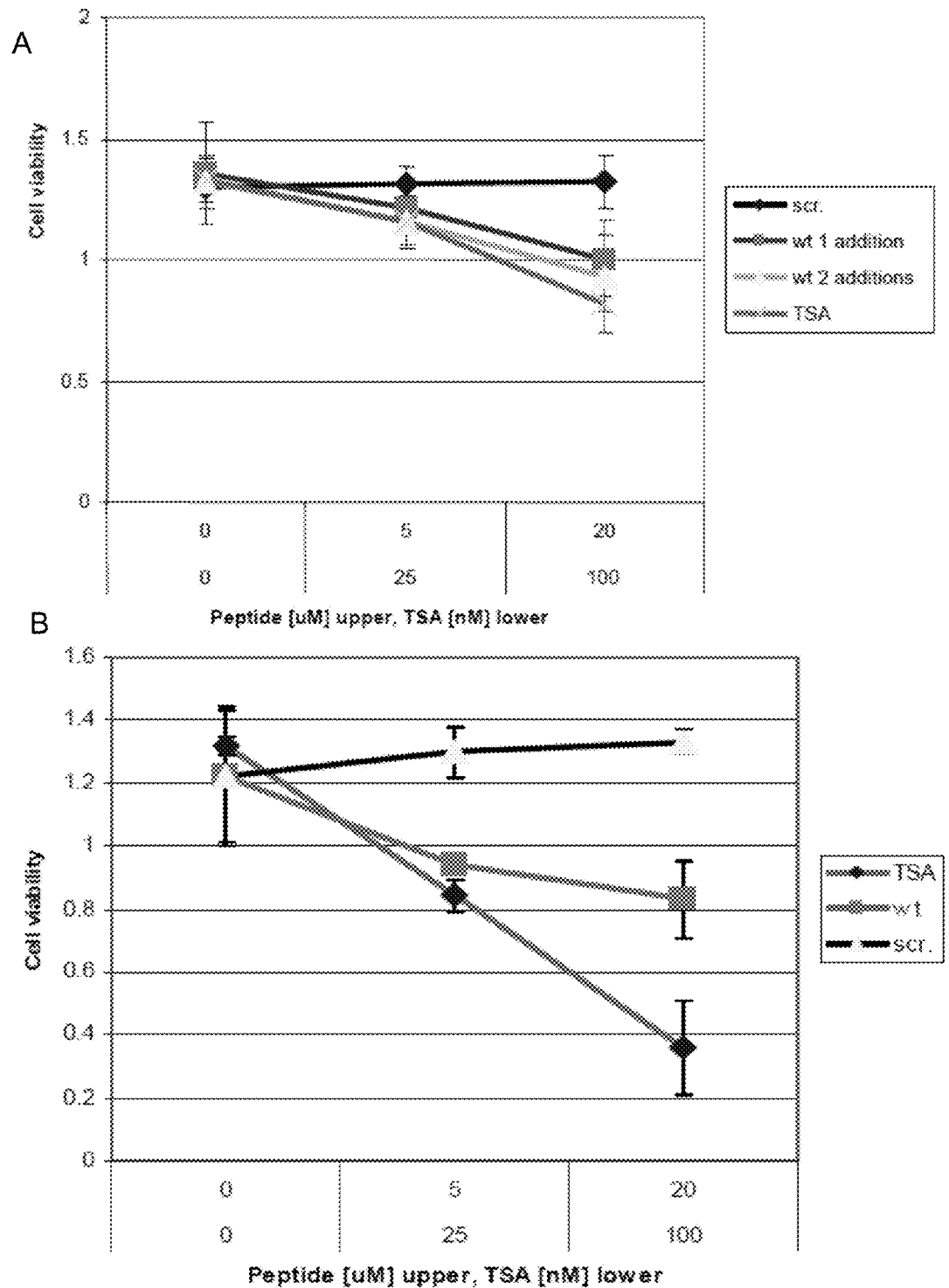
FIGS. 3A-3F: Peptide reduces proliferation of tumor cell lines in PTEN and SALL4 dependent manner, assessed with MTT assay. (3A) In HL 60 cell acute myeloid leukemia cells the peptides easily penetrated the cell membrane and the wild type peptide reduces the number of the living cells, whereas the mutant peptide has no effect on the cell viability. Addition of a new dose of peptide 24 h after the first addition potentiates the effect. (3B) MCF 7 breast carcinoma cell line which is also penetrable by peptides displayed the same effect with the wild type peptide on the cell viability. (3C) HuH-7 hepatocelluar carcinoma cells are high expressers of SALL4 and the wt peptide reduced the cell viability. In this experiment scrambled peptide was introduced as an additional control of the specificity of the peptide action (change to other cell line). (3D) SNU-398 cell line with high expression of SALL4, and wt peptide reduced the amount of living cells in dose dependent manner. (3E) For SNU-387 cells with low SALL4 levels, the wt peptide did not affect the cell viability. (3F) For AN3CA, a uterus cancer cell line, with high SALL4 expression but negligible amount of PTEN, the peptides have no effect on the viability.
Figure 3C:
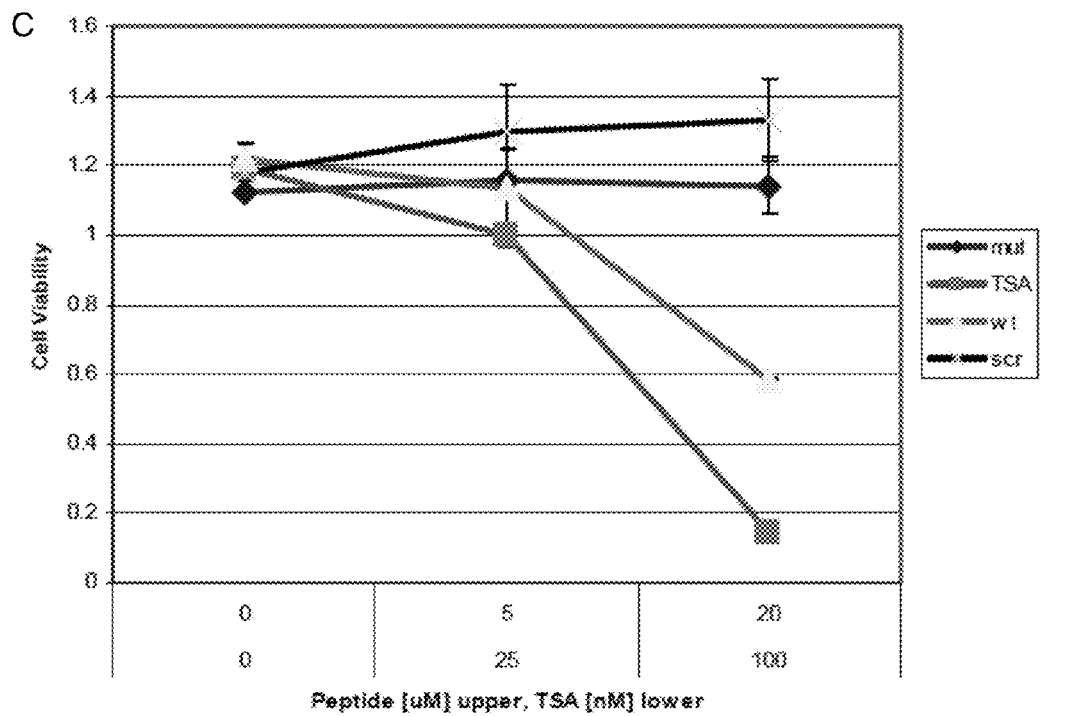
Figure 3D:
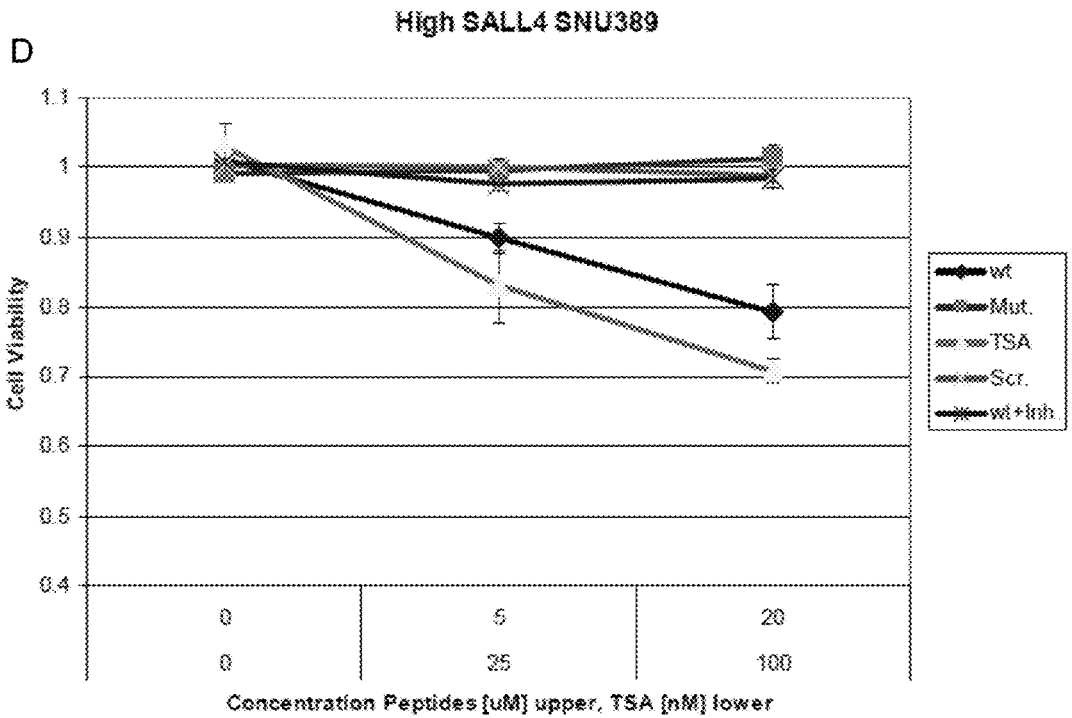
Figure 3E:
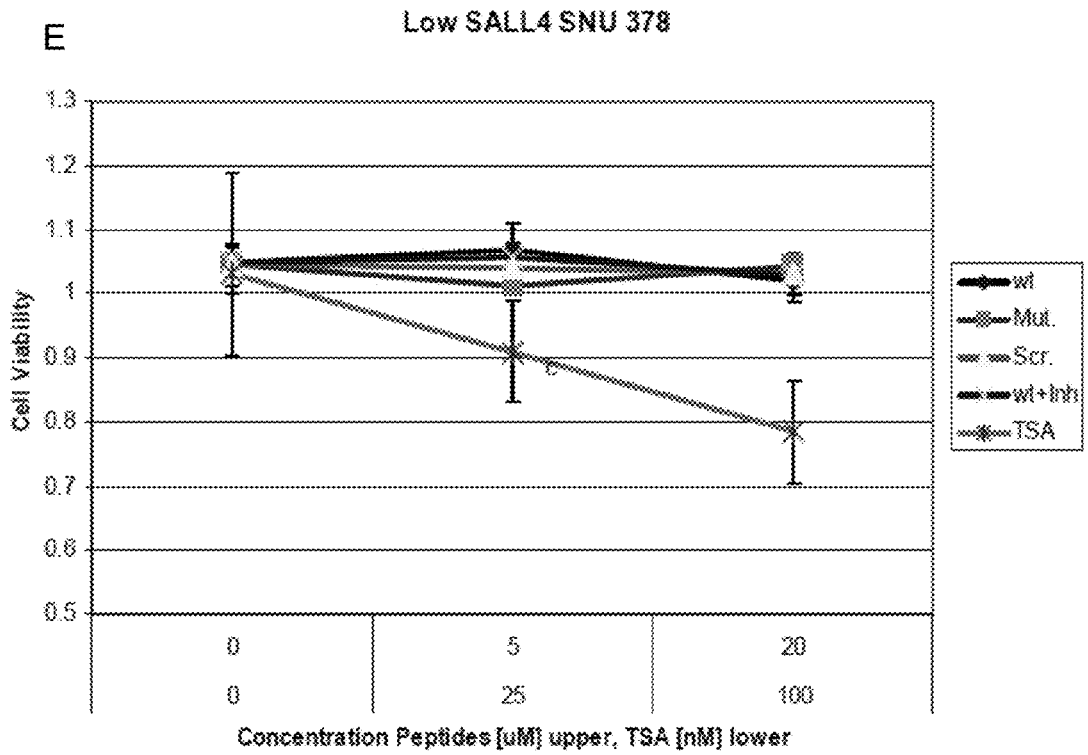
Figure 3F:
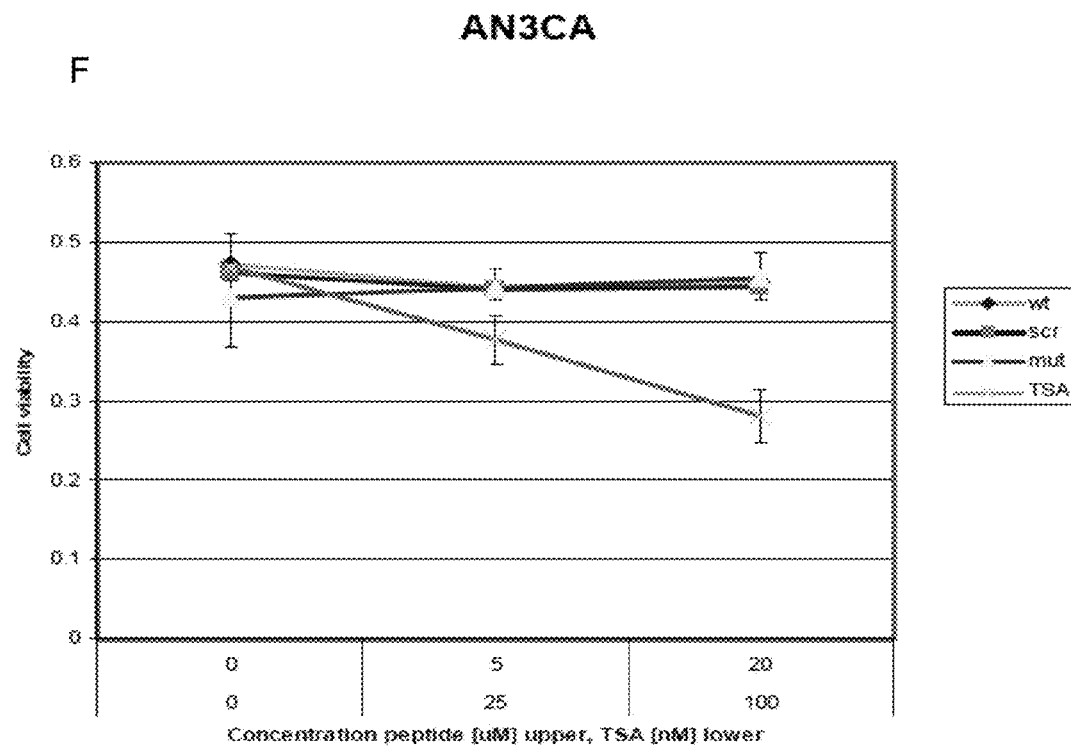

It was surprising to see that the wt peptide had no effect on a SALL4-expressing uterus cancer cell line, AN3CA (FIG. 3F). This prompted a check on whether Pten, a gene being repressed by SALL4 through its interaction with NuRD, was present in this cell line. According to the model herein, to ensure the function of wt peptide, a SALL4 expressing cell system with intact SALL4 downstream target genes was needed. It is possible that even though the wt peptide can still compete with endogenous SALL4 in interacting with HDAC complex, in tumor cells with Pten deletion an anti-proliferative effect may not be seen. The expression of Pten was evaluated in the AN3CA cells along with SNU-398 and SNU387. While Pten protein was present in both SNU-398 and SNU387, it was absent in AN3CA cells.

To further test whether the effect of wt peptide on tumor cells is related to both SALL4 and Pten, a Pten inhibitor (SF-1670) was used for rescue experiments. While the SALL4-expressing SNU-398 cells treated with wt peptide alone showed decreased cell viability, co-treatment with a Pten inhibitor restored the cell viability to a baseline level, same as that post Mut or Scr peptide treatment. As a control for the specificity of SALL4, SNU387 cells, non-SALL4 expressing cells, were also treated with this Pten inhibitor. While wt, Mut, and Scr peptide treatment showed no change in cell viability, co-treatment of this Pten inhibitor with wt peptide in this cell line showed no effect as well.

Figures 4A, 4B, 4C:
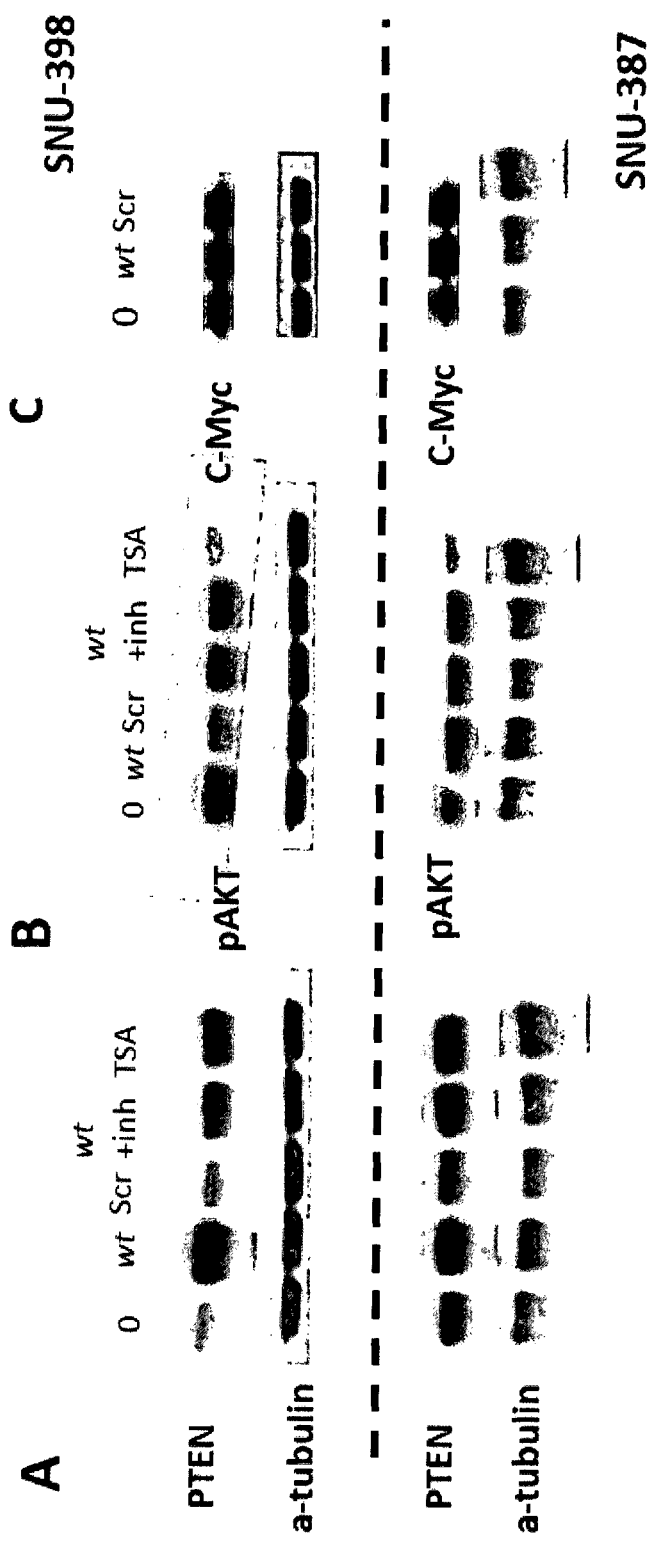
FIGS. 4A-4C: Wt peptide can affect the Pten/Akt pathway. (4A) Wt peptide can effect the PTEN expression level in cells with high level of SALL4 (panel A SNU 398), but not in the cells with low expression levels of SALL4 (panel A, SNU 378). (4B) The pAKT levels in the same cell types were modulated in a corresponding manner. (4C) The expression of c-Myc was not affected by the peptide treatments.

In summary, the anti-proliferative effect of this wt peptide was only observed in SALL4 and Pten expressing tumor cells. Pten and its Downstream AKT Pathway were Affected by this Peptide Treatment Since the wt peptide showed SALL4/Pten specificity, whether wt peptide treatment could affect the expression of Pten and its downstream V-akt murine thymoma viral oncogene homolog 1 (AKT) pathway was next investiagated. It was noticed that Pten was expressed at a low level in untreated SNU-398 cells, and its expression was noticeably higher when the cells were treated with wt peptide, an effect not observed in Scr peptide treated cells. The induction of Pten expression was not affected when wt peptide was administrated together with a Pten inhibitor. AKT, a molecule with levels of phosphorylation controlled by the expression of Pten was affected by the wt peptide addition accordingly. Levels of phosphorylated AKT (pAKT) on Ser 473 residue were significantly reduced by wt or TSA treatment (FIGS. 4A&B). The effect of wt peptide on pAKT was abrogated by the Pten inhibitor. No effect of Scr peptide was observed in SNU-398 cells. In contrast, the protein expression level of endogenous Pten was very high in the none-SALL4 expressing SNU387 cells. Treatment of these cells with wt peptide did not seem to change the expression of Pten significantly, and more importantly wt peptide had little or no effect on the pAKT in this cell line (FIGS. 4A&4B).

Also tested was whether wt peptide could affect genes that were known to be activated by SALL4, such as c-Myc. SNU-398 cells treated with wt or Scr peptide were evaluated for c-Myc protein expression. No change was observed among SNU-398 cells that were not treated or treated with either wt, Scr or TSA. When combined, the observation on the biological effects of the peptide treatment and the expression of Pten/Akt pathway in these cells, it was noticed that the wt peptide and its role in cell death promotion was correlated to its effect on the expression levels of Pten/Akt.

Figure 5:
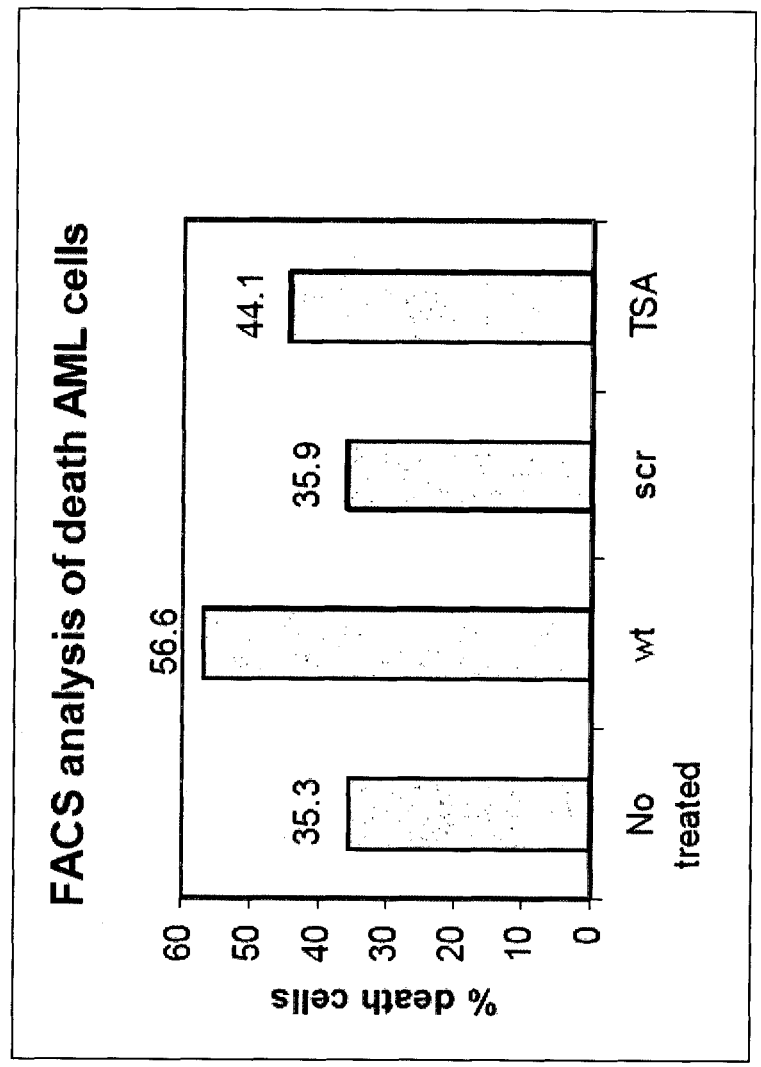
FIG. 5: Treatment of SALL4 peptide in primary AML led to cell death. The wild type peptide killed 56% of the leukemic cells, whereas the scr peptide had the same value as the untreated (no treated) cells.

Treatment of SALL4 Peptide in Primary AML LED to Cell Death, Similar to that of Down-Regulation of SALL4 in these Cells by shRNA Whether a therapeutic effect could be achieved by using this wt peptide on primary AML samples was then tested. Ninety-six hours after the first treatment of peptides (wt, Mut, or Scr) or TSA in the primary AML cells collected from a patient, the remaining alive cells were measured by FACS analysis using Annexin V/PI staining. During the treatment the wt and control peptides (Mut or Scr) were re-introduced twice at the 24-hour and the 48-hour time points along with the Chariot (Active Motif) transfection agent. A significant effect of the wt peptide on the cell viability of primary AML cells was observed. While there was a 56% cell death rate with wt peptide treatment at the end of the fourth day, the cell death rate was only 35% in the non-treated or treated with the control peptide, and the cell death rate was 44% in cells treated with TSA (FIG. 5).

Figures 6A, 6B:
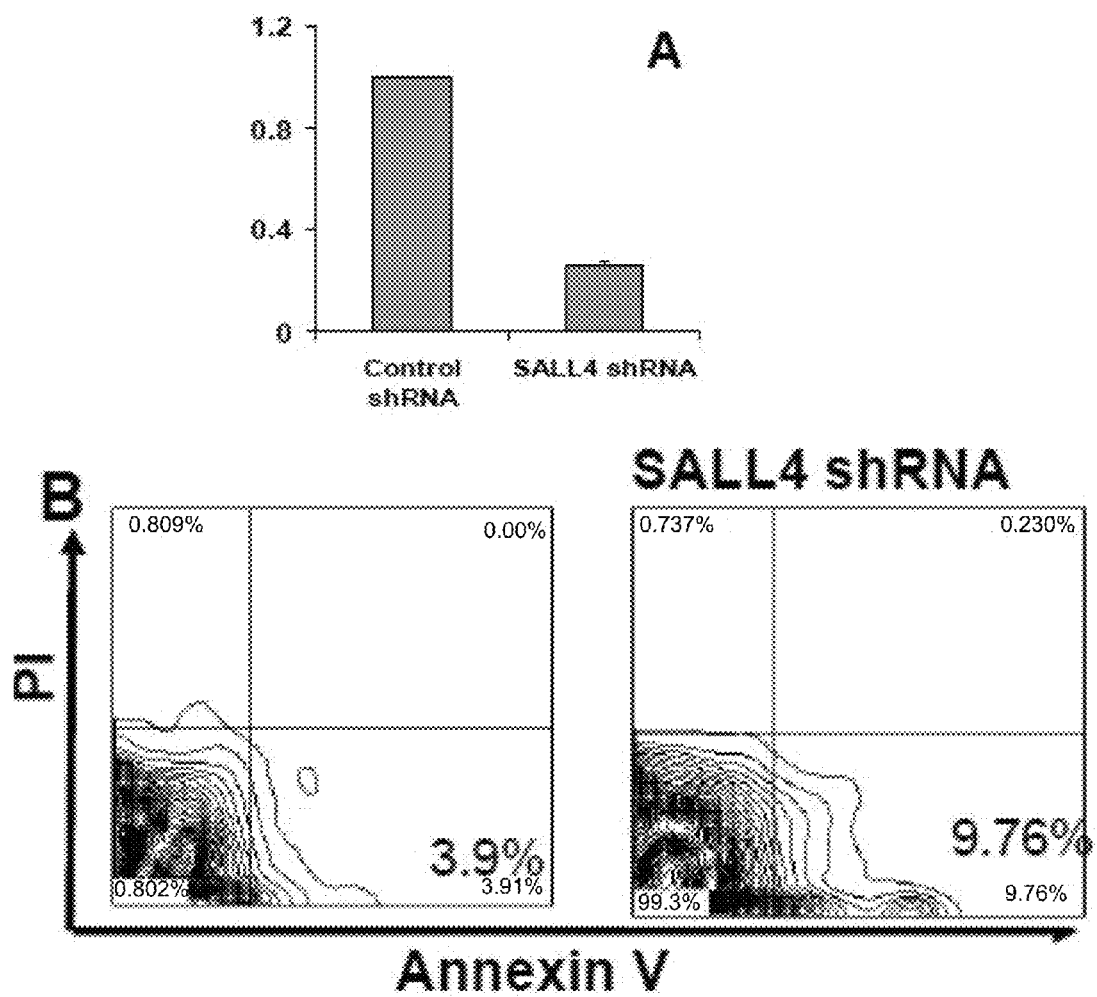
FIG. 6: Down-regulation of SALL4 in primary AML led to cell death. (6A) Down-regulation of SALL4 in primary AML cells. The ability of shRNA constructs 7412 to knock down SALL4 mRNA in AML cells were confirmed by qRT-PCR with normalization to GAPDH. The expression of SALL4 RNA in AML cells that were infected with SALL4 shRNA (7412)-expressing retroviruses was reduced to 35% of those infected with scrambled pRS control vectors, a shRNA pRS against non-effective GFP sequence from OriGene Technologies, Inc., Rockville Md. (N=3, Error Bars: +/−SD). (6B) Increased apoptosis and cell death were observed via flow cytometry in AML cells upon SALL4 knock down by Annexin V/PI staining. Control scrambled shRNA-infected cells and SALL4 shRNA-infected cells were analyzed 24 to 48 h post transduction. Data were derived from four independent experiments. (6C-6F) Leukemia development in xenotransplant recipient mice. AML is defined as blast count more than 20% in peripheral blood and/or bone marrow with multiple organ involvements observed in recipient mice. Blasts were present in liver (6C, ×200), spleen (6D, ×200), and bone marrow (6E, ×200), and were human CD45 positive (6F). (G) Four of six of SALL4 knock down recipients did not develop leukemia and had less than 0.5% human CD45 stain detected in their peripheral blood or bone marrow and were considered negative for engraftment since the background stain of human CD45 in the untreated mice was about 0.5%. (6H) Xenotransplantation showed increased survival of mice receiving SALL4-reduced leukemic cells. While the median survival of recipient mice with control retrovirus-infected primary human AML cells (N=7) was 33 days, the median survival of recipient mice with SALL4 shRNA retrovirus-infected primary human AML cells (N=6) was 109 days. The p-value of Log rank was 0.03 and the p-value of Gehan-Breslow-Wilcoxon was 0.01.
Figures 6C, 6D, 6E, 6F, 6G, 6H:
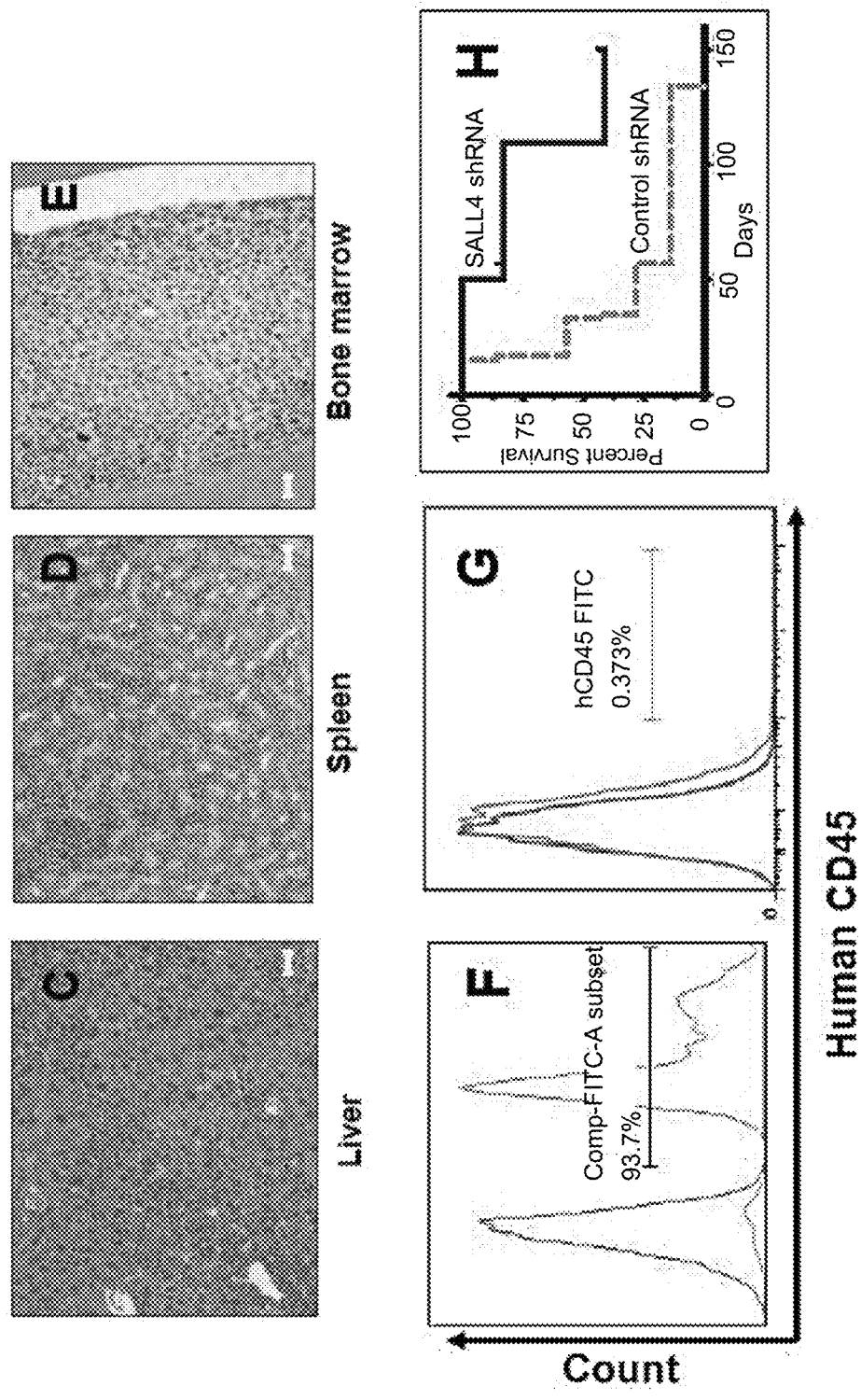

The phenotype of wt peptide treatment was then compared with that of downregulation of SALL4 in primary AML cells. SALL4-specific shRNA (7210 and 7412, FIG. 6A) validated by previous studies were used for these experiments. FACS analysis with Annexin V/PI staining confirmed that there was a 2-fold increase in cell apoptosis and cell death in vitro in primary AML cells when SALL4 expression was reduced (FIG. 6B). In addition, there was an increased survival of leukemic recipient mice in vivo upon knocking down of SALL4 expression in these primary AML samples (FIG. 6C). $1.5 \times 10^6$ SALL4 shRNA or control retrovirus-treated primary human AML cells were transplanted into sublethally irradiated (1.0 Gy) NOD/SCID/IL2rγ-null mice by tail vein injection. Fatal AML with onset ranging from one to three months developed in all control recipient (7 out of 7) and some SALL4 shRNA recipient (2 out of 6) mice after transplantation. The transplanted leukemia disease was characterized by immature blasts with human CD45 expression in peripheral blood, bone marrow, and tissues such as liver and spleen (FIGS. 6C-6F). Interestingly, four out of six SALL4 shRNA recipient mice were still healthy four months after the transplantation, and had no detection of human CD45 cells (FIG. 6G). While the median survival of control recipient mice (N=7) was 33 days, the median survival of SALL4 shRNA recipient mice (N=6) was 109 days. Both the Log rank (also called Mantel-Cox, P=0.03 (FIG. 4H) and Gehan-Breslow-Wilcoxon (P=0.01)) tests were used for survival analysis and were statistically significant. Since the leukemic initiation ability or leukemic stem cell property of human primary leukemic cells was tested by xenotransplantation, the prolonged survival of SALL4 shRNA-treated recipient mice as well as the lack of engraftment of human leukemic cells in these mice indicated that SALL4 is essential for the survival of leukemic stem cells or leukemia initiation cells.

TABLE 1

| Cell Line | Wt | Wt (Chariot) | Mut |
|---|---|---|---|
| MCF7 | ~50% | 70% | 70% (Ch) |
| AML3 | ~5% | 50% | ~10% |
| NP4 | >1% | >5% | NA |
| HL60 | ~50% | 70% | ~50% |
| KG1a | >10% | 60% | >15% |
| HeLa | 0 | 80% | NA |
| SNU387 | 0 | 40% | 60% (Ch) |
| SNU-398 | 0 | 40% | 60% (Ch) |
| HuH-7 | 0 | 60% | 60% (ch) |
| CD34+ | 0 | 50% | 50% (Ch) |
| AML | 0 | 50% | 50% (Ch) |

Discussion

Histone deacetylase (HDAC) inhibitors have been used in various cancer treatments with variable effects. The best therapeutic results to date are observed in hematological malignancies. Their anti-neoplastic effects and functional mechanisms are likely tissue specific and context dependent depending on transcription factors. Transcription factors play a key role in normal hematopoiesis and leukemogenesis. Most of the existing HDAC inhibitors are targeting the enzymatic activities of histone deacetylases.

Figures 7A, 7B:
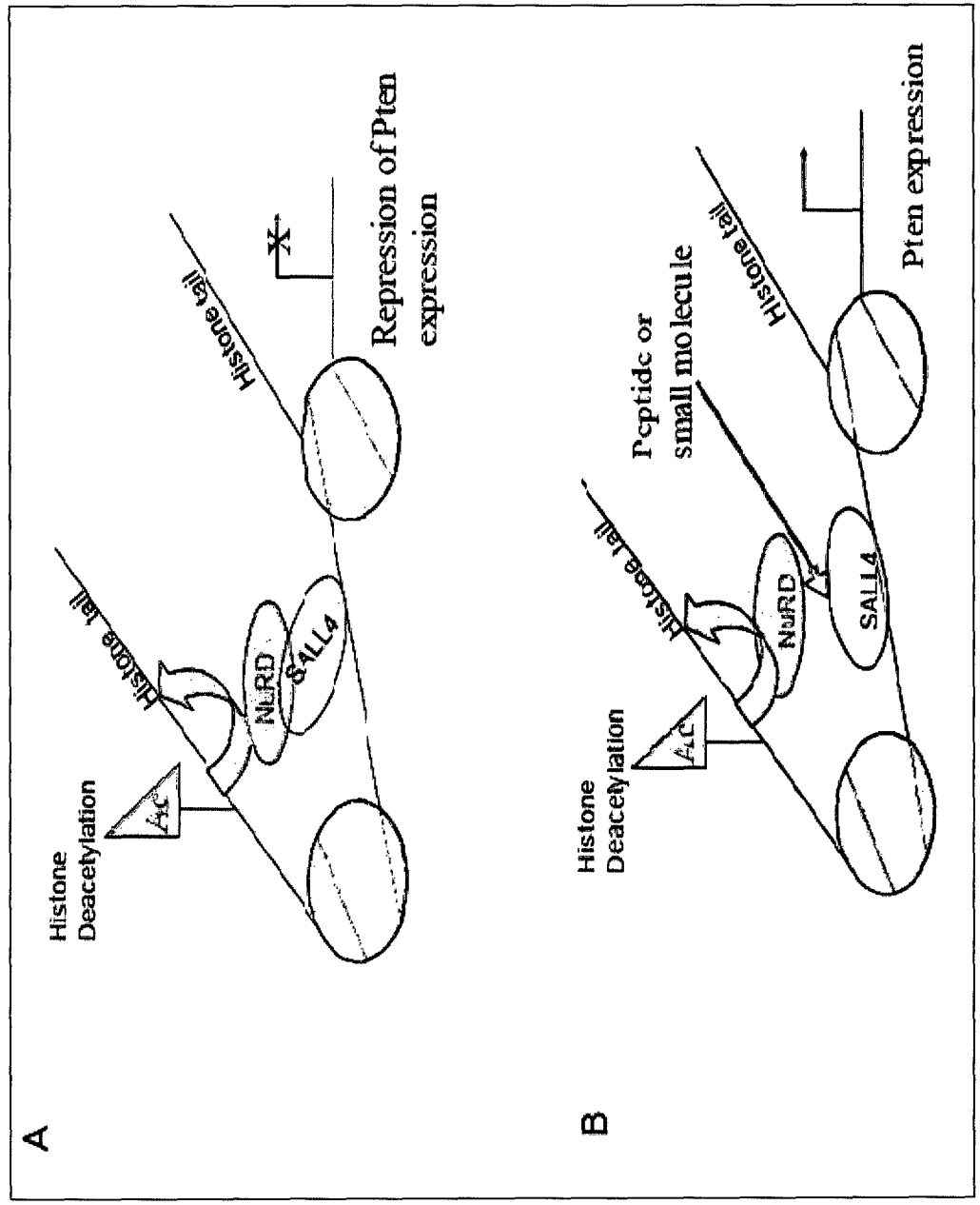
FIG. 7: Working model on HDAC inhibitors that target the interaction between HDAC complex and its transcription factor recruiter SALL4. (A) SALL4 represses its downstream targets by recruiting NuRD, a HDAC complex, to the specific promoter regions, such as Pten promoter region, that results in histone deacetylation and transcription repression. (B) Peptide or small molecules can compete with SALL4 in interacting with NuRD, and therefore, can release SALL4 from recruiting NuRD. The repression of Pten by SALL4 is lost, and the Pten expression is activated.

The important role of SALL4 in normal HSC and leukemic stem or initiating cells (LICs) is supported by its interactions with several key players in the self renewal of HSCs and LICs, particularly by repression of Pten expression. The mechanism of SALL4 repressing Pten is at least in part through its interaction with NuRD, a HDAC complex. In this study, whether blocking the SALL4 interaction with its epigenetic complex NuRD could have a biological effect in cancer cells, such as AML and hepatocarcinoma cells, was tested. It washypothesized that HDAC inhibitors (either by targeting the enzymatic activities of HDAC and/or disrupting the interaction between the HDAC and its transcription factor recruiter) can impair SALL4's repressor function, and negatively affect the self-renewal and survival of leukemic cells by re-activating the expression of Pten (FIG. 7). The prediction was proved to be true. The SALL4 NuRD recruiting region contains a stretch of 12 critical amino acids, and this 12-AA peptide has demonstrated growth inhibition of leukemic cells similar to that of classic HDAC inhibitors such as trichostatin A (TSA) as well as that of downregulation of SALL4 gene by shRNA. This supported the proposal herein that the HDAC inhibitors have therapeutic effects on hematological malignancies through the specific effect on transcription factor SALL4.

In summary, the study described herein demonstrated that a peptide that can be used to target the interaction between a transcription factor SALL4 and its epigenetic complex NuRD in regulating its target gene, such as Pten, can be used to target SALL4 in cancer, e.g., leukemia, liver cancer. Furthermore, this peptide can also be used as a cell-type specific, a SALL4 gene-specific HDAC inhibitor or a SALL4/Pten inhibitor in cancer treatment.

Example 2

Targeting Transcription Facto r SALL4 in Acute Myeloid Leukemia by Interrupting its Interaction with an Epigenetic Complex (Example 2 is the Same as Example 1, However, the Results of Example 1 were Reviewed and Reworked and are Described Below)

An exciting recent approach to target transcription factors in cancer is to block formation of oncogenic complexes. Described herein is the testing of whether interfering with the interaction of the transcription factor SALL4, which is critical for leukemic cell survival, and its epigenetic partner complex represents a novel therapeutic approach. The mechanism of SALL4 in promoting leukemogenesis is at least in part mediated by its repression of the tumor suppressor PTEN through its interaction with a histone deacetylases (HDAC) complex. Demonstrated herein is that a peptide can compete with SALL4 in interacting with the HDAC complex and reverse its effect on PTEN repression. Treating SALL4-expressing malignant cells with this peptide led to cell death that can be rescued by a PTEN inhibitor. The anti-leukemic effect of this peptide was confirmed on primary human leukemia cells in culture and in vivo, and was identical to that of down-regulation of SALL4 in these cells using an RNAi approach. In summary, the study herein demonstrates a novel peptide that blocks the specific interaction between SALL4 and its epigenetic HDAC complex in regulating its target gene PTEN. Furthermore, targeting SALL4 by this approach provides an innovative approach in treating leukemia.

In this study, it is demonstrated that the HDAC recruiting region of SALL4 contains 12 amino acids (AA) and that this 12-AA peptide promoted growth inhibition of SALL4-expressing leukemic cells, similar to that observed following treatment with a classic HDAC inhibitor, trichostatin A (TSA), as well as following down-regulation of SALL4 by shRNA. The anti-tumor effect of this peptide was rescued by a PTEN inhibitor. The studies herein demonstrated a novel therapeutic strategy for inhibition of growth of tumor cells dependent on SALL4 pathways.

Materials and Methods

Peptide Synthesis, Binding Affinity and Delivery Assays

Peptides were synthesized by Biosynthesis Inc., Lewisville, Tex., using standard solid face peptide synthesis chemistry and purified by the manufacturer typically to 95% purity. Peptides were dissolved in deionized $H_2O$ to concentration of 20 mM, diluted in sterile PBS to final concentration of 2 mM and aliquoted and stored at −80° C. For experiments in which peptide was added to nuclear extracts, 20 mM of peptide was added directly to 100 µl of nuclear extract from 1×106 cells to final concentration of 0.5, 1.0, 1.5 or 2.0 mM, respectively. For delivery of peptide into adherent cell lines, cells were grown in 6-well plates (35 mm dish) to 50% confluence and various concentrations of peptides were added. For each treatment with Pep-1 peptide carrier (Chariot reagent, Catalogue #30025, Active Motif), 10 µl of 2 mM diluted peptide was mixed with 10 µl of 10-fold diluted Pep-1 for 30 min on ice. Medium was removed, followed by addition of peptides and Pep-1 mixture to the cells along with 400 µl serum-free medium. The cells were incubated further for 1 h at 37° C. after which 500 µl complete medium (with 10% serum) was added. Alternatively, for nonadherent cells, such as HL-60, 20 mM peptide diluted in 10 µl PBS was mixed with 10 µl of diluted Pep-1, incubated 30 min on ice and added directly to the cell suspension (1 ml of 3×105 cells). Primary AML cells were treated the same way as HL-60, by scaling up the peptide and carrier reagent accordingly.

Culture of Primary AML Samples

Three frozen primary AML patient samples were used for this study, and were obtained from Brigham and Women's Hospital at Boston, Mass., USA, under approved IRB protocol (No. 2011-P-000096/1). Culture conditions were adapted from a published protocol 28-31. In brief, the frozen AML samples were incubated in RPMI1640 medium without serum for 1 to 3 h after thawing and DNA fragments from dead cells were removed by washing. After three washes with the medium, 1×106 cells per well of 12-well plate were maintained in 1 ml of serum-free medium (StemSpan-H3000, Catalogue #09800, StemCell Technologies) supplied with StemSpan CC 100 cytokine cocktail (Catalogue #02690, StemCell Technologies) that supports 40-50% viability at 72 hours postthaw culturing based on our experience. These cells were then used for the down-regulation of SALL4 (see details below) and peptide treatment experiments.

Lentiviral Production

SALL4 shRNA construct (Puri-7412) and scrambled shRNA control vectors have been verified in Yand et al., *PLoS One*, 5:e10766 (2010); Yang et al., *Blood*, 112:805-813 (2008); Yang et al., *PNAS, USA*, 104:10494-10499 (2007). The SALL4 shRNA sequence is as follows 5'-GCCT-TGAAACAAGCCAAGCTA-3' (SEQ ID NO: 3); Lentiviral supernatants were obtained in 293T cell cultures by cotransfection of the shRNA plasmids with packaging plasmids containing VSV-G and pHR8.9. For lentiviral infection of primary human AML patient samples, 1×105 cells were seeded in 12-well plates (200 µl per well) with the appropriate culture media. Polybrene (hexadimethrine bromide; Sigma-Aldrich, St Louis, Mo.) was added at a final concentration of 8 µg/ml. After adding 1 ml of lentiviral particles (titer of each lentiviral particles was pre-adjusted to 1×106 transducing unit/ml to achieve a multiplicity of infection of 10), spinoculation was performed at 1800 rpm for 90 minutes at 37° C. Then cells were brought back to 500 µl in volume using the appropriate fresh culture media and incubated at 37° C., 5% $CO_2$ until use for subsequent experiments.

Xenotransplantation

NSG (NOD.Cg-Prkdcscid Il2rgtm 1Wjl/SzJ, The Jackson Laboratory, ME, USA) mice were bred and maintained in the Children's Hospital Boston animal facility. All animal work has been approved by and done according to the guidelines of the IACUC under protocol 10-10-1832. Human primary AML cells exposed to various peptides or carrier only (1.0× 106 cells per mouse) or transduced with SALL4-shRNA or control lentivirus (1.5×106 cell per mouse) were transplanted into 10- to 12-week old mice received 135 cGy sublethal irradiation 2-4 h before the injection via the dorsal tail vein. Mice were euthanized when they became ill or at 78 days post-transplantation. BM was removed from the two femurs by flushing with RPMI1640 medium, spleen cells were abstained by mincing and filtering through a cell strainer and peripheral blood was collected from the heart. These samples were subsequently subjected to flow cytometry analysis utilizing FITC-conjugated anti-human CD45 antibody and APC-conjugated anti-mouse CD45 antibody (eBiosciences, CA, USA). The percentage of human CD45+ cells was calculated as follows: % human CD45+ cells=No. human CD45+ cells/(No. human CD45+ cells+No. mouse CD45+ cells)×100. In addition, both Mantel-Cox and Gehan-Breslow-Wilcoxon tests were used for survival analyses. Additional information on methods can be found in supplemental material.

Figures 8A, 8B, 8C, 8D:
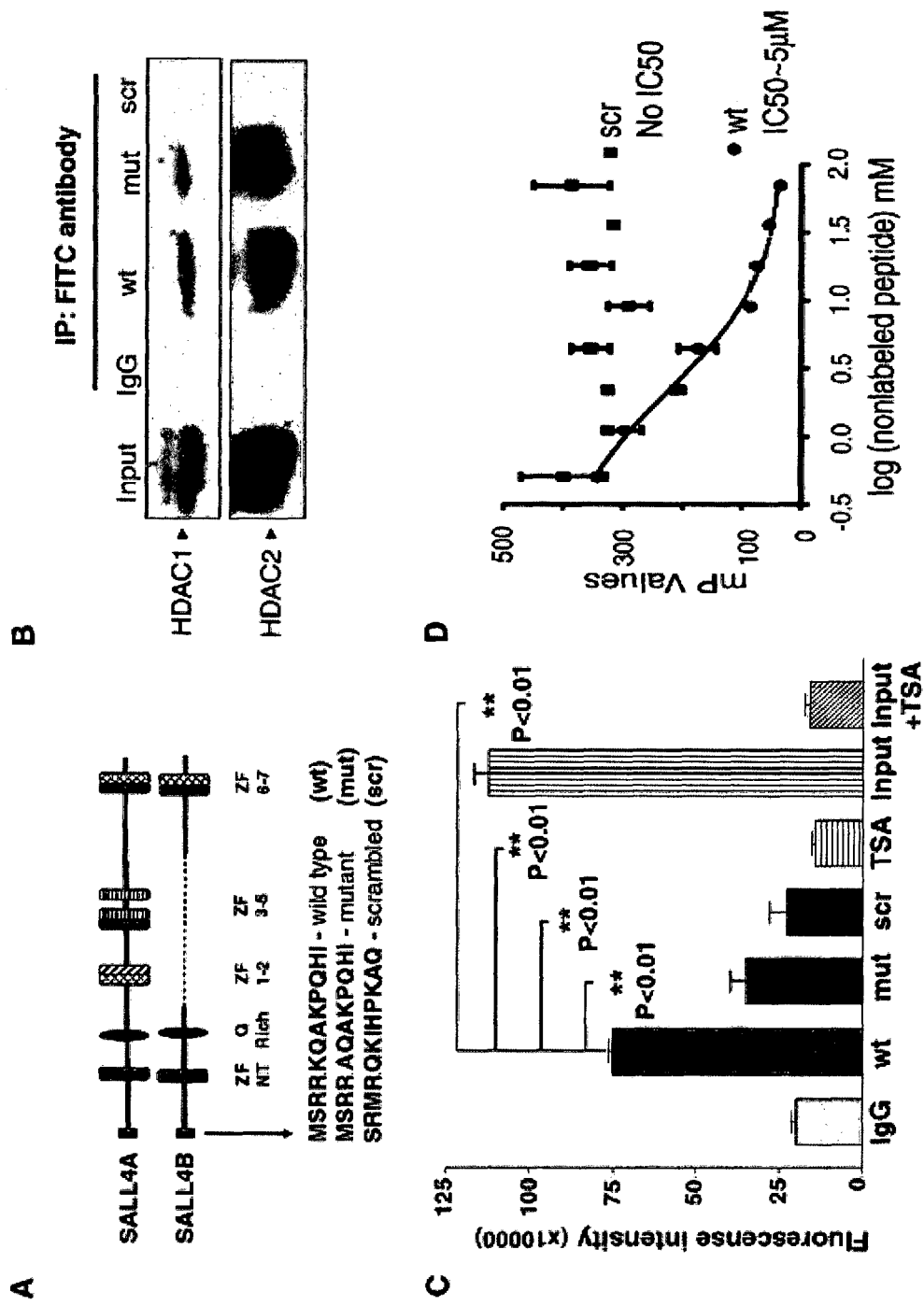
FIGS. 8A-8D: A peptide derived from the amino terminus of SALL4 can interact with the NuRD complex components, HDAC1/HDAC2. (8A) The top diagram compares the structures of the two SALL4 isoforms, SALL4A and SALL4B, demonstrating the conserved amino terminus. Below are the amino acid sequences of the peptides used in this study. In the mutant peptide (mut), Lys 5 is replaced with an alanine residue. (8B) The wild type peptide associates with HDAC1 and HDAC2. Nuclear extracts from 1×106 SNU-398 cells were incubated with 20 µM FITC-labeled wild type (wt), mutant (mut), or scrambled (scr) peptides and then immunoprecipitated with anti-FITC or non-immune IgG followed by western blotting with anti-HDAC1 (upper panel) or anti-HDAC2 (lower panel) antibodies. In the first lane marked "Input", 10% of the extracts were subjected to western blot analysis without immunoprecipitation. (8C) The wild type peptide associates with HDAC activity. Nuclear extracts from 1×106 SNU-398 cells were incubated with 20 µM FITC-labeled wild type, mutant, or scrambled peptides. Extracts were subsequently immunoprecipitated with anti-FITC antibody and the complexes pulled down were subjected to an HDAC activity assay as described in the methods. TSA was added at a concentration of 100 nM. Input is the sample in which 10% of the extract was assayed for HDAC activity without the immunoprecipitation step. (8D) The wild type peptide binds with high affinity to protein complexes in SNU-398 nuclear extracts. Competitive binding of nonlabeled wild type or scrambled peptides was measured by fluorescent polarization. 1 µM of FITC-labeled wild type peptide was added to nuclear extracts from 2×107 SNU-398 cells along with increasing concentrations of non-labeled scrambled or wild type peptide. The fluorescent polarization (y axis) is decreased if the FITC-labeled peptide is displaced from a larger complex.

Results:

A Peptide Derived from the Amino Terminal 12 Amino Acids Sequence of SALL4 Interacts with the HDAC Complex SALL4 interacts with NuRD ( ) Lu, et al., *PLoS One*, 4:e5577 (2009), and others have suggested that another SALL gene family member, SALL1, can recruit the NuRD complex through interaction with a conserved 12 amino acid sequence at its N-terminus (Kiefer, et al., *J Biol Chem*, 277: 14869-14876 (2002); Lauberth et al., *J Biol Chem*, 281: 23922-23931 (2006); Lauberth et al., *J Biol Chem*, 282: 34858-34868 (2007))). As the N-termini of SALL1 and SALL4 are almost identical, it is hypothesized herein that the N-terminus of SALL4 is involved in the recruitment of HDAC/NuRD (the 12 amino acid peptide at the N terminus of SALL4 is referred to herein as wild type (wt)). It has been shown by others that mutating amino acids 3 to 5 of this 12-AA wt peptide abrogates its binding to the NuRD complex. Among these three amino acids, mutation of residue 5 (Lys) alone abolishes NuRD/HDAC interaction to the greatest extent (Lauberth et al., *J Biol Chem*, 281:23922-23931 (2006); Hong et al., *Embo J*, 24:2367-2378 (2005); Lejon et al., *J Biol Chem*, 286:1196-1203). Therefore, residue 5 was mutated by converting Lys to Ala in the context of the 12 wt amino acid peptide, to act as a negative control (mut). A second negative control, scrambled peptide (scr), was designed with the same 12 amino acids as that of the wt peptide, but in a scrambled sequence. Designing the scrambled peptide in this manner can maintain the overall net charge of this peptide, which affects cellular uptake of the peptide (FIG. 8A).

First evaluated was whether the wild type peptide or the mutant or scrambled controls could bind to HDAC1 and HDAC2, which comprise part of the NuRD complex 38. The hepatocellular carcinoma (HCC) cell line SNU-398 expresses abundant amount of SALL4 and was chosen for the following 9 experiments. Pull-down by an anti-fluorescein isothiocyanate (FITC) antibody on nuclear extracts from SNU-398 cells pre-treated with FITC-labeled wild type, mutant, or scrambled peptides revealed that HDAC1 and HDAC2 could be easily detected in nuclear complexes obtained from the cells treated with wild type peptide. Much reduced HDAC binding to the mutant peptide was observed, and binding to the scrambled peptide was undetectable (FIG. 8B). It was further hypothesized that if the peptide interacted with HDAC1 and/or HDAC2, then the peptide pull-down could exhibit HDAC activity. To test this possibility, the histone deacetylase activity of the peptide pull-down complex was measured using a fluorescent assay kit (FIG. 8C). The active enzymatic activity of the HDACs tested by this assay corresponded to the amount of the HDAC proteins in the sample. While the wild type peptide pull-down had the most HDAC activity and the mutant showed some residual activity, the scrambled peptide, which did not bind to HDAC, exhibited no HDAC activity in the pull-down, comparable to that observed with the IgG control.

Next tested was the binding affinity of the wild type and scrambled peptides to the HDAC complex. For this, Fluorescent Polarization (FP), a technology based on molecular movement and rotation in which fluorescent molecules are excited with polarized light, was used. If the fluorescent molecules are part of a large complex, they rotate less and the emitted light has high polarity. In contrast, smaller molecules rotate faster and have low polarity ("depolarized"). FP has long been a valuable biophysical research tool for investigating proteinprotein or peptide-protein interactions at the molecular level. When a fluorescent labeled peptide binds to a target protein or a complex, it becomes part of the large molecular complex and becomes less mobile and has high polarization. However, excessive amount of unlabeled peptide added to the abovementioned mixture will displace the labeled peptide and the free labeled peptide will have low polarization. Using this approach, FITC-labeled wild type or scrambled peptides were first mixed with nuclear extracts from SNU-398 cells. Serial dilutions of unlabeled wild type or scrambled peptides were then added as competitors respectively, and measured by FP assay. While wild type peptide had an IC50 of 5 µM, the IC50 for the scrambled peptide could not be calculated due to the lack of binding activity (FIG. 8D). In summary, the 12 amino acid wild type peptide derived from the amino terminus of SALL4 can bind to an active HDAC complex.

Figures 9A, 9B:
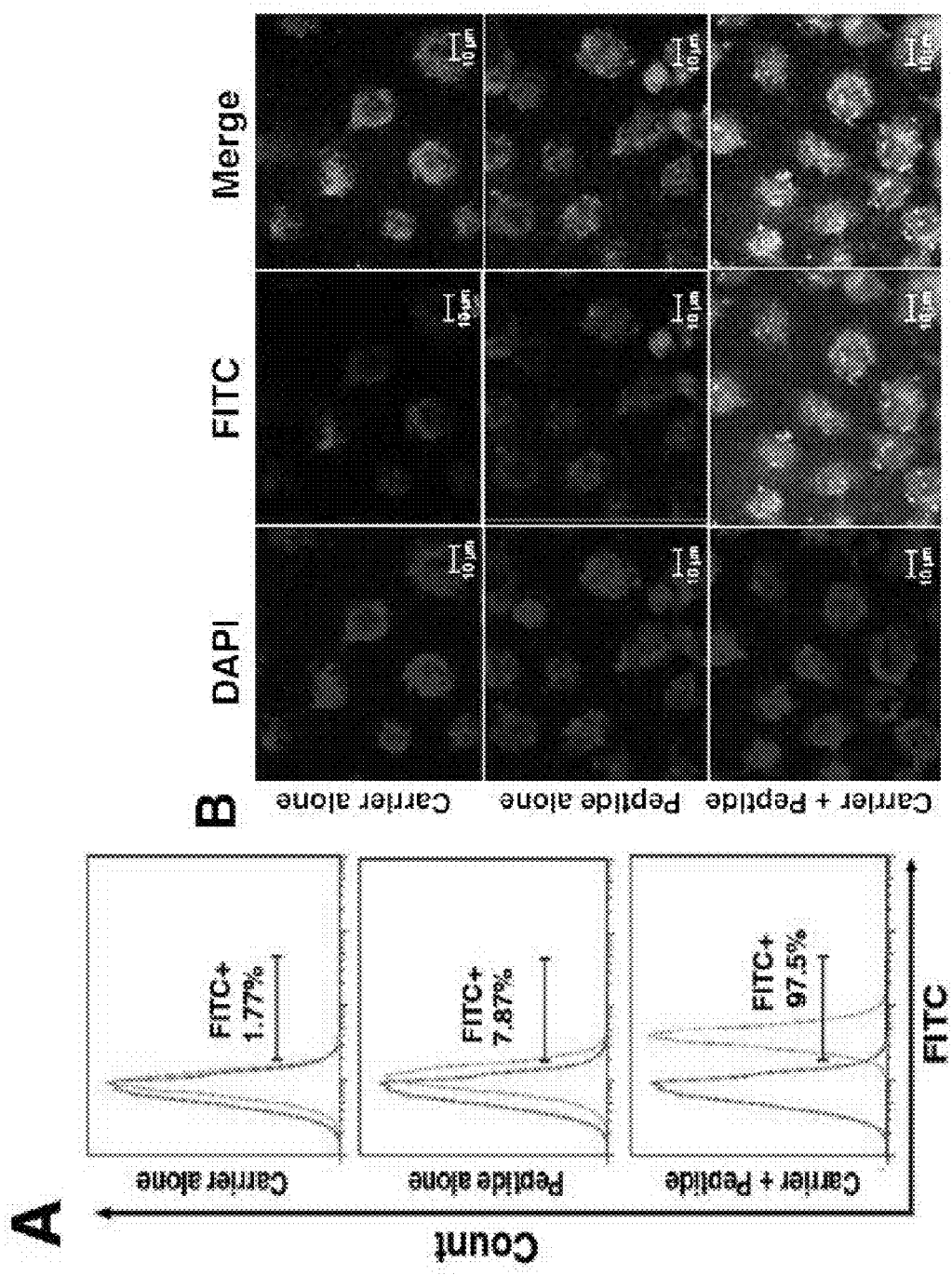
FIGS. 9A-9E: The wild type peptide blocks SALL4 repression of PTEN. (9A) Flow cytometry analysis on SNU-398 cells treated with Pep-1 carrier peptide alone (top panel), wild type peptide alone (middle panel), or Pep-1 carrier+peptide (lower panel). Over 90% of cells showed FITC-labeled peptide uptake after the use of Pep-1 carrier. (9B) Confocal images of the distribution of FITC-labeled peptide in SNU-398 cells treated as shown in (9A). (9C) The endogenous SALL4 interaction with HDAC is blocked by wild type (wt) but not scrambled (scr) peptide. SALL4 was immunoprecipitated from SNU-398 nuclear extracts (1×106 cells) pre-treated with wild type or scrambled peptides as indicated using an anti-SALL4 antibody. Immunoprecipitates were analyzed by Western blot using HDAC1 (top panel) or SALL4 (lower panel) antibodies. The interaction was completely abrogated by pre-treatment with 20 µM wild type peptide (wt, lane 2) but not scrambled peptide (scr, lane 3). Equal amount of SALL4 protein was present in all samples. In Lane 4 ("10% input"), 10% of the amount of nuclear extract used in lanes 1-3 was subjected to Western blot analysis without immunoprecipitation. (9D) Western blot showed increased PTEN expression after wild type peptide treatment compared to scrambled, α-tubulin was used as a loading control. (9E) Chip-qPCR showed increased H3 acetylation markers in SNU-398 cells upon wild type peptide treatment. Enrichment with control IgG was set at 1.

The Wild Type Peptide Competes with Endogenous SALL4 to Block Interaction with HDAC and Repression of PTEN Next tested was the cellular uptake and localization of these peptides in various types of cells using FITC-labeled wild type or scrambled peptides. Despite the net positive charge of these peptides, their penetration into cells is cell type-specific. Some cell lines, such as HL-60 (an AML cell line), allowed peptide entry without any modification or facilitator, while others such as SNU-398 were not penetrable at all. In order to achieve a similar level of peptide delivery across a range of cell types, a 21 amino acid residue peptide carrier, Pep-1, was used (Morris et al., *Nat Biotechnol*, 19:1173-1176 (2001)). The overall success rate of peptide uptake by the cells was above 95% with Pep-1, as evaluated by flow cytometry (FIG. 9A). In addition, confocal microscopic studies confirmed the uptake of these peptides throughout the cell, including nuclei (as evidenced by the DAPI overlay in FIG. 9B). It was further confirmed that Pep-1 could facilitate peptide entry into all cell types at high levels and Pep-1 was thus utilized in subsequent studies.

Figures 9C, 9D, 9E:
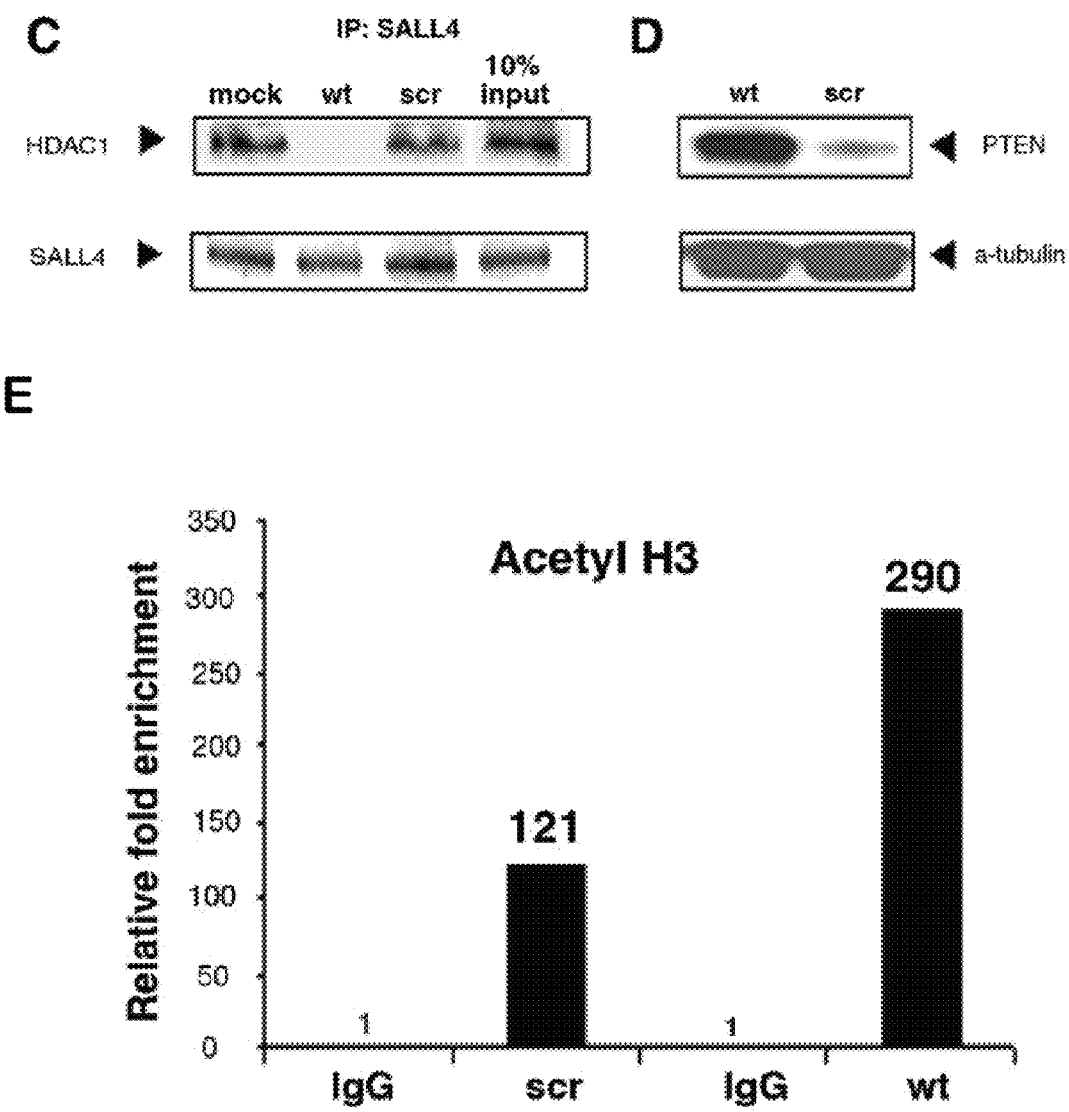

Next tested was whether wild type peptide could compete for the interaction of endogenous SALL4 with HDAC1. SNU-398 cells were treated with wild type or scrambled peptides along with the peptide carrier Pep-1. Binding to HDAC1 by endogenous SALL4 was completely abrogated when cells were treated with the wild type, but not the scrambled peptide (FIG. 9C). This result demonstrated that wild type peptide can compete with SALL4 in recruiting HDACs.

Then tested was whether this peptide could reverse the repressive effect of SALL4 on its target genes. The focus was on PTEN, since it is implicated in SALL4-mediated leukemogenesis (Yang et al., *Blood*, 112:805-813 (2008); Lu et al., *PLoS One*, 4:e5577 (2009)). In addition, it was previously reported that SALL4 could specifically bind to the PTEN promoter region in a chromatin immunoprecipitation (ChIP) assay (Lu et al., *PLoS One*, 4:e5577 (2009)). When SALL4 was overexpressed in 293T cells, an enrichment of SALL4 as well as decreased H3 acetylation at this binding site was observed, which correlated with decreased PTEN RNA expression (Lu et al., *PLoS One*, 4:e5577 (2009))). Therefore, it was hypothesized that SALL4 could recruit the HDAC/NuRD complex to repress PTEN, and that the wild type peptide would compete with endogenous SALL4 in recruiting the HDAC/NuRD complex to the PTEN promoter, and release the repression effect of SALL4 on PTEN. Furthermore, this model would predict that wild type peptide treatment of SALL4-expressing cells would lead to increased epigenetic markers of gene activation, such as H3 acetylation, at the PTEN promoter binding site, as well as an increase in PTEN expression. To test this possibility, SNU-398 cells were treated with scrambled or wild type peptide and subsequently evaluated for PTEN expression and H3 acetylation at the SALL4 binding site at the PTEN promoter region. Wild type peptide-treated SNU-398 cells demonstrated increased PTEN protein (FIG. 9D) as well as increased H3 acetylation on the PTEN promoter region (FIG. 9E), which was not observed with scrambled peptide-treated SNU-398 cells (FIGS. 9D&9E). Therefore, the results herein are compatible with the model that SALL4 recruits HDACs to repress PTEN expression, and blocking the SALL4-HDAC interaction with the wild type peptide results in increased expression of PTEN.

Figures 10A, 10B, 10C:
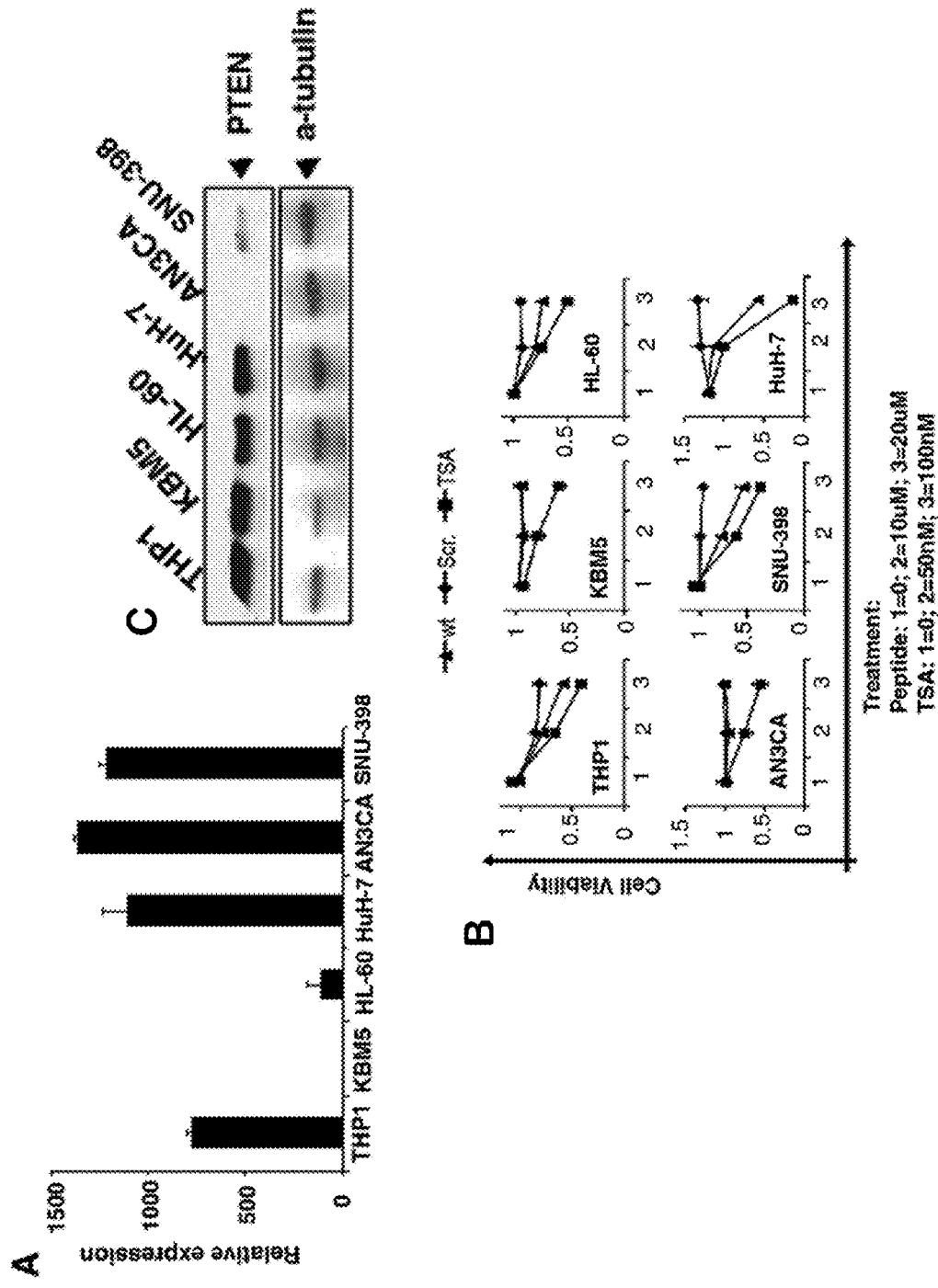
FIGS. 10A-10E: The wild type peptide reduces tumor cell viability in a SALL4/PTEN dependent manner. (10A) SALL4 expression in various tumor cell lines. SALL4 RNA expression was measured by qRT-PCR and normalized to GAPDH. Expression of SALL4 in KBM5 cells was set as 1. (10B) Reduced viability of tumor cells treated with wild type peptide and TSA at various concentrations was observed in SALL4-expressing THP1, HL-60, SNU-398, and HuH-7 cell lines, but not in non-SALL4-expressing KBM5 cells at 72 hours. Surprisingly, AN3CA, a uterine cancer cell line with high SALL4 expression, did not respond to wild type peptide treatment. Cell viability (y axis) represents the relative result of the MTS assay, the value for each cell line with Pep-1 treatment alone was set as 1. (10C) Western blot on endogenous PTEN protein expression in various untreated cancer cell lines. Notably, AN3CA has no detectable endogenous PTEN. (10D) Peptide treatment can affect the PTEN/AKT pathway. Western blot on protein expression level of PTEN, pAKT, and total AKT after peptide treatments. (10E) A PTEN inhibitor (SF1670) can reverse wild type peptide effects on viability of THP1 (SALL4+) cells, but has no effect on KBM5 (SALL4−) cells. The graph shows the results of MTS analysis of cells treated with wild type peptide (wt), scrambled peptide (scr), TSA (100 nM) or wild type peptide+PTEN inhibitor SF1670 (wt+inh).

The Wild Type Peptide Exerts an Anti-Proliferative Effect on SALL4-Expressing Cancer Cells Multiple leukemic and solid tumor cancer cell lines with high or low/no SALL4 expression (FIG. 10A) were chosen to test the biological effect(s) of the wild type peptide. Wild type or scrambled peptide was delivered into tumor cells at various concentrations, and their effects on cells were evaluated 72 hours post-treatment by the MTS cell viability assay. Since it was demonstrated that the wild type peptide could compete with SALL4 in recruitment of the HDAC-containing NuRD complex, and could potentially work as a HDAC inhibitor, the HDAC inhibitor trichostatin A (TSA) was used as a positive control in the same group of experiments. All SALL4-expressing leukemic or solid tumor cell lines, including HL-60, THP1, HuH-7 and SNU-398 exhibited decreased cell viability when treated with wild type peptide, but remained unaffected with treatment of scrambled peptide (FIG. 10B). TSA treatment led to a similar anti-proliferative effect on these cancer cells. The effect of wild type peptide is SALL4-specific, as it had no effect on KBM5, an AML cell line with undetectable endogenous SALL4 expression. We were surprised to see that the wild type peptide had no effect on a high SALL4-expressing endometrioid cancer cell line, AN3CA. This prompted checking whether PTEN, a gene repressed by SALL4 through its interaction with NuRD 27, was present in this cell line. According to the model herein, the function of wild type peptide requires both the expression of SALL4 and intact SALL4 downstream target genes, such as PTEN. In tumor cells with PTEN deletion, even though wild type peptide could compete with endogenous SALL4 in interacting with the HDAC complex, an anti-proliferative effect might not be observed. Therefore, expression of PTEN was evaluated in AN3CA cells along with other cell lines. While PTEN protein was present in all the other cell lines, it was absent in AN3CA cells (FIG. 10C), with reported deletion mutation of the gene in this cell line 40,41. These results indicate that the action of the peptide requires expression of SALL4, and that in cells such as KBM5 lacking SALL4, it is not effective. Furthermore, the anti-proliferative effect also required certain downstream targets, such as PTEN.

Figures 10D, 10E:
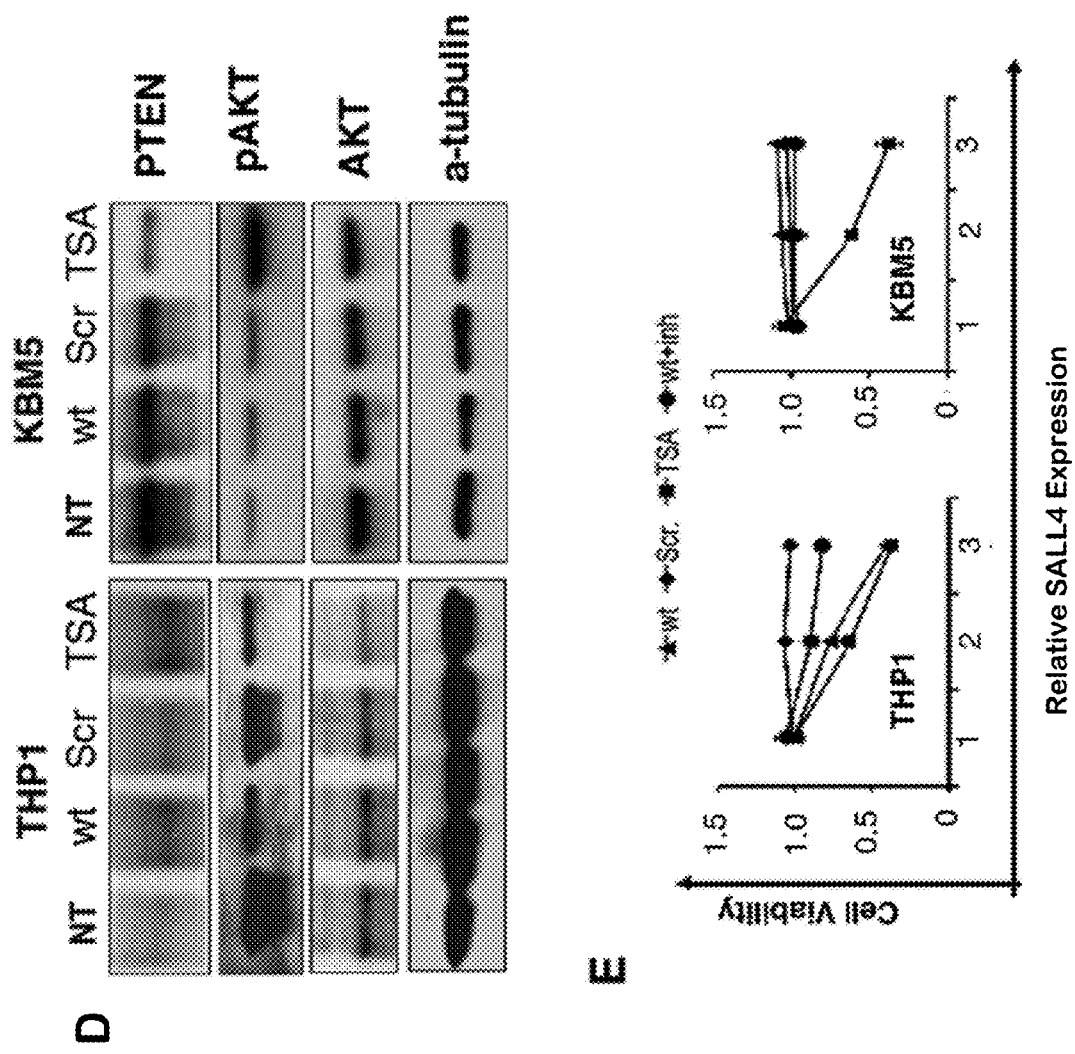

The Wild Type Peptide Affects Both PTEN and its Downstream Target Phosphorylated AKT To further evaluate the specificity of the SALL4/PTEN pathway, next investigated was whether wild type peptide treatment could affect the expression of PTEN and its downstream target, phosphorylated AKT (pAKT). Indeed, increased PTEN expression was observed upon wild type peptide or TSA treatment of SALL4-expressing THP1 cells, while the corresponding levels of pAKT on Ser 473 were significantly reduced. No effect on the PTEN/pAKT pathway after scrambled peptide treatment was observed in THP1 cells (FIG. 10D, left panel). In contrast, treatment of the non-SALL4-expressing KBM5 cells with wild type peptide had little or no effect on the levels of PTEN and pAKT in this cell line (FIG. 10D, right panel) when compared to scrambled peptide treatment.

To further test whether the effect of wild type peptide on tumor cells is related to PTEN, a PTEN inhibitor (SF1670) was used (Li et al., *Blood*, 117:6702-6713). This PTEN inhibitor does not affect the expression level of PTEN, but can reverse the effect of PTEN on dephosphorylation of its downstream target pAKT (Li et al., *Blood*, 117:6702-6713). While SALL4-expressing THP1 cells treated with wild type peptide alone showed decreased cell viability, co-treatment with this PTEN inhibitor restored the cell viability to the baseline levels, similar to that of scrambled peptide treatment (FIG. 10E, left panel). As a control for the specificity of SALL4, KBM5, a non-SALL4-expressing cell line was also treated with PTEN inhibitor. Both wild type and scrambled peptide treatment showed no change in cell viability, and co-treatment of this PTEN inhibitor with wild type peptide in this cell line showed no effect as well (FIG. 10E, right panel). Results similar to that observed in THP1 were noticed in HCC cell lines such as SNU-398 cells (high SALL4 expression); while SNU-387 cells (with 15 undetectable SALL4 expression) demonstrated a pattern similar to KBM5 cells (data not shown).

In summary, the anti-proliferative effect of this wild type peptide was only observed in SALL4-expressing tumor cells with intact PTEN gene, and was rescued with a PTEN inhibitor. Combining the observation herein on the biological effects of the peptide treatment and the expression of PTEN and pAKT in these cells, it was concluded that the role of the wild type peptide in promotion of tumor cell death is correlated to its effect on expression levels of PTEN and pAKT, indicating that at least in part, it is working specifically through the PTEN/AKT pathway.

Treatment of Primary AML Cells with SALL4 Peptide Leads to Impaired Leukemic Engraftment In Vivo, Similar to that of Down-Regulation of SALL4

Figures 11E, 11F:
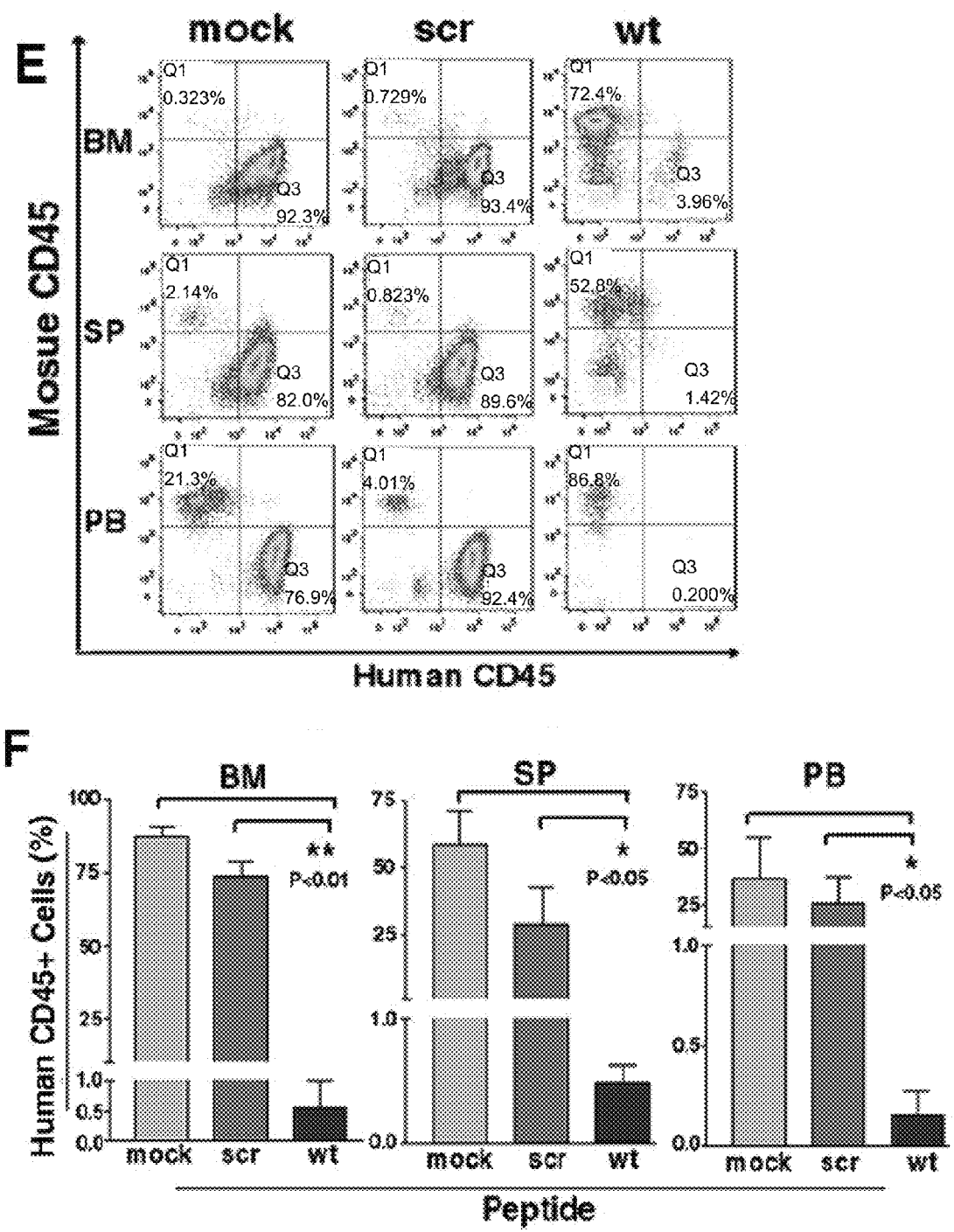

SALL4 is critical for leukemic cell survival in the AML cell line NB4 (Yang, et al., *Blood*, 112:805-813 (2008)). Asked herein was whether this is also the case for primary human AML samples. Three SALL4/PTEN-expressing AML samples were selected for experiments in which cells were first tested under culture conditions that maintain/promote viability of AML cells 28-31. The SALL4-specific shRNA that has been validated in previous studies (Yang et al., *PLoS One*, 5:e10766 (2010); Yang, et al., *Blood*, 112:805-813 (2008); Yang et al., *PNAS USA*, 104:10494-10499 (2007)) was utilized in these AML patient samples (FIG. 11A). 48 hours after transduction, the viability of cells was determined by flow cytometry after staining with Annexin V and propidium iodide (PI). Live cells are Annexin V negative and PI negative, the double negative population. When normalized the living cell percentage to 100% in the control scrambled shRNA-treated group, decreased viability was observed following reduction of SALL4 expression in primary AML cells in culture (80.9%, N=3, +/−SD=2.75%. P=0.0002, FIG. 11B). Furthermore, in a xenotransplant model, increased survival of leukemic cell recipient NOD/SCID/IL2rγ-null (NSG) mice following knocking down SALL4 expression in the primary AML samples was observed (FIG. 11C). Fatal AML with onset ranging from one to three months developed in all recipients receiving AML cells transduced with a scrambled control shRNA (n=7), while only 2 out of 6 mice receiving SALL4 shRNA-treated primary AML developed leukemia. While the median survival of scrambled shRNA control recipient mice (n=7) was 33 days, the median survival of SALL4 shRNA recipient mice (n=6) was 109 days (P=0.01). The transplanted leukemia disease was characterized by immature blasts with human CD45 expression in peripheral blood, bone marrow, and tissues such as liver and spleen (FIG. 11D to 11F). In contrast, non-leukemic SALL4 shRNA recipient mice showed less than 0.5% human CD45 positive cells (FIG. 11E) in the bone morrow or spleen samples.

Next tested was whether a therapeutic effect could be achieved by using the wild type peptide in primary human AML samples. The same SALL4/PTEN expressing primary AML samples were selected for experiments under the same culture conditions as mentioned above. Leukemic cells were subjected to three treatment regimes: peptide (wild type or scrambled), peptide plus PTEN inhibitor, or HDAC inhibitor (TSA). To assist peptide delivery into cells, a carrier agent, Pep-1 was used for all the experiments, and control treated cells were given pep-1 alone (mock). At 96 hours from the commencement of first treatment dose, cellular viability was determined by flow cytometry after staining with Annexin V and PI. A significant decrease in cell viability of primary AML cells after wild type peptide treatment which could be rescued by the PTEN inhibitor SF1670 was observed (FIG. 9A). Cells treated with either scrambled peptide or the Pep-1 peptide carrier (Mock) had over 97% cell viability, similar to that of non-treated cells at the end of the fourth day. However, only 55.3% cell viability was observed upon wild type peptide treatments (N=3, +/−SD=12.02%, P=0.006), which could in part be rescued by the PTEN inhibitor SF1670, which restored cell viability back to 78.3% (N=3, +/−SD=11.7%). Similar to wild type peptide treatment, TSA also induced cell death, with cell viability of 54.7% observed at fourth day posttreatment (N=3, +/−SD=21.6%, P=0.041, FIG. 12A).

Subsequently tested was the ability of peptide treatment to inhibit the development of AML in vivo utilizing xenografts. Consistent with the cell culture observations, reduced engraftment of human AML cells treated with wild type peptides following xenotransplantation was observed. Pep-1-treated only, or Pep-1 plus wild type or scrambled peptide-treated primary human AML cells were transplanted into sublethally irradiated NSG mice by tail vein injection. 11 weeks after transplantation, Pep-1-alone or scrambled peptide recipient mice became moribund, and all mice were euthanized for analysis (FIG. 12B). The recipients from either the Pep-1 alone or Pep-1 plus scrambled peptide-treated group had blasts on bone marrow cytospin, splenomegaly, and leukemic infiltration of the kidneys (FIGS. 12C&12D). In addition, the engraftment of human CD45+ cells was evaluated by flow cytometry (FIG. 12E). While the average engraftment of Pep-1 alone or Pep-1 plus scrambled peptide-treated cells was greater than 74% in bone marrow, the average engraftment of the Pep-1 plus wild type peptide-treated group was only 0.5%. Similar differences were observed in spleen and peripheral blood (FIG. 12F). These results demonstrate that blocking the SALL4 interaction with HDAC/NuRD inhibited the leukemic properties of human AML cells both in culture and in xenograft models, and similar to what was observed after down-regulation of SALL4 in these cells.

Discussion

Approximately 13,000 new cases and 9,000 deaths from AML were estimated to occur in the United States in 2010. This is a disease in which standard chemotherapy has not changed in over 25 years, and survival remains extremely poor. To develop effective therapeutics, it is important to understand the mechanism(s) driving the development of AML and translate that knowledge into more targeted and effective therapy. Transcription factors play a key role in tumor development including leukemogenesis, and some of these transcription factors are being used as diagnostic and prognostic markers in cancers. Targeting transcription factors in cancer through blocking of oncogenic complexes formation has been an exciting recent approach 43-46.

Histone deacetylase (HDAC) inhibitors have been used in various cancer treatments with variable results. The best therapeutic outcomes to date are observed in hematological malignancies. Most of the existing HDAC inhibitors target the enzymatic activities of histone deacetylases, which are in general nonspecific and indiscriminately re-express silenced genes in normal and tumor cells. The anti-neoplastic effects and functional mechanisms of HDACi are likely tissue-specific and context-dependent depending on transcription factors. Targeting the transcription factor(s) that recruits HDACs in cancers could potentially achieve more specific therapeutic effects.

The embryonic stem cell gene SALL4 encodes a zinc finger transcription factor. Its expression is down-regulated during development, and absent in most adult tissues, but aberrantly re-expressed in cancer cells, including AML. Knocking down the SALL4 gene by shRNA in leukemia and solid tumors leads to cell death and growth inhibition both in vitro and in vivo (Kobayashi et al., *Int J Oncol*, 38:933-939; Yang, et al., *Blood*, R2:805-813 (2008); Yang et al., *PNAS USA*, 104:10494-10499 (2007); Bard, *Faseb J*, 23:1405-1414 (2009); Kobayashi et al., *Oncol Rep*, 26:965-970). The unique expression pattern of SALL4 and its essential functional role for cancer cell survival makes it an ideal candidate for targeting cancer cells.

The important role of transcription factor SALL4 in leukemic stem or initiating cells (LICs) is supported by its interactions with several key players in the self-renewal of embryonic stem cells and LICs, particularly by repression of PTEN expression. Described herein is that SALL4 mainly acts as a repressor by interacting with an epigenetic HDAC/NuRD complex, and that the oncogenic role of SALL4 in cancer development in part is through its repressive function on the tumor suppressor PTEN by recruiting the HDAC/NuRD complex. In this study described herein, whether blocking the SALL4 interaction with the HDAC/NuRD complex could have a biological effect in cancer cells, particular AML cells, was tested. It was hypothesized that HDAC inhibitors (either by targeting the enzymatic activities of HDAC and/or disrupting the interaction between the HDAC and its transcription factor recruiter) can impair SALL4's repressor function, and negatively affect the self-renewal and survival of leukemic cells by re-activating the expression of PTEN (FIG. 13). In the study herein, data is presented that supports this hypothesis. First, demonstrated herein is that the SALL4 HDAC/NuRD recruiting region is located at the N-terminus of SALL4, and contains 12 critical AA. Furthermore, shown herein is that this 12-AA peptide has demonstrated growth inhibition of leukemic cells similar to that of classic HDAC inhibitors such as TSA, as well as that of down-regulation of SALL4 gene by shRNA. This supports the proposal that some of the therapeutic effects of HDAC inhibitors on hematological malignancies are probably mediated by the specific effect(s) of transcription factor SALL4. These studies not only led to a novel approach in treating AML, but also new understanding of the mechanisms of action of HDAC inhibitors in AML.

To test whether targeting SALL4 with this peptide can be used in treating solid tumors, such as HCC, an HCC cell line was treated with wild type and control scrambled and mutant peptides. Similar to our observations in AML, it was found that treating SALL4-expressing HCC cell lines can lead to cell death in culture and decreased tumorigenesis in murine xenograft models, identical to the phenotype generated by loss-of-function of SALL4 by a shRNA approach. These findings indicate targeting SALL4 can be used as an innovative approach in treating solid tumors as well.

Taken together, the studies herein demonstrate that this peptide can be used as a cell type-specific, SALL4 gene-specific HDAC inhibitor, and/or SALL4/PTEN modulator in cancer treatment. This approach, targeting the interaction between a transcription factor (SALL4) and its epigenetic complex (HDAC/NuRD) serves as a paradigm for targeting other transcription factors in other malignancies, both in solid tumors and leukemia, and thus provides a new direction in targeted cancer therapy.

Example 3

SALL4 is Reactivated in Human Adult Liver and Induces Heapatocarcinogenesis

Methods/Materials
Clinical Samples

Permission to perform this study was obtained from NUS Institutional Review Boards (NUS IRB 09-261). HCC tissue microarrays (TMAs) were constructed with the tissues collected from the National University Hospital (NUH) of Singapore with permission from NUS Institutional Review Boards (NUS IRB 10-133).

Immunohistochemistry

Paraffin tissue sections of 4 μm were deparaffinized with Histoclear and hydrated in graded ethanols. Antigen retrieval was performed by boiling at 120° C. in high pH target retrieval solution for 10 minutes in a pressure cooker. Nonspecific signal was blocked by peroxidase block for 10 minutes at room temperature, followed by protein block for 30 minutes at room temperature. Primary antibodies were incubated at room temperature for one hour in a humidified chamber, followed by HRP-conjugated secondary antibody incubation for 30 minutes at room temperature. Antibody binding was revealed by DAB and reaction was stopped by immersion of tissue sections in distilled water once brown color appeared. Tissue sections were conterstained by hematoxylin, dehydrated in graded ethanols and mounted. SALL4 IHC was done using primary SALL4 antibody from Santa Cruz Inc. All reagents for immunohistochemistry were from Dako (Denmark). Appropriate positive and negative controls were included for each run of IHC. Only nuclear staining was considered positive for SALL4. For IHC on TMAs, SALL4 expression was scored according to the percentage of tumor cells stained positive for SALL4, with 0 denotes less than 5% of tumor cells stained, 1 denotes 5-30% of tumor cells stained, 2 denotes 31-50% of tumor cells stained, 3 denotes 51-80% of tumor cells stained, 4 denotes >80% of tumor cells stained. SALL4 expression in TMAs was scored by a pathologist and two researchers independently.

Cell Culture

HCC cell lines were maintained in either Dulbecco's Modified Eagle Medium (DMEM) or RPMI media supplemented with 10% fetal bovine serum (FBS) at 37° C. in a humidified atmosphere of 5% $CO_2$. Immortalized hepatocyte cell lines, THLE-2 and THLE-3, were maintained in BEGM medium (Lonza) in pre-coated tissue culture flasks at 37° C. in a humidified atmosphere of 5% $CO_2$ as recommended by ATCC.

Genomic Quantitative Real-Time PCR

Real-time PCR was carried out using genomic DNA extracted from various cell lines. To determine CNV, a target assay or the DNA segment being interrogated for copy number variation (SALL4) and a reference assay for an internal control segment (GAPDH), which is typically a known single copy gene were employed. By normalizing the threshold cycle values (CT) of the target assay to that of the reference assay, relative gene copy number were calculated by calibrating SALL4 gene copies in HCC cell lines to SALL4 gene copies in an immortalized non-transformed human hepatocytes cell line, THLE-3.

Viral Transduction

Lentiviruses expressing scrambled shRNA or E5 SALL4-specific shRNA were packaged by treansfection of 293T cells with lentiviral vector pLL3.7. 24 hours and 48 hours post-transfection, viruses were harvested and filtered through 0.45 filters. Virus titers were determined by FACS analysis of GFP expression using infected 3T3 cells by the conventional ways. MOI 0.5 to 5 was used dependent on individual cell lines. Transduction of HCC cells were carried out using spinoculation protocol, virus was added to the trypsinized cells and let settle for an hour at 37° C. in a humidified atmosphere of 5% $CO_2$, centrifuged at 2,200 RPM at 37° C. for 90 mins and incubated overnight at 37° C. in a humidified atmosphere of 5% $CO_2$. Transduction efficiency was determined by GFP expression by FACS analysis.

Cell Viability Assays 7000 cells were seeded in each wells of a microtiter plate in 100 μL of complete medium. Cells from each treatment were seeded in duplicate. Controls using the same medium without cells were set up in parallel. At various time points, 317 μg/mL of 3-(4,5-dimethylthiazol-2-yl)-5-(3-carboxymethoxyphenyl)-2-(4-sulfophenyl)-2H-tetrazolium (CellTiter96® AQueous One Solution Cell Proliferation Assay, Promega) was added to each well. After four hours incubation of the tetrazolium salt, absorbance at 490 nm was read by a microplate reader.

In Vivo Tumorigenicity Assay 4- to 8-week-old NOD/SIC mice were used. Animal work was done at the Childrens Hospital Boston (CHB) with approval from IACUC. $10 \times 10^6$ SNU-398 or $6 \times 10^6$ HuH-7 cells infected with viruses expressing scrambled shRNA or E5 shRNA specific for SALL4 (total 300 μL of cell suspension and matrigel in 1:1 ratio) were injected subcutaneously (s.c.) into NOD/SCID mice on the right flank. After injection, mice were examined and tumor volumes were measured at various time points. Tumor volume=π/6×larger diameter× (smaller diameter)$^2$. Tumor samples were processed for routine histology examination.

Significance

The study described herein establishes that the stem cell factor SALL4 plays an important role in hepatocarcinogenesis. Shown herein is that SALL4 is expressed in human fetal liver, silenced in adult liver and re-expressed as an oncofetal protein in hepatocellular carcinoma, through genomic amplification and epigenetic modifications. The analysis further shows that the expression of SALL4 in HCC correlates with an unfavorable outcome, namely, an advanced tumor stage and poorer survival. Also demonstrated in this study is that the repression of PTEN by SALL4 is one of the mechanisms underlying SALL4-induced HCC. A novel 12-amino acid peptide restored PTEN expression by antagonizing the oncogenic role of SALL4 and hence is of therapeutic relevance in SALL4-positive HCCs.

Summary

SALL4, the human homologue of *Drosophila* homeotic gene spalt, is a stem cell factor that plays an important role during early development. SALL4 is a C2H2 zinc finger transcription factor that critically participates in the embryonic stem cell transcriptional regulatory network. Sall4 is important during mouse liver development; the expression of Sall4 gradually diminishes during liver development and eventually becomes undetectable in murine adult hepatocytes. It has been suggested that the expression of Sall4 in murine fetal liver has a role in the differentiation of hepatoblasts, by driving their differentiation to the cholangiocyte lineage and away from the hepatocyte lineage. SALL4 has also been implicated in human diseases. Mutations of SALL4 account for Okihiro Syndrome/Duane Radial Ray Syndrome, an autosomal dominant disorder in which patients have an association of Duane syndrome (eye retraction) with forearm malformation and deafness. Intriguingly, there has been increasing awareness of SALL4 as a novel oncogene. SALL4B transgenic mice develop leukemia, suggesting a role for SALL4 in leukemogenesis. Extensive studies have been carried out in the past two years to establish the role of SALL4 as a specific diagnostic and prognostic marker for various solid tumors, especially germ cell tumors.

In this study, it was hypothesized that in human liver, SALL4 follows the expression pattern observed in its murine counterpart and plays crucial roles in hepatocarcinogenesis when it is re-expressed in adult hepatocytes. By immunohistochemistry and microarray analysis, it is shown herein that SALL4 is expressed in human fetal liver, silenced in adult liver and re-expressed as an oncofetal protein in hepatocellular carcinoma. SALL4 expression in HCC correlates with an advanced tumor stage and an unfavorable prognosis. Shown herein is that SALL4 gene amplification is one of the mechanisms of re-activation of SALL4 in HCC, as 28.9% of the primary HCC tissues (n=228) showed gain of SALL4 by genotyping assay and 70% of HCC cell lines analyzed (n=10) showed gain of SALL4 gene copy by genomic qPCR analysis. Knocking down of SALL4 by RNA interference led to a decrease in the number of viable HCC cells in vitro and tumorigenecity of HCC cells in vivo, indicating a functional role of SALL4 in HCC. Also demonstrated herein in this study is that the repression of PTEN expression by SALL4 represents a mechanism underlying SALL4-induced HCC. A novel 12-amino acid peptide restored PTEN expression by antagonizing the oncogenic role of SALL4 and hence is of therapeutic relevance in SALL4-positive HCCs.

Introduction

Hepatocellular carcinoma is the fourth leading cause of cancer-related deaths globally. The major risk factors for HCC, which include chronic viral infection, chronic alcohol consumption and aflatoxin B-contaminated food, have been identified decades ago. Despite advances in treatment for HCC, prognosis remains bleak, with more than 90% of patients eventually succumbing to the disease within 5 years. While the epidemiological risk factors for HCC are well known, the molecular mechanisms underlying hepatocarcinogenesis are still not well characterized. Elucidating these mechanisms will enable identification of novel candidates for therapeutic targeting.

Most HCCs arise in the setting of liver cirrhosis secondary to chronic hepatitis viral infections. The underlying liver lesions render treatment of HCC with chemotherapeutic agents ineffective. Hence, studying the molecular pathogenesis of HCC is the current trend which might potentially lead to the development of effective targeted therapies for HCC. Thus far, there is no established molecular classification of HCC, unlike in the case of breast cancer, where Her2/nu status is used to guide treatment decision. Sorafenib, an oral multikinase inhibitor, is the only approved agent for patients with advanced HCC, who are not the candidates for potentially curative treatment or transarterial chemoembolization. However, the effectiveness of Sorafenib for advanced HCC is debatable. This accentuates a need for scientists to develop more effective targeted therapies for HCC.

The human homologue of Drosophila spalt homeotic gene, SALL4, encodes a C2H2 zinc finger transcription factor that contains several zinc finger domains within the protein. Drosophila spalt was first discovered by mutational studies—mutation of spalt gave rise to homeotic transformation in which posterior head segments of the embryo are transformed into anterior thoracic structures and anterior tail segments are transformed into posterior abdominal structures. The spalt gene family is evolutionarily conserved and is found in various species including Drosophila, C. elegans and vertebrates. Vertebrate spalt has been shown to play important roles during development.

Sall4, together with Oct4, Nanog, Sox2 and other stem cell factors, forms an extensive interconnected autoregulatory transcriptional regulatory network important in embryonic stem (ES) cell biology. It plays important roles during early mammalian development by maintaining the pluripotency and self-renewal capability of ES cells. Sall4 has been shown to physically interact with Oct4 and Nanog; it also has been demonstrated to be an activator of Oct4. Sall4 is important in maintaining the inner cell mass-derived lineages in mouse and the depletion of Sall4 induces differentiation of ES cells. Given its important roles in development, it is not surprising that Sall4 null mice are embryonic lethal, due to failure of inner cell mass formation. The function of Sall4 as a potent stem cell factor is further highlighted by its ability to enhance reprogramming of somatic cells to pluripotent cells.

In mouse liver specifically, Sall4 expression diminishes gradually during development, and is eventually silenced in adult hepatocytes, suggesting a role of Sall4 during early to midfetal liver development. It has been proposed that Sall4 is essential in controlling the lineage commitment of murine hapatoblasts, promoting cholangiocytic differentiation while suppressing hepatocytic differentiation. Interestingly, the observation that only one of the Sall4 isoforms, Sall4a, is present in murine hepatoblasts and regulates lineage commitment corroborates with a recent report of the differential roles of Sall4a homodimers in regulating differentiation, as opposed to the roles of Sall4a/Sall4b heterodimers and Sall4b homodimers in regulating pluripotency genes.

Apart from its essential roles during early mammalian development, SALL4 is implicated in various human diseases. The earliest reports of the involvement of SALL4 in human diseases pertain to Okihiro Syndrome, (also known as Duane-radial ray syndrome), an autosomal dominant condition characterized by radial malformations and congenital eye movement disorders, stemming from (congenital) SALL4 mutations.

In 2006, SALL4 was reported to be a novel oncogene and responsible for leukemogenesis. SALL4 expression was showed to be constitutively active in human acute myeloid leukemia (AML) and SALL4B transgenic mice developed AML that was transplantable. Following this, SALL4 was reported to be aberrantly expressed in B-cell lymphoblastic leukemias/lymphomas. In AML, SALL4 acts as a key regulator of cell survival and apoptosis. Subsequently, over the past two years, many reports proposed the use of SALL4 as a diagnostic marker in various cancers, especially in germ cell tumors that are diagnostically difficult to identify. Early this year, Ushiky et al. suggested that SALL4 can be used as a marker to differentiate hepatoid gastric carcinoma from HCC.

Based on the importance of Sall4 during murine liver development and the oncogenic roles of SALL4 in carcinogenesis, it was hypothesized that in human liver, SALL4 follows the expression pattern of its murine counterpart and plays crucial roles in hepatocarcinogenesis when it is re-expressed in adult hepatocytes.

Results

Figures 21A, 21B, 21C, 21D:
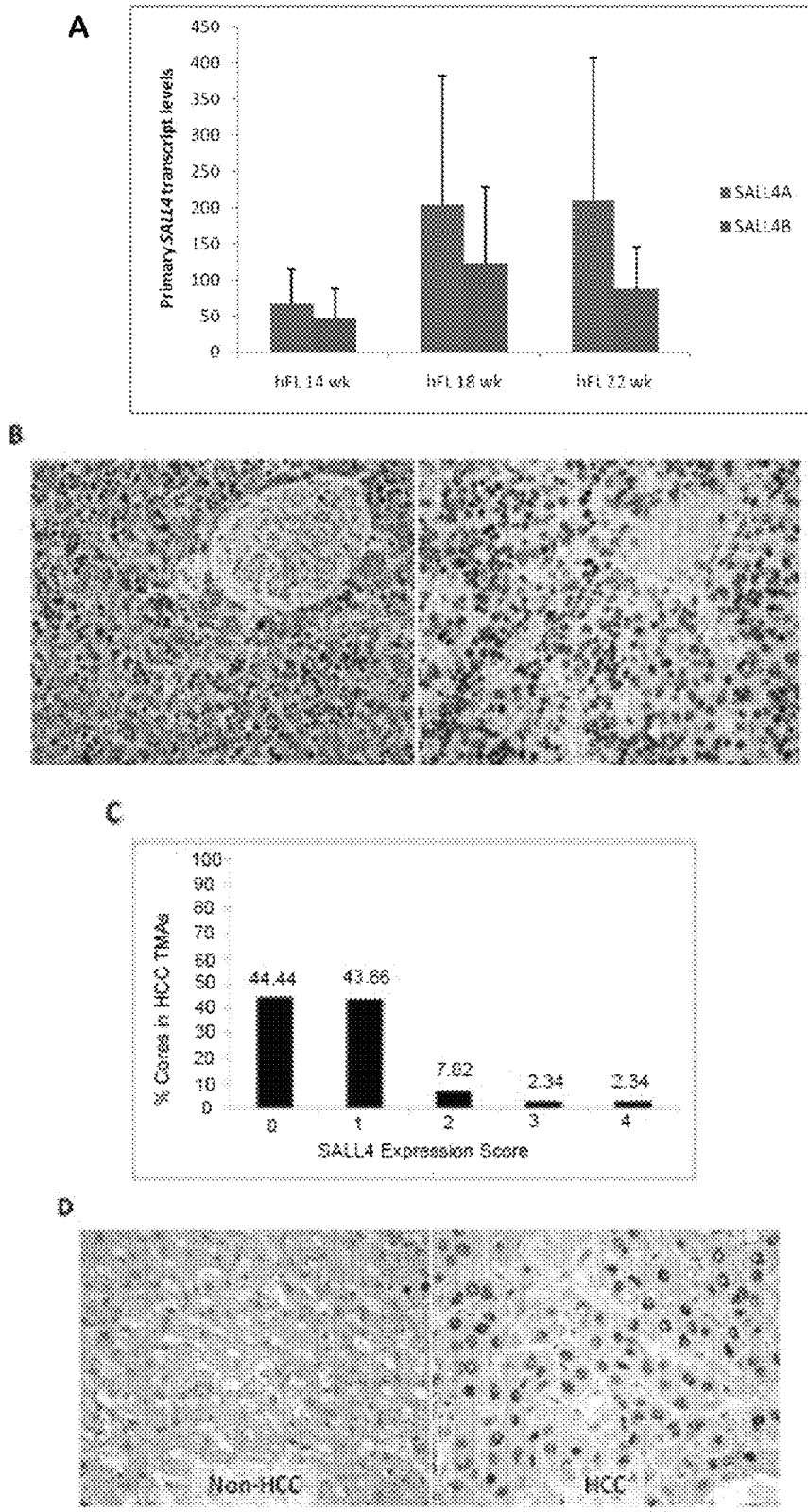
FIGS. 21A-21H. Expression of SALL4 in human fetal livers, adult livers, HCC livers and HCC cell lines. (21A) Quantitative RT-PCR analysis of SALL4A and SALL4B expression in human fetal liver of various gestation periods. All values were normalized to GAPDH and plotted relative to the expression levels in THLE-2 immortalized human hepatocyte cell line. Both isoforms of SALL4 are present in human fetal liver. Error bars indicate standard error of three replicates. (21B) IHC staining of formalin-fixed paraffin-embedded (FFPE) human fetal liver tissue section shows that SALL4 is expressed in human fetal liver and localized to the nucleus. Left panel is the H&E staining of the same FFPE human fetal liver section. (21C) IHC analysis of SALL4 expression in primary HCC tissues on TMA consisting 171 HCC tissue cores. X-axis represents the scoring of SALL4 expression, score 0: <5% of tumor cells stained positive for SALL4; 1: 5-30% of tumor cells stained positive for SALL4; 2: 31-50% of tumor cells stained positive for SALL4; 3: 51-80% of tumor cells stained positive for SALL4; 4: >80% of tumor cells stained positive for SALL4. (21D) Representative immunohistochemistry images show high SALL4 expression in HCC region (right) and absence of SALL4 in the adjacent non-HCC region (left). (21E) Microarray analysis reveals significant differential SALL4 expression in HCC tumor region and the adjacent normal liver region. p<0.001. (21F) Quantitative RT-PCR analysis of SALL4 expression in 10 human HCC cell lines. All values were normalized to GAPDH and plotted relative to the expression of THLE-2 human immortalized hepatocytes cell line. (21G) Quantitative RT-PCR analysis of SALL4A expression in 10 human HCC cell lines. All values were normalized to GAPDH and plotted relative to the expression of THLE-2 human immortalized hepatocytes cell line. (21H) Quantitative RT-PCR analysis of SALL4B expression in 10 human HCC cell lines. All values were normalized to GAPDH and plotted relative to the expression of THLE-2 human immortalized hepatocytes cell line.

SALL4 is Expressed in Human Fetal Liver, Silenced in Adult Liver and Re-Expressed in Hepatocellular Carcinoma Sall4 expression in murine fetal livers at various developmental stages has been established previously. However, the expression pattern of SALL4 in human liver remains unknown. Shown herein is the expression of SALL4 at both mRNA and protein levels in human fetal liver tissues. SALL4 mRNA was detected in human fetal livers from various gestation stages by qPCR. Unlike mouse fetal liver, where only Sall4a was detected, both SALL4A and SALL4B isoforms were detected in human fetal livers at gestational week of 14, 18 and 22 (FIG. 21A). SALL4 protein expression was also detected in a 19 week old fetal liver by immunohistochemistry (FIG. 21B). Sall4 expression has been previously reported to be present in mouse fetal liver and gradually fall during liver development and finally absent in adult hepatocytes. Described herein is the detection of both isoforms of SALL4 in human fetal liver.

After the expression of SALL4 in human fetal livers was confirmed, the expression of SALL4 in adult human livers, in both normal livers and tumor tissues, was then investigated. A panel of tissue microarrays (TMAs) consisting of both hepatocellular carcinoma (HCC) tissues and the matched non- HCC tissues from the same patient (n=171) was constructed. By immunohistochemistry (IHC), differential expression of SALL4 in primary HCC tissues and the matched non-HCC tissues, with higher SALL4 expression in HCC than the matched non-HCC tissues (p=0.000), was observed. Detailed analysis of the NC data revealed slightly more than half of the HCC tissues analyzed expressed SALL4, albeit at variable expression levels. The expression of SALL4 was scored according to published scoring criteria for SALL4 IHC in germ cell tumors, with some modifications (for detailed scoring criteria see material and methods). Score 0 was given when only less than 5% of the HCC cells stained positive for SALL4, and these cases were regarded as SALL4-negative HCC (FIG. 21C). Generally, SALL4 expression was absent in most of the non-HCC adult liver tissues examined (FIG. 21D).

Figure 21E:
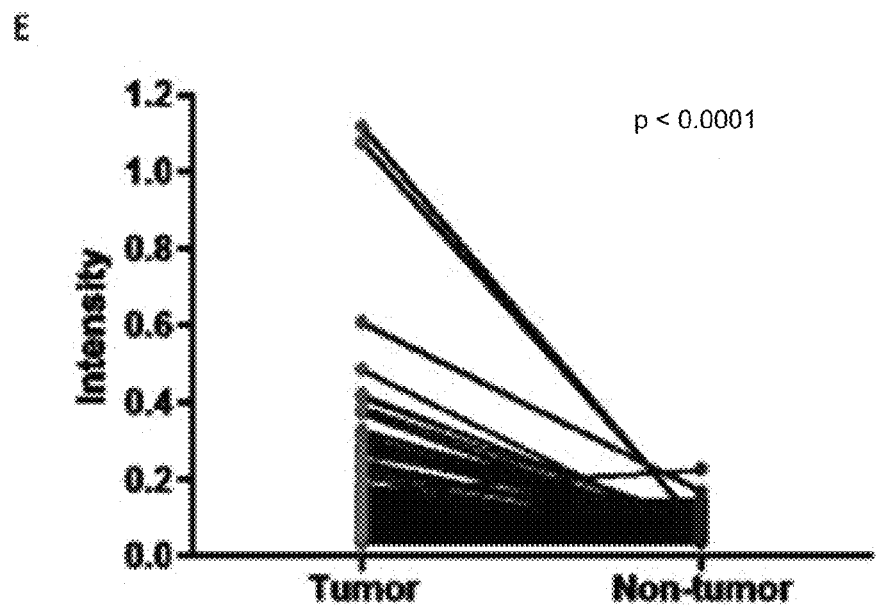

SALL4 expression at mRNA level was also analyzed in another cohort of primary HCC samples from Hong Kong (n=228) by microarray analysis. Similarly, microarray data showed differential expression of SALL4 in HCC and the adjacent normal (AN) tissues (p<0.0001), with SALL4 being expressed higher in HCC than the AN tissues (FIG. 21E). Hence, from these two independent sizable sets of HCC and matched normal liver tissues, it was established that SALL4 was re-expressed in a subgroup of HCC livers, but remained silent in the matched adult non-HCC livers, at both mRNA and protein levels.

Figure 21F:
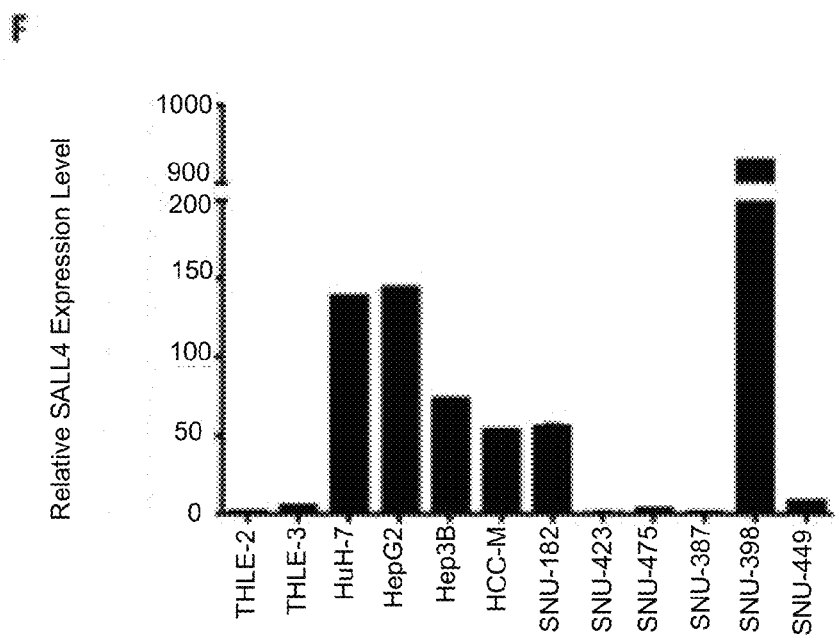
Figure 21G:
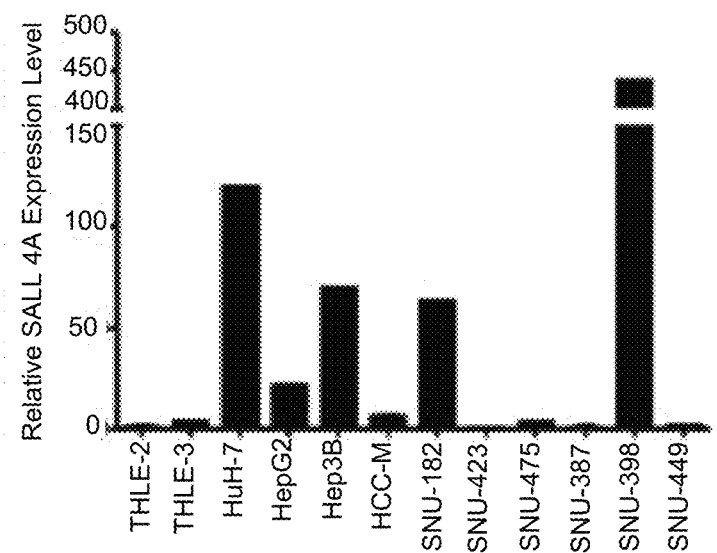
Figure 21H:
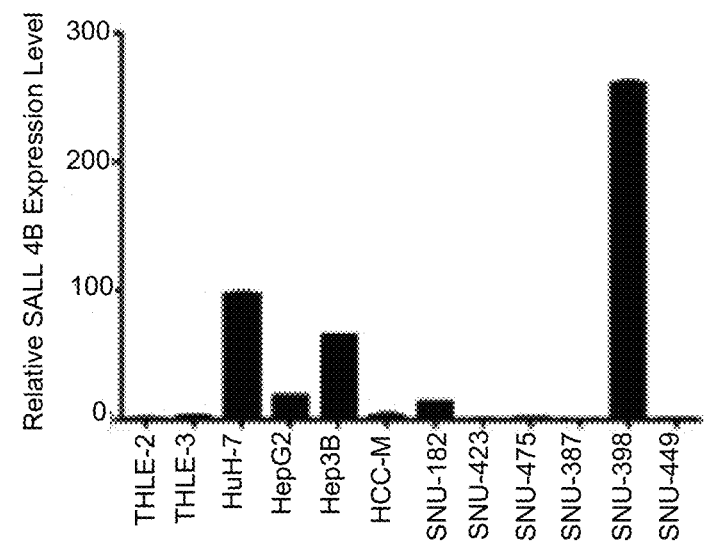

Analysis of endogenous SALL4 expression across a panel of 10 HCC cell lines by qPCR showed the expression of SALL4 at high, moderate or low levels in these HCC cell lines, an expression pattern that recapitulated that of the primary human HCC tissues (FIG. 21F). This data indicates that HCC cell lines are an appropriate model for further testing of the hypothesis, it also substantiated the hypothesis that SALL4 was re-expressed in a subgroup of HCC.

Demonstrated herein is that SALL4 is expressed in human fetal liver, silenced in human adult liver and re-expressed in HCC liver.

Figures 22A, 22B:
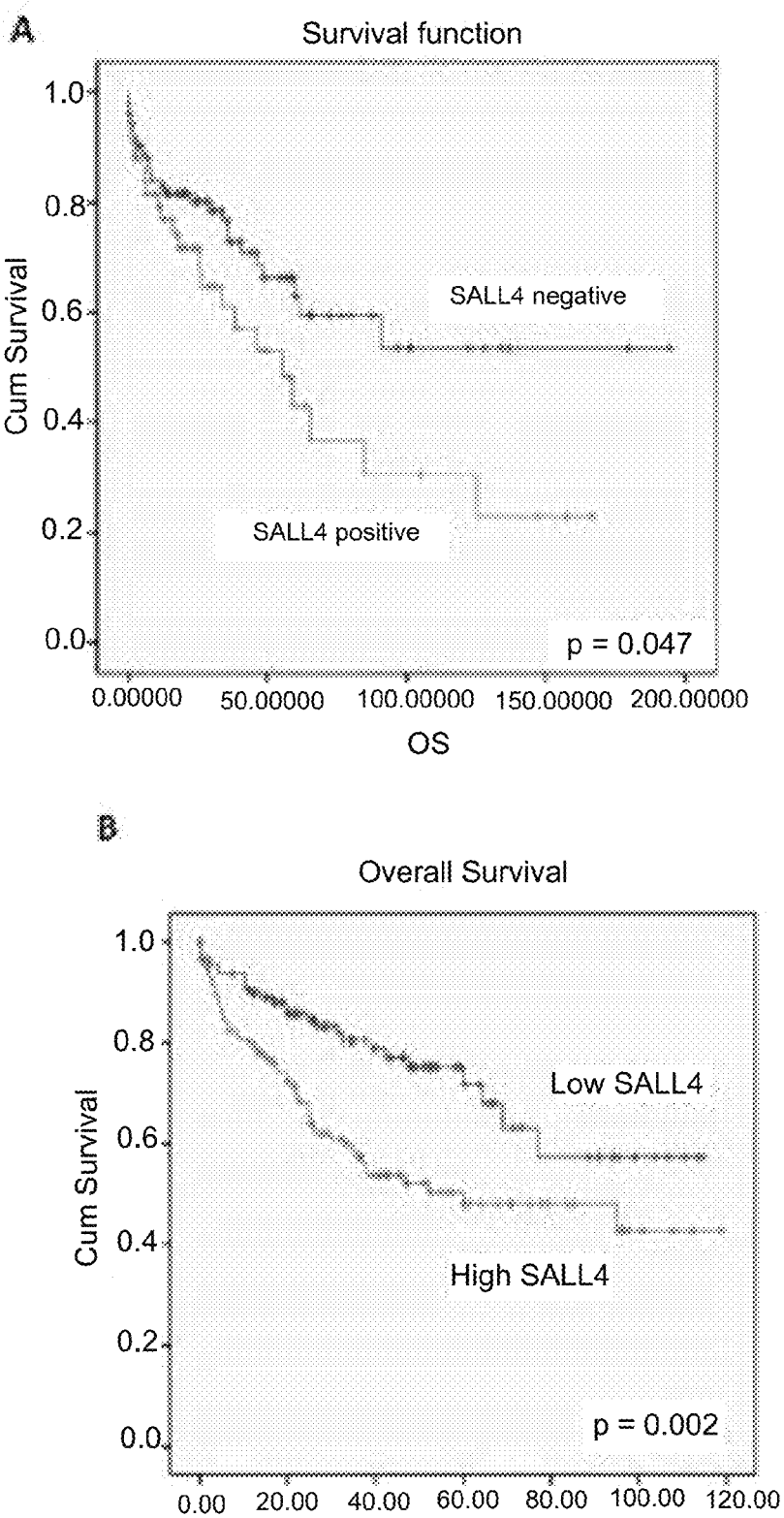
FIGS. 22A-22C: SALL4 expression in HCC predicts poor prognosis. (22A) Kaplan-Meier curve shows poorer survival advantage for SALL4-positive HCC (IHC score 1-4), as compared to SALL4-negative HCC (IHC score 0) in 171 primary HCC cases. p=0.047. (22B) Kaplan-Meier curves show poorer overall survival advantage for SALL4-high HCC in another cohort of primary HCC samples (clinical specimens from Hong Kong). N=228; p=0.002. (22C) Kaplan-Meier curves show poorer disease-free, survival advantage for SALL4-high HCC in the Hong Kong cohort of primary HCC samples. N=228; p=0.001.
Figure 22C:
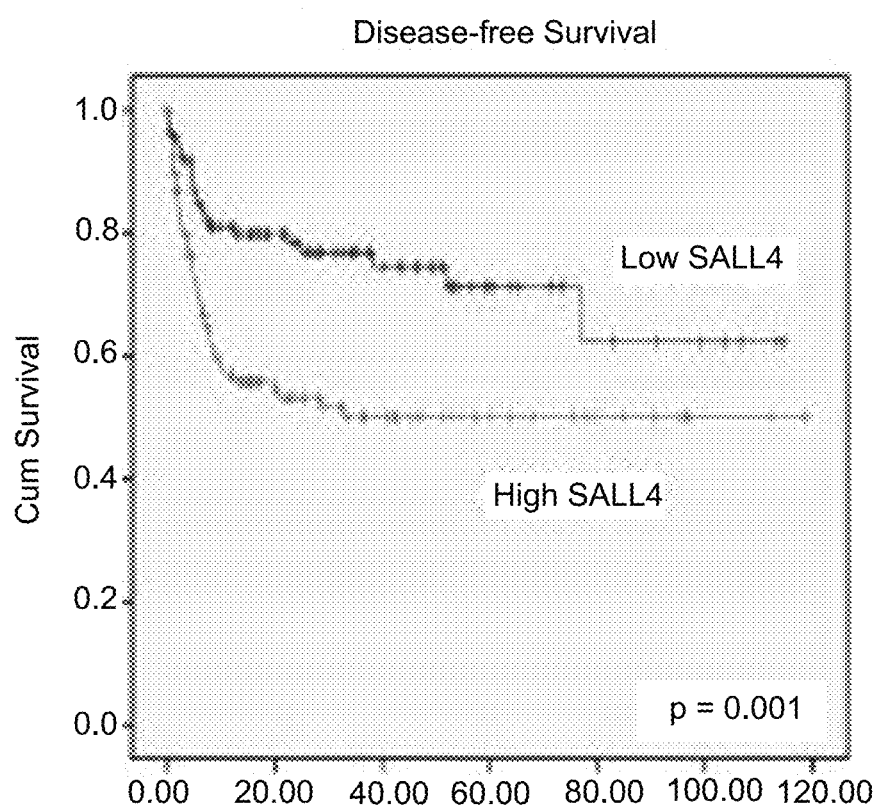

Patients with SALL4-Positive HCC have Worse Prognosis Compared to Patients with SALL4-Negative or SALL4-Low HCC Clinicopathological analyses from both sizable cohorts of primary HCC samples revealed poorer prognosis for patients with SALL4-overexpressed HCC. Comparing the survival status of 171 HCC patients, absence of SALL4 protein (IHC score 0) conferred significant survival advantage (p=0.047), as compared to SALL4-positive HCC (FIG. 22A). From this batch of primary HCC samples, a significant positive correlation of SALL4 expression with Ki67, a proliferative marker (r=0.234, p=0.002), was observed indicating a more aggressive phenotype for HCC with higher SALL4 expression.

Similarly, poorer survival (both overall and disease-free survival) was observed in the group of patients with SALL4-overexpressed HCC (p=0.001), as compared to the group of patients with SALL4-low/null HCC, in the 228 primary HCC samples from Hong Kong (FIG. 22B). Furthermore, SALL4 was found to be expressed higher at more advanced tumor stage. From our microarray analysis of this 228 clinical specimens, SALL4 was found to be positively correlated to HCC tumor stage (r=0.142, p=0.01989).

From the clinicopathological analyses of these two independent sets of primary HCC samples described herein, it was concluded+ that the expression of SALL4 in HCC predicts poorer prognosis for HCC patients, as SALL4 expression was significantly correlated to poorer survival, more aggressive tumor phenotype, and more advanced tumor stage.

Figure 23A:
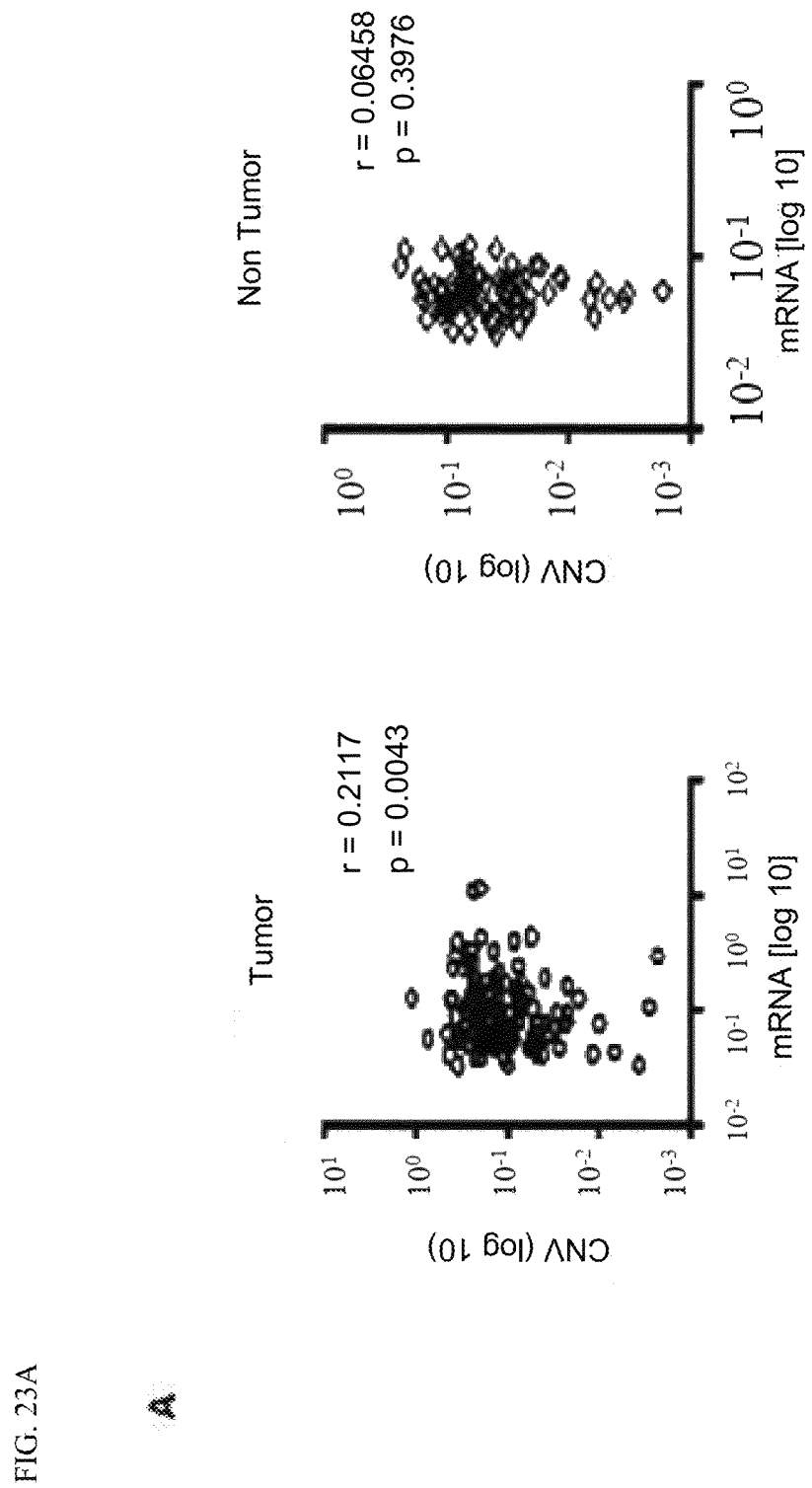
FIGS. 23A-23B: SALL4 gene amplification and epigenetic modifications as the mechanisms of SALL4 re-expression in HCC. (23A) SALL4 CNV significantly positively correlates with SALL4 gene expression in HCC tissues but not in the adjacent normal liver regions. (23B) Positive correlation of SALL4 gene copy number and SALL4 gene expression of 10 HCC cell lines and one immortalized hepatocyte cell line.

SALL4 is Re-Expressed in HCC Livers as a Result of Genomic Amplification and Epigenetic Modifications After establishing the expression pattern of SALL4 in human livers at various stages, including in the disease state in HCC, the mechanism(s) of SALL4 re-expression in HCC was explored. Two possible mechanisms, SALL4 gene amplification and a change in SALL4 promoter methylation status, were proposed. SALL4 sits on chromosome 20q13.13-13.2, this locus is frequently reported to be amplified in HCC, indicating gene amplification might be one of the mechanisms underlying SALL4 re-activation in HCC. Indeed, Illumina genotyping assay confirmed SALL4 copy number gain in 28.9% of the 228 primary HCC tissues from Hong Kong. Further analysis demonstrated positive correlation of SALL4 copy number gain with SALL4 gene expression in this set of primary HCC tissues (r=0.2117, p=0.0043), this correlation was not observed in the adjacent non-HCC tissues (FIG. 23A)

Figure 23B:
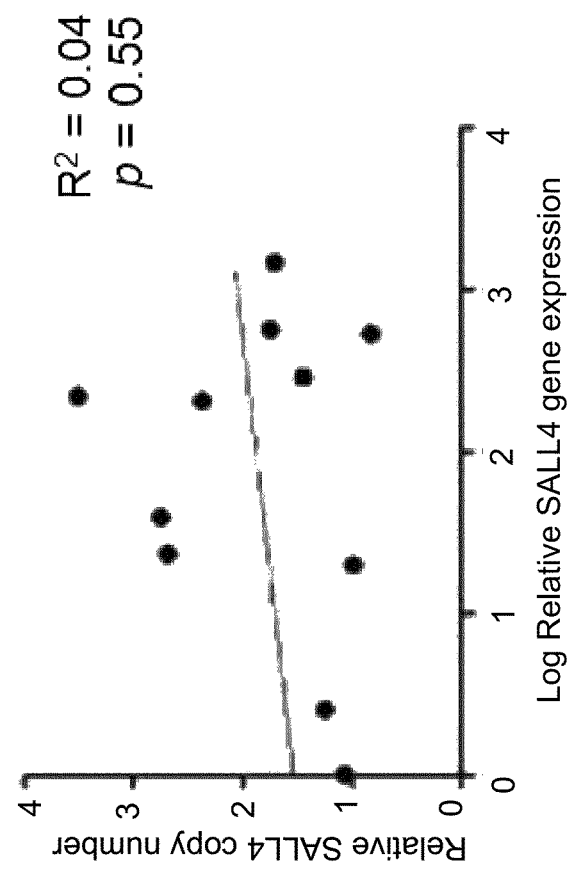

To further verify the hypothesis that SALL4 gene amplification is one of the mechanisms responsible for SALL4 re-expression in HCC, genomic qPCR assay was employed to investigate copy number variation (CNV) of SALL4 in 10 HCC cell lines. Using an immortalized human non-transformed hepatocyte cell line, THLE-3, as a calibrator, relative SALL4 gene copy number in the 10 HCC cell lines was derived. Amplification of SALL4 in THLE-3 was not assumed, as it is a non-transformed hepatocyte cell line with minimal or no expression of SALL4. By normalizing SALL4 gene copy as 1 in THLE-3 cells, relative gene copy number of more than one indicated amplification. In order to exclude background noise and false positive results, a cutoff value of 1.25 was set to distinguish real SALL4 gene amplification from noise. From this analysis, amplification of SALL4 in seven out of the ten (70%) HCC cell lines analyzed was demonstrated (FIG. 23B).

Recently, a collection of data obtained from Affymetrix 250K Sty human genotyping array and published databases reported somatic copy-number alterations in 3131 cancers of various origins, as compared to 1480 normal tissue specimens, of which, SALL4 gene status in eight out of the ten HCC cell lines included in this study was reported. The qPCR data was normalized and compared with this set of published data and no significant discrepancy was observed between these two sets of data, further confirming SALL4 gene amplification in HCC.

In addition, no SALL4 deletion was detected in these HCC cell lines; this observation is in concordance with published literature and online databases. Noteworthy was the positive correlation between SALL4 copy number gain and SALL4 overexpression in HCC. It was concludes that SALL4 amplification is one of the mechanisms underlying re-activation of SALL4 expression in HCC.

Overexpression of SALL4

Figure 24A:
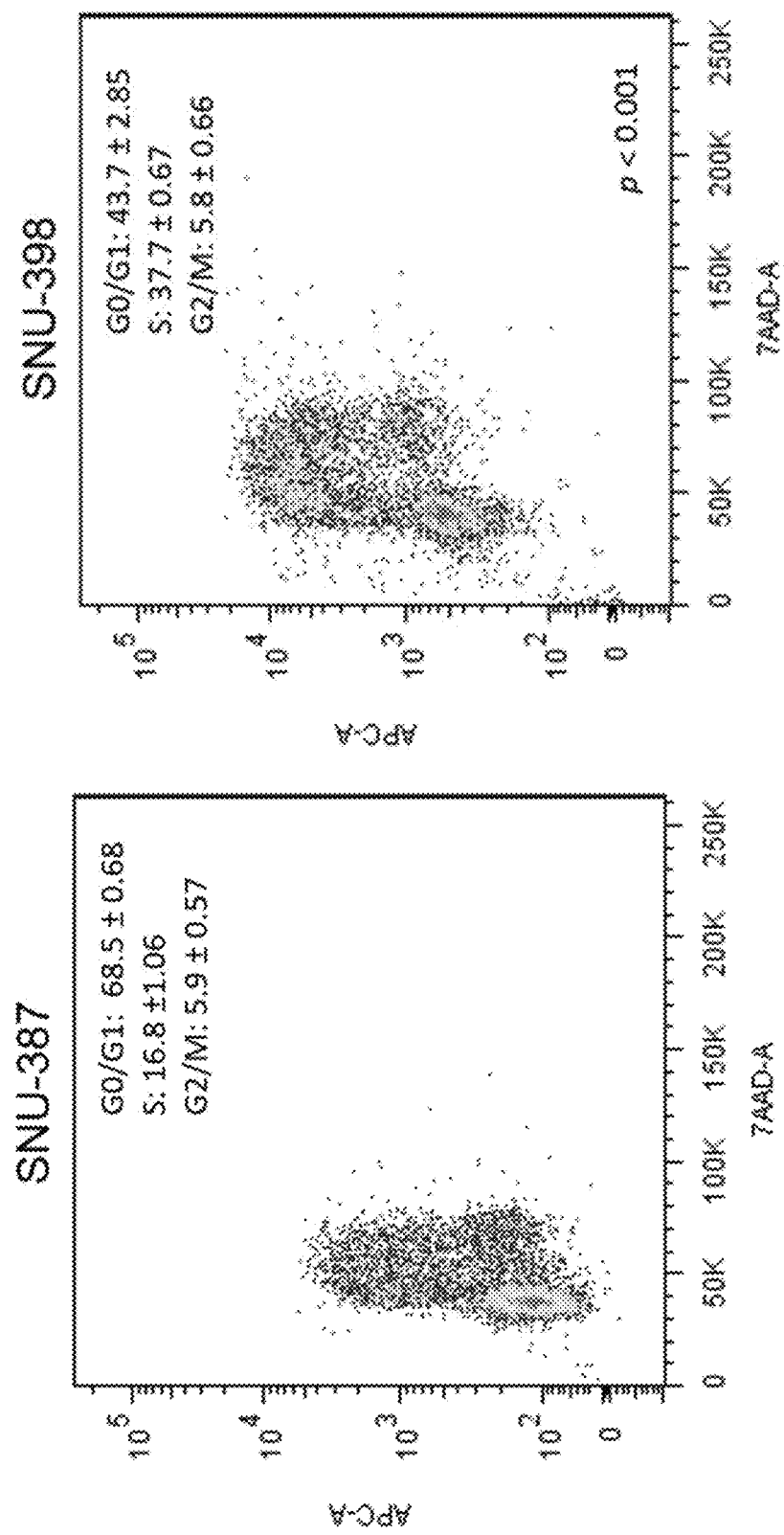

Whether the expression of SALL4 has a functional role in HCC was investigated. The proliferation rate of SNU-398 cells with high endogenous SALL4 expression was significantly higher than that of the low/undetectable SALL4 SNU-387 cells (FIG. 24A). In order to determine if the increased proliferation rate of SNU-398 was merely due to the overexpression of SALL4 or if there were other contributing factors, gain-of-function studies were carried out. SALL4 was overexpressed by lentiviral transduction/transient transfection in SNU-387 cells and the immortalized hepatocyte cell lines THLE-2 and THLE-3.

Figures 25A, 25B, 25C:
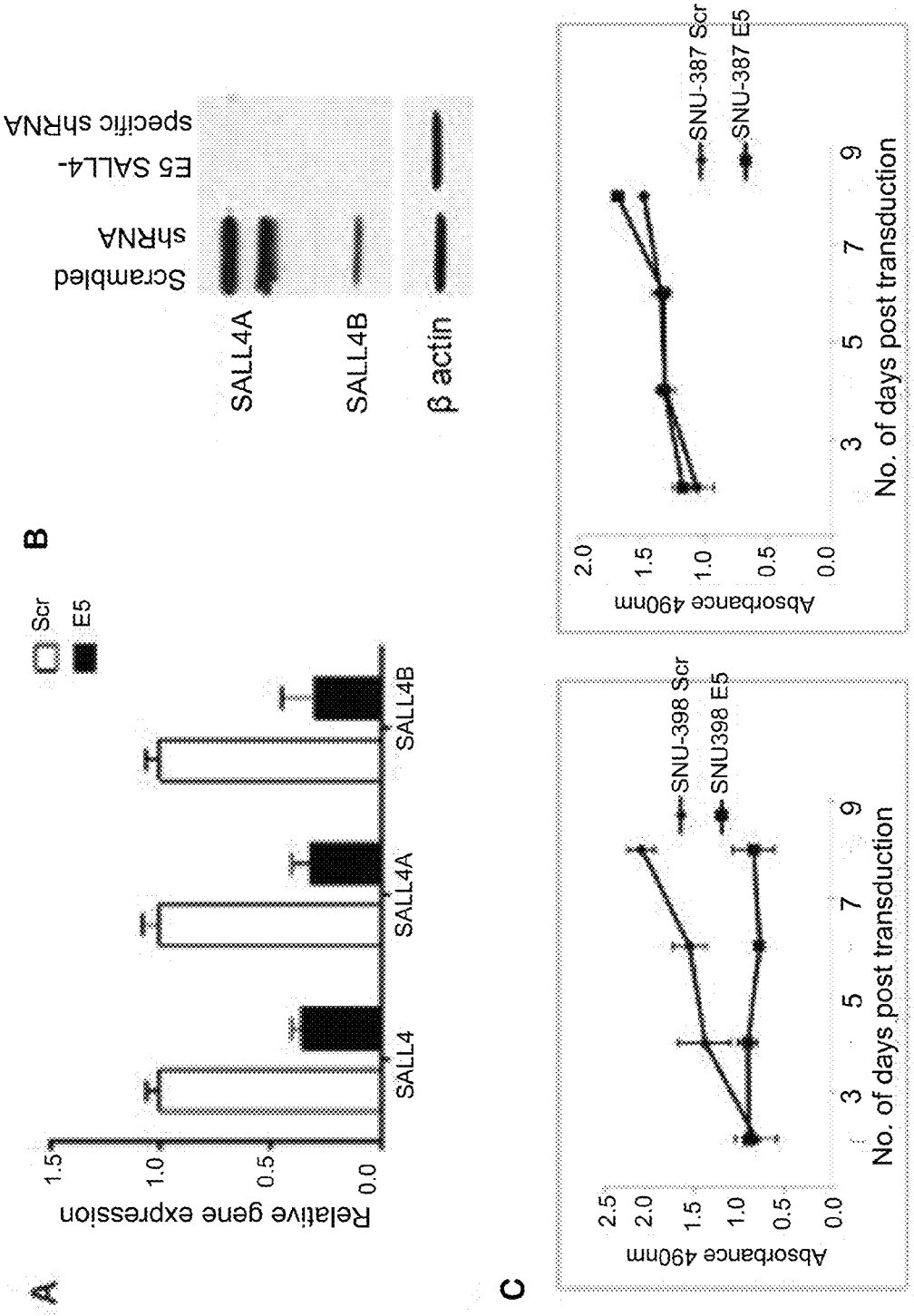
FIGS. 25A-25G: Functional roles of SALL4 in HCC. (25A) qPCR analysis of relative SALL4A and SALL4B expression on SNU-398 cells four days post-transduction. Error bars indicate standard error of three replicates. (25B) Western blot analysis of SALL4 expression on SNU-398 cells four days post-transduction. (25C) MTS analysis of cell viability upon gene knockdown by scrambled control shRNA (Scr) or E5 shRNA targeting SALL4 (E5) on SNU-398 (left) or SNU-387 (right) cells. Error bars indicate standard error of three replicates. (25D) Cell counting assay using trypan blus stain. (25E) Caspase 3/7 assay showing an increase in apoptosis activity in SALL4-knockdown (E5) SNU-398 cells at various time points post-transduction. (25F) Effects of SALL4 gene knockdown on tumorigenecity of HuH-7 cells. Representative images of mice transplanted with HuH-7 cells infected with virus expressing scrambled shRNA or E5 shRNA (top).

Knockdown of SALL4 by RNA Interference Leads to Decrease of Number of Viable HCC Cells In Vitro and Decrease Tumorigenicity Capacity of HCC Cells In Vivo After successfully establishing the expression pattern of SALL4 in human livers at various stages and the clinical significance of SALL4 in HCC, the functional roles of SALL4 in HCC was investigated. Lentiviral-mediated RNAi was carried out by introducing shRNAs specifically targeting SALL4 into various HCC cell lines. E5 shRNA was used to knock down both SALL4A and SALL4B in HCC cells. In order to exclude the off-target effect of RNAi as well as the effect of virus transduction on HCC cells, a scrambled shRNA was used as a negative control. The efficiency of virus transduction was assessed by FACS analysis of GFP expression. High transduction efficiency was constantly obtained, with GFP expression frequently >80% (FIG. 25A). By using E5 shRNA, knockdown both SALL4 isoforms to 70% at mRNA level was obtained. At protein level, almost all SALL4 proteins were gone upon gene knockdown (FIG. 25B).

Phenotypic changes of HCC cells upon SALL4 gene knockdown were then investigated. In the HCC cell line that expresses high endogenous SALL4, SNU-398, number of viable cells decreased upon SALL4 gene knockdown, as assessed by MTS assay. In contrast, the number of viable cells was similar in scrambled-shRNA-transduced and E5 shRNA-transduced SNU-387 cells, a HCC cell line that has low/no endogenous SALL4 (FIG. 25C). This data indicated that the E5 SALL4-targeting shRNA that used in this study was specific to SALL4, with no off-target effects. Most importantly, the differences in phenotype of the HCC cells with high and low endogenous SALL4 upon SALL4 gene knockdown indicated that the disruption of this gene has effects only in cells that express high SALL4 level, which indicated that SALL4 was a good candidate molecule for targeted therapy in HCC.

Figures 25D, 25E:
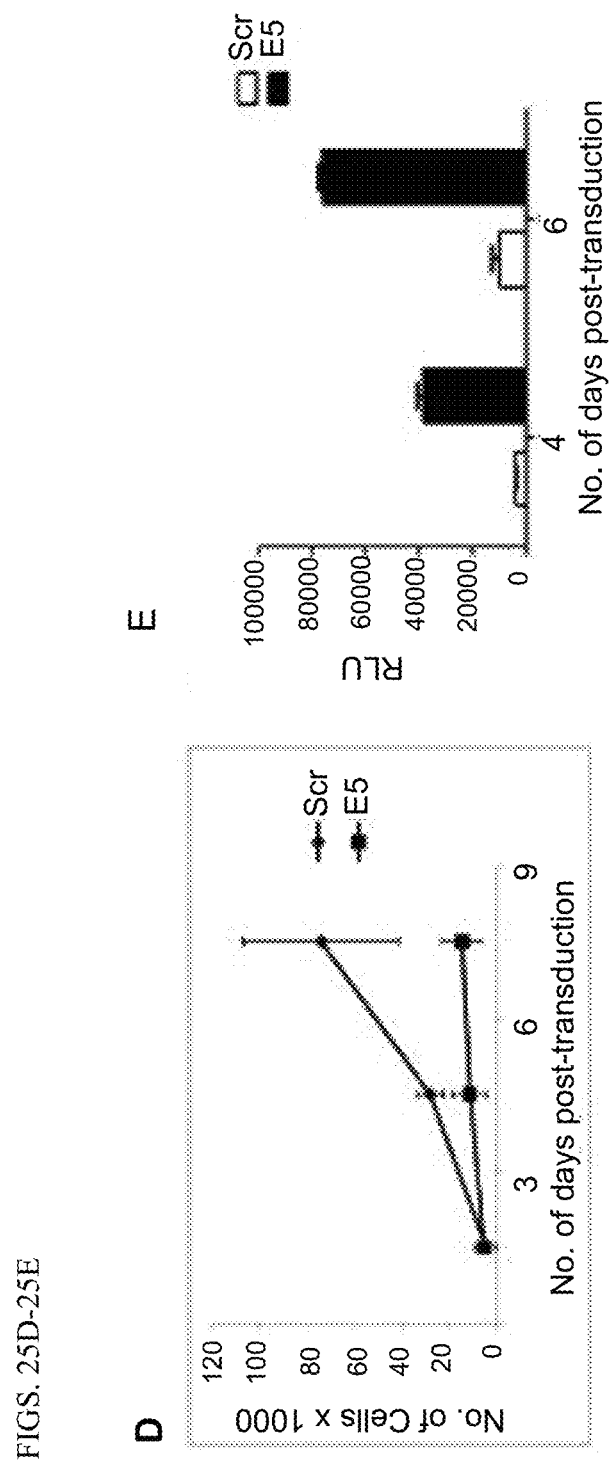
Figure 25F:
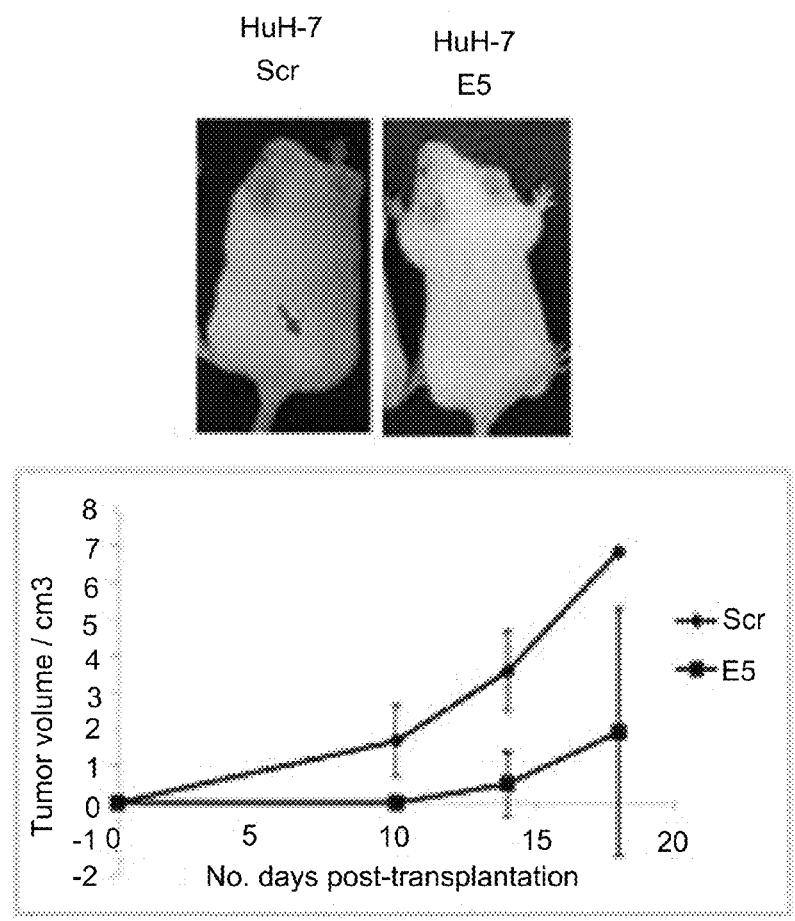
Figure 25G:
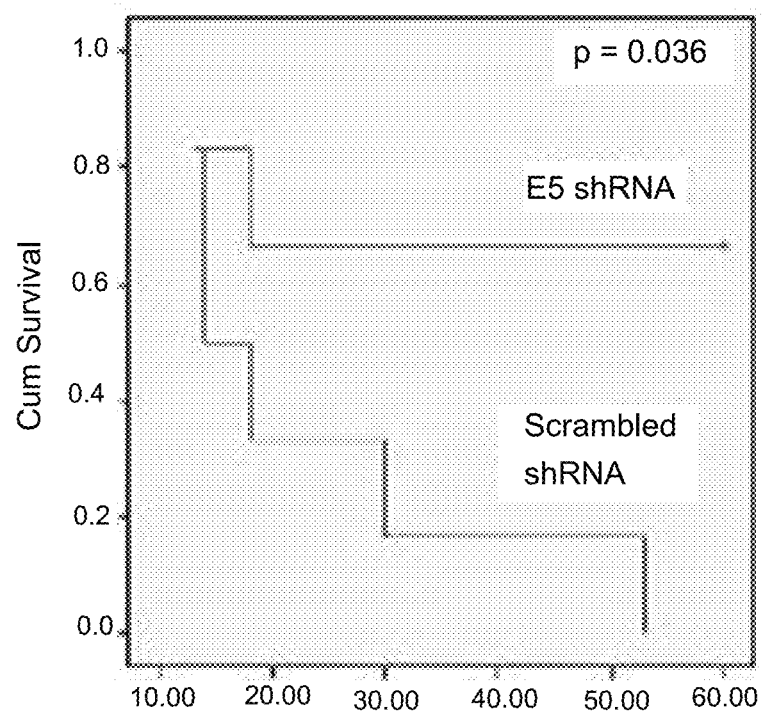

A decrease in tumorigenicity in SALL4-knockdown HCC cells was anticipated and an in vivo transplantation assay was carried out to confirm this hypothesis. HuH-7, another HCC cell line with considerably high endogenous SALL4 expression, and SNU-398 cells were transduced with lentivirus expressing either E5 shRNA or control scrambled shRNA and transplanted subcutaneously into right flank of NOD/SCID mice. Knocking down of SALL4 in these two HCC cell lines greatly reduced the ability of these cells to propagate tumors in immunocompromised mice. SALL4-knockdown HuH-7 cells generated smaller tumor at a later onset, as compared to the control cells; only one out of the three mice that received SALL4-knockdown HuH-7 had tumor formation at the right flank, while all the three mice that received scrambled shRNA-treated HuH-7 developed subcutaneous tumors (FIG. 25D). Moreover, NOD/SCID mice that received SALL4-knockdown HuH-7 and SNU-398 cells had significant survival advantage as compared to the mice that received scrambled shRNA-treated HCC cells (FIG. 25E).

The loss-of-function studies demonstrated that SALL4 is essential in the maintenance of cell viability in HCC, and reduction of SALL4 diminishes the ability of HCC cells to propagate tumors in immunocompromised mice, emphasizing a functional role of SALL4 in hepatocarcinogenesis.

Loss of PTEN as a Possible Mechanism Underlying SALL4-Induced HCC

The conserved 12 amino acid domain at the N-terminal of SALL4 has been shown to be able to recruit and interact with the Mi-2/Nucleosome Remodeling and Deacetylase (NuRD) complex and exert its transcriptional repression function. PTEN and SALL1 are among the downstream targets repressed by SALL4 through the recruitment of NuRD complex. Described herein is the investigation of whether PTEN repression and the resultant increased in phosphorylated AKT and activation of PI3K signalling pathway was one of the mechanisms underlying SALL4-induced hepatocarcinogenesis.

PTEN expression upon SALL4 gene knockdown was investigated by qPCR and western blot. At day 4 post-transduction, PTEN mRNA increased by 16.5% (FIG. 26A), while densitometry analysis of western blot showed an increase in cytoplasmic PTEN protein expression by 60% and total PTEN by 70% (FIG. 26B). This indicated that SALL4 represses PTEN in HCC cells.

Targeting of SALL4 by a 12-Amino Acid Peptide Leads to Decreased Number of Viable HCC Cells as a Result of Increased PTEN Expression and Decreased PI3K Cell Survival Signaling As mentioned herein, the conserved N-terminal domain of SALL4 is essential for its transcriptional repression function, by recruiting NuRD complex and deacetylating histones. Provided herein is evidence that SALL4 represses PTEN expression in HCC cells. A 12-amino acid peptide (SALL4 peptide) (FIG. 1A) effective in blocking the recruitment of NuRD complex at SALL4 N-terminal was synthesized. SALL4 peptide was effective in targeting SALL4 and inducing a decrease in the number of viable HCC cells when it was added to the cultures. When 5 µM or 20 µM of SALL4 peptide (wt) was given to SNU-398 cells with high endogenous SALL4 expression, the number of viable cells was reduced, as compared to SNU-398 cells treated with control mutant peptide (Mut) and scrambled peptide (Scr). Trichostatin A (TSA) is a general HDAC inhibitor, it was used as a positive control drug in this assay and indeed it also effectively induced reduction in the number of viable HCC cells at 5 µM and 20 µM dose. PTEN inhibitor was able to rescue the phenotypes when it was added to the cells treated with SALL4 peptide (wt+Inh), as evidenced by the maintenance of the number of viable cells (FIG. 27A), indicating PTEN has a role in SALL4 peptide-induced lost of viable HCC cells.

Figures 27A, 27B:
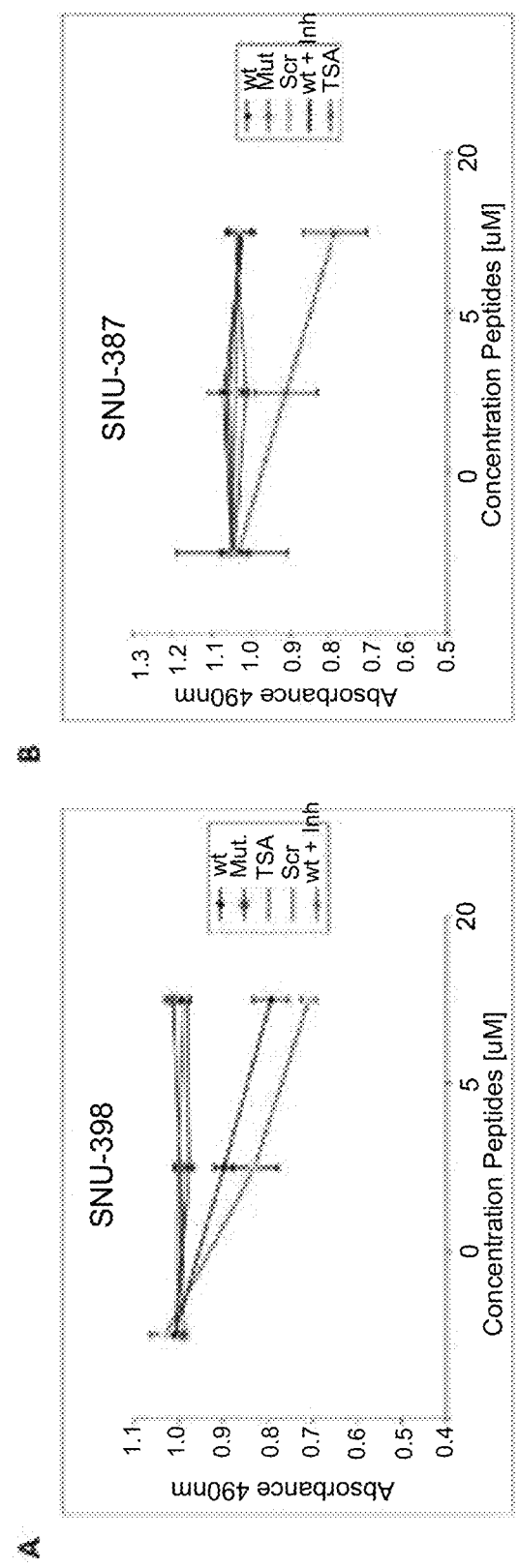

In contrast, SALL4 peptide had no effect on SNU-387 cells which have low/undetectable endogenous SALL4 expression (FIG. 27B). There was no change in the number of viable SNU-387 cells when SALL4 peptide (wt) was given to the cells, as compared to the controls (Mut. Or Scr.). However, similar reduction in the number of viable SNU-387 cells was observed in cells treated with TSA at 5 µM and 20 µM doses. This indicates that SALL4 peptide can be used as a specific drug for high SALL4-expressing cancerous cells to eradicate tumors, with minimal toxicity, as compared to TSA inhibitor.

Figure 27C:
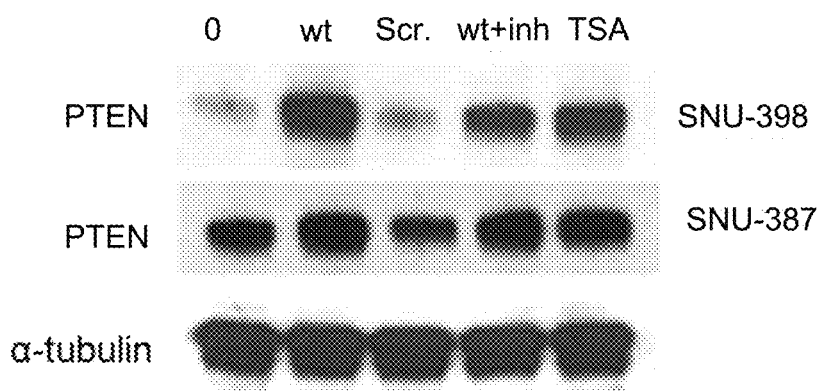
Figure 27D:
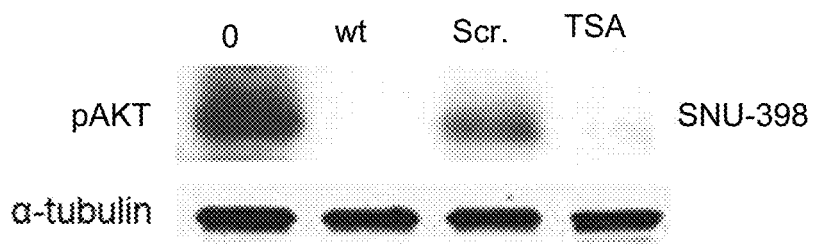

To confirm the involvement of PTEN tumor suppressor in SALL4 peptide-induced reduction of number of viable HCC cells, PTEN expression was analyzed by western blot upon drug treatment. SALL4 peptide (wt) induced extensive increased in PTEN expression in SNU-398 cells, compared to controls (cells without treatment, or cells treated with scrambled peptide). Similarly, TSA also induced PTEN expression in SNU-398 cells (FIG. 27C). SALL4 peptide also induced a slight increase in PTEN expression in SNU-387 cells, however there is no significant biological effect following this slight PTEN induction, as seen in the CitoTox 96 cell viability assay (FIG. 27B). Whether the increase in PTEN expression upon SALL4 peptide treatment has an effect in PI3K signalling by dephosphorylating AKT was examined. Western blot analysis of pAKT expression showed significant reduction of pAKT level upon SALL4 peptide treatment in SNU-398 cells (FIG. 27D), indicating that the increase in PTEN expression level has a functional role in blocking the PI3K survival signalling by dephosphorylating AKT.

These data herein indicate that SALL4 peptide can be used as a powerful targeted therapy for a subgroup of HCC, as it effectively and specifically reduces viable SALL4-positive HCC cells, by activating PTEN tumor suppressor and inhibiting PI3K survival signalling in HCC cells.

Discussion

SALL4 is one of the important transcription factors implicated in the extensive interconnected autoregulatory transcriptional regulatory network essential in maintaining embryonic stem cell characteristics. It is important in murine liver development, as Sall4a regulates differentiation of hepatoblasts to the cholangiocytic lineage. Shown herein is that the expression pattern of SALL4 in human livers at various stages—activated in fetal liver, silenced in non-transformed adult livers, and re-expressed in hepatocellular carcinoma as a oncofetal protein. The re-expression of SALL4 in HCC has its clinical significance, as HCC patients with overexpressed SALL4 tend to have poorer prognosis, in terms of survival, tumor stage and the aggressiveness of tumors.

Herein, two mechanisms for SALL4 re-expression in HCC were proposed—gene amplification and promoter hypomethylation. In the study herein, it was confirmed that SALL4 gene amplification is one of the mechanisms underlying SALL4 reactivation in HCC, by genomic qPCR and SNP array.

This expression of SALL4 has a functional role, as determined by the loss-of-function studies. Knocking down of SALL4 decreased the number of viable HCC cells and their tumorigenicity. SALL4 has been shown previously to be a major regulator of cell survival and apoptosis in human leukemic cells.

HCC is one of the most deadliest diseases. There is an increasing trend of HCC incidence in the European countries, as well as the United States. Thus far there is no satisfactory treatment for HCC patients besides surgical intervention. As not all HCC patients are candidates for surgical intervention and the underlying liver lesions often render HCC resistant to chemotherapy, the mortality and morbidity rates of this disease are high. There is no effective targeted therapy for HCC, as it is a complex disease arises from multiple hits at the genetic levels. Sorafenib, an oral multikinase inhibitor, is the only approved agent for patients with advanced HCC. The effectiveness of Sorafenib for advanced HCC is questionable. Given the clinical importance of SALL4, targeting SALL4 is a promising intervention for HCC. Shown herein is that a short peptide effective in targeting SALL4 can be used for HCC targeted therapy. SALL4 peptide targeted SALL4 specifically, only tumor tissues that express high SALL4 will be affected. SALL4 peptide worked by blocking the recruitment of NuRD complex at the N-terminal of SALL4, and hence antagonized the transcriptional repression function of SALL4. This activated PTEN transcription and the PI3K survival signaling.

Conclusion

The data herein establishes that the stem cell factor SALL4 plays an important role in hepatocarcinogenesis. Shown herein is that SALL4 is expressed in human fetal liver, silenced in adult liver and re-expressed as an oncofetal protein in hepatocellular carcinoma, in part through genomic amplification. The expression of SALL4 in HCC has been shown to correlate to unfavorable prognoses, in terms of tumor stages and survival, in our analysis. Also demonstrated herein is that the repression of PTEN by SALL4 is one of the mechanisms underlying SALL4-induced HCC. A 12-amino acid peptide blocked the oncogenic roles of SALL4 by restoring PTEN expression and hence has therapeutic implication in SALL4-positive HCCs.

Example 4

Oncofetal Protein SALL4 as a Novel Prognostic Marker and Therapeutic Target for the Aggressive Stem/Progenitor-Like Subgroup of Hepatocellular Carcinoma (Example 4 is the Same as Example 3, However, the Results of Example 3 were Reviewed and Reworked and are Described Below)

Hepatocellular carcinoma (HCC) is the third leading cause of cancer-related deaths worldwide. Cancers with embryonic stem cells (ESCs)/progenitor cells gene expression characteristics are known to have poor prognosis. In the study described herein, the clinical relevance SALL4, an ESC factor and emerging oncogene, as a prognostic marker and therapeutic target for the progenitor-like subgroup of HCC was evaluated.

Methods

The expression of SALL4 in primary HCC was first screened and clinicopathological analysis was carried out. Loss-of-function studies were then performed to evaluate the role of SALL4 in hepatocarcinogenesis and its potential as a molecular target for therapy. To assess the therapeutic effects of a peptide that targets SALL4, in vitro functional and in vivo xenograft assays were carried out.

Results

SALL4 is expressed in human fetal liver, silenced in adult liver, but re-expressed in a subgroup of HCC patients with unfavorable prognosis, representing an oncofetal protein. Gene expression analysis reveals the enrichment of progenitor-like gene signatures in SALL4-positive HCCs. Loss-of function studies confirmed that SALL4 is essential for human HCC cell survival and tumorigenicity. Importantly, demonstrated herein is that a peptide can block the oncogenic function of SALL4 in HCC by modulating at least one of its targets, the PTEN/AKT pathway.

Conclusions

Shown herein is that SALL4 is a prognostic marker for aggressive HCC. Because of its functional roles in hepatocarcinogenesis and absence in adult liver, SALL4 also represents an attractive drug target. This is further validated by the proof-of-concept approach of utilizing a peptide to block the oncogenic function of SALL4 in HCC described herein.

It was hypothesized that SALL4 can contribute to the development and maintenance of HCC when it is expressed in adult hepatocytes. Indeed, in humans, it was observed that the expression of SALL4 follows the pattern of its murine counterpart during normal liver development, and that SALL4 is expressed in a subgroup of HCC as a result of genomic amplification. From the clinicopathological analysis described herein, SALL4 expression has been found to be correlated with poor prognosis for HCC patients. Additional loss-of-function studies confirmed a functional role for SALL4 in hepatocarcinogenesis. Importantly, a novel 12-amino acid peptide blocks SALL4 oncogenic function, leading to decreased HCC cell viability and tumorigenicity, further supporting the hypothesis that SALL4 is a therapeutic target in HCC. In summary, shown herein is that SALL4 is a prognostic marker and therapeutic target for a subgroup of HCC patients with aggressive progenitor-like tumors.

Methods

Patient Samples

Permission to perform this study was obtained from NUS Institutional Review Boards (NUS IRB 09-261). HCC tissue microarrays (TMAs) were constructed with the tissues collected from the National University Hospital (NUH) of Singapore with permission from NUS Institutional Review Boards (NUS IRB 10-133).

Datasets

For profiling HCC samples versus normal controls, datasets from the GEO database with the accession numbers of GSE6222, GSE6864, & GSE29721 were used. For comparing HCC samples of high and low SALL4 expression with primary hepatocytes (Hep) and human fetal liver (HFL) samples, appropriate samples from the following GEO datasets (GSE6222, GSE6764, GSE9843, GSE15238, GSE18269, GSE23343, GSE29721, & GSE33606) were utilized. For comparison of SNU-398 samples with primary hepatocytes and human fetal liver samples, Hep and HFL samples were taken from GEO datasets, GSE23034 & GSE23413, respectively. SNU-398 samples with SALL4 knocked down were submitted to GEO database with the following accession number: GSE35965. The CNV data were taken from both GEO (GSE25097) and the TCGA (TCGA-G3-A25Z) databases. Only HCC samples in which SALL4 expression exceeded the threshold of expression intensity of 40 were included for the SALL4 copy number and gene expression correlation study.

Data Analysis

For Affymetrix data, all CEL files were analyzed together using the Robust Multichip Average method to obtain the gene expression intensities. For Illumina Beadchip data, raw data with background subtraction were used for all samples. Normalization was then performed across all samples based on the Cross Correlation method, and normalized data were further log 2-tranformed. Gene set enrichment analysis (GSEA) was performed by using normalized data using GSEA v2.0 tool http://<www.broad.mit.edu/gsea/>. For GSEA, we analyzed 12 high SALL4 primary HCCs and 43 low SALL4 HCCs.

Clustering and Heatmaps

Hierarchical clustering with average linkage was used in all clustering. For clustering HCC SALL4 high and low samples with human fetal liver and hepatocyte samples, the mean of the four group means (HCC SALL4 high, HCC SALL4 low, human fetal liver, and hepatocyte) was subtracted from the log 2-transformed normalized data prior to clustering. For clustering SNU-398 SALL4 knocked down data, human fetal liver and hepatocyte genes with differential expression between the cell line and primary cells were excluded by using only genes with no significant changes between any one of SUN-398 SALL4 knocked down (KD) and wildtype control (WT) and any one of primary cells. The cutoff for no significant fold change used is 1.5. The mean of the four group means (SNU-398 KD, SNU-398 WT, hepatocyte and human fetal liver) was then also subtracted from the log 2-transformed normalized data prior to clustering. Genes with no significant changes between the four groups of samples were not represented in both heatmaps to show clear patterns.

Cell Culture

HCC cell lines were maintained in either Dulbecco's Modified Eagle Medium (DMEM) or RPMI medium supplemented with 10% fetal bovine serum (FBS) at 37° C. in a humidified atmosphere of 5% CO2. Immortalized hepatocyte cell lines, THLE-2 and THLE-3, were maintained in BEGM medium (Lonza, Basel, Switzerland) in pre-coated tissue culture flasks at 37° C. in a humidified atmosphere of 5% CO2 as recommended by ATCC.

Statistical Analysis

All experiments were done in triplicate, unless otherwise stated, standard deviation and statistical significance were determined. Statistical analysis was performed using SPSS v 15.0 for Windows (SPSS Inc., Chicago, Ill., USA). Chi-square test was used to examine the association between the biomarkers expression and clinicopathological features. Cumulative overall and disease-free survival was analyzed by the Kaplan-Meier method and analysed by the log-rank test. Factors that were identified as statistically significant were included in the subsequent multivariate analyses using Cox proportional hazard regression model. The correlation significance was analysed by Spearman and Pearson correlation analysis. The chi square test and Student t test were used for comparison between groups. A p value ≤0.05 was considered statistically significant.

Results

Figures 28A, 28B:
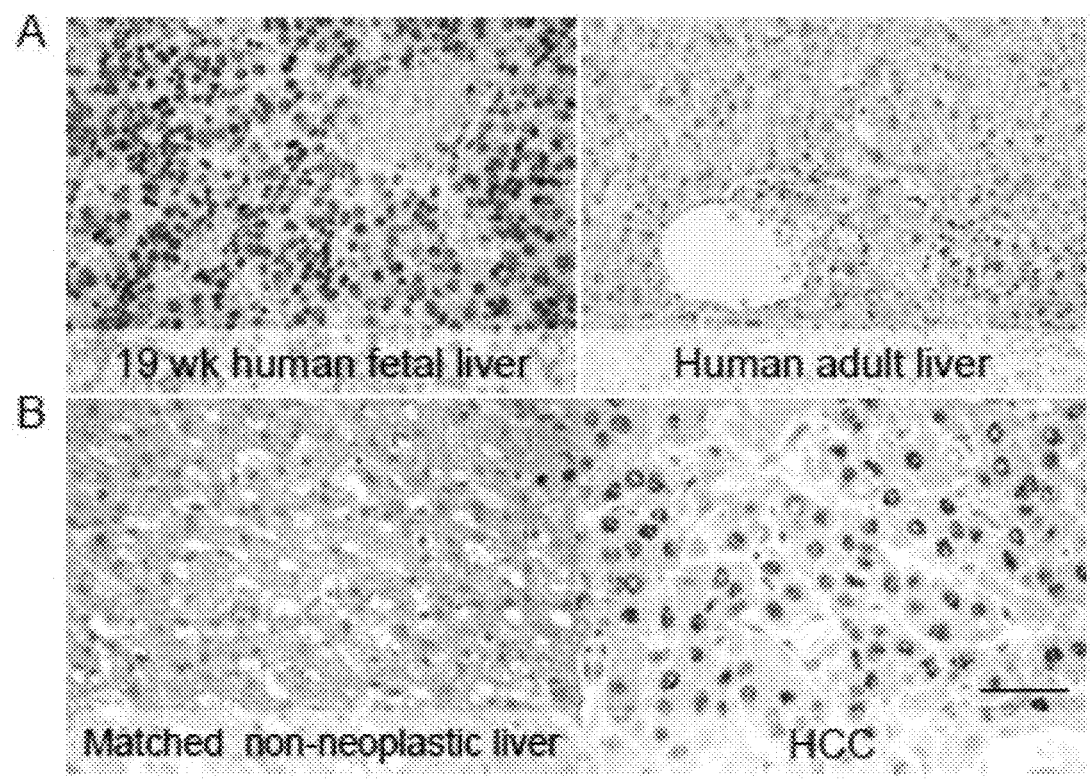

Sall4 is Expressed in Human Fetal Liver, Silenced in Adult Liver, and Reexpressed in Hepatocellular Carcinoma The expression of Sall4 in murine liver at various developmental stages has been reported previously (Oikawa et al., $Gastroenterology$, 136:1000-1011 (2009)), but its expression pattern in human liver and HCC has not been well studied. To test the hypothesis that SALL4 is re-expressed in a subgroup of HCC, the expression of SALL4 in primary human HCC specimens at both the mRNA and protein levels was examined. In order to determine if there is aberration of SALL4 expression in HCC livers, first investigated was SALL4 expression in normal human livers at both the fetal and adult stages. By immunohistochemistry (IHC), detected SALL4 expression in human fetal but not adult liver was detected (FIG. 28A).

Subsequently, the expression of SALL4 in human HCC was investigated. A panel of tissue microarrays (TMAs) consisting of 179 surgically resected primary HCCs and their matched non-neoplastic liver tissues was constructed from the archives of the National University Hospital Department of Pathology, Singapore (Singapore cohort). By IHC, differential expression of SALL4 was observed in matched primary HCC and the non-HCC tissues, with more SALL4-expressing cells in HCC than the matched non-neoplastic livers (P<0.05) (FIG. 28B). Detailed analysis of the IHC data revealed SALL4 positivity in 55.6% (95/171) of the HCC tissues analyzed, albeit at variable expression levels.

Figures 28C, 28D, 28E:
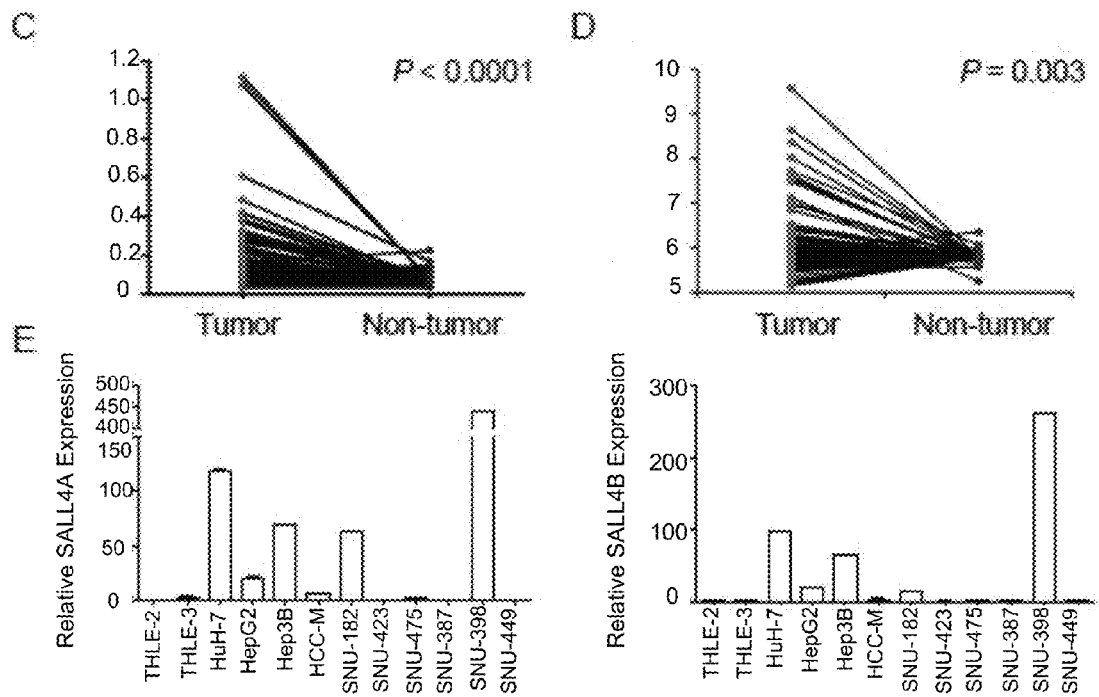

To further confirm that SALL4 is upregulated in a subgroup of HCC, SALL4 expression was analyzed by gene expression microarray in, various independent cohorts of primary HCC samples. In a cohort of 228 matched primary HCC and non-neoplastic liver samples from Hong Kong (Hong Kong cohort), differential SALL4 expression (P<0.0001), similar to what we observed in the Singapore cohort, was observed with SALL4 being upregulated in HCCs compared to the non-tumor tissues (FIG. 28C). Furthermore, various global gene expression data was pooled from public databases (details on the datasets are described in Supplementary Appendix) and similar differential SALL4 expression in the HCC and non-tumor liver tissues was observed (P=0.003) (FIG. 28D). From these independent sizable cohorts of primary HCC and matched non-neoplastic liver tissues, it was established that SALL4 is upregulated in a subgroup of human HCC livers, but remained silenced in their matched adult nonneoplastic livers.

Analysis of endogenous SALL4 expression across a panel of 10 human HCC cell lines by qPCR showed the expression of SALL4 at high, moderate or low levels in these HCC cell lines, an expression pattern that recapitulates that of the primary human HCC tissues (FIG. 28E). Moreover, SALL4 expression was not detected in the two immortalized non-transformed liver cell lines, THLE-2 and THLE-3. This data indicates that these cell lines are appropriate models for further testing of our hypothesis, and also confirmed the findings that SALL4 is re-expressed in a subgroup of HCC.

After establishing the expression pattern of SALL4 in human livers at various stages, including in the diseased state of HCC, it was then asked how SALL4 is re-activated in HCC. The SALL4 gene is located on chromosome 20q13.13-13.2, a locus that has been frequently reported to be amplified in HCC (Beroukhim et al., Nature, 463:899-905 (2010); Tabach et al., PLoS One, 6:e14632 (2011)) Hence, it was hypothesized that SALL4 gene amplification is one of the mechanisms underlying SALL4 re-activation in HCC. Indeed, Illumina genotyping assay confirmed SALL4 copy number gain in 28.9% of the 228 primary HCC tissues from the Hong Kong cohort. To investigate if the genomic status of SALL4 was correlated with expression level, CNV data deposited in the Gene Expression Omnibus (GEO) (Accession: GSE25097) and The Cancer Genome Atlas (TCGA) (Accession: TCGA-G3-A25Z) databases was extracted. A significant positive correlation between SALL4 copy number and SALL4 expression (r=0.7356; P<0.0001) in these primary HCC tissues was observed (FIG. 28F). Collectively, these data indicate that SALL4 genomic amplification represents one of the mechanisms underlying re-expression of SALL4 in HCC.

In summary, the results obtained from a number of different assays and cohorts of clinical specimens demonstrated that SALL4 is expressed in human fetal livers, silenced in adult livers, and re-expressed in many HCC livers.

Patients with SALL4-Positive HCC have Worse Prognosis Compared to Patients with SALL4-Negative/Low HCC To analyze the clinical relevance of SALL4 re-activation in HCC, clinicopathological analysis was carried out. HCC patients with SALL4 overexpression demonstrated worse prognosis compared to SALL4-low HCC, as revealed from the clinicopathological analyses of the two cohorts of primary HCC samples from Singapore and Hong Kong. Comparing survival status of HCC patients from Singapore, absence of SALL4 protein (IHC score 0) confers significant survival advantage (Overall survival: P=0.036, HR 1.79; Disease-free survival: P=0.014, HR 1.79), from a univariate analysis (FIG. 29A). The relatively longer survival observed in the patients from the Singapore cohort can be attributed to the fact that the primary HCC tissues were from patients who underwent curative surgery. Interesting, from this batch of primary HCC samples, a significant positive correlation of SALL4 expression with Ki-67, a proliferative marker (r=0.234, P=0.002), was also observed indicating a more aggressive phenotype for HCCs with higher SALL4 expression.

Similarly, SALL4 expression was associated with poor survival outcome in the Hong Kong cohort of primary HCC samples (Poverall=0.002; PDisease-free=0.001) (FIG. 29B). Furthermore, the analysis of these 228 clinical specimens also revealed significant positive correlation of SALL4 expression and HCC tumor stages (r=0.142, P=0.01989), indicating that HCCs that are positive for SALL4 tend to be the ones at late stages.

In a multivariate Cox regression model, SALL4 has shown to be an independent prognostic factor for disease-free survival (P=0.045, HR 1.86, 95% CI 1.01 to 3.44), after adjusting for other clinicopathological features that have been reported to have prognostic value in HCC.

Recent studies have compared gene expression profiles of various cancers with ESC/hepatic progenitor gene expression signatures (Ben-Porath et al., Nat Genet, 40:499-507 (2008); Lee et al., nat Med, 12:410-416 (2006); Woo et al., Cancer Res, 70:3034-3041)2010)). Results acquired from these studies indicated that cancer patients with ESC/hepatic progenitor cell-like gene expression signatures have poor prognosis. A plausible hypothesis is that tumors evolved either from the stem/progenitor cells or dedifferentiated into an early developmental stage are more aggressive. To investigate if SALL4-positive HCCs share gene expression pattern with fetal hepatoblasts, global gene expression data of human hepatocytes, human fetal livers, and human HCCs was extracted from the GEO database and carried out hierarchical cluster analysis. From the analysis, high SALL4 HCCs clustered tightly with human fetal livers, while low SALL4 HCCs clustered with hepatocytes (FIG. 29C), indicating that HCCs expressing SALL4 share similar gene expression pattern with hepatic progenitor cells, hence are poorly differentiated, more aggressive, and have poor prognosis.

To further prove that SALL4 predicts worse prognosis in HCC, gene set enrichment analysis (GSEA) was carried out to investigate the enrichment of a few pathways that have prognostic value in SALL4-high/low HCCs. From our GSEA analysis, it was found that genes that are upregulated in HCC with poor survival were significantly enriched in our high SALL4 HCC subgroup (NES=1.795, P=0.013). Moreover, an embryonic stem cell signature was also significantly enriched in the high SALL4 HCC group (NES=1.822, P=0.013). These data recapitulate the previous clinicopathological and hierarchical cluster analyses, and further strengthen the idea of SALL4 being a prognostic marker that is enriched in the more aggressive progenitor-like HCC with poor prognosis. Furthermore, a significant enrichment of genes upregulated in metastasis in the high SALL4 HCC (NES=1.736, P=0.006), while genes downregulated in metastasis were enriched in the low SALL4 HCC, was also observed (NES=−1.598, P=0.005). The upregulation of genes that are important in promoting metastasis in high SALL4 HCC, and enrichment of metastasis suppressor genes in low SALL4 HCC indicate that the high SALL4 HCC group has the potential to be metastatic. Also, a significant enrichment of genes upregulated in hepatoblastoma, a malignant embryonal liver tumor, in high SALL4 HCC (NES=1.950, P=0.002), and an enrichment of genes downregulated in hepatoblastoma in low SALL4 HCC was also observed (NES=−1.522, P=0.048). Interestingly, a significant enrichment of genes upregulated in Chiang et al. proliferation subclass of HCC in our high SALL4 HCC (NES=1.579, P=0.049), while genes downregulated in the proliferation subclass were enriched in low SALL4 HCC (NES=−1.473, P=0.054) were also observed, indicating that high SALL4 HCC is more proliferative than the low SALL4 HCC. Undoubtedly, these data further substantiate that SALL4 expression predicts poor prognosis in HCC (FIGS. 32A-32F).

Taken together, it was concluded that the expression of SALL4 in HCC predicts poor prognosis for HCC patients, as SALL4 expression is significantly correlated with poorer survival, more aggressive tumor phenotype, and more advanced tumor stages. These data strongly support SALL4 having prognostic value for HCC.

Figure 30A:
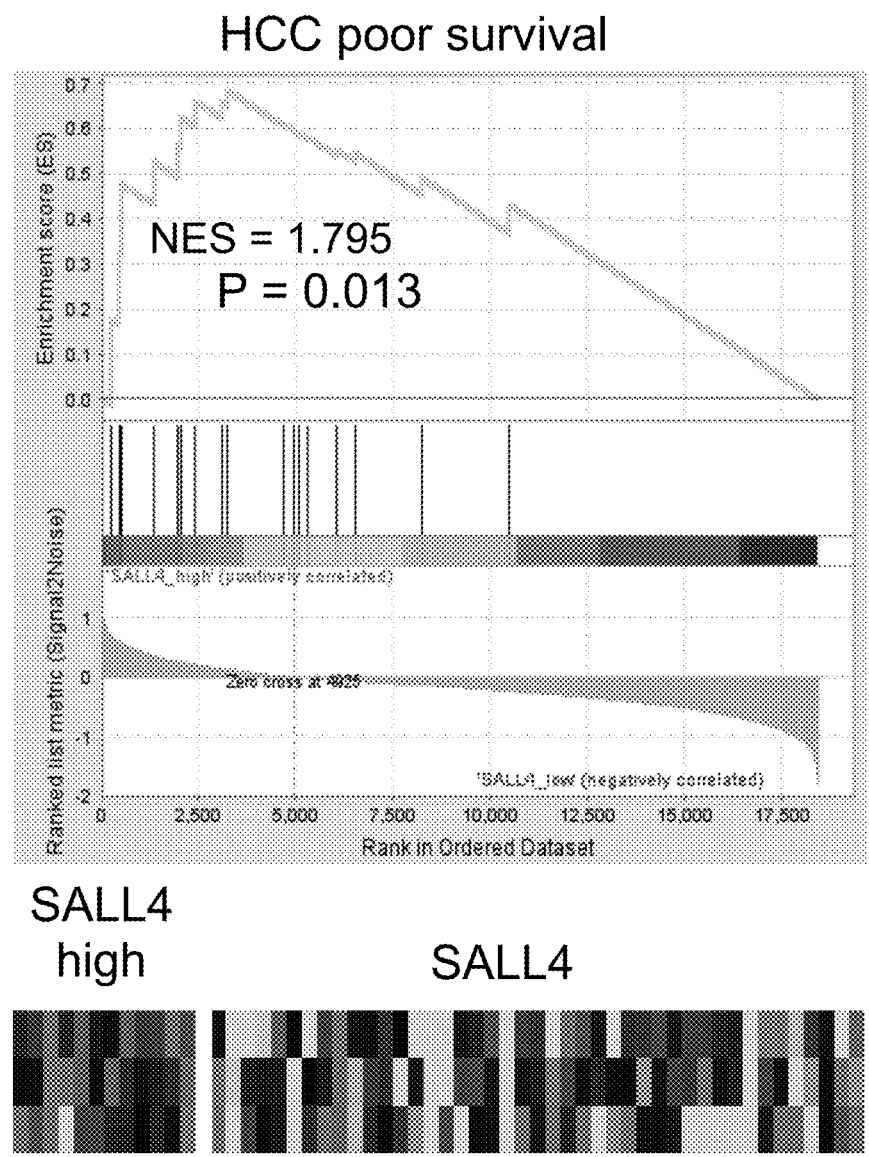

Loss of SALL4 by RNA Interference (RNAi) Leads to Decreased HCC Cell Viability In Vitro and Impaired HCC Cell Tumorigenicity In Vivo Next, the potential of SALL4 as a molecular target for therapeutic intervention in HCC was examined by performing loss-of-function studies. To knock down SALL4 expression, lentiviral-mediated RNAi was carried out by introducing shRNAs specifically targeting SALL4 into various human HCC cell lines. Two SALL4-specific shRNAs, denoted as shSALL4 1 and shSALL4 2, were used to knock down both SALL4A and SALL4B in HCC cells. In order to exclude the off-target effect of RNAi as well as the effect of virus transduction on HCC cells, scrambled shRNAs, denoted Scr shRNA 1 and Scr shRNA 2, were used as negative controls. The efficiency of virus transduction was assessed by the percentage of cells expressing GFP by flow cytometry. High transduction efficiency was consistently obtained, with GFP expression frequently >80% (data not shown). By using both shSALL4 1 and shSALL4 2, both SALL4 isoforms were knocked down to 30% of wild type RNA levels. At the protein level, both shSALL4 1 and shSALL4 2 were efficient in knocking down SALL4 protein to nearly undetectable levels (FIG. 30A).

Figure 30B:
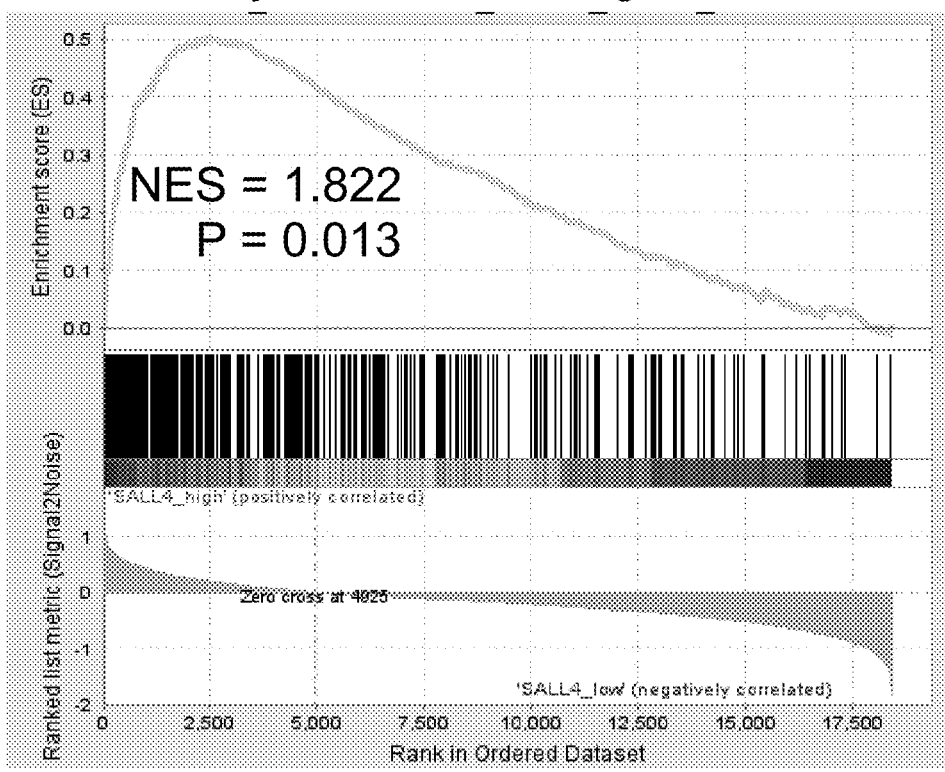
Figure 30B:
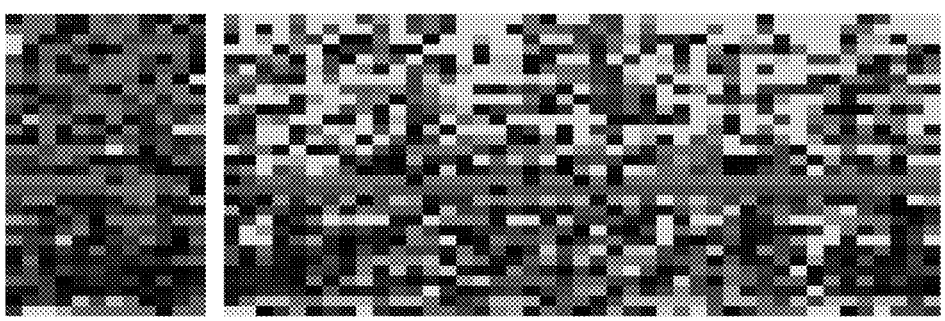

To investigate the phenotypic changes of HCC cells upon SALL4 gene knockdown, SALL4 was knocked down in three HCC cell lines with high (SNU-398), moderate (HuH-7), and undetectable (SNU-387) endogenous SALL4 expression and assessed cell viability by MTS assay. Remarkably, in HCC cell lines that express moderate to high endogenous SALL4 expression, cell viability was significantly decreased upon SALL4 gene knockdown (FIG. 30B). This implicates that SALL4 is essential in maintaining HCC cell viability. In contrast, HCC cell viability was not affected by SALL4 RNAi in the SNU-387 cell line that does not express SALL4 (FIG. 30B), indicating that the effects of the shRNAs used in this study were specific to SALL4 and not a result of off-target effects.

Figure 30C:
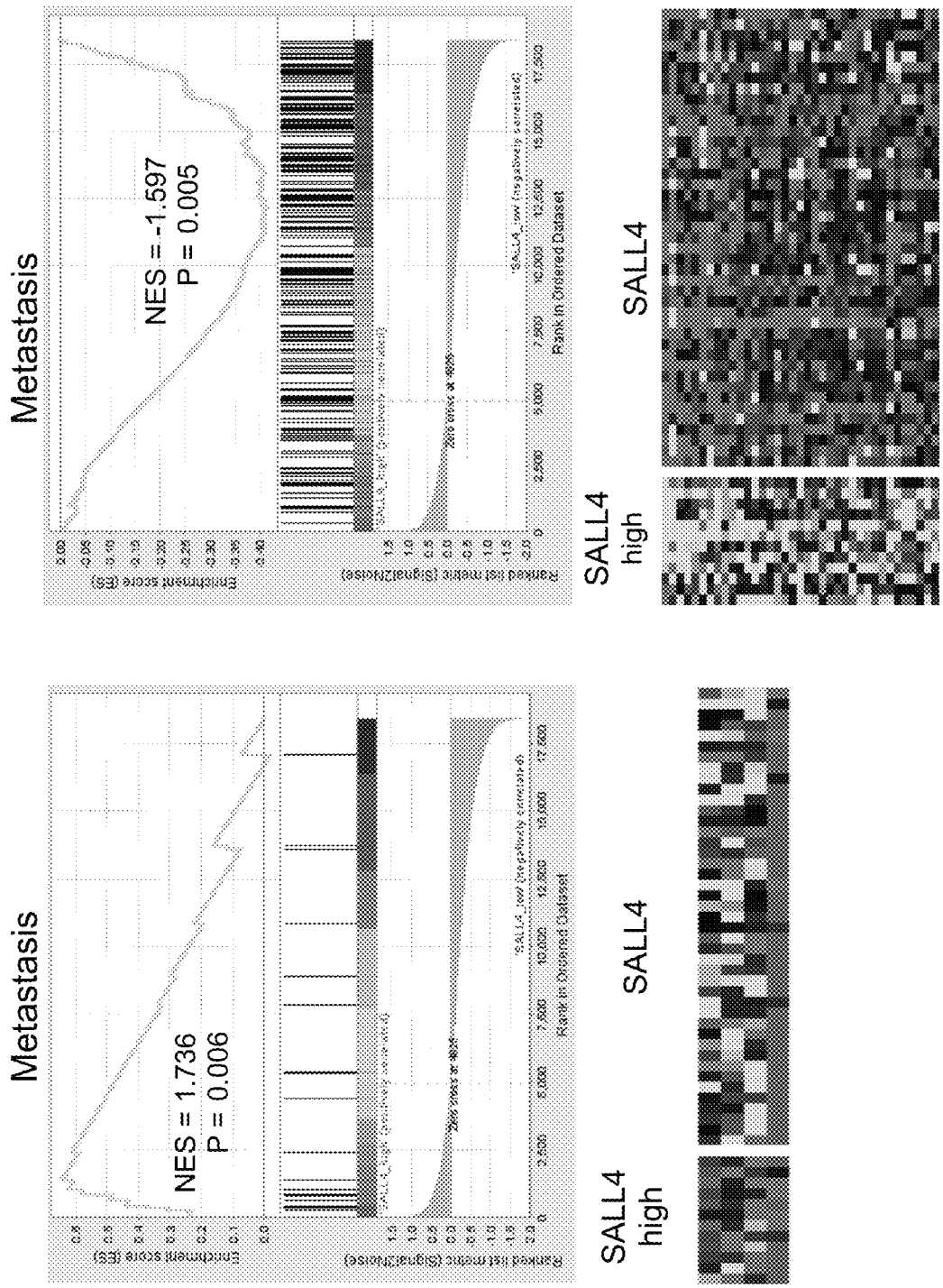
Figure 30:
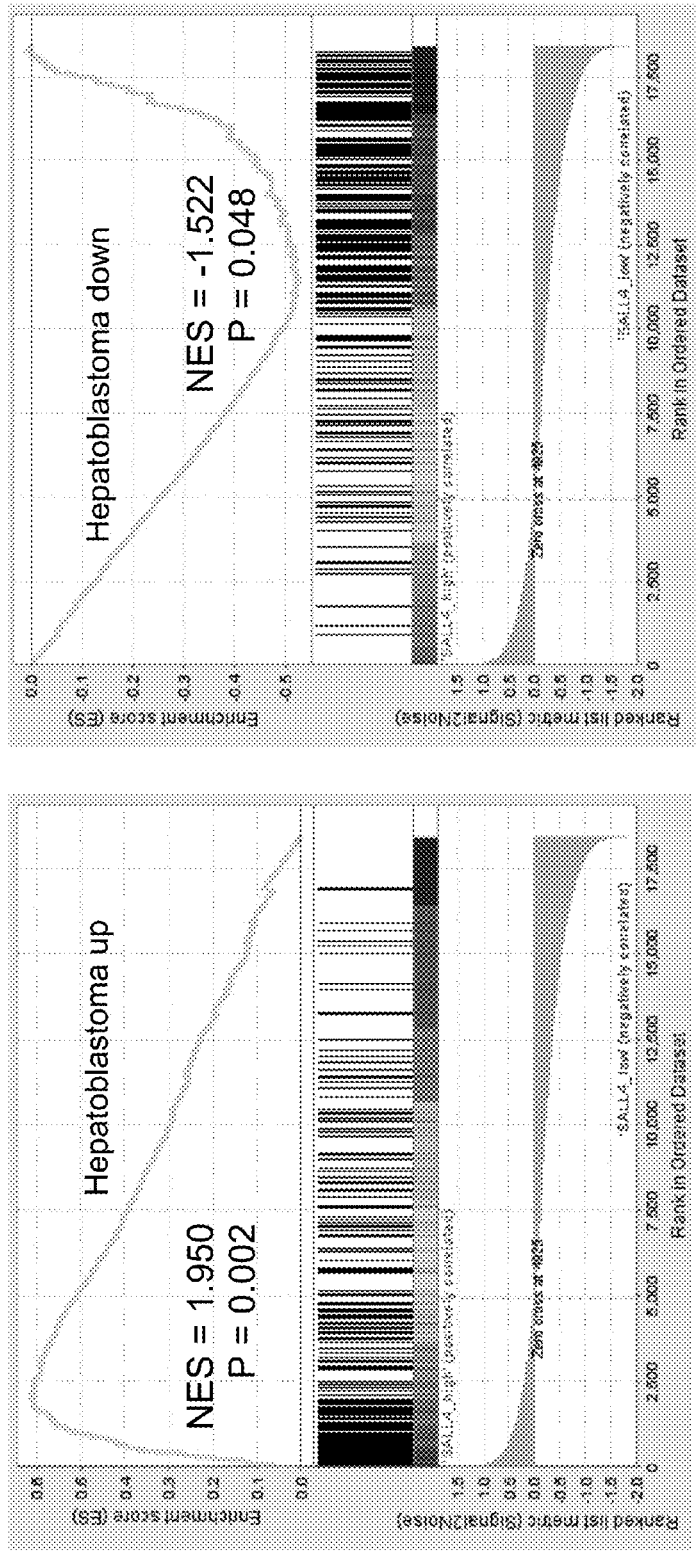
Figure 30:
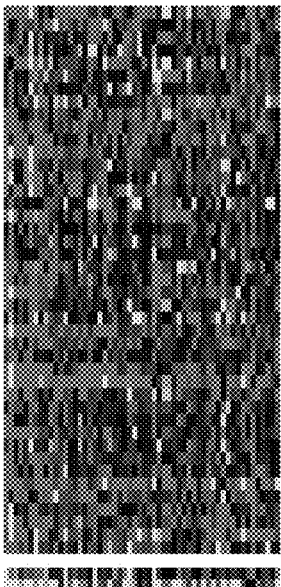
Figure 30:
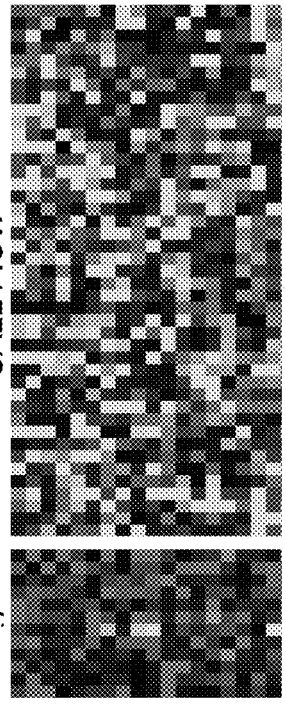
Figure 30E:
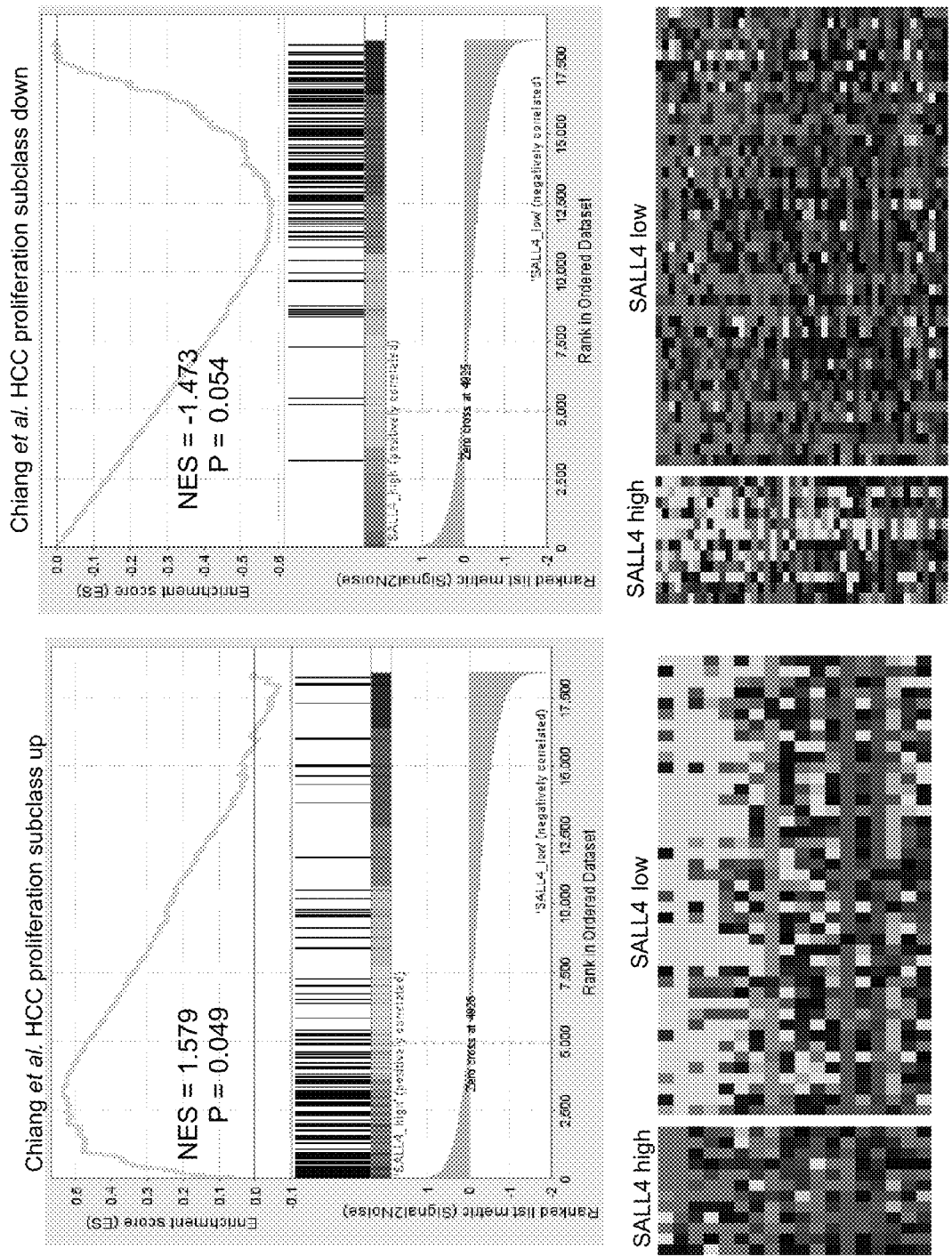

To further characterize the effects of loss of SALL4 in HCC cells, more functional assays in SNU-398 cells, which express high SALL4, were carried out. The decrease in cell viability of HCC cells expressing high levels of SALL4 following SALL4 knockdown was confirmed by cell counting with trypan blue (FIG. 30C). Furthermore, increased apoptosis in SALL4-knockdown HCC cells was observed by assessing caspase activities. Increased caspase 3/7 activities was observed upon loss of SALL4 in SNU-398 HCC cells (FIG. 30D), as well as increased cleaved caspase 3 (FIG. 30E). These data further confirm that SALL4 plays a crucial role in maintaining survival of those HCC cells in which it is expressed.

To examine if SALL4 has a role in maintaining tumorigenicity of HCC cells, in vivo xenotransplantation assays were carried out. HuH-7 and SNU-398 cells were transduced with lentviruses expressing either shSALL4 1 or Scr shRNA 1 and transplanted subcutaneously into the flanks of NOD/SCID mice. Knocking down SALL4 in these two HCC cell lines greatly reduced the ability of these cells to propagate tumors in immunocompromised mice. SALL4 knockdown conferred survival advantage to the mice, as seen from the Kaplan-Meier analysis. Furthermore, SALL4-knocked down HuH-7 cells generated smaller tumors at a later onset, as compared to the control cells; only one out of the three mice that received SALL4-knocked down HuH-7 had tumor formation, while all the three mice that received Scr shRNA 1-treated HuH-7 developed large subcutaneous tumors. These data indicate that SALL4 is required for tumorigenicity of HCC cells.

As high SALL4-expressing HCCs share gene expression patterns with fetal hepatic cells and have a poorer prognosis, it was asked if loss of SALL4 in these cells reversed this phenotype. To answer this, microarray analysis of gene expression profiles of Scr shRNA 1- and shSALL4 1-treated SNU-398 were carried out, and then hierarchical clustering of these gene expression profiles along with those derived from normal human hepatocytes and fetal livers was carried out. As expected, SNU-398 cells treated with Scr shRNA 1 clustered closely with human fetal livers, as both express high levels of SALL4. Interestingly, SALL4-knocked down SNU-398 cells clustered with human hepatocytes, indicating downregulation of SALL4 can render HCC less aggressive.

In summary, these loss-of-function studies demonstrated that SALL4 is essential in maintaining the viability of HCC cells, and that reduction of SALL4 diminishes the ability of HCC cells to propagate tumors in xenotransplants, emphasizing a functional role for SALL4 in hepatocarcinogenesis. More importantly, the studies show that SALL4 is an important therapeutic target in HCC, as loss of SALL4 reversed the aggressive phenotypes of HCCs.

Targeting SALL4 by a Novel Peptide Affects HCC Cell Survival

As SALL4 is potentially a good therapeutic target for HCC, a targeted therapy to antagonize the oncogenic role of SALL4 was developed. It is known that SALL4 functions as a transcription repressor by recruiting a HDAC-containing NuRD complex, and that the tumor suppressor PTEN is among the target genes repressed by SALL4.26 SALL gene family members share a conserved 12-amino acid (12-AA) N-terminal domain, which has been implicated in the interaction with components of the NuRD complex (Kiefer et al., *J Biol Chem*, 277:14869-14876 (2002); Lauberth et al., *J Biol Chem*, 282:34858-34868 (2007); Laubert et al., *J Biol Chem*, 281:23922-23931 (2006)). It was hypothesized that this 12-AA peptide could be used as a competitive inhibitor to block the interaction between SALL4 and NuRD and as a result block the NuRD mediated SALL4 repression function. It was also predicted that upon treatment with peptide, PTEN expression would be upregulated and that effects on HCC cell growth and survival similar to those observed in SALL4 knockdown studies would be observed.

Figure 31A:
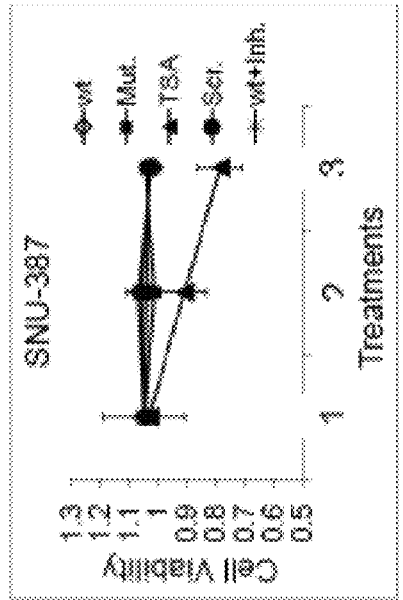

Consistent with this hypothesis, when added to cultures, this 12-AA SALL4 peptide was effective in targeting SALL4 pathways and resulted in a decrease in HCC cell viability. When 5 µM or 20 µM of SALL4 peptide (wt) was given to SNU-398 cells (high SALL4), the number of viable cells was reduced, as compared to SNU-398 cells treated with control mutant peptide (Mut.) and scrambled peptide (Scr.). Trichostatin A (TSA), a general HDAC inhibitor, was used as a positive control drug in this assay. Importantly, the PTEN inhibitor SF1670 was shown to be able to rescue the phenotype when it was added to the cells treated with SALL4 peptide (wt+Inh.), as evidenced by the maintenance of cell viability (FIG. 31A). These results indicate that PTEN plays an important role in the SALL4 peptide-induced loss of HCC cell viability.

Figure 31B:
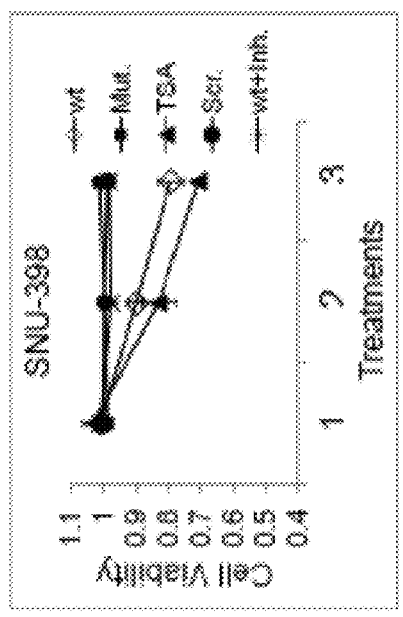

In contrast, SALL4 peptide had no effect on SNU-387 cells that have undetectable endogenous SALL4 expression (FIG. 31B). There was no change in the number of viable SNU-387 cells when treated with SALL4 peptide (wt), similar to the controls (Mut. or Scr.). However, a similar reduction in the number of viable SNU-387 cells was observed in cells treated with TSA at 50 nM and 100 nM doses. This indicated that SALL4 peptide is a specific drug for SALL4-overexpressing HCC cells with minimal toxicity on SALL4-negative cells, as compared to the HDAC inhibitor TSA.

Figure 31C:
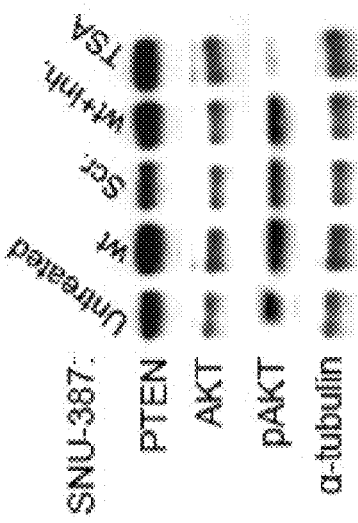
Figure 31D:
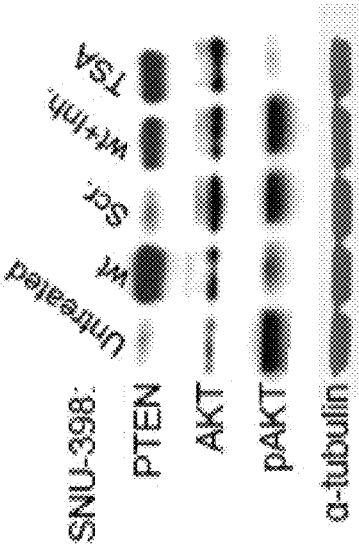

To confirm the involvement of the PTEN tumor suppressor in the SALL4 peptide-induced reduction of HCC cell viability, PTEN expression was analyzed by western blot upon drug treatment. SALL4 peptide treatment induced an extensive increase in PTEN protein in SNU-398 cells, compared to control untreated cells and Scr. peptide-treated cells. Expectedly, TSA also induced PTEN upregulation in SNU-398 cells (FIG. 31C). In contrast, SALL4 peptide has negligible effect on PTEN expression in SNU-387 cells (FIG. 31D). If the increase in PTEN expression has an effect in PI3K signaling was next examined. PTEN functions as a phosphatase to dephosphorylate AKT. Western blot analysis demonstrated a marked reduction of phospho AKT protein levels upon SALL4 peptide treatment in high SALL4 SNU-398 cells (FIG. 31C), but not in low SALL4 SNU-387 cells (FIG. 31D), indicating that the increase in PTEN expression level has a functional role in blocking the PI3K survival signaling by dephosphorylating AKT. Furthermore, this effect can be rescued by the PTEN inhibitor, consistent with the role of SALL4 regulating this pathway.

Figures 31E, 31F, 31G, 31H:
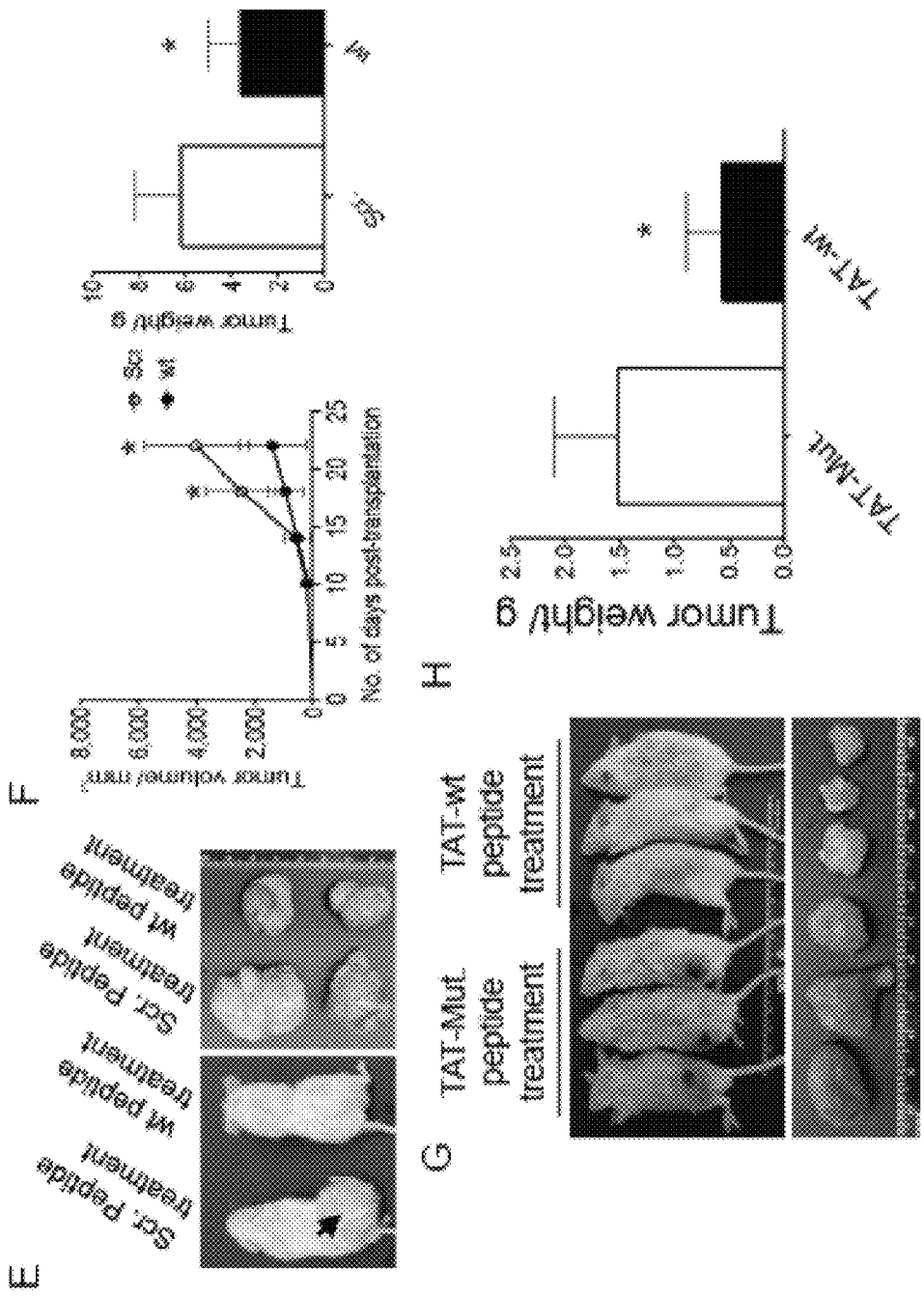
Figures 32A, 32B:
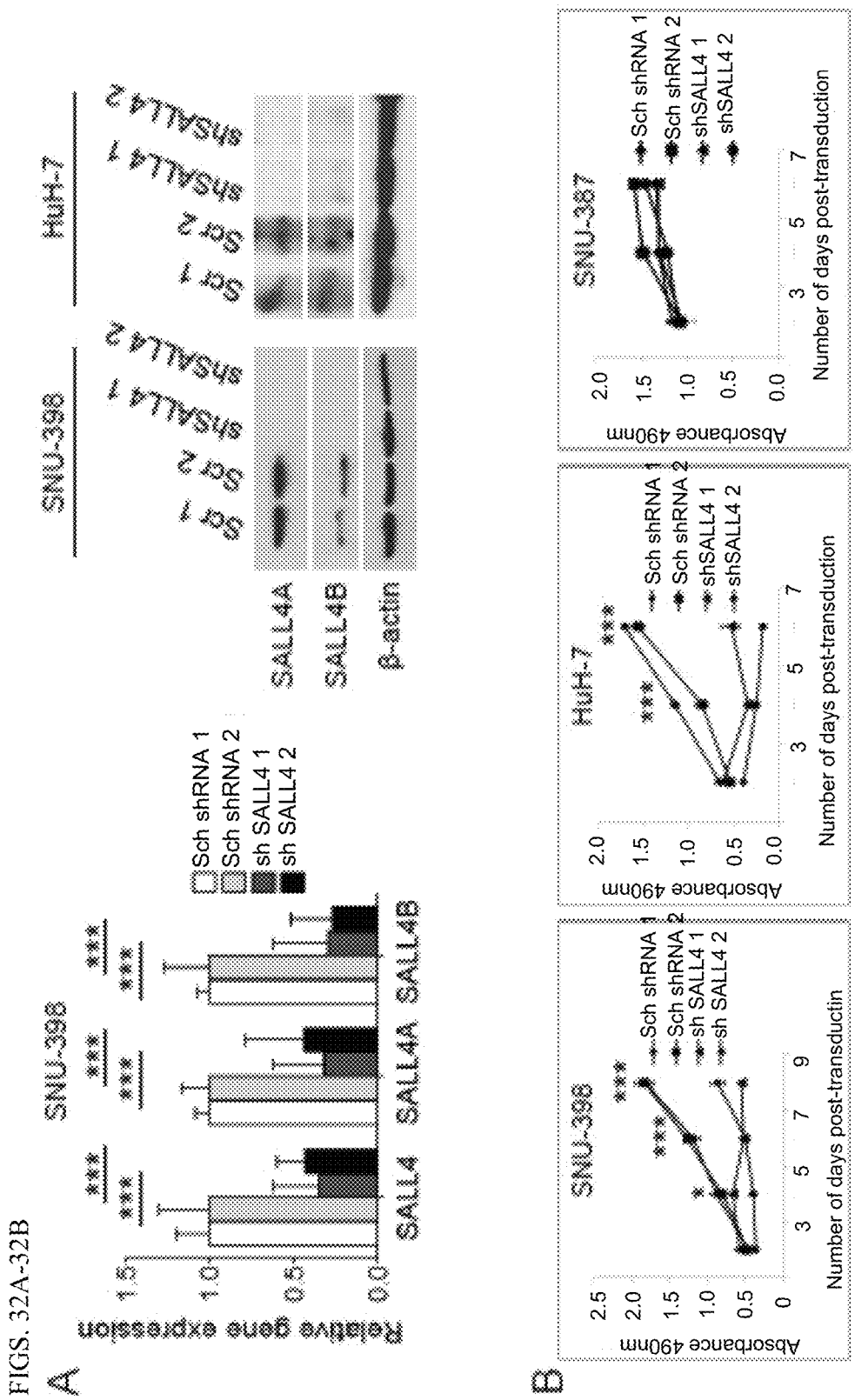
Figure 32C:
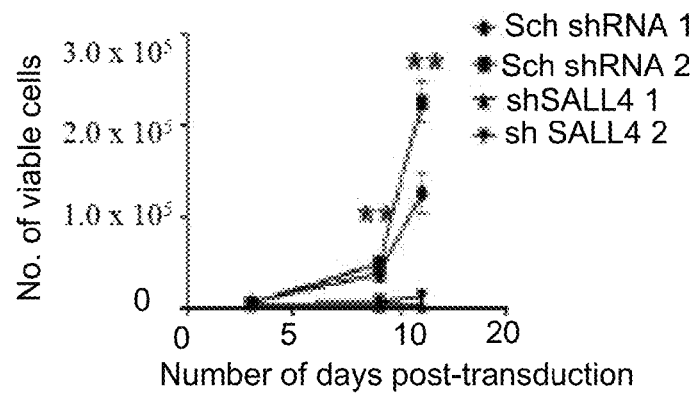
Figure 32D:
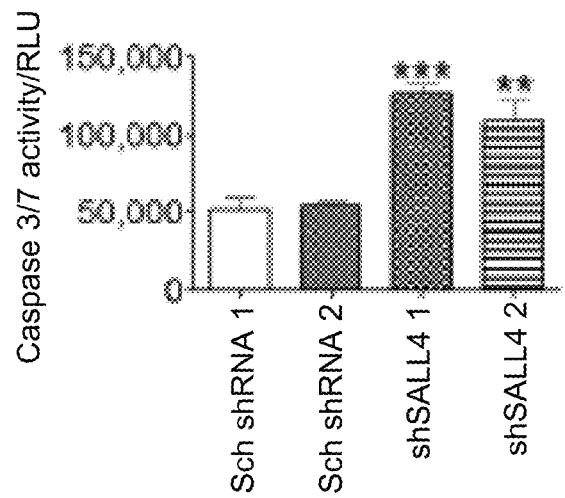
Figure 32E:
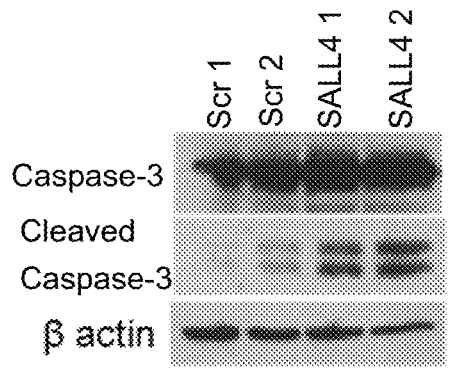
Figure 32F:
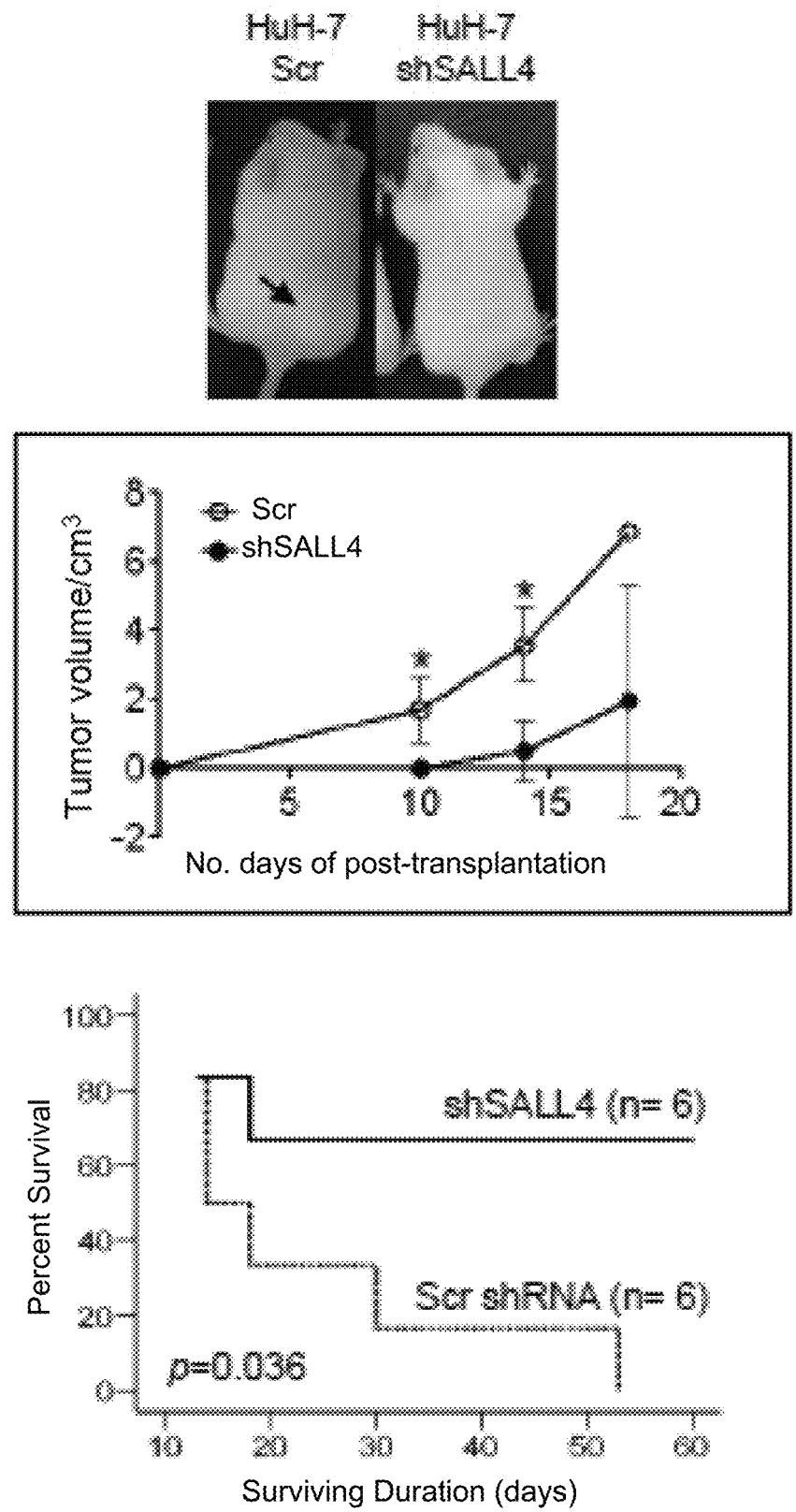

To test the therapeutic effect of this peptide in vivo, SNU-398 cells were subjected to in vitro treatment with 20 µM of wt or Scr. peptide and transplanted the peptide-treated cells subcutaneously into the flanks of NOD/SCID mice. Interestingly, SALL4 peptide treatment compromised tumorigenicity of the HCC cells, as Scr peptide-treated cells grew into larger subcutaneous tumors when compared to that of wt peptide-treatment (FIG. 31E). Tumor volume in the wt peptide-treated group was significantly reduced compared to Scr. peptide treatment (FIG. 31F). Moreover, the tumor burden (weight post-dissection at day 26) further confirmed that the tumor load was reduced with wt peptide treatment (FIG. 31F).

Direct intracellular delivery of peptides has long been a problem associated with peptide- or protein-mediated treatment. To overcome the membrane-mediated permeability barriers and enable efficient delivery of the peptides into cells in vivo, therapeutic peptides can be conjugated to protein transduction domains, such as the HIV-1 TAT motif (Cerchietti et al., *Bold,* 113:3397-3405 (2009)). The TAT protein transduction domain is able to promote efficient cellular uptake of peptides and acts as a nuclear localization signal, which is useful for the delivery of inhibitors of transcription factors (Wadia et al., 57:579-596 (2005)). This technology was used to develop a model of in vivo treatment of HCC more like that encountered in human patients. Mut and wt peptides were conjugated with TAT and delivered the TAT-Mut or TAT-wt peptides intraperitoneally into NOD/SCID mice transplanted subcutaneously with SNU-398 cells. Similar to previous experiments, in which HCC cells were treated in vitro with unconjugated peptides prior to transplantation, TAT fusion wild type peptides were able to reduce the tumorigenicity of SNU-398 HCC cells (FIG. 31G). The tumor loads (weight post-dissection) at 18 days post-treatment of TAT-wt peptide treated mice were significantly smaller than tumors in TAT-Mut. peptide treated mice (FIG. 31H). These experiments confirm that the SALL4 peptide has biological activity both in vitro and in vivo in a xenotransplant model.

Together, the data indicates that the SALL4 peptide can be used as a potential targeted therapy for a subgroup of HCC, as it effectively and specifically reduces viable SALL4-positive HCC cells by activating the PTEN tumor suppressor and inhibiting PI3K/AKT survival signaling in HCC cells.

Discussion

HCC is one of the deadliest cancers, with a mortality to incidence ratio of almost 1.1 Although previously considered a dominant disease mostly in developing countries, in which hepatitis B is endemic, there has been an increasing trend of HCC incidence in developed nations like Europe and United states, with increasing prevalence of hepatitis C and alcoholism. While surgical intervention is curative, most patients are not good candidates due to late stage of presentation and/or poor liver function owing to underlying liver cirrhosis. In the United States, less than 5% of patients are candidates for hepatic resection (El-Serag et al., *NEJM,* 365:1118-1127 (2011)). To date, even the most effective chemotherapy drug for advanced HCC, sorafenib, has limited efficacy (Yang et al., *Infect Dis Clin North Am* 24:899-919 (2010); Keating et al., *Drugs,* 69:223-240 (2009)), possibly due to the disease complexity and heterogeneity in hepatocarcinogenesis. Therefore, there is an urgent need for better understanding of the underlying mechanism in hepatocarcinogenesis, and more effective therapies for HCC.

SALL4 is one of the important transcription factors implicated in the transcriptional regulatory network essential for the maintenance of embryonic stem cell characteristics (Yang et al., *PLoS One,* 5 (2010); Rao et al., *Mol Cell Biol,* 30:5364-5380 (2010); Ynag et al., *PNAS USA,* 105:19756-19767 (2008); Wu et al., *J Bio Chem,* 281:24090-4 (2006)). It is important in murine liver development, as Sall4 regulates differentiation of hepatoblasts to the cholangiocytic lineages (Oikawa et al., *Gasteroenterology,* 136:1000-11 (2009)). Genes involved in liver development and regeneration are likely to be implicated in the development of HCC. In this report, the unique expression pattern of SALL4 in human livers at various developmental stages—activated in fetal liver, silenced in adult livers, and reexpressed in HCC as an oncofetal protein was established (FIG. 33).

Two earlier reports, however, documented negative SALL4 expression in HCC by IHC staining (Cao, et al., *cancer,* 115:2640-51 (2009); Ushiku et al., *Am J Surg Pathol,* 34:533-40 (2010)). The discrepancy in SALL4 staining can possibly be attributed to the difference in antibodies used. Also, a larger cohort of primary HCC tissues was analyzed herein, compared to a total of seven and 60 cases analyzed by Cao et al. and Ushiku et al., respectively. Despite the difference, the results provided herein are reliable because of the rigorous testing of the specificity the antibody used in the study herein by including positive and negative controls, and the IHC data was supported by gene expression microarray data.

Many mechanisms can account for re-activation of oncogenes in malignancies. Chromosome 20q13 is frequently amplified and implicated in cancer initiation (Tabach et al., *PLoS One,* 6:e14632 (2011)). The frequent gain of chromosomal locus 20q13.13-20q13.223,24, where SALL4 is located, led to the hypothesis that genomic amplification of SALL4 is a mechanism leading to SALL4 reactivation. From the analysis of high throughput genomics data from various cohorts of primary human HCC described herein, copy number gain of SALL4 in HCC was confirmed. This data not only confirmed the mechanism underlying SALL4 re-activation, it also identified a novel oncogene located in this frequently amplified chromosomal region in cancers.

Identification of robust biomarkers that can be used to prognosticate patients ensures more effective clinical management. As shown herein, SALL4 is a prognostic marker for HCC. The reexpression of SALL4 in HCC is clinically significant, as HCC patients with overexpressed SALL4 have enriched hepatic progenitor-like gene signature and tend to have poorer prognosis in terms of survival, tumor stage, and the aggressiveness of tumors. Immunohistochemistry and other in situ hybridization (ISH) assays like FISH or chromogenic ISH (CISH) can be developed and standardized to identify HCC patients that have elevated SALL4 expression and/or genomic amplification in the clinical settings.

Overexpression of a particular gene in tumor tissues can play a role as a driver in the cancer development or a bystander expressed only as a result of carcinogenesis. The loss of function studies described herein substantiate that SALL4 has a functional role in human HCC and is not merely a bystander. Knocking down of SALL4 led to decreased HCC cell viability, slower growth, increased apoptosis, and impaired tumorigenicity, indicating that SALL4 is required and essential for maintaining the malignant state. Furthermore, loss of SALL4 did not affect HCC cells that do not express SALL4, further highlighting SALL4 as a good candidate for therapeutic targeting.

In addition to our loss-of-function studies, gain-of-function studies were also conducted to investigate the contributory roles of SALL4 in HCC development. Spontaneous liver tumor formation in SALL4B transgenic mice was observed, which indicates a functional role for SALL4 in HCC. The contributory role of SALL4 in liver tumor formation was also confirmed by employing a two-stage chemical carcinogenesis protocol to induce preneoplastic lesions in the livers. Using the two well-characterized hepatotoxins, alkylating agent Nnitrosodiethylamine as an initiator and phenobarbital as a promoter, accelerated liver adenoma and carcinoma development in SALL4B livers subjected to this treatment regime was demonstrated. The increased sensitivity of liver tumor formation in our SALL4B DEN/PB model can possibly be attributed to increased hepatic proliferation promoted by SALL4, as evidenced by increased liver/body weight ratio, increased Ki-67 expression and increased mitosis.

Traditionally, oncofetal antigens are surface proteins that are expressed only in defined fetal organs during development normally, but are re-expressed in cancers that originated from those specific organs. Given their unique expression pattern, they can be used for diagnosis of certain cancers, such as a positive alpha-fetoprotein expression in a tumor can help the clinician to diagnose HCC and also use this marker to follow up for disease relapse. Some of them are even targets for vaccination against cancers. However, most of these proteins do not have functional roles in the induction or promotion of carcinogenesis. Proposed herein is that SALL4 represents a new class of oncofetal proteins with great prognostic and therapeutic values. Unlike alpha-fetoprotein, SALL4 can be a direct drug target owing to its functional roles in hepatocarcinogenesis, besides being a prognostic marker for HCC. Other ESC factors, such as Nanog, would be alternative candidate genes to be tested for this new oncofetal protein concept.

Reviews of the pathways involved in pathogenesis of HCC have revealed that the Ras/Raf/MAPK, PI3K/AKT/mTOR, and Wnt/□-catenin pathways are critical pathways for hepatocarcinogenesis (Farazi et al., *nat Rev Cancer* 6:674-687 (2006); Llovet et al., *J Hepatol,* 48 Suppl 1:S20-37 (2008)). While the Ras/Raf/MAPK pathway is currently being clinically targeted by sorafenib, molecular targeted therapies against the others are still in preclinical or early phase clinical trials. Of these, some have shown promising results, including the mTOR inhibitor AZD8055 and HDAC inhibitor vorinostat. The study herein has emphasized that SALL4 is clinically important in HCC, and targeting SALL4 with the peptide is a promising intervention for HCC, especially for the more advanced stage HCCs. The SALL4 peptide works by blocking the recruitment of a HDAC-containing complex, NuRD, at the N-terminal of SALL4, and hence antagonizing the transcriptional repression function of SALL4. This activates PTEN transcription and represses the PI3K/AKT survival signaling. The studies herein indicate that the SALL4 peptide exerts its therapeutic effect through both the HDAC and PI3K/AKT/mTOR signaling pathways; it works as a gene-specific or cell-type specific HDAC inhibitor that can affect the PTEN/PI3K/AKT/mTOR pathway.

The discovery of a role for SALL4 in HCC, its association with prognosis, and a peptide blocker has potential therapeutic significance in HCC. Testing for the presence of SALL4 at diagnosis may be helpful not only in prognosis, but also allows specific selection of patients who are likely to be responsive to treatment. In addition, given the mechanism of action of the peptide, patients with SALL4 may be responsive to therapies which include HDAC and/or PI3 kinase inhibitors. Furthermore, the SALL4-expressing HCC patients would likely benefit from treatment with SALL4 peptide. Given the specific expression of SALL4 in HCC cells but not in normal adult hepatocytes, treatment with SALL4 peptide will likely carry less tissue toxicity, which is especially beneficial in patients with underlying cirrhosis whose baseline liver function is already compromised.

It is also noteworthy that SALL4 is known to be enriched in "side population cells", a putative stem cell population, and its expression is associated with drug resistance in leukemia and other solid tumors such as breast cancer (Jeong et al., *PLoS One,* 6:e18372 (2011)). SALL4 also upregulates Bmi139, a gene that is important for the maintenance of the HCC side population (Chiba et al., *cancer Res,* 68:7742-9 (2008)).

In summary, the study herein reveals a novel role of the oncofetal protein SALL4 in the extensive network of heterogeneous cellular pathways underlying hepatocarcinogesis. A 12-amino acid peptide has been shown to be able to block the oncogenic role of SALL4, and hence has therapeutic potential in SALL4-positive HCCs. The study herein also shows that SALL4 is a prognostic marker and therapeutic target in HCC, laying a foundation for a more vigorous development of SALL4-specific targeted therapy to treat more aggressive HCCs.

Example 5

A Novel SALL4/c-Myc Pathway Mediates Metastasis and Drug Resistance in Endometrial Cancer Aggressive cancers and embryonic stem (ES) cell share a common gene expression signature. Identify key factor/pathway(s) within this ES signature that are responsible for the aggressiveness of cancers can lead to potential cure. In the study herein, it was found that SALL4, a top-ranked ES signature gene, is aberrantly expressed in more than 40% of primary human endometrial cancer samples. More importantly, SALL4 expression was positively correlated with worse patient survival and aggressive features such as metastasis in endometrial carcinoma. Further functional studies have shown that loss of SALL4 inhibits endometrial cancer cell growth in vitro and tumorigenicity in vivo, as a result of inhibition of cell proliferation and increased apoptosis. In addition, down-regulation of SALL4 significantly impedes migration and invasion of endometrial cancer cells in vitro and their metastatic potential in vivo. It was further confirmed that SALL4 plays an essential role in endometrial cancer survival by regulating c-Myc expression via direct binding to its promoter region. Further manipulation of SALL4 expression affected drug sensitivity of endometrial cancer cells to carboplatin. In summary, demonstrated herein is that one of the ES signature genes, SALL4, plays functional role(s) in metastasis and drug resistance in aggressive endometrial cancers, and the SALL4/c-Myc pathway is a therapeutic target for this patient population.

In this study, by screening SALL4 expression in a large cohort of endometrial cancer samples, it was found that SALL4 is aberrantly expressed in endometrial cancer patient samples when compared to normal controls. More importantly, high SALL4 expression was significantly correlated with worse patient survival and metastasis capacity. Using human endometrial cancer cell lines, extensive investigations on the biological role of SALL4 in endometrial carcinogenesis were conducted. Both the in vitro and in vivo data strongly indicate that SALL4 expression is essential in endometrial cancer survival and progression by promoting tumor metastasis and chemoresistance through activation of c-Myc. Therefore, the studies show that SALL4 should be targeted as a therapeutic option for endometrial cancer patients, especially for those with advanced or recurrent disease.

Experimental Procedures

Lentiviral Constructs and Lentivirus Generation

In brief, the expression plasmids for human SALL4A and SALL4B were constructed using FUW-Luc-mCh-puro vector (FIG. 43A). SALL4A or SALL4B mutant preserving the same amino acid sequence, but containing triple-point mutations within the SALL4shRNA1 target nucleotide sequence, which renders the transgenes resistant to SALL4 shRNA targeting, were generated using QuikChange site-directed mutagenesis kit (Stratagene) and confirmed by sequencing. Short hairpin RNAs set for human SALL4 in pLKO.1-puro vector were purchased from Open Biosystems (RHS3979) and knockdown efficiency was further evaluated. Two of them, designated as SALL4shRNA1 and SALL4shRNA 2, were selected for subsequent experiments. The sequences for SALL4 shRNAs and Scramble shRNA are listed as following: SALL4shRNA1: GCCTTGAAACAAGCCAAGCTA (SEQ ID NO: 3); SALL4shRNA 2: CTATTTAGCCAAAG-GCAAA (SEQ ID NO: 2); Scr-shRNA: CCTAAGGT-TAAGTCGCCCTCG (SEQ ID NO: 14)

Cell Culture and Stable Cell Lines

Cell lines AN3CA, HEC-1A, and KLE were kindly provided by Dr. Patricia Donahoe (Massachusetts General Hospital, MA, USA) (31). HEC-1B, Ishikawa, RL-95-2 and SKUTB were kindly provided by Dr. Immaculata De Vivo (Brigham and Women's Hospital, MA, USA) (32). Cell lines were maintained in a 37° C., 5% CO2 humidified incubator, DMEM, McCoy's 5A, EME, and DMEM-F12 growth media along with supplements were purchased from Gibco-Invitrogen (Carlsbad, Calif.). Cells were infected at various multiplicities of infection with lentivirus expressing SALL4 or SALL4shRNAs, and then selected with puromycin. Stable overexpression or knockdown of SALL4 was determined by real-time PCR and western blot. Stable cell lines were continuously cultured in medium containing 1 µg/ml puromycin (Sigma, Cat No. P9620).

Wound-Healing, Migration and Invasion Assays

An artificial "wound" was created on a confluent cell monolayer and photographs were taken at the indicated time. A permeable filter of transwell system (8-µm pores size, Transwell Permeable supports, Cat. No. 3422, Corning Incorporated, MA) was used for migration assays and 24-well plates with Matrigel-coated inserts (8-µm pores; BD Biosciences) were used for matrigel invasion assays. Stable shRNAs-infected cells were added to inserts in accordance with the manufacturer's protocol. Cells were incubated for the indicated time periods under standard culture conditions. Tumor cells remaining on the top-side of the membrane were removed by cotton swab. Cells that migrated to the underside were fixed and stained with crystal violet solution. After taking pictures, the stained cells were solubilized with 10% acetic acid and quantitated on a microplate reader at 600 nm.

GSEA Analysis

Prior to GSEA, we first divided all EC samples into two groups according to their SALL4 expression: SALL4 high and SALL4 low. GSEA was then performed based on normalized data using GSEA v2.0 tool http://<www.broad.mit-.edu/gsea/> for identification of enriched gene sets between SALL4 high & SALL4 low groups.

qChIP (Chromatin Immunoprecipitation) and qRT-PCR

AN3CA cells were grown and processed for qChIP as described previously (33) using monoclonal anti-SALL4 antibody. Real-time PCR was performed with two sets of c-Myc primers listed in Table S3, to validate pulldown DNA fragment. Mouse IgG was used as negative control. Total RNA was extracted with Trizol reagent (Invitrogen) or RNeasy kit (Qiagen). Real-time PCR for SALL4A and B was performed with the TaqMan PCR core reagent kit (Applied Biosystems) as described previously (7). c-Myc mRNA expression was measured using iScript One-step RT-PCR Kit with SYBR Green (Bio-Rad). C-Myc primers are as follows:

```
                                              (SEQ ID NO: 15)
    Forward 5'TCAAGAGGCGAACACACAAC-3';

(SEQ ID NO: 16)
    Reverse: 5'-GGCCTTTTCATTGTTTTCCA-3'
```

Chemoresistance Assay

Carboplatin was purchased from Sigma (Sigma-Aldrich, Cat. No. C2538). Cultured cells were plated in 6-well plates to allow for colony formation for 2-3 weeks, or cells were seeded on coverslips overnight. Then, cells were treated with indicated dosages of carboplatin for 72 hours. Cell proliferation and apoptosis were evaluated by Ki-67 staining or TUNEL assay.

Statistical Analysis

Results are expressed as mean±SD from at least three independent experiments. Statistical significance between two groups was determined by student t-test (GraphPad Prism Software). The value of $p<0.05$ was considered significant (*).

Patient Samples

Twenty one cases of normal endometrial tissues, five cases of endometrial hyperplasia and 147 cases of endometrial carcinoma tissues from Brigham and Women's Hospital and the National University Hospital (NUH) of Singapore were selected for the study. Ethics approval was obtained from Brigham and Women's Hospital Institutional Review Board (2011-P-000096/1) as well as from the National University of Singapore Institutional Review Board (NUS IRB 09-261).

SALL4 Immunohistochemistry (IHC) Analysis

Immunohistochemical staining was performed according to standard techniques. Briefly, paraffin tissue sections of 4 µm were deparaffinized with Histoclear and hydrated in graded ethanols. Antigen retrieval was performed by boiling at 120° C. in high pH target retrieval solution for 10 minutes in a pressure cooker. Primary antibodies were incubated at room temperature for 1 hour in a humidified chamber, followed by HRP-conjugated secondary antibody incubation for 30 minutes at room temperature. Antibody binding was revealed by DAB and reaction was stopped by immersion of tissue sections in distilled water once brown color appeared. Tissue sections were counterstained by hematoxylin, dehydrated in graded ethanol and mounted. Both polyclonal antibody as we described before (1) and monoclonal anti-SALL4 antibody (Santa Cruz, Calif., USA #sc-101147) were used. All reagents for immunohistochemistry were from Dako (Dako, Denmark A/S). Appropriate positive and negative controls were included for each run of IHC. For IHC on TMAs, SALL4 expression was scored according to the percentage of tumor cells stained positive for SALL4, with 0 denotes less than 5% of tumor cells stained, +1 denotes 5-30% of tumor cells stained, +2 denotes 31-50% of tumor cells stained, +3 denotes 51-80% of tumor cells stained.

Western Blot

Whole-cell lysates were prepared in lysis buffer [1% Nonidet P-40, 50 mM Tris-HCl (pH 8.0), 100 mM sodiumfluoride, 30 mM sodium, pyrophosphate, 2 mM sodium molybdate, 5 mM EDTA, and 2 mM sodium orthovanadate] containing protease inhibitors (10 μg/mL aprotinin, 10 μg/mL leupeptin, and 1 mM phenylmethylsulfonyl fluoride). Protein concentrations were determined by using the Bio-Rad Protein Assay. 30 μg of protein was loaded on a 4-12% Bis-Tris gel (NuPAGE; Invitrogen) and blotted onto a nylon membrane. Adequate protein transfer was demonstrated by staining the membranes with Ponceau S (Sigma Chemical). The following primary antibodies were used for staining: antibody raised against SALL4 (mouse monoclonal, Santa Cruz Inc SC-101147), anti-c-Myc (Rabbit polyclonal, cell signaling D84C12) and α-tubulin (mouse monoclonal Sigma T6074). Detection was by ECL (Amersham Pharmacia Biotechnology) with a Fuji LAS 1000 Plus chemiluminescence imaging system.

Xenotransplant Murine Model

All experimental procedures involving animals were conducted in accordance with the institutional guidelines set forth by the Children's Hospital Boston (CHB animal protocol number 11-09-2022). Eight to ten-week-old NOD/SCID mice were housed in a specific pathogen-free facility. To generate a xenograft mouse model, NOD/SCID mice were injected with 2×106 cells into right flanks. Cells were resuspended in 0.1 ml of PBS and then mix with 0.1 ml of matrigel. Two cell lines were prepared for xenografts: AN3CA and HEC-1A. Tumor sizes were measured weekly. As for metastasis mouse model, 1×106 AN3CA cells—were injected via the retro-orbital sinus as described previously (2). After 6 weeks, mice were killed and all the organs were checked for metastasis. Metastatic liver were collected and fixed in 10% neutral buffered formalin for further routine histology examination. Cell proliferation in tumor was determined by staining histological sections with monoclonal antibody against Ki-67 (BD, Cat. No. 556003), and apoptosis was evaluated by terminal uridine deoxynucleotidyl transferase dUTP nick end labeling (TUNEL) assay (in situ cell death detection kit, Promega, Cat. No. G3250) according to manufacturer's protocol.

Clonogenic Assay and MTS Assay

For clonogenic assay, cells of the respective cell line were seeded in 6-well plates (NUNC) and grown under the indicated conditions. In the case of HEC-1A cells, 3000 cells/well were seeded and cultured for 15 days. Ishikawa cells were seeded at 1000 cells/well and cultured for 20 days. Plates were fixed and stained using crystal violet solution. For quantification of apoptotic cells, and cellular proliferation, cells were gown on sterilized coverslip for overnight, fix with 4% paraformaldehyde for 10 min, stained with Ki-67 antibody or TUNEL kit as described above. MTS viability assay was performed as described previously (3).

Statistical Analysis

Results are expressed as mean±SD from at least three independent experiments. Statistical significance between two groups was determined by student t-test (GraphPad Prism Software). The value of p<0.05 was considered significant (*).

Results

To examine SALL4 expression in endometrial cancer, a panel of tissue microarrays consisting of 147 endometrial cancer samples was constructed and screened. Twenty one normal endometrial and five hyperplasia samples were used as controls. SALL4 expression was scored according to the percentage of tumor cells stained positive for SALL4, with 0 denotes less than 5% of tumor cells stained, +1 denotes 5-30% of tumor cells stained, +2 denotes 31-50% of tumor cells stained, +3 denotes 51-100% of tumor cells stained. Among the 147 endometrial cancer cases, 47% were positive for SALL4 expression, albeit at variable expression levels. In contrast, SALL4 expression was not detected in hyperplasia and normal endometrial tissues. Representative images are shown in FIG. 34A and FIG. 38A. In addition, SALL4 mRNA expression in endometrial cancers was also investigated. Using snap-frozen patient samples, SALL4 mRNA expression was further validated in endometrial carcinomas using quantitative real-time PCR. Since it was previously identified that human SALL4 has two isoforms (SALL4A and SALL4B) (Ma et al., *Blood*, 108:2726-35 (2006)), isoform-specific primers and Taqman probes were used for qRT-PCR. By qRT-PCR, it was established that both isoforms were elevated in a subgroup of primary endometrial cancers compared to normal (FIG. 38B).

To examine if the upregulation of SALL4 has clinical significance in endometrial carcinoma, clinicopathological analysis was carried out to see if SALL4 expression predicts poor prognosis. Clinicopathological and demographic data of 120 endometrial carcinoma cases was retrieved from the NUH cohort. From the analysis described herein, it was found that SALL4 expression was significantly correlated with poor survival of EC patients (P=0.015) (FIG. 34B). In addition, Gene Set Enrichment Analysis (GSEA) was carried out to investigate if gene sets that have prognostic values are enriched in SALL4-expressing endometrial carcinomas. Indeed, enrichment of gene sets upregulated in cancers with poor survival (P<0.001), metastasis (P<0.001), advanced tumor stage (P<0.001), and proliferation (P<0.001) in SALL4-expressing endometrial carcinoma (FIG. 34C and FIGS. 39A-39C) were observed. On the other hand, gene sets that are enriched in cancers with good survival (P<0.001), downregulated in cancers of advanced stage (P<0.001), proliferation (P=0.006) and metastasis (P=0.047) were enriched in SALL4-negative endometrial carcinomas (FIG. S2). These data collectively demonstrate that SALL4 has prognostic value in endometrial carcinoma.

To assess the biological functional role of SALL4 in endometrial cancer, first evaluated was SALL4 expression in a panel of six endometrial cancer cell lines using quantitative real-time PCR to select for appropriate models for our functional studies (FIG. 40). Three of them, AN3CA, HEC-1A and Ishikawa were selected for subsequent studies based on their endogenous SALL4 expression of high, moderate or undetectable levels, which reflected best for the differential SALL4 expression levels encountered in primary human endometrial cancer tissues. To suppress SALL4 expression in endometrial cancer cells, two short hairpin RNAs (shRNAs) specifically targeting both SALL4A and SALL4B isoforms, designated as SALL4-sh1 and SALL4-sh2, were chosen and optimized from 5 constructs. AN3CA and HEC-1A cells were infected with lentivirus expressing shRNAs. On day 4 after infection, loss of SALL4 induced substantial cell death in both the AN3CA and HEC-1A cells, the changes in cell morphology and apoptotic phenotypes were visible by light microscopy (FIG. 41). Knockdown efficiency of the two shRNAs was verified by Western blot and qRT-PCR (FIG. 35A and FIG. 42), both shRNAs could down-regulate SALL4A and SALL4B efficiently in AN3CA and HEC-1A cells. To further verify that the effects of shRNAs are specific, SALL4A and SALL4B overexpression constructs that carry triple-point mutation within the 21-bp sequence targeted by SALL4-sh1 were prepared. These mutations did not lead to amino acid sequence change of SALL4 protein but rendered the overexpression constructs insensitive to inhibition by SALL4-sh1, therefore, they could be used as rescue mutants to test the specificity of the shRNA. After co-infection of AN3CA cells with SALL4-sh1 and rescue mutants SALL4A or SALL4B lentivirus, it was observed that mutant SALL4A alone or SALL4B alone was able to partially rescue SALL4 shRNA knockdown phenotypes (FIG. 43A-43C), indicating that loss of SALL4 expression was detrimental to the survival of endometrial cancer cells.

Figures 35A, 35B, 35C:
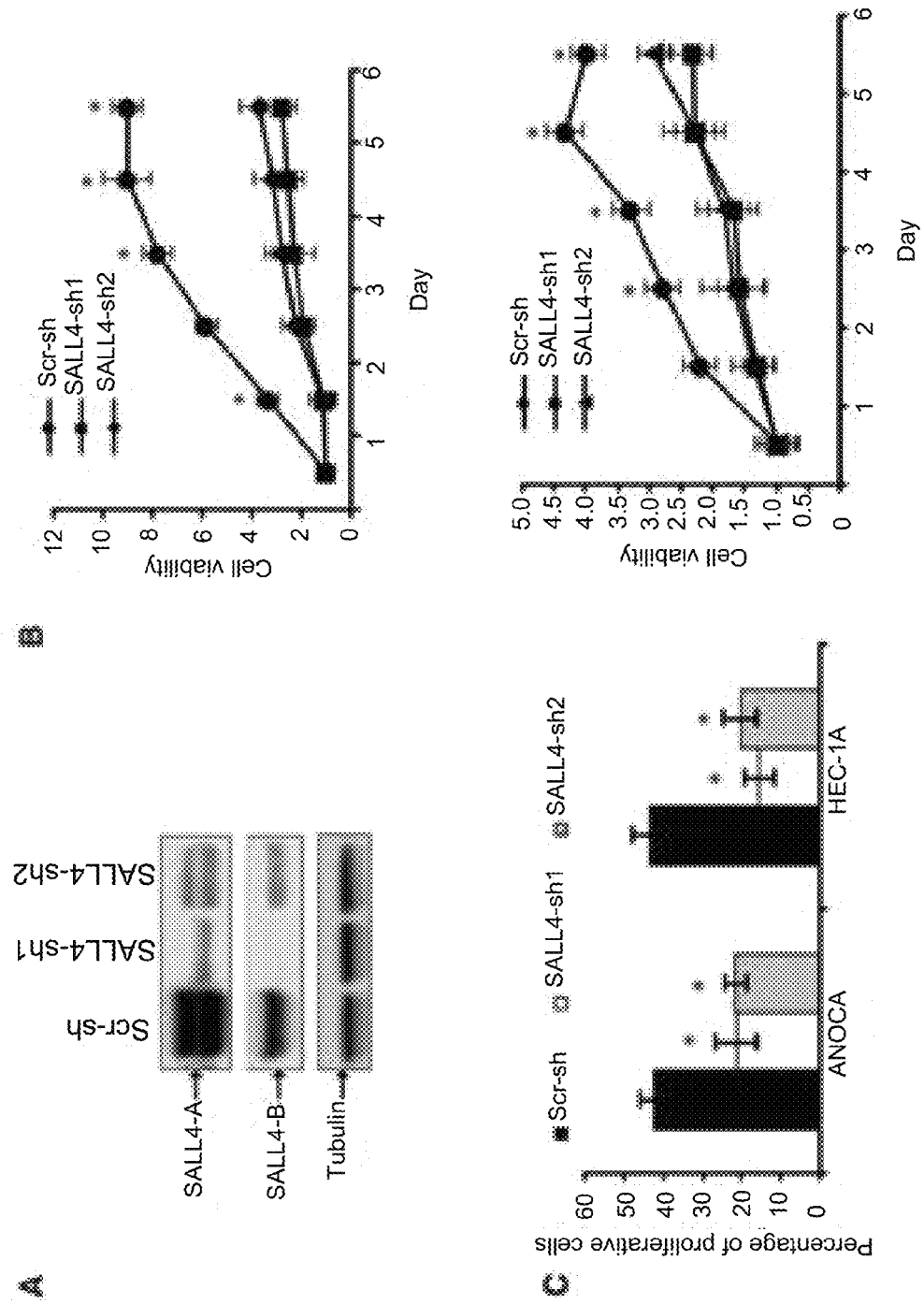
Figures 35D, 35E, 35F:
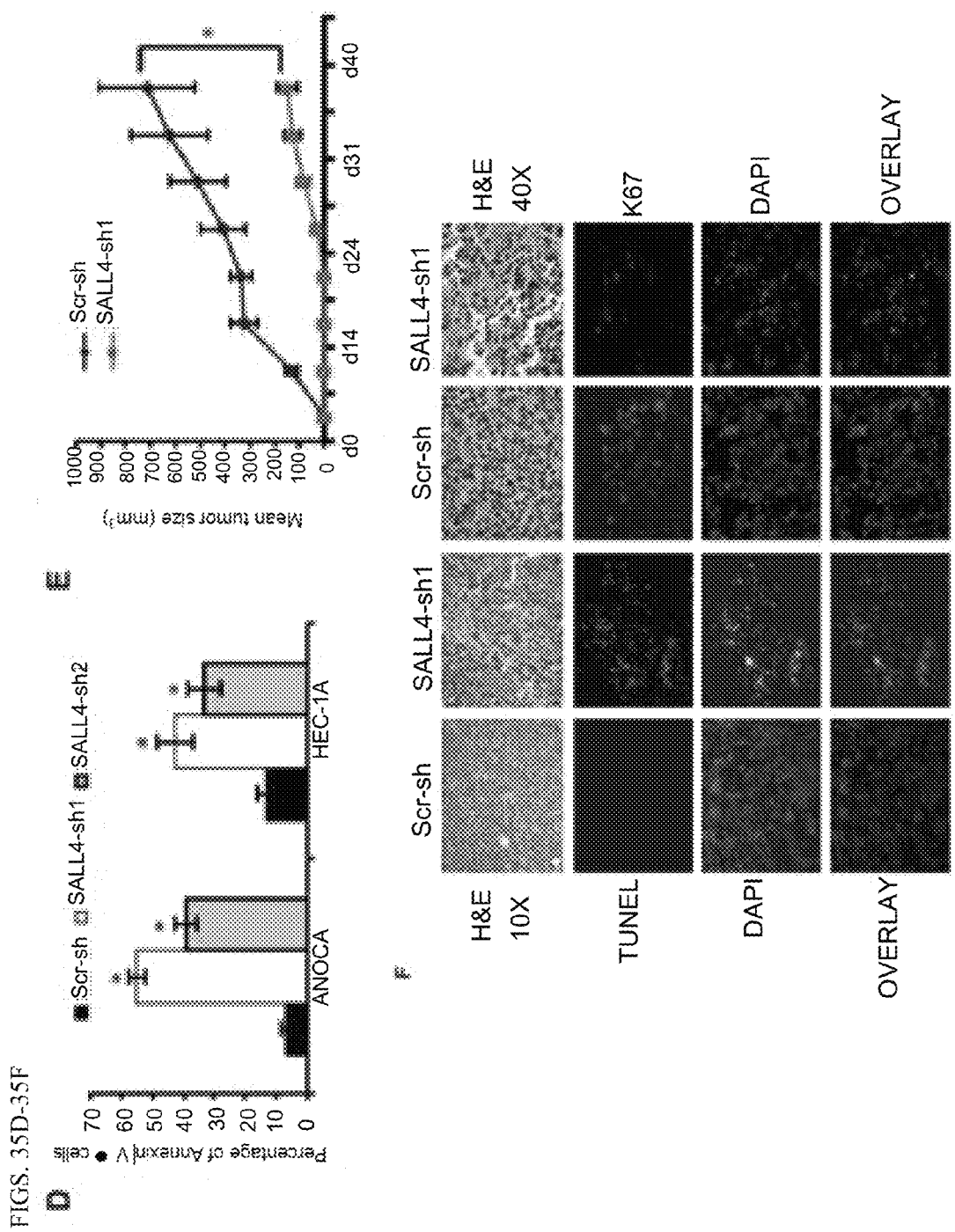

To elucidate the role of SALL4 in endometrial cancer survival, the viability of lentivirus-infected AN3CA and HEC1-A cells were first examined by a MTS assay over a period of time. FIG. 35B showed that the growth rate for SALL4-knockdown cells was significantly decreased compared to those of scrambled shRNA-treated control cells (AN3CA cells in upper panel and HEC-1A cells in lower panel). In contrast, there was no effect of SALL4 knockdown in Ishikawa cells, which had undetectable SALL4 expression endogenously (data not shown). Decreased cell growth curve could be due to impaired proliferation and/or increased cell death. To determine the effect of SALL4 knockdown on cell proliferation, BrdU incorporation in vitro by flow cytometry was measured. The data in FIG. 35C showed that SALL4 knockdown could significantly decrease the proportions of BrdU-positive proliferating endometrial cancer cells. Next assessed was the effect of SALL4 depletion on the apoptotic activity of the endometrial cancer cells using AnnexinV staining. The data in FIG. 35D illustrated that the percentages of Annexin V-positive cells were much higher in SALL4 knockdown groups than the scramble control groups. Collectively, these data indicate that loss of SALL4 inhibits cell proliferation and triggers cell apoptosis in vitro.

To further confirm the role of SALL4 in tumorigenicity of endometrial cancer, a xenograft model was used. Two millions AN3CA cells after treated with either scramble control or SALL4 shRNA lentiviruses were injected subcutaneously into the right flank region of NOD/SCID mice and monitored for tumor development. As shown in FIG. 35E, tumor growth induced by SALL4 knockdown group was dramatically slower than that induced by scramble shRNA-treated cells. The excised tumors were subjected to routine histology processing and used for immunostaining analysis. Cellular proliferation in tumor tissues was assessed by immunostaining with anti-Ki-67 antibody (FIG. 35F, right panel), indicating that loss of SALL4 could significantly inhibit cell proliferation when compared to that of scramble shRNA-treated tumors. On the other hand, subcutaneous tumors induced by SALL4-knocking down cells showed a marked increase in the number of apoptotic cells as detected by TUNEL analysis (FIG. 35F, left panel). Taken together, these results clearly demonstrate that silencing SALL4 inhibits endometrial cancer cell growth in vitro and tumorigenicity in vivo by inhibiting proliferation and triggering apoptosis.

Figures 36A, 36B, 36C, 36D, 36E:
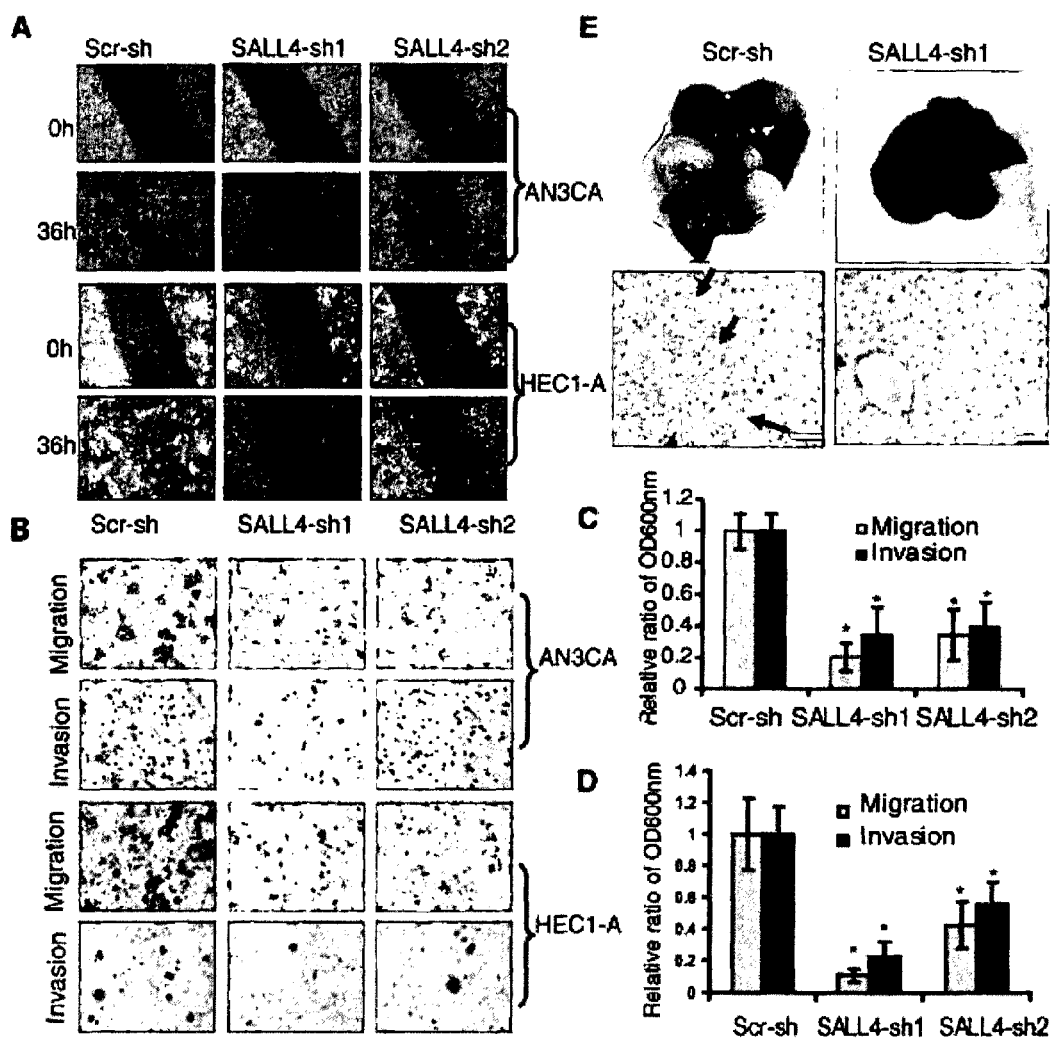

Metastasis is a central problem in cancer therapeutics, also the data above showed that SALL4 expression was positively correlated with tumor metastatic ability. Next assessed was whether loss of SALL4 could affect tumor invasiveness. In a wound-healing assay, a much slower wound closure rate was observed in the SALL4 knockdown AN3CA and HEC-1A cells as compared to the scramble shRNA-treated cells (FIG. 36A). In transwell migration and invasion assays, significantly reduced migration and invasion were also observed in AN3CA and HEC-1A cells upon SALL4 knockdown (FIGS. 36B, 36C and 36D). It was further asked whether loss of SALL4 could influence cell migration and metastasis formation in vivo. The invasive potential of these three cell lines in vitro: AN3CA, HEC-1A and Ishikawa cells was compared, and a strong association between SALL4 expression and invasive capacity was detected, with Ishikawa showing the least migration/invasion ability (data not shown). The most invasive cell line AN3CA with high endogenous SALL4 expression was then chosen for the in vivo metastasis assay. SALL4-knockdown or scramble shRNA-treated AN3CA cells were injected into NOD/SCID mice through eye injection. Metastasis of the tumor in all organs was evaluated 6 weeks later when scramble shRNA-treated recipient mice became morbid. Four out of five scramble shRNA-treated AN3CA recipients had markedly enlarged tumor-bearing livers (FIG. 36E, left upper panel), with tumor morphology recapitulating that of the tumors found in patients with poorly differentiated invasive endometrial carcinoma (FIG. 36E, left lower panel). In contrast, SALL4-knockdown cells were significantly impaired in their ability to generate any tumor both macroscopically and microscopically in all organs, including liver. These data strongly indicate that SALL4 is essential to maintain the invasive state of endometrial cancer cells.

Figures 37A, 37B, 37C, 37D:
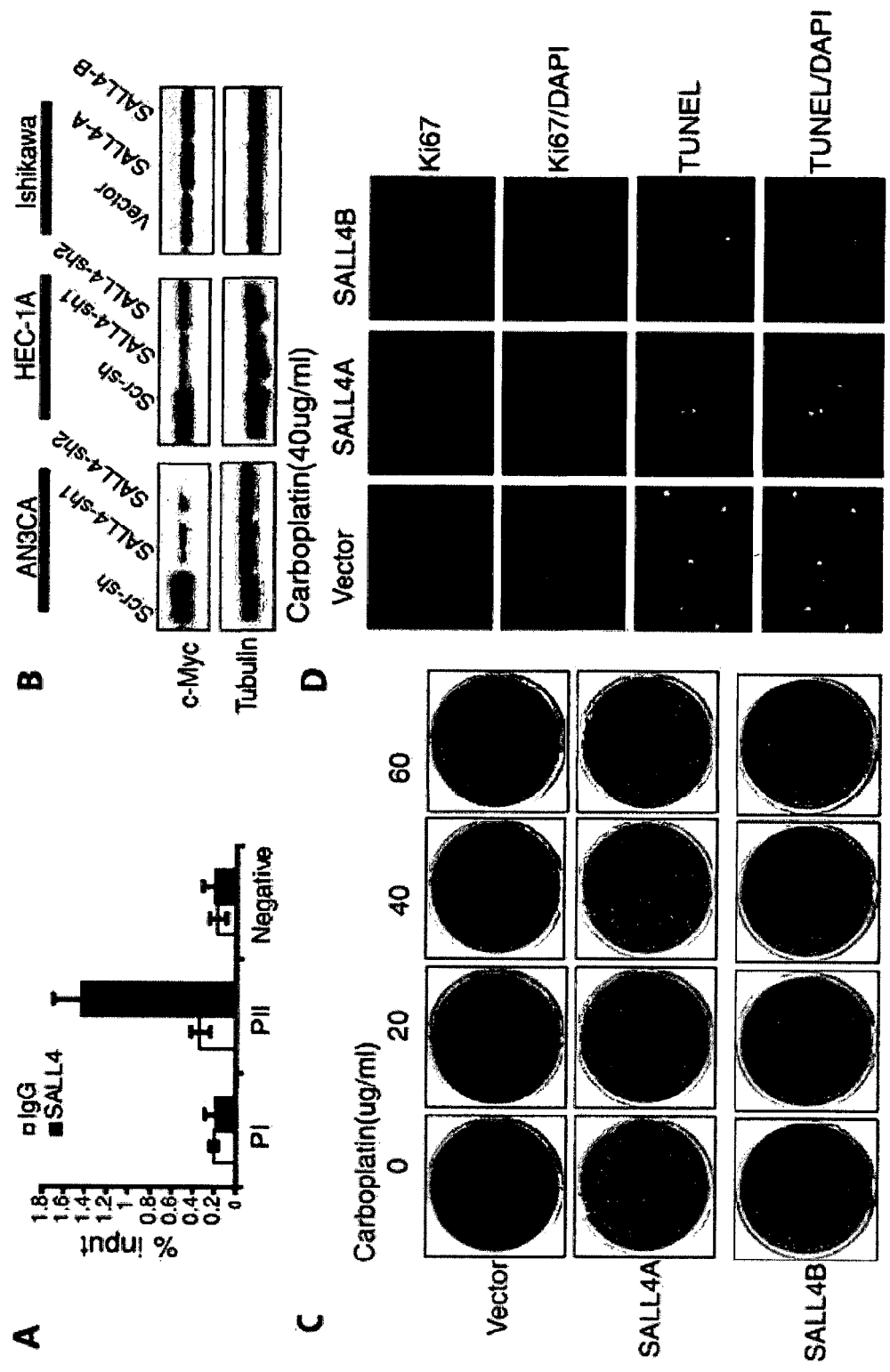

A genome-wide analysis of SALL4 target genes in myeloid leukemic NB4 cells as well as murine ES cells was performed using chromatin immunoprecipitation followed by microarray on the promoter regions (ChIP-chip) approach (Yang et al., *PNAS, USA*, 105:19756-61 (2008)). Re-analyzing these ChIP-chip data sets, it was found that SALL4 could bind to the c-Myc promoter region in NB4 and murine ES cells (FIG. 44). It is possible that SALL4 regulates c-Myc in endometrial cancer as well. To test this hypothesis, the ChIP-chip result was verified quantitatively using a regular ChIP coupled with qPCR approach. It was demonstrated that SALL4 indeed could bind to the promoter region of c-Myc in AN3CA cells (FIG. 37A). To examine the regulatory effect of SALL4 on c-Myc expression, western blot and quantitative real-time PCR analysis was performed after SALL4 knockdown in AN3CA and HEC-1A cells. SALL4 silencing in these two cell lines significantly decreased the protein and mRNA expression of c-Myc compared to scramble control (FIG. 37B and FIG. 45). A parallel ectopic SALL4 expression was carried out in Ishikawa cells, which has negligible endogenous SALL4 expression. As shown in FIG. 37B and FIG. 46A-46B, both SALL4A and SALL4B overexpression could significantly increase c-Myc protein and mRNA expression. These data indicate that SALL4 can directly regulate c-Myc in endometrial cancer, and this may be at least in part responsible for its role in endometrial cancer tumorigenesis.

It has been documented that elevated c-Myc expression confers drug resistance to several types of tumor cells (Hermeking et al., *Curr cancer Drug Targets*, 3:163-75 (2003: Knaoo et al., *Anticancer Drugs*, 14:39-47 (2003); Van Waardenburg et al., *Anticancer Res*, 16:1963-70 (1996)). In light of the role of SALL4 in regulating c-Myc expression, next asked was whether SALL4 expression could affect the sensitivity of endometrial cancer cells to carboplatin treatment. Clonogenic assays revealed that overexpression of SALL4 in a carboplatin-sensitive Ishikawa cells could promote carboplatin-resistance in a dose dependent manner (FIG. 37C and FIG. 47). Furthermore, it was observed that both SALL4A and SALL4B-transfected Ishikawa showed increased proliferation after carboplatin treatment compared to empty vector control as demonstrated by Ki-67 staining (FIG. 37D, upper panel). In addition, SALL4-overexpression could significantly protect cells from apoptosis induced by carboplatin treatment, assayed by TUNEL staining as shown in FIG. 37D (lower panel). On the contrary, in carboplatin resistant HEC-1A cells, knocking-down SALL4 significantly restored the sensitivity of these cells to carboplatin treatment (FIG. 48A-48B). Altogether, the data indicate that in endometrial cancer, upregulation of SALL4 expression can contribute to chemotherapy resistance.

Discussion

It has been proposed that human preimplantation embryonic cells share similar phenotypes with cancer cells. Both types of cells are at a proliferative stem/undifferentiated cell state and are potentially immortal (Reya et al., *Nature*, 414 (6859):105-11 (2001); Daley et al., *CSHL Quant Biol*, 73:171-4 (2008)). Furthermore, cancer cells with an ES cell gene expression signature has poor prognosis (Ben-Porath et al., *Nat Genet*, 40:499-507 (2008)). Sall4 is a key factor of the transcriptional core network essential for the maintenance of stemness of ES cells (Wu et al., *J Biol Chem*, 281:24090-4 (2006); Zhang et al., *Nat Cell Biol*, 8:1114-23 (2006)). SALL4 is also abnormally expressed in germ cell tumors and used as a diagnostic marker for these tumors (Cao et al., *cancer*, 115:2640-51 (2009)). However, more comprehensive and systematic studies on the functional role(s) of SALL4 in human solid tumors are still lacking.

Shown herein is that SALL4 is re-expressed in solid cancer cells and contributes to cancer cell tumorigenic properties, focusing on the endometrial cancer model. The study herein indicates that the ES cell signature gene SALL4 is re-expressed in majority of endometrial cancers at both the mRNA and protein levels, but not in the pre-neoplastic endometrial hyperplasia or normal endometrial tissues. More importantly, the clinical data herein also show that aberrant SALL4 expression is positively correlated with aggressive tumor features including worse survival, metastasis and advanced stages. Recently, Levan et al. have reported a gene signature that can predict poor prognosis of endometrial carcinoma, and SALL4 is among the 218 genes which are associated with poor prognosis (Levan et al., *Gene Expr*, 14:361-70 (2010)). In their report, the authors followed 45 endometrial cancer patients over a period of five years. While 21 patients survived, 24 patients died. Overall, the deceased patients had high grade and more advanced stages of disease at the time of surgical intervention. The authors then evaluated and compared the gene expression profiled of tumor samples between survivors and non-survivors. As described herein, the gene expression profiled was extracted and the data was re-analyzed in order to examine if SALL4 is differentially expressed in these two groups of patients. From the analysis described herein, it was found that SALL4 expression was significantly higher in the non-survivor (more aggressive cases) compared to the survivor group (FIG. 49). Since the non-survivor group had more advanced stage diseases, it is possible that SALL4 expression is also correlated with more aggressive endometrial subtype. Indeed, from the immunohistochemistry study described herein, it was observed that elevated SALL4 expression in 71% of serous carcinomas (n=7), a endometrial carcinoma subtype that have conventionally been viewed as the more aggressive subtype, while none of the clear cell carcinoma cases demonstrated SALL4 expression (n=3).

The ability of tumor cells to acquire metastatic potential and spread in their host organism is one of the main issues in cancer treatment, as metastasis accounts for more than 90% of human cancer-related deaths (Mehlan et al., *Nat Rev cancer*, 6:449-58 (2006)). The GSEA data described herein strongly indicated that SALL4 is positively correlated with tumor metastatic capacity. Additionally, both the in vitro and in vivo data herein confirmed that SALL4 expression was critical for tumor invasive capacity and metastatic ability, strongly indicating that SALL4 is a potential therapeutic target, and that blocking of the oncogenic role of SALL4 could significantly benefit patients with more advanced endometrial cancer, whose prognosis are very poor in general, with a median survival of less than 1 year (Elit et al., *Curr Opin Obstet Gynecol*, 14:67-73 (2002)).

Demonstrated herein is that c-Myc is one of SALL4 target genes by ChIP-qPCR assay. Furthermore, the loss- and gain-of-function studies described herein have shown that c-Myc expression level is regulated directly by SALL4, and manipulation of SALL4 expression can affect drug sensitivity of endometrial cancer cells. Therefore, shown herein is that c-Myc is one of the most important target genes of SALL4 in endometrial cancer, which likely contributes to SALL4-mediated metastasis and drug resistance.

In summary, the study herein has revealed several novel and important findings: (I) SALL4, an ES cell signature gene, is aberrantly expressed in 47% of endometrial carcinoma, and its expression was positively correlated with aggressive tumor features. (II) SALL4 is critical for endometrial cancer cell survival and tumor progression. (III) A SALL4/c-Myc pathway is involved in promoting aggressive features of the tumor, such as metastasis and cancer drug resistance. Among these finding, the connection between SALL4 expression and tumor invasiveness is most intriguing.

Example 6

Modification of WT-Peptide with TAT Showed Effective Binding and Nuclear Localization in SNU398 Cells Peptide Modifications A 12 amino acid sequence (MSRRKQAKPQHI (SEQ ID NO 1)) previously described was shown to be effective in antagonistic action against the effect of SALL4 on SNU398 cells. However, this sequence requires a peptide carrier for drug delivery into cells, and also restricted in vivo administration of the drug. As such, modification to the peptide sequence with TAT was carried out. It is believed that amino acids 3 to 5 are the vital amino acids interacting with the NuRD complex, and thus to show specificity of the peptide sequence, an additional mutant sequence (TAT-Mut) was synthesized on top of the TAT-WT sequence (FIG. 51).

The sequences for peptides used are as below:

```
                                         (SEQ ID NO: 17)
TAT: NH2-YGRKKRRQRRR-COOH (SEQ ID NO: 1)
WT: NH2-MSRRKQAKPQHI-COOH (SEQ ID NO: 18)
TAT-WT: NH2-YGRKKRRQRRR-MSRRKQAKPHI-COOH (SEQ ID NO: 19)
TAT-Mut: NH2-YGRKKRRQRRR-MSAAAQAKPHI-COOH (SEQ ID NO: 18)
Biotinylated TAT-WT: Btn-YGRKKRRQRRR-MSRRKQAKPHI-
COOH (SEQ ID NO: 19)
Biotinylated TAT-Mut: Btn-YGRKKRRQRRR-MSAAAQAKPHI-
COOH
```

Binding studies carried out by florescent polarization (FP) assays showed that the binding affinity of TAT-WT was similar to that of WTChariot (FIG. 51) whereas TAT-Mut showed minimal binding. This confirms the importance of amino acids 3 to 5 in binding of WT to the RbAP 48 component of the NuRD complex, and also established TATMut as a suitable negative control in subsequent experiments. Confocal microscopy was next used to study cellular uptake of TAT-WT by SNU398 cells in vitro. Consistent with previous studies, we note that the peptide sequence, when conjugated with TAT, is able to localize within the nucleus within 15 minutes of addition to cell culture plates (FIG. 52).

TAT-WT Peptide Showed Similar Cell Killing Effect In Vitro Compared to WT Peptide Sequence In vitro studies were next carried out to determine biological activity of TAT-WT peptide against HCC cells. When 20 uM of TAT-WT peptide was added to SNU398 culture plates, a decrease in cell number that was comparable to WT peptide was observed, whereas TAT-Mut did not exhibit such cell killing effect (FIG. 53). Trichostatin A (TSA), a general HDAC inhibitor, was used as a positive control drug in this study. In addition, several other peptides including D-form wt-peptide (termed as D), six amino acids (termed as 6aa). The sequences of the peptides were listed below:

```
                                              (SEQ ID NO: 20)
6aa: NH2-MSRRKQ-COOH (SEQ ID NO: 1)
WT: NH2-MSRRKQAKPQHI-COOH (SEQ ID NO: 1)
D: NH2-MSRRKQAKPQHI-COOH (D-form of wt-peptide)

(SEQ ID NO: 17)
TAT: NH2-YGRKKRRQRRR-COOH (SEQ ID NO: 18)
TAT-WT: NH2-YGRKKRRQRRRMSRRKQAKPHI-COOH (SEQ ID NO: 19)
TAT-Mut: NH2-YGRKKRRQRRRMSAAAQAKPHI-COOH
```

As the WT peptide sequence is targeted against the NuRD complex of SALL4, it was hypothesizes that the drug should only work in cell lines with high SALL4 expression levels and not those with low SALL4 expression levels. Consistent with the hypothesis, the cell killing effect of TAT-WT was negligible in a cell line that had low SALL4 expression levels, SNU387 cells (FIG. 53).

TAT-WT Peptide was Effective in Decreasing Tumor Volume In Vivo when Injected Directly into Mice Next tested was the in vivo efficacy of drug delivery with TAT-WT peptide. NOD/SCID mice were transplanted subcutaneously with SNU398 cells and allowed to grow till tumors were palpable. Both TAT-WT and TAT-Mut were then injected subcutaneously into mice for 5 consecutive days, and their tumor sizes then measured every 3 days until mice had to be sacrificed when tumor burden became too large such that they were incompatible with life.

The studies herein showed that TAT-WT peptide was effective in slowing down tumor growth in mice compared to TAT-Mut peptide (FIG. 54A). At 18 days post treatment with TAT-WT, tumor weight was also observed to be lower in mice treated with TATWT peptide compared to TAT-Mut peptide (FIGS. 54B&54C).

For tumorigenicity studies, cells were prepared and injected into mice as described above. 56 mg/kg body weight of TAT-Mut or 60 mg/jg of TAT-WT were administered intraperitoneally for five consecutive days starting from the day of subcutaneous HCC cell transplantation. Mice were then examined regularly and tumor volumes were measured at various time points as described in the results section. Tumor volume was calculated using the formula, tumor volume=□/6×largest diameter×(smallest diameter)2. When tumors were too large to be compatible with life, mice were sacrificed and tumor was harvested and weighed, followed by processing for routine histology.

Wt-Peptide Usage have been Tested on Leukemic Cell Lines and Primary Cells, Liver Cancer, Lung Cancer and Ovary Cancer Wt-peptide usage have been tested so far on leukemic cell lines and primary cells (Examples 1 and 2). Wt-peptide usage have been tested so far on liver cancer cell lines (Examples 3 and 4). Wt-peptide usage have been tested on lung cancer cell lines.

Lung cancer is the second most common cancer in the United States with an estimated 221,130 newly diagnosed cases in 2011. The majority subtype of lung cancer is non-small cell lung cancer (NSCLC), which comprises of 80% of all lung cancer cases. Molecular targeted therapy including EGFR and ALK inhibitor has resulted in some improvement in the treatment response in selected groups of NSCLC patients. However, EGFR and ALK collectively account for about 15% of all NSCLC, and the over all survival rate for lung cancer patients remains extremely poor (~15% over 5 years). Lung cancer is still the leading cause of cancer death in the US, and more effective therapy is needed.

The gene expression database was analyzed and a significant higher level of SALL4 expression in all sub-types of NSCLC cancer tissue compared to normal lung control was found (FIG. 55A), which was validated by using immunohistochemistry (IHC) approach at the protein level (FIG. 55B). Furthermore, we screened SALL4 expression in a panel of lung cancer cell lines and performed loss of function study using SALL4 specific shRNAs. the data showed that knocking-down of SALL4 could induce significant cell growth arrest and dramatic cell apoptosis in multiple lung cell lines including H661, H522, H292 and PC9, but not in HCC827 cells which lacks SALL4 expression (FIG. 56A-56F).

Further studies using H661, H522 and PC9 cells in a xenograft mouse model demonstrated that down-regulation of SALL4 inhibits tumor growth in vivo. A small peptide has been generated to block the oncogenic function of SALL4. Targeting SALL4 in lung cancer cell lines with this peptide resulted in cell death, similar to the effects of down-regulation of SALL4 (FIG. 56A-56F). Therefore, shown herein is that SALL4 plays a crucial role in tumor initiation and development of NSCLC, and targeting SALL4 may provide an innovated therapeutic approach in the treatment of lung cancer.

Ovarian cancer is the fifth-leading cause of cancer death among all cancers in women in western countries and is the leading cause of death from female reproductive tract malignancies. Early stage disease often remains undetected due to the lack of symptoms and reliable biomarkers. Dissecting molecular pathways underlying tumor initiation of the ovarian cancer can provide early detection and new prevention strategies that would inhibit early progression of this fatal disease. Impaired genome stability is one of the hallmarks of cancer. Several chromosomal duplications have been frequently observed in many types of cancer. Noticeably, the chromosomal region, 20q12-13, is commonly amplified in ovarian cancer, which was previously reported in more than 50% of sporadic ovarian cancers and in four of four (100%) of familial ovarian cancers. The high frequency of gene amplification at 20q12-q13 suggests that the genes amplified within that region may play a central role in the tumor initiation of ovarian carcinoma. The human SALL4 gene is located on chromosome 20q13.2, and is known to be important in human malformation syndromes and embryonic stem self-renewal. It is hypothesizes that SALL4 is an important candidate gene of the 20q12-q13 amplicon that plays an essential role in ovarian cancer initiation.

Further analysis of gene expression profiling database has showed a significant higher level of SALL4 expression in ovarian epithelial cancer when compared to that of normal ovarian surface epithelial cells (FIG. 57A), and there is no significant difference of SALL4 expression between low and high grade of ovarian tumor (FIG. 57B). The immunohistochemistry (IHC) stain data described herein has confirmed that SALL4 expresses in more than 20% of ovarian tumor, but not in normal ovarian epithelial cell (FIG. 57C). The potential role of SALL4 in ovary tumorigenesis is further supported by the studies herein on a cell model of progressive ovarian cancer. SALL4 expression was monitored during ovarian surface epithelial cells undergoing malignant transformation in a cell culture condition. The data showed that SALL4 expression was significantly increased at the intermediate malignant stage (FIG. 58A).

Since high SALL4 expression was observed in primary ovarian cancer samples, a loss of function study was performed using short hairpin RNA technology in several ovarian epithelial cell lines. It was found that SALL4 deletion dramatically induced cell apoptosis and completely inhibited cell growth in SALL4 expression cell lines such as TOV112D and OV90 (FIG. 59A-59C), but had no effect on the non-SALL4 expression line such as IGROV-1 (data not shown).

The above data indicate that SALL4 also plays an important role in maintenance of ovarian tumor.

To understand the mechanism(s) of SALL4 function(s), SALL4-associated proteins were identified by tandem mass spectrometry. Components of the Mi-2/nucleosome remodeling and deacetylase (NuRD) complex were found in SALL4-immunocomplexes along with HDAC activity in ESCs with endogenous SALL4 expression and 293T cells overexpressing SALL4. The SALL4-mediated transcriptional regulation was tested on one potential target gene: Phosphatase and Tensin Homolog (Pten). Pten was confirmed as SALL4 downstream targets by chromatin-immunoprecipitation (ChIP), and its expression level, when tested by quantitative reverse transcription polymerase chain reaction (qRT-PCR), was decreased in 293T cells overexpressing SALL4. Moreover, SALL4 binding sites at the promoter regions of Pten were co-occupied by NuRD components, indicating that SALL4 represses the transcription of Pten through its interactions with NuRD9. A small peptide that can block the oncogenic role of SALL4 in repressing Pten has been generated. Treating SALL4 in cancer cell line OV90 with this peptide resulted in cell death, similar to what we observed for down-regulation of SALL4 (FIG. 60).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of treating a solid tumor which expresses Spalt-Like Transcription Factor 4 (SALL4) and Phosphatase and Tensin Homolog (PTEN) in an individual in need thereof, comprising administering to the individual an effective amount of a composition that inhibits SALL4 repression of PTEN expression, wherein the composition comprises a peptide having the amino acid sequence MSRRKQAKPQHI (SEQ ID NO: 1).

2. The method of claim 1, wherein the composition inhibits the activity of SALL4.

3. The method of claim 1, wherein the solid tumor expresses high levels of SALL4 as compared to a level of SALL4 in a non-tumor cell.

4. The method of claim 1, wherein the solid tumor is a liver tumor, a lung tumor, a brain tumor, a uterine tumor, a breast tumor, a gastric tumor, a germ cell tumor, an ovarian tumor, an endometrial tumor or a combination thereof.

5. The method of claim 4, wherein the lung tumor comprises cells that are epidermal growth factor receptor (EGFR)-mutation positive, EGFR-mutation negative or a combination thereof.

6. The method of claim 4, wherein the brain tumor is a glioblastoma multiforme brain tumor.

7. The method of claim 1, wherein the composition is administered using a peptide carrier.

8. A method of treating a tumor which expresses Spalt-Like Transcription Factor 4 (SALL4) and Phosphatase and Tensin Homolog (PTEN) in an individual in need thereof, comprising administering to the individual an effective amount of a composition that inhibits SALL4 repression of PTEN expression, wherein the composition is a peptide having the amino acid sequence MSRRKQAKPQHI (SEQ ID NO: 1).

9. The method of claim 8, wherein the composition inhibits the activity of SALL4.

10. The method of claim 8, wherein the tumor is a liver tumor, an ovarian epithelial tumor or an endometrial tumor.

* * * * *

SEQUENCE LISTING

```
<160> NUMBER OF SEQ ID NOS: 20

<210> SEQ ID NO 1
<211> LENGTH: 12
<212> TYPE: PRT
<213> ORGANISM: unknown
<220> FEATURE:
<223> OTHER INFORMATION: SALL4 peptide

<400> SEQUENCE: 1

Met Ser Arg Arg Lys Gln Ala Lys Pro Gln His Ile
 1               5                  10

<210> SEQ ID NO 2
<211> LENGTH: 19
<212> TYPE: DNA
<213> ORGANISM: unknown
<220> FEATURE:
<223> OTHER INFORMATION: shRNA targeting SALL4, E5

<400> SEQUENCE: 2
ctatttagcc aaaggcaaa                                                    19

<210> SEQ ID NO 3
<211> LENGTH: 21
<212> TYPE: DNA
<213> ORGANISM: unknown
<220> FEATURE:
<223> OTHER INFORMATION: shRNA targeting SALL4, 507

<400> SEQUENCE: 3
gccttgaaac aagccaagct a                                                 21

<210> SEQ ID NO 4
<211> LENGTH: 29
<212> TYPE: DNA
<213> ORGANISM: unknown
```

```
<220> FEATURE:
<223> OTHER INFORMATION: shRNA targeting SALL4, 7210

<400> SEQUENCE: 4
gccgacctat gtcaaggttg aagttcctg                                        29

<210> SEQ ID NO 5
<211> LENGTH: 29
<212> TYPE: DNA
<213> ORGANISM: unknown
<220> FEATURE:
<223> OTHER INFORMATION: shRNA targeting SALL4, 7412

<400> SEQUENCE: 5
gatgccttga acaagccaa gctacctca                                         29

<210> SEQ ID NO 6
<211> LENGTH: 12
<212> TYPE: PRT
<213> ORGANISM: unknown
<220> FEATURE:
<223> OTHER INFORMATION: SALL4 mutant peptide

<400> SEQUENCE: 6

Met Ser Arg Arg Ala Gln Ala Lys Pro Gln His Ile
 1               5                  10

<210> SEQ ID NO 7
<211> LENGTH: 12
<212> TYPE: PRT
<213> ORGANISM: unknown
<220> FEATURE:
<223> OTHER INFORMATION: SALL4 scramble peptide

<400> SEQUENCE: 7

Ser Arg Met Arg Gln Lys Ile His Pro Lys Ile Gln
 1               5                  10

<210> SEQ ID NO 8
<211> LENGTH: 20
<212> TYPE: DNA
<213> ORGANISM: unknown
<220> FEATURE:
<223> OTHER INFORMATION: cMyc-PI-f primer

<400> SEQUENCE: 8
aaggaggtgg ctggaaactt                                                  20

<210> SEQ ID NO 9
<211> LENGTH: 20
<212> TYPE: DNA
<213> ORGANISM: unknown
<220> FEATURE:
<223> OTHER INFORMATION: cMyc-PI-r primer

<400> SEQUENCE: 9
cgttcaggtt tgcgaaagta                                                  20

<210> SEQ ID NO 10
<211> LENGTH: 20
<212> TYPE: DNA
<213> ORGANISM: unknown
<220> FEATURE:
<223> OTHER INFORMATION: cMyc-PII-f primer

<400> SEQUENCE: 10
```

```
ggaaagagga cctggaaagg                                              20

<210> SEQ ID NO 11
<211> LENGTH: 20
<212> TYPE: DNA
<213> ORGANISM: unknown
<220> FEATURE:
<223> OTHER INFORMATION: cMYc-PII-r primer

<400> SEQUENCE: 11
gggaccggac ttcctaaaag                                              20

<210> SEQ ID NO 12
<211> LENGTH: 20
<212> TYPE: DNA
<213> ORGANISM: unknown
<220> FEATURE:
<223> OTHER INFORMATION: Negative-f primer

<400> SEQUENCE: 12
agcaggtgga tcatgaggtc                                              20

<210> SEQ ID NO 13
<211> LENGTH: 20
<212> TYPE: DNA
<213> ORGANISM: unknown
<220> FEATURE:
<223> OTHER INFORMATION: Negative-r primer

<400> SEQUENCE: 13
ctggagtgca gtggtgtgat                                              20

<210> SEQ ID NO 14
<211> LENGTH: 21
<212> TYPE: DNA
<213> ORGANISM: unknown
<220> FEATURE:
<223> OTHER INFORMATION: shRNA targeting SALL4 scramble peptide

<400> SEQUENCE: 14
cctaaggtta agtcgccctc g                                            21

<210> SEQ ID NO 15
<211> LENGTH: 20
<212> TYPE: DNA
<213> ORGANISM: unknown
<220> FEATURE:
<223> OTHER INFORMATION: c-Myc forward primer

<400> SEQUENCE: 15
tcaagaggcg aacacacaac                                              20

<210> SEQ ID NO 16
<211> LENGTH: 20
<212> TYPE: DNA
<213> ORGANISM: unknown
<220> FEATURE:
<223> OTHER INFORMATION: c-Myc reverse primer

<400> SEQUENCE: 16
ggccttttca ttgttttcca                                              20

<210> SEQ ID NO 17
<211> LENGTH: 11
<212> TYPE: PRT
<213> ORGANISM: unknown
```

```
<220> FEATURE:
<223> OTHER INFORMATION: TAT

<400> SEQUENCE: 17

Tyr Gly Arg Lys Lys Arg Arg Gln Arg Arg Arg
 1               5                  10

<210> SEQ ID NO 18
<211> LENGTH: 22
<212> TYPE: PRT
<213> ORGANISM: unknown
<220> FEATURE:
<223> OTHER INFORMATION: TAT-SALL4 wild type

<400> SEQUENCE: 18

Tyr Gly Arg Lys Lys Arg Arg Gln Arg Arg Arg Met Ser Arg Arg Lys
 1               5                  10                  15

Gln Ala Lys Pro His Ile
             20

<210> SEQ ID NO 19
<211> LENGTH: 22
<212> TYPE: PRT
<213> ORGANISM: unknown
<220> FEATURE:
<223> OTHER INFORMATION: TAT-SALL4 mutant

<400> SEQUENCE: 19

Tyr Gly Arg Lys Lys Arg Arg Gln Arg Arg Arg Met Ser Ala Ala Ala
 1               5                  10                  15

Gln Ala Lys Pro His Ile
             20

<210> SEQ ID NO 20
<211> LENGTH: 6
<212> TYPE: PRT
<213> ORGANISM: unknown
<220> FEATURE:
<223> OTHER INFORMATION: 6aa peptide

<400> SEQUENCE: 20

Met Ser Arg Arg Lys Gln
 1               5
```